(12) United States Patent
Benenato et al.

(10) Patent No.: US 11,220,476 B2
(45) Date of Patent: *Jan. 11, 2022

(54) COMPOUNDS AND COMPOSITIONS FOR INTRACELLULAR DELIVERY OF THERAPEUTIC AGENTS

(71) Applicant: ModernaTX, Inc., Cambridge, MA (US)

(72) Inventors: Kerry E. Benenato, Sudbury, MA (US); Mark Cornebise, Arlington, MA (US)

(73) Assignee: ModernaTX, Inc., Cambridge, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 16/555,045

(22) Filed: Aug. 29, 2019

(65) Prior Publication Data

US 2020/0123100 A1  Apr. 23, 2020

Related U.S. Application Data

(63) Continuation of application No. 15/846,084, filed on Dec. 18, 2017, now Pat. No. 10,442,756, which is a
(Continued)

(51) Int. Cl.
| | | |
|---|---|---|
| *C07C 229/12* | (2006.01) | |
| *C07C 271/20* | (2006.01) | |
| *C07C 279/12* | (2006.01) | |
| *C07C 279/28* | (2006.01) | |
| *C07C 279/32* | (2006.01) | |
| *C07D 233/72* | (2006.01) | |
| *C07D 249/04* | (2006.01) | |
| *C07D 263/20* | (2006.01) | |
| *C07D 265/33* | (2006.01) | |
| *C07D 271/06* | (2006.01) | |
| *C07D 271/10* | (2006.01) | |
| *C07D 207/27* | (2006.01) | |
| *C07D 277/38* | (2006.01) | |

(Continued)

(52) U.S. Cl.
CPC .......... *C07C 229/12* (2013.01); *A61K 9/0019* (2013.01); *A61K 9/0043* (2013.01); *A61K 9/0073* (2013.01); *A61K 9/127* (2013.01); *A61K 9/1272* (2013.01); *A61K 9/1617* (2013.01); *A61K 9/1641* (2013.01); *A61K 9/5123* (2013.01); *A61K 9/5146* (2013.01); *A61K 31/7105* (2013.01); *A61K 38/1725* (2013.01); *A61K 38/1816* (2013.01); *A61K 47/543* (2017.08); *A61K 47/6911* (2017.08); *A61K 48/005* (2013.01); *A61K 48/0033* (2013.01); *C07C 227/16* (2013.01); *C07C 227/18* (2013.01); *C07C 229/16* (2013.01); *C07C 233/36* (2013.01); *C07C 233/72* (2013.01); *C07C 235/10* (2013.01); *C07C 255/24* (2013.01); *C07C 263/20* (2013.01); *C07C 271/20* (2013.01); *C07C 275/14* (2013.01); *C07C 279/12* (2013.01); *C07C 279/24* (2013.01); *C07C 279/28* (2013.01); *C07C 279/32* (2013.01); *C07C 311/05* (2013.01); *C07C 335/08* (2013.01); *C07D 207/27* (2013.01); *C07D 233/72* (2013.01); *C07D 249/04* (2013.01); *C07D 263/20* (2013.01); *C07D 265/33* (2013.01); *C07D 271/06* (2013.01); *C07D 271/10* (2013.01); *C07D 277/38* (2013.01); *C07F 9/091* (2013.01); *C07K 14/505* (2013.01); *A61K 9/1271* (2013.01); *A61K 48/00* (2013.01); *C07C 2601/02* (2017.05); *C07C 2601/04* (2017.05); *C07C 2601/14* (2017.05); *C07C 2601/18* (2017.05)

(58) Field of Classification Search
CPC ... C12N 15/111; C12N 15/113; A61K 47/543; A61K 48/00; A61K 48/0008; A61K 9/127; A61K 9/1271; A61P 35/00
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 3,872,171 A | 3/1975 | Cronin et al. |
| 4,125,544 A | 11/1978 | Dygos |
| | (Continued) | |

FOREIGN PATENT DOCUMENTS

| | | |
|---|---|---|
| AU | 652831 B2 | 9/1994 |
| CN | 102068701 A | 5/2011 |
| | (Continued) | |

OTHER PUBLICATIONS

Abdelwahed et al., "Freeze-drying of nanoparticles: Formulation, process and storage considerations," Advanced Drug Delivery Reviews 58 (2006) 1688-1713.

Akinc et al., Development of Lipidoid-siRNA Formulations for Systemic Delivery to the Liver, Molecular Therapy, May 2009, vol. 17, No. 5, pp. 872-879.

Akinc et al., Targeted Delivery of RNAi Therapeutics With Endogenous and Exogenous Ligand-Based Mechanisms, Mol Ther. 2010 18(7):1357-1364.

(Continued)

*Primary Examiner* — Jane J Zara
(74) *Attorney, Agent, or Firm* — Cooley LLP; Heidi A. Erlacher; Christine C. Pemberton

(57) ABSTRACT

The disclosure features novel lipids and compositions involving the same. Nanoparticle compositions include a novel lipid as well as additional lipids such as phospholipids, structural lipids, and PEG lipids. Nanoparticle compositions further including therapeutic and/or prophylactics such as RNA are useful in the delivery of therapeutic and/or prophylactics to mammalian cells or organs to, for example, regulate polypeptide, protein, or gene expression.

22 Claims, 11 Drawing Sheets

Specification includes a Sequence Listing.

Related U.S. Application Data continuation of application No. 15/476,253, filed on Mar. 31, 2017, now Pat. No. 9,868,691, which is a continuation of application No. PCT/US2016/052352, filed on Sep. 16, 2016.

(60) Provisional application No. 62/393,940, filed on Sep. 13, 2016, provisional application No. 62/382,740, filed on Sep. 1, 2016, provisional application No. 62/333,557, filed on May 9, 2016, provisional application No. 62/266,460, filed on Dec. 11, 2015, provisional application No. 62/253,433, filed on Nov. 10, 2015, provisional application No. 62/252,316, filed on Nov. 6, 2015, provisional application No. 62/220,091, filed on Sep. 17, 2015, provisional application No. 62/220,085, filed on Sep. 17, 2015.

(51) Int. Cl.

| | | |
|---|---|---|
| *C07C 275/14* | (2006.01) | |
| *C07C 279/24* | (2006.01) | |
| *C07C 311/05* | (2006.01) | |
| *C07C 229/16* | (2006.01) | |
| *C07C 335/08* | (2006.01) | |
| *C07C 233/36* | (2006.01) | |
| *C07C 235/10* | (2006.01) | |
| *C07C 255/24* | (2006.01) | |
| *C07F 9/09* | (2006.01) | |
| *A61K 47/54* | (2017.01) | |
| *A61K 47/69* | (2017.01) | |
| *A61K 9/00* | (2006.01) | |
| *A61K 9/127* | (2006.01) | |
| *C07C 233/72* | (2006.01) | |
| *C07C 263/20* | (2006.01) | |
| *A61K 9/16* | (2006.01) | |
| *A61K 38/18* | (2006.01) | |
| *A61K 48/00* | (2006.01) | |
| *C07K 14/505* | (2006.01) | |
| *C07C 227/16* | (2006.01) | |
| *A61K 9/51* | (2006.01) | |
| *A61K 31/7105* | (2006.01) | |
| *A61K 38/17* | (2006.01) | |
| *C07C 227/18* | (2006.01) | |

(56) References Cited

U.S. PATENT DOCUMENTS

| | | | |
|---|---|---|---|
| 4,957,735 | A | 9/1990 | Huang |
| 5,807,861 | A | 9/1998 | Klein et al. |
| 6,143,276 | A | 11/2000 | Unger |
| 6,303,378 | B1 | 10/2001 | Bridenbaugh et al. |
| 6,395,253 | B2 | 5/2002 | Levy et al. |
| 6,652,886 | B2 | 11/2003 | Ahn et al. |
| 6,696,038 | B1 | 2/2004 | Mahato et al. |
| 7,268,120 | B1 | 9/2007 | Horton et al. |
| 7,371,404 | B2 | 5/2008 | Panzner et al. |
| 7,943,168 | B2 | 5/2011 | Schlesinger et al. |
| 8,058,069 | B2 | 11/2011 | Yaworski et al. |
| 8,158,601 | B2 | 4/2012 | Chen et al. |
| 8,420,123 | B2 | 4/2013 | Troiano et al. |
| 8,440,614 | B2 | 5/2013 | Castor |
| 8,449,916 | B1 | 5/2013 | Bellaire et al. |
| 8,450,298 | B2 | 5/2013 | Mahon et al. |
| 8,460,696 | B2 | 6/2013 | Slobodkin et al. |
| 8,460,709 | B2 | 6/2013 | Ausborn et al. |
| 8,563,041 | B2 | 10/2013 | Grayson et al. |
| 8,568,784 | B2 | 10/2013 | Lillard et al. |
| 8,569,256 | B2 | 10/2013 | Heyes et al. |
| 8,580,297 | B2 | 11/2013 | Essler et al. |
| 8,603,499 | B2 | 12/2013 | Zale et al. |
| 8,603,500 | B2 | 12/2013 | Zale et al. |
| 8,603,501 | B2 | 12/2013 | Zale et al. |
| 8,603,534 | B2 | 12/2013 | Zale et al. |
| 8,603,535 | B2 | 12/2013 | Troiano et al. |
| 8,609,142 | B2 | 12/2013 | Troiano et al. |
| 8,613,951 | B2 | 12/2013 | Zale et al. |
| 8,613,954 | B2 | 12/2013 | Zale et al. |
| 8,617,608 | B2 | 12/2013 | Zale et al. |
| 8,618,240 | B2 | 12/2013 | Podobinski et al. |
| 8,637,083 | B2 | 1/2014 | Troiano et al. |
| 8,642,076 | B2 | 2/2014 | Manoharan et al. |
| 8,652,487 | B2 | 2/2014 | Maldonado |
| 8,652,528 | B2 | 2/2014 | Troiano et al. |
| 8,663,599 | B1 | 3/2014 | Sung et al. |
| 8,663,700 | B2 | 3/2014 | Troiano et al. |
| 8,668,926 | B1 | 3/2014 | Mousa et al. |
| 8,685,368 | B2 | 4/2014 | Reineke |
| 8,691,750 | B2 | 4/2014 | Constein et al. |
| 8,697,098 | B2 | 4/2014 | Perumal et al. |
| 8,703,204 | B2 | 4/2014 | Bloom et al. |
| 8,709,483 | B2 | 4/2014 | Farokhzad et al. |
| 8,715,736 | B2 | 5/2014 | Sachdeva et al. |
| 8,715,741 | B2 | 5/2014 | Maitra et al. |
| 8,728,527 | B2 | 5/2014 | Singh |
| 8,734,832 | B2 | 5/2014 | O'Hagan et al. |
| 8,734,846 | B2 | 5/2014 | Ali et al. |
| 8,734,853 | B2 | 5/2014 | Sood et al. |
| 8,802,644 | B2 | 8/2014 | Chen et al. |
| 9,006,487 | B2 | 4/2015 | Anderson et al. |
| 9,029,590 | B2 | 5/2015 | Colletti et al. |
| 9,394,234 | B2 | 7/2016 | Chen et al. |
| 9,717,690 | B2 | 8/2017 | Guild et al. |
| 9,738,593 | B2 | 8/2017 | Ansell et al. |
| 9,867,888 | B2 | 1/2018 | Benenato |
| 9,868,691 | B2 * | 1/2018 | Benenato ............ A61K 38/1725 |
| 9,868,692 | B2 | 1/2018 | Benenato |
| 9,868,693 | B2 | 1/2018 | Benenato |
| 10,106,490 | B2 | 10/2018 | Du |
| 10,166,298 | B2 | 1/2019 | Ansell et al. |
| 10,392,341 | B2 | 8/2019 | Benenato et al. |
| 10,442,756 | B2 * | 10/2019 | Benenato ............ A61K 31/7105 |
| 10,799,463 | B2 | 10/2020 | Benenato et al. |
| 10,857,105 | B2 * | 12/2020 | Benenato ............... C07C 229/12 |
| 2003/0073619 | A1 | 4/2003 | Mahato et al. |
| 2003/0092653 | A1 | 5/2003 | Kisich et al. |
| 2004/0142474 | A1 | 7/2004 | Mahato et al. |
| 2005/0222064 | A1 | 10/2005 | Vargeese et al. |
| 2006/0008910 | A1 | 1/2006 | Maclachlan et al. |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2007/0252295 | A1 | 11/2007 | Panzner et al. |
| 2009/0042825 | A1 | 2/2009 | Matar et al. |
| 2009/0042829 | A1 | 2/2009 | Matar et al. |
| 2011/0009641 | A1 | 1/2011 | Anderson et al. |
| 2011/0200582 | A1 | 8/2011 | Baryza et al. |
| 2011/0244026 | A1 | 10/2011 | Guild et al. |
| 2012/0136073 | A1 | 5/2012 | Yang et al. |
| 2012/0177724 | A1 | 7/2012 | Irvine et al. |
| 2012/0178702 | A1 | 7/2012 | Huang |
| 2012/0226085 | A1 | 9/2012 | Ishihara et al. |
| 2012/0295832 | A1 | 11/2012 | Constien et al. |
| 2013/0017223 | A1 | 1/2013 | Hope et al. |
| 2013/0064894 | A1 | 3/2013 | Martin et al. |
| 2013/0065942 | A1 | 3/2013 | Matar et al. |
| 2013/0090372 | A1 | 4/2013 | Budzik et al. |
| 2013/0108685 | A1 | 5/2013 | Kuboyama et al. |
| 2013/0115273 | A1 | 5/2013 | Yang et al. |
| 2013/0115274 | A1 | 5/2013 | Knopov et al. |
| 2013/0116307 | A1 | 5/2013 | Heyes et al. |
| 2013/0122104 | A1 | 5/2013 | Yaworski et al. |
| 2013/0123338 | A1 | 5/2013 | Heyes et al. |
| 2013/0129785 | A1 | 5/2013 | Manoharan et al. |
| 2013/0130348 | A1 | 5/2013 | Gu et al. |
| 2013/0142868 | A1 | 6/2013 | Hoekman et al. |
| 2013/0142876 | A1 | 6/2013 | Howard et al. |
| 2013/0150625 | A1 | 6/2013 | Budzik et al. |
| 2013/0156845 | A1 | 6/2013 | Manoharan et al. |
| 2013/0156849 | A1 | 6/2013 | de Fougerolles et al. |

(56) References Cited

U.S. PATENT DOCUMENTS

| | | |
|---|---|---|
| 2013/0164400 A1 | 6/2013 | Knopov et al. |
| 2013/0171241 A1 | 7/2013 | Geall |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189351 A1 | 7/2013 | Geall |
| 2013/0195759 A1 | 8/2013 | Mirkin et al. |
| 2013/0195765 A1 | 8/2013 | Gho et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236550 A1 | 9/2013 | Ausborn et al. |
| 2013/0243827 A1 | 9/2013 | Troiano et al. |
| 2013/0243848 A1 | 9/2013 | Lobovkina et al. |
| 2013/0243867 A1 | 9/2013 | Mohapatra et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0266617 A1 | 10/2013 | Mirosevich et al. |
| 2013/0273117 A1 | 10/2013 | Podobinski et al. |
| 2013/0274504 A1 | 10/2013 | Colletti et al. |
| 2013/0274523 A1 | 10/2013 | Bawiec, III et al. |
| 2013/0280334 A1 | 10/2013 | Karp et al. |
| 2013/0280339 A1 | 10/2013 | Zale et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0017327 A1 | 1/2014 | Cheng et al. |
| 2014/0017329 A1 | 1/2014 | Mousa |
| 2014/0037573 A1 | 2/2014 | Eliasof et al. |
| 2014/0037660 A1 | 2/2014 | Folin-Mleczek et al. |
| 2014/0037714 A1 | 2/2014 | Quay et al. |
| 2014/0039032 A1 | 2/2014 | Kumboyama et al. |
| 2014/0044772 A1 | 2/2014 | Maclachlan et al. |
| 2014/0044791 A1 | 2/2014 | Basilion et al. |
| 2014/0045913 A1 | 2/2014 | Kumboyama et al. |
| 2014/0050775 A1 | 2/2014 | Slobodkin et al. |
| 2014/0057109 A1 | 2/2014 | Mechen et al. |
| 2014/0065172 A1 | 3/2014 | Echeverri et al. |
| 2014/0065204 A1 | 3/2014 | Hayes et al. |
| 2014/0065228 A1 | 3/2014 | Yarowoski et al. |
| 2014/0079774 A1 | 3/2014 | Brinker et al. |
| 2014/0093575 A1 | 4/2014 | Hammond et al. |
| 2014/0093579 A1 | 4/2014 | Zale et al. |
| 2014/0113137 A1 | 4/2014 | Podobinski et al. |
| 2014/0121263 A1 | 5/2014 | Fitzgerald et al. |
| 2014/0121393 A1 | 5/2014 | Manoharan et al. |
| 2014/0134260 A1 | 5/2014 | Heyes et al. |
| 2014/0141070 A1 | 5/2014 | Geall et al. |
| 2014/0141089 A1 | 5/2014 | Liang |
| 2014/0141483 A1 | 5/2014 | Bossard et al. |
| 2014/0142165 A1 | 5/2014 | Grayson et al. |
| 2014/0142254 A1 | 5/2014 | Fonnum et al. |
| 2014/0161830 A1 | 6/2014 | Anderson et al. |
| 2014/0288160 A1 | 9/2014 | Guild et al. |
| 2014/0308304 A1 | 10/2014 | Manoharan et al. |
| 2015/0174260 A1 | 6/2015 | Yang et al. |
| 2015/0174261 A1 | 6/2015 | Kuboyama et al. |
| 2015/0239926 A1 | 8/2015 | Payne et al. |
| 2015/0284317 A1 | 10/2015 | Colletti et al. |
| 2015/0343062 A1 | 12/2015 | Kuboyama et al. |
| 2015/0376115 A1 | 12/2015 | Ansell et al. |
| 2016/0002178 A1 | 1/2016 | Fenton et al. |
| 2016/0009657 A1 | 1/2016 | Anderson et al. |
| 2016/0151284 A1 | 6/2016 | Heyes et al. |
| 2017/0119904 A1 | 5/2017 | Ansell et al. |
| 2018/0201572 A1 | 7/2018 | Benenato |
| 2018/0273467 A1 | 9/2018 | Benenato |
| 2018/0303925 A1 | 10/2018 | Weissman et al. |
| 2018/0333366 A1 | 11/2018 | Benenato et al. |
| 2018/0369419 A1 | 12/2018 | Benenato et al. |
| 2019/0016669 A1 | 1/2019 | Benenato et al. |
| 2019/0314292 A1 | 10/2019 | Benenato et al. |
| 2019/0314524 A1 | 10/2019 | Ansell et al. |
| 2019/0336452 A1 | 11/2019 | Brader et al. |
| 2020/0069599 A1 | 3/2020 | Smith et al. |
| 2020/0129445 A1 | 4/2020 | Patel |
| 2020/0131116 A1 | 4/2020 | Almarsson et al. |
| 2021/0087135 A1 | 3/2021 | Benenato et al. |

FOREIGN PATENT DOCUMENTS

| | | |
|---|---|---|
| CN | 102204920 A | 10/2011 |
| CN | 102813929 A | 12/2012 |
| CN | 104644555 A | 5/2015 |
| EP | 737750 | 10/1996 |
| EP | 1404860 B1 | 5/2002 |
| EP | 2073848 B1 | 8/2013 |
| JP | 2000-169864 A | 6/2000 |
| WO | WO 1993/014778 | 8/1993 |
| WO | WO 1999/014346 A2 | 3/1999 |
| WO | WO 1999/052503 | 10/1999 |
| WO | WO 1999/54344 A1 | 10/1999 |
| WO | WO 2003/086280 | 10/2003 |
| WO | WO 2005/034979 A2 | 4/2005 |
| WO | WO 2006/063249 A2 | 6/2006 |
| WO | WO 2008/042973 A2 | 4/2008 |
| WO | WO 2009/024599 | 2/2009 |
| WO | WO 2009/053686 A1 | 4/2009 |
| WO | WO 2009/086558 A1 | 7/2009 |
| WO | WO 2009/127060 A1 | 10/2009 |
| WO | WO 2009/129385 A1 | 10/2009 |
| WO | WO 2009/129395 A1 | 10/2009 |
| WO | WO 2010/030739 A1 | 3/2010 |
| WO | WO 2010/042877 A1 | 4/2010 |
| WO | WO 2010/053572 A2 | 5/2010 |
| WO | WO 2010/054406 A1 | 5/2010 |
| WO | WO 2010/088537 A2 | 8/2010 |
| WO | WO 2010/129709 A1 | 11/2010 |
| WO | WO 2011/058990 A1 | 5/2011 |
| WO | WO 2011/068810 A1 | 6/2011 |
| WO | WO 2011/127255 A1 | 10/2011 |
| WO | WO 2012/000104 A1 | 1/2012 |
| WO | WO 2012/006376 A2 | 1/2012 |
| WO | WO 2012/006378 A1 | 1/2012 |
| WO | WO 2012/030901 A1 | 3/2012 |
| WO | WO 2012/031043 A1 | 3/2012 |
| WO | WO 2012/031046 A2 | 3/2012 |
| WO | WO 2012/054365 A2 | 4/2012 |
| WO | WO 2012/129483 A1 | 9/2012 |
| WO | WO 2012/149252 A2 | 11/2012 |
| WO | WO 2012/149255 A2 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149376 A2 | 11/2012 |
| WO | WO 2012/149393 A2 | 11/2012 |
| WO | WO 2012/153338 A2 | 11/2012 |
| WO | WO 2012/170889 A1 | 12/2012 |
| WO | WO 2012/170930 A1 | 12/2012 |
| WO | WO 2013/006825 A1 | 1/2013 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/016058 A1 | 1/2013 |
| WO | WO 2013/033438 A2 | 3/2013 |
| WO | WO 2013/033563 A1 | 3/2013 |
| WO | WO 2013/036835 A1 | 3/2013 |
| WO | WO 2013/049328 A1 | 4/2013 |
| WO | WO 2013/052167 A2 | 4/2013 |
| WO | WO 2013/056132 A2 | 4/2013 |

(56) References Cited

FOREIGN PATENT DOCUMENTS

| | | |
|---|---|---|
| WO | WO 2013/057715 A1 | 4/2013 |
| WO | WO 2013/059496 A1 | 4/2013 |
| WO | WO 2013/059922 A1 | 5/2013 |
| WO | WO 2013/064911 A2 | 5/2013 |
| WO | WO 2013/066903 A1 | 5/2013 |
| WO | WO 2013/067537 A1 | 5/2013 |
| WO | WO 2013/070872 A2 | 5/2013 |
| WO | WO 2013/072929 A2 | 5/2013 |
| WO | WO 2013/086322 A1 | 6/2013 |
| WO | WO 2013/086354 A1 | 6/2013 |
| WO | WO 2013/086373 A1 | 6/2013 |
| WO | WO 2013/086526 A1 | 6/2013 |
| WO | WO 2013/087083 A1 | 6/2013 |
| WO | WO 2013/087791 A1 | 6/2013 |
| WO | WO 2013/093648 A2 | 6/2013 |
| WO | WO 2013/135359 A1 | 9/2013 |
| WO | WO 2013/143555 A1 | 10/2013 |
| WO | WO 2013/143683 A1 | 10/2013 |
| WO | WO 2013/148186 A1 | 10/2013 |
| WO | WO 2013/148541 A1 | 10/2013 |
| WO | WO 2013/149141 A1 | 10/2013 |
| WO | WO 2013/151650 A1 | 10/2013 |
| WO | WO 2013/155487 A1 | 10/2013 |
| WO | WO 2013/155493 A9 | 10/2013 |
| WO | WO 2013/158127 A1 | 10/2013 |
| WO | WO 2013/158579 A1 | 10/2013 |
| WO | WO 2013/166498 A1 | 11/2013 |
| WO | WO 2013/173693 A1 | 11/2013 |
| WO | WO 2013/177419 A2 | 11/2013 |
| WO | WO 2013/177421 A2 | 11/2013 |
| WO | WO 2013/185069 A1 | 12/2013 |
| WO | WO 2014/007398 A1 | 1/2014 |
| WO | WO 2014/008334 A1 | 1/2014 |
| WO | WO 2014/026284 A1 | 2/2014 |
| WO | WO 2014/028487 A1 | 2/2014 |
| WO | WO 2014/028763 A1 | 2/2014 |
| WO | WO 2014/047649 A1 | 3/2014 |
| WO | WO 2014/052634 A1 | 4/2014 |
| WO | WO 2014/054026 A1 | 4/2014 |
| WO | WO 2014/071072 A2 | 5/2014 |
| WO | WO 2014/072997 A1 | 5/2014 |
| WO | WO 2014/089486 A1 | 6/2014 |
| WO | WO 2014/144196 A1 | 9/2014 |
| WO | WO 2014/160243 A1 | 10/2014 |
| WO | WO 2014/172045 A1 | 10/2014 |
| WO | WO 2011/136368 A1 | 11/2014 |
| WO | WO 2014/182661 A2 | 11/2014 |
| WO | WO 2014/210356 A1 | 12/2014 |
| WO | WO 2015/011633 A1 | 1/2015 |
| WO | WO 2015/130584 A2 | 9/2015 |
| WO | WO 2015/154002 A1 | 10/2015 |
| WO | WO 2015/199952 A1 | 12/2015 |
| WO | WO 2016/004202 A1 | 1/2016 |
| WO | WO 2016/004318 A1 | 1/2016 |
| WO | WO 2016/118697 A1 | 7/2016 |
| WO | WO 2016/118724 A1 | 7/2016 |
| WO | WO 2016/176330 A1 | 11/2016 |
| WO | WO 2017/015630 A2 | 1/2017 |
| WO | WO 2017/031232 A1 | 2/2017 |
| WO | WO 2017/070616 A2 | 4/2017 |
| WO | WO 2017/070626 A2 | 4/2017 |
| WO | WO 2017/075531 A1 | 5/2017 |
| WO | WO 2017/099823 A1 | 6/2017 |
| WO | WO 2017/100744 A1 | 6/2017 |
| WO | WO 2017/112865 A1 | 6/2017 |
| WO | WO 2017/127750 A1 | 7/2017 |
| WO | WO 2017/180917 A2 | 10/2017 |
| WO | WO 2017/192470 A1 | 11/2017 |
| WO | WO 2017/201317 A1 | 11/2017 |
| WO | WO 2017/201325 A1 | 11/2017 |
| WO | WO 2017/201328 A1 | 11/2017 |
| WO | WO 2017/201332 A1 | 11/2017 |
| WO | WO 2017/201333 A1 | 11/2017 |
| WO | WO 2017/201340 A2 | 11/2017 |
| WO | WO 2017/201342 A1 | 11/2017 |
| WO | WO 2017/201346 A1 | 11/2017 |
| WO | WO 2017/201347 A1 | 11/2017 |
| WO | WO 2017/201348 A1 | 11/2017 |
| WO | WO 2017/201349 A1 | 11/2017 |
| WO | WO 2017/201350 A1 | 11/2017 |
| WO | WO 2017/201352 A1 | 11/2017 |
| WO | WO 2017/218704 A1 | 12/2017 |
| WO | WO 2018/078053 A1 | 5/2018 |
| WO | WO 2018/081480 A1 | 5/2018 |
| WO | WO 2018/081638 A1 | 5/2018 |
| WO | WO 2018/089540 A1 | 5/2018 |
| WO | WO 2018/170260 A1 | 9/2018 |
| WO | WO 2018/170270 A1 | 9/2018 |
| WO | WO 2018/170306 A1 | 9/2018 |
| WO | WO 2018/170322 A1 | 9/2018 |
| WO | WO 2018/170336 A1 | 9/2018 |
| WO | WO 2018/191719 A1 | 10/2018 |
| WO | WO 2018/232120 A1 | 12/2018 |
| WO | WO 2019/046809 A1 | 3/2019 |
| WO | WO 2019/089828 A1 | 5/2019 |
| WO | WO 2019/152557 A1 | 8/2019 |
| WO | WO 2019/193183 A2 | 10/2019 |
| WO | WO 2019/202035 A1 | 10/2019 |
| WO | WO 2020/002525 A1 | 1/2020 |
| WO | WO 2020/061457 A1 | 3/2020 |
| WO | WO 2020/123300 A2 | 6/2020 |

OTHER PUBLICATIONS

Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Andries, O., et al., Comparison of the gene transfer efficiency of mRNA/GL67 and pDNA/GL67 complexes in respiratory cells. Mol Pharmaceutics. 2012; 9: 2136-2145.

Ashizawa et al., "Liposomal delivery of nucleic acid-based anti-cancer therapeutics: BP-100-1.01," Expert Opin. Drug Deliv., (2014) 12(7):1107-1120.

Bag, J., Recovery of normal protein synthesis in heat-shocked chicken myotubes by liposome-mediated transfer of mRNAs. Can. J. Biochem. Cell Biol. 1985; 63(3): 231-235.

Belliveau, N.M., et al., Microfluidic synthesis of highly potent limit-size lipid nanoparticles for in vivo delivery of siRNA. Mol Ther Nucleic Acids. Aug. 2012; 1(8): e37.

Bettinger, T. et al., Peptide-mediated RNA delivery: a novel approach for enhanced transfection of primary and post-mitotic cells. Nucleic Acids Res. Sep. 15, 2001;29(18):3882-91.

Bolhassani A., et al., Improvement of Different Vaccine Delivery Systems For Cancer Therapy, Molecular Cancer, Biomed Central, London, GB, 2011, vol. 10, No. 3, pp. 1-20.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bouxsein, N.F., et al., Structure and gene silencing activities of monovalent and pentavalent cationic lipid vectors complexed with siRNA. Biochem. 2007; 46(16): 4785-4792.

Chen, D., et al., Rapid discovery of potent siRNA-containing lipid nanoparticles enabled by controlled microfluidic formulation. J Am Chem Soc. 2012; 134: 6948-6951.

Chen, S. et al., "Development of lipid nanoparticle formulations of siRNA for hepatocyte gene silencing following subcutaneous administration," J Control Release, 2014, 196, 106-112.

Cun, Dongmei, et al., Preparation and characterization of poly(DL-lactide-co-glycolide) nanoparticles for siRNA delivery. International Journal of Pharmaceutics 390 (2010) 70-75.

Dahlman, James E. et al., In vivo endothelial siRNA delivery using polymeric nanoparticles with low molecular weight, Nature Nanotechnology, 2014, No. vol. #, pp. 1-8.

Delehanty, James B., Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.

(56) References Cited

OTHER PUBLICATIONS

El Ouahabi, A., et al., Double long-chain amidine liposome-mediated self replicating RNA transfection. FEBS Letters. Feb. 1996; 380(1-2): 108-112.
Felgner, PL Cationic lipid/polynucleotide condensates for in vitro and in vivo polynucleotide delivery—the cytofectins. J. of Liposome Research. 1993; 3(1): 3-16.
Felgner, PL Particulate systems and polymers for in vitro and in vivo delivery of polynucleotides. Adv. Drug Delivery Rev. 1990; 5(3): 163-187.
Felgner, PL, et al., Lipofection: a highly efficient, lipid-mediated DNA-transfection procedure. Proc Natl Acad Sci U SA. Nov. 1987;84(21):7413-7.
Gao, X. et al., Nonviral gene delivery: what we know and what is next. AAPS J. Mar. 23, 2007;9(1):E92-104.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
He, K. et al., Synthesis and Separation of Diastereomers of Ribonucleoside 5'-(alpha-P-Borano)triphosphates. J Org Chem. Aug. 21, 1998;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hoerr, I. et al., In vivo application of RNA leads to induction of specific cytotoxic T lymphocytes and antibodies. EurJ Immunol. Jan. 2000;30(1):1-7.
Jayaraman et al., "Maximizing the Potency of siRNA Lipid Nanoparticles for Hepatic Gene Silencing In Vivo," Angew. Chem. Int. Ed. 2012, 51, 8529-8533.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., Phosphate-enhanced transfection of cationic lipid-complexed mRNA and plasmid DNA. Biochimica et Biophysica Acta. 1998. 1369:320-34.
Kariko, K., et al., In vivo protein expression from mRNA delivered into adult rat brain. J. of Neuroscience Methods. Jan. 2001; 105(1): 77-86.
Kariko, K., et al., Incorporation of pseudouridine into mRNA yields superior nonimmunogenic vector with increased translational capacity and biological stability, Molecular Therapy, Nature Publishing Group, GB, vol. 16, No. 11, Nov. 1, 2008 (Nov. 1, 2008), pp. 1833-1840.
Keown, WA, et al., Methods for Introducing DNA into Mammalian Cells. Methods in Enzymology, 1990, 185:527-37.
Kirpotin, D.B., et al., Antibody targeting of long-circulating lipidic nanoparticles does not increase tumor localization but does increase internalization in animal models. Cancer Res. 2006; 66: 6732-6740.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8,' No. 4 ',pp. 3232-3241.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.
Lee, Justin B. et al., Lipid Nanoparticle siRNA Systems for Silencing The Androgen Receptor In Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Leung et al., "Lipid Nanoparticles for Short Interfering RNA Delivery", Advances in Genetics, vol. 88, Chapter 4, pp. 71-110.

Lewis, David, Dynamic Polyconjugates (DPC) Technology: An elegant solution to the siRNA delivery problem. Arrowhead Research Corp (NASDAQ: ARWR). Nov. 2011.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008;31(7):924-31. Epub Aug. 14, 2008.
Lian, T. et al., Trends and developments in liposome drug delivery systems. J Pharm Sci. Jun. 2001;90(6):667-80.
Lopez-Berestein, G. et al., Treatment of systemic fungal infections with liposomal amphotericin B. Arch Intern Med. Nov. 1989;149 (11 ):2533-6.
Love et al., Lipid-like materials for low-dose, in vivo gene silencing, PNAS vol. 107 No. 5, pp. 1864-1869, Feb. 2, 2010.
M. Kanapathipillai, et al., Nanoparticle targeting of anti-cancer drugs that alter intracellular signaling or influence the tumor microenvironment, Adv. Drug Deliv. Rev. (2014), , pp. 1-12.
Magee, W .E. et al., Marked stimulation of lymphocyte-mediated attack on tumor cells by target-directed liposomes containing immune RNA, Cancer Res., 1978, 38(4):1173-6.
Malone, R.W. et al., Cationic liposome-mediated RNA transfection. Proc Natl Acad Sci U S A. Aug. 1989;86 (16):6077-81.
Martinon, F. et al., Induction of virus-specific cytotoxic T lymphocytes in vivo by liposome-entrapped mRNA. Eur J Immunol. Jul. 1993;23(7):1719-22.
Maskarinec et al., "Direct Observation of Poloxamer 188 Insertion into Lipid Monolayers," Biophys J., Mar. 2002, vol. 82, 1453-1459.
Maurer, N., et al., Spontaneous entrapment of polynucleotides upon electrostatic interaction with ethanol-destabilized cationic liposomes. Biophys J. May 2001; 80(5):2310-2326.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review .
Mishra, R.K. et al., Improved leishmanicidal effect of phosphorothioate antisense oligonucleotides by LDL-mediated delivery. Biochim Biophys Acta. Nov. 7, 1995;1264(2):229-37.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Morissette et al., "High-throughput crystallization: polymorphs, salts, co-crystals and solvates of pharmaceutical solids," Advanced Drug Delivery Reviews 56 (2004) 275-300.
Müller et al, "Solid lipid nanoparticles (SLN) for controlled drug delivery—a review of the state of the art," European Journal of Pharmaceutics and Biopharmaceutics, 50 (2000) 161-177.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Pollard, C., et al., Type I IFN counteracts the induction of antigen-specific immune responses by lipid-based delivery of mRNA vaccines. Mol Ther. Jan. 2013; 21(1): 251-259.
Pulford, B., et al., Liposome-siRNA-peptide complexes cross the blood-brain barrier and significantly decrease PrP∧C on neuronal cells and PrP∧RES in infected cell cultures. PLoS ONE. 2010; 5(6): e11085.
Sahay, G. et al., "Efficiency of siRNA delivery by lipid nanoparticles is limited by endocytic recycling," Nat Biotechnol. Jul. 2013 ; 31(7): 653-658.

(56) References Cited

OTHER PUBLICATIONS

Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Schott, J.W., et al., Viral and non-viral approaches for transient delivery of mRNA and proteins. Current Gene Ther. 2011; 11 (5): 382-398.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Shah et al., "Lipid Nanoparticles: Production, Characterization and Stability," Springer International Publishing, 2014, 23 pages.
Shea, R.G. et al., Synthesis, hybridization properties and antiviral activity of lipid-oligodeoxynucleotide conjugates. Nucleic Acids Res.Jul. 11, 1990;18(13):3777-83.
Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Svinarchuk, F.P. et al., Inhibition of HIV proliferation in MT-4 cells by antisense oligonucleotide conjugated to lipophilic groups. Biochimie. 1993;75(1-2):49-54.
Tam et al., "Advances in Lipid Nanoparticles for siRNA Delivery," Pharmaceutics 2013, 5, 498-507; doi:10.3390/pharmaceutics5030498.
Tavernier, G., et al., mRNA as gene therapeutic: How to control protein expression. J. of Controlled Release. Mar. 2011; 150(3): 238-247.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Torchilin, Vladimir et al., Multifunctional and Stimuli-Sensitive Pharmaceutical Nanocarriers, Eur J. Pharm Biopharm, 2009, vol. 71, No. 3, pp. 431-444.
Tracy, M., "Progress in the Development of LNP Delivery for siRNA Advancing LNPs to the Clinic," International Liposome Research Days Meeting, Vancouver, Canada. Aug. 2010, pp. 1-52.
Treat, J. et al., in Liposomes in the Therapy of Infectious Disease and Cancer, Lopez-Berestein and Fidler (eds.), Liss, New York, 1989. 353-65.
Uzgun, S., et al., PEGylation improves nanoparticle formation and transfection efficiency of messenger RNA. Pharm Res. Sep. 2011; 28(9); 2223-2232.
Van Tendeloo, V.F. et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Wan et al., Lipid nanoparticle delivery systems for siRNA-based therapeutics. Drug Deliv Transl Res. Feb. 2014;4(1):74-83. doi:10.1007/s13346-013-0161-z.
Wang et al., Systemic delivery of modified mRNA encoding herpes simplex virus 1 thymidine kinase for targeted cancer gene therapy. Mol Ther. Feb. 2013;21 (2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Yamamoto et al., Current prospects for mRNA gene delivery, European Journal of Pharmaceutics and Biopharmaceutics 71 (2009) 484-489.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann, E. et al., Electrolyte- and pH-stabilities of aqueous solid lipid nanoparticle (SLN™) dispersions in artificial gastrointestinal media. Eur J Pharm Biopharm. Sep. 2001;52(2):203-10.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1): 373-378.
Dong et al.,"Lipopeptide nanoparticles for potent and selective siRNA delivery in rodents and nonhuman primates," PNAS, Mar. 2014, vol. 111, No. 11, 3955-3960; 5753-5754.
Hashiba et al., "pH-labile PEGylation of siRNA-loaded lipid nanoparticle improves active targeting and gene silencing activity in hepatocytes," Journal of Controlled Release (2017) vol. 262, 239-246.
Heurtault et al., "Physico-chemical stability of colloidal lipid particles," Biomaterials, 2003, 24: 4283-4300.
Jaiswal et al., "Nanostructured lipid carriers and their current application in targeted drug delivery," Artificial Cells, Nanomedicine, and Biotechnology (2016) 44: 27-40.
Lewis, R., et al., "Studies of the Thermotropic Phase Behavior of Phosphatidylcholines Containing 2-Alkyl Substituted Fatty Acyl Chains: A New Class of Phosphatidylcholines Forming Inverted Nonlamellar Phases," Biophysical Journal, Apr. 1994, vol. 66, pp. 1088-1103.
Mohtar et al., "Solid Lipid Nanoparticles of Atovaquone Based on $2^4$ Full-Factorial Design," Iranian Journal of Pharmaceutical Research (2015) 14(4): 989-1000.
Müller et al., "Solid lipid nanoparticles (SLN) as potential carrier for human use: interaction with human granulocytes," Journal of Controlled Release, 1997, 47: 261-269.
Ramteke, K. H. et al., "Solid Lipid Nanoparticle: A Review," IOSR Journal of Pharmacy, Nov.-Dec. 2012, 2(60): 34-44.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Yadava, P. et al., "Effect of Lyophilization and Freeze-thawing on the Stability of siRNA-liposome Complexes," AAPS PharmSciTech, Jun. 2008, 9(2): 335-341.
Zhang et al., "A novel cationic cardiolipin analogue for gene delivery," Pharmazie, 2006, 61: 10-14.

* cited by examiner

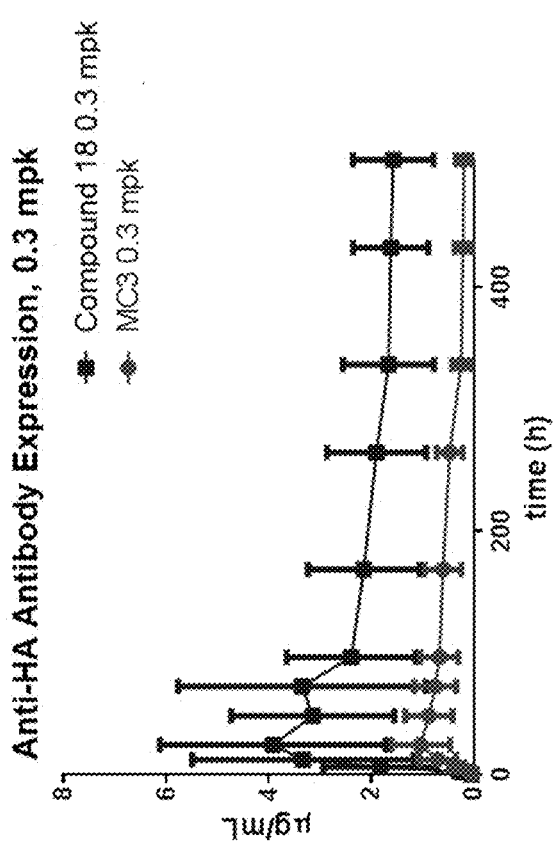
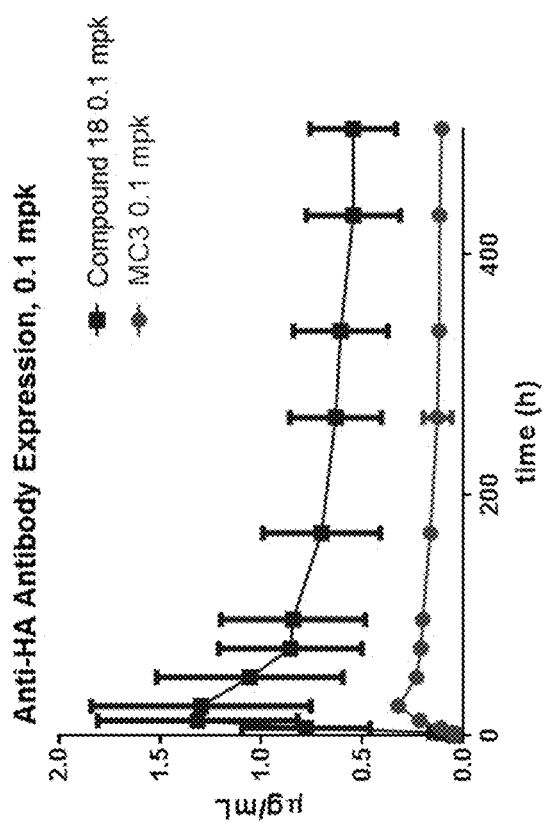
Fig. 11B
Fig. 11A

SEQUENCE LISTING

<160> NUMBER OF SEQ ID NOS: 6

<210> SEQ ID NO 1
<400> SEQUENCE: 1
000

<210> SEQ ID NO 2
<400> SEQUENCE: 2
000

<210> SEQ ID NO 3
<400> SEQUENCE: 3
000

<210> SEQ ID NO 4
<400> SEQUENCE: 4
000

<210> SEQ ID NO 5
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 5
caaaggctct tttcagagcc acca        24

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
caaaggcucu uuucagagcc acca        24

COMPOUNDS AND COMPOSITIONS FOR INTRACELLULAR DELIVERY OF THERAPEUTIC AGENTS

RELATED APPLICATIONS

This application is a continuation of U.S. Ser. No. 15/846,084, filed on Dec. 18, 2017, now allowed, which is a continuation of U.S. Ser. No. 15/476,253 filed on Mar. 31, 2017, now U.S. Pat. No. 9,868,691, issued on Jan. 16, 2018, which is a continuation application of International Application PCT/US2016/052352, having an international filing date of Sep. 16, 2016, which claims priority to, and the benefit of, U.S. Provisional Application Nos. 62/220,085, filed Sep. 17, 2015; 62/220,091, filed Sep. 17, 2015; 62/252,316, filed Nov. 6, 2015; 62/253,433, filed Nov. 10, 2015; 62/266,460, filed Dec. 11, 2015; 62/333,557, filed May 9, 2016; 62/382,740, filed Sep. 1, 2016; and 62/393,940, filed Sep. 13, 2016; the entire contents of each of which are incorporated herein by reference in their entireties.

INCORPORATION-BY-REFERENCE OF SEQUENCE LISTING

The contents of the text file named "MRNA014001WOST25.txt", which was created on Dec. 2, 2016 and is 1 KB in size, are hereby incorporated by reference in their entireties.

FIELD OF DISCLOSURE

The present disclosure provides novel compounds, compositions comprising such compounds, and methods involving lipid nanoparticle compositions to deliver one or more therapeutic and/or prophylactics to and/or produce polypeptides in mammalian cells or organs. In addition to a novel lipid, lipid nanoparticle compositions of the disclosure may include one or more cationic and/or ionizable amino lipids, phospholipids including polyunsaturated lipids, PEG lipids, structural lipids, and/or therapeutic and/or prophylactics in specific fractions.

BACKGROUND OF THE DISCLOSURE

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutic and/or prophylactics such as nucleic acids to cells.

Lipid-containing nanoparticle compositions, liposomes, and lipoplexes have proven effective as transport vehicles into cells and/or intracellular compartments for biologically active substances such as small molecule drugs, proteins, and nucleic acids. Such compositions generally include one or more "cationic" and/or amino (ionizable) lipids, phospholipids including polyunsaturated lipids, structural lipids (e.g., sterols), and/or lipids containing polyethylene glycol (PEG lipids). Cationic and/or ionizable lipids include, for example, amine-containing lipids that can be readily protonated. Though a variety of such lipid-containing nanoparticle compositions have been demonstrated, improvements in safety, efficacy, and specificity are still lacking.

SUMMARY OF THE DISCLOSURE

The present disclosure provides novel compounds and compositions and methods involving the same.

A first aspect of the disclosure relates to compounds of Formula (I):

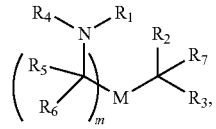

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R)OR, and —$C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-8}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-8}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)

$N(R)_2$, —C(=$NR_9$)R, —C(O)N(R)OR, and —C(=$NR_9$)N$(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-8}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In certain embodiments, a subset of compounds of Formula (I) includes those of Formula (IA):

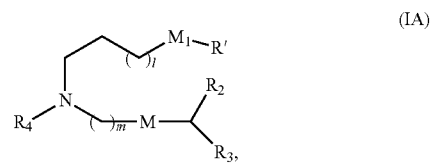

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=$NR_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

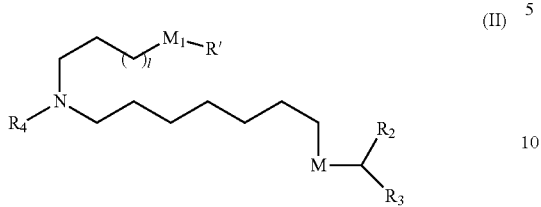

(II)

R$_3$ (II) or a salt or isomer thereof, wherein 1 is selected from 1, 2, 3, 4, and 5; M$_1$ is a bond or M'; R$_4$ is unsubstituted C$_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In certain embodiments, a subset of compounds of Formula (I) includes those of Formula (IIa), (IIb), (IIc), or (IIe):

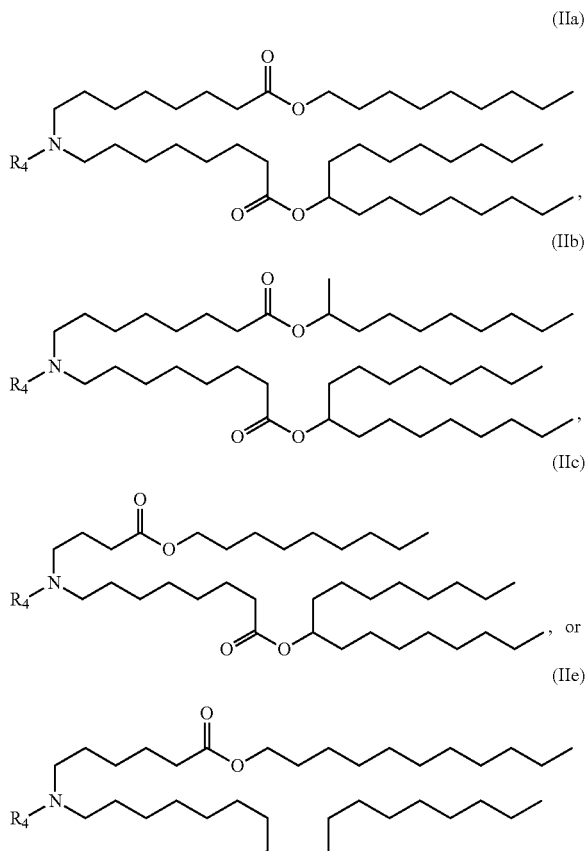

(IIa)

(IIb)

(IIc)

, or (IIe)

or a salt or isomer thereof, wherein R$_4$ is as described herein.

In certain embodiments, a subset of compounds of Formula (I) includes those of Formula (IId):

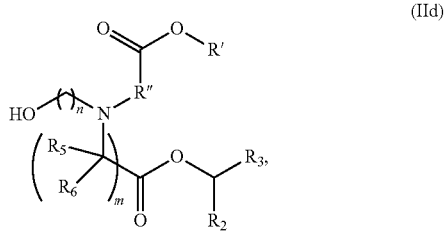

(IId)

or a salt or isomer thereof, wherein n is 2, 3, or 4; and m, R', R'', and R$_2$ through R$_6$ are as described herein. For example, each of R$_2$ and R$_3$ may be independently selected from the group consisting of C$_{5-14}$ alkyl and C$_{5-14}$ alkenyl.

In another aspect, the disclosure features a nanoparticle composition including a lipid component comprising a compound as described herein (e.g., a compound according to Formula (I), (IA), (II), (IIa), (IIb), (IIc), (IId) or (IIe)).

In yet another aspect, the disclosure features a pharmaceutical composition comprising a nanoparticle composition according to the preceding aspects and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In another aspect, the disclosure provides a method of delivering a therapeutic and/or prophylactic (e.g., an mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In another aspect, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In another aspect, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In another aspect, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In another aspect, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In yet another aspect, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

BRIEF DESCRIPTION OF THE DRAWINGS

FIGS. 11A and 11B show the results of anti-HA (anti-hemagglutinin) antibody expression measured after intravenous administration of various nanoparticle compositions including MC3 and Compound 18 at a 0.1 mpk (FIG. 11A) or 0.3 mpk (FIG. 11B) dose with 60 minutes infusion to naive cynomolgus monkeys.

DETAILED DESCRIPTION

Figure 1:
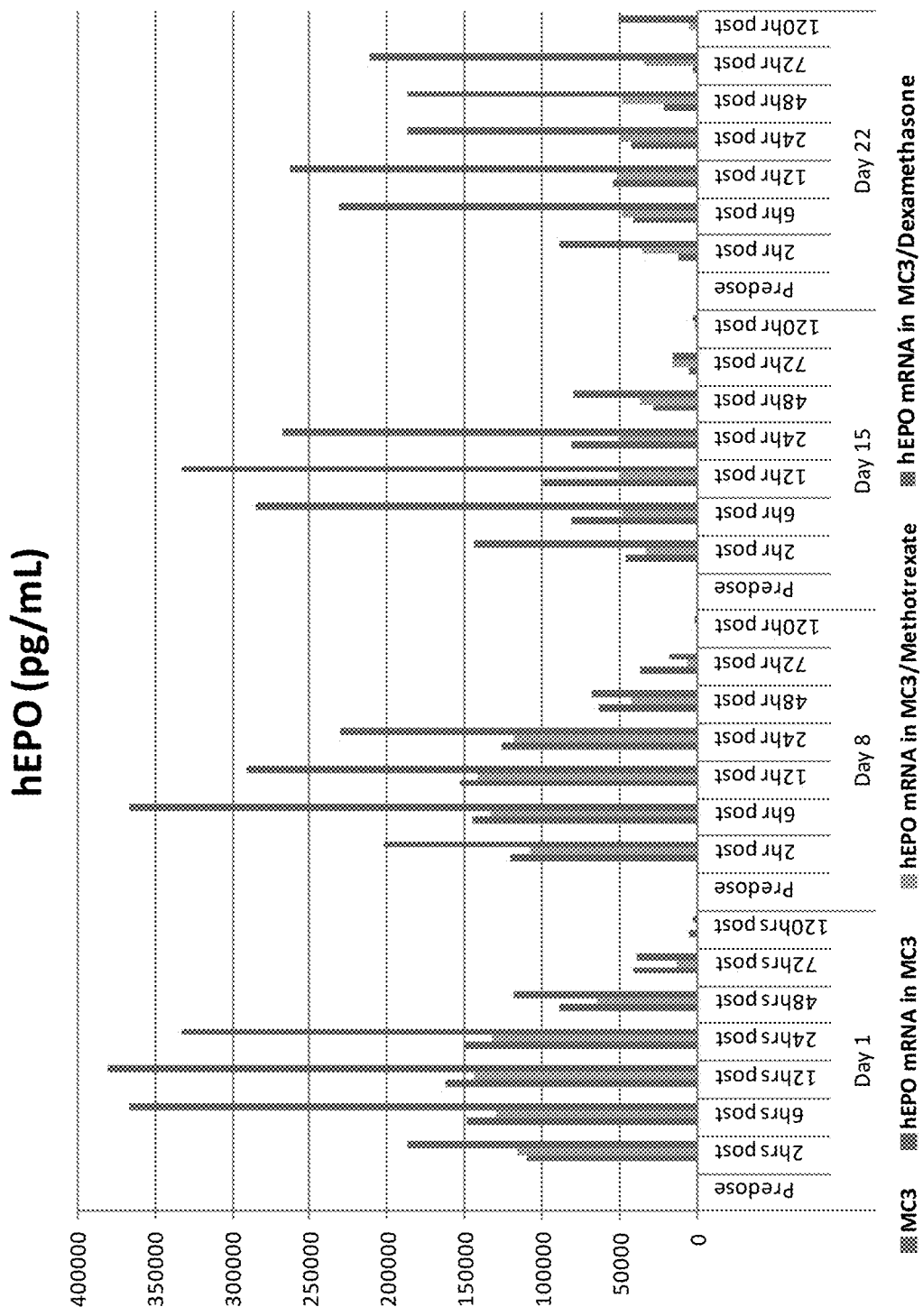
FIG. 1 shows the results of pretreating non-human primates with methotrexate or dexamethasone prior to administration of a nanoparticle composition including MC3.

The disclosure relates to novel lipids and lipid nanoparticle compositions including a novel lipid. The disclosure also provides methods of delivering a therapeutic and/or prophylactic to a mammalian cell, specifically delivering a therapeutic and/or prophylactic to a mammalian organ, producing a polypeptide of interest in a mammalian cell, and treating a disease or disorder in a mammal in need thereof. For example, a method of producing a polypeptide of interest in a cell involves contacting a nanoparticle composition comprising an mRNA with a mammalian cell, whereby the mRNA may be translated to produce the polypeptide of interest. A method of delivering a therapeutic and/or prophylactic to a mammalian cell or organ may involve administration of a nanoparticle composition including the therapeutic and/or prophylactic to a subject, in which the administration involves contacting the cell or organ with the composition, whereby the therapeutic and/or prophylactic is delivered to the cell or organ.

Lipids

The present disclosure provides lipids including a central amine moiety and at least one biodegradable group. The lipids described herein may be advantageously used in lipid nanoparticle compositions for the delivery of therapeutic and/or prophylactics to mammalian cells or organs. For example, the lipids described herein have little or no immunogenicity. For example, the lipid compound of any of Formula (I), (IA), (II), (IIa), (IIb), (IIc), (IId) or (IIe) has a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprise a reference lipid (e.g., MC3, KC2, or DLinDMA) and the same therapeutic or prophylactic agent.

In a first aspect of the invention, the compounds described herein are of Formula (I):

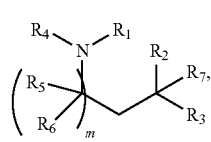

(I)

or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2$H, —$CXH_2$, —CN, —$N(R)_2$, —$C(O)N(R)_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

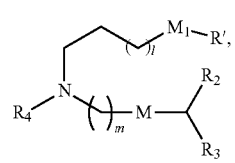

(IA)

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S)N(R)$_2$, or —NHC(O)N(R)$_2$. For example, Q is —N(R)C(O)R, or —N(R)S(O)$_2$R.

In certain embodiments, a subset of compounds of Formula (I) includes those of Formula (II):

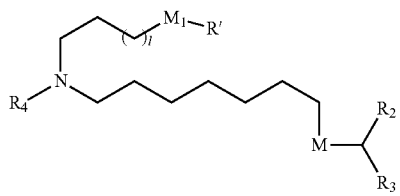

(II)

or a salt or isomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

The compounds of any one of formula (I) or (IA) include one or more of the following features when applicable.

In some embodiments, $M_1$ is M'.

In some embodiments, M and M' are independently —C(O)O— or —OC(O)—.

In some embodiments, at least one of M and M' is —C(O)O— or —OC(O)—.

In some embodiments, M and M' are independently —S—S—.

In some embodiments, at least one of M and M' is —S—S.

In some embodiments, one of M and M' is —C(O)O— or —OC(O)— and the other is —S—S—. For example, M is —C(O)O— or —OC(O)— and M' is —S—S— or M' is —C(O)O— or —OC(O)— and M is —S—S—.

In some embodiments, l is 1, 3, or 5.

In some embodiments, $R_4$ is unsubstituted methyl or —$(CH_2)_nQ$, in which Q is OH, —NHC(S)N(R)$_2$, —NHC(O)N(R)$_2$, —N(R)C(O)R, or —N(R)S(O)$_2$R.

In some embodiments, Q is OH.
In some embodiments, Q is —NHC(S)N(R)$_2$.
In some embodiments, Q is —NHC(O)N(R)$_2$.
In some embodiments, Q is —N(R)C(O)R.
In some embodiments, Q is —N(R)S(O)$_2$R.
In some embodiments, Q is —O(CH$_2$)$_n$N(R)$_2$.
In some embodiments, Q is —O(CH$_2$)$_n$OR.
In some embodiments, Q is —N(R)R$_8$.
In some embodiments, Q is —NHC(=NR$_9$)N(R)$_2$.
In some embodiments, Q is —NHC(=CHR$_9$)N(R)$_2$.
In some embodiments, Q is —OC(O)N(R)$_2$.
In some embodiments, Q is —N(R)C(O)OR.
In some embodiments, n is 2.
In some embodiments, n is 3.
In some embodiments, n is 4.
In some embodiments, M$_1$ is absent.
In some embodiments, R' is C$_{1-18}$ alkyl, C$_{2-18}$ alkenyl, —R*YR", or —YR".
In some embodiments, R$_2$ and R$_3$ are independently C$_{3-14}$ alkyl or C$_{3-14}$ alkenyl.

In one embodiment, the compounds of Formula (I) are of Formula (IIa),

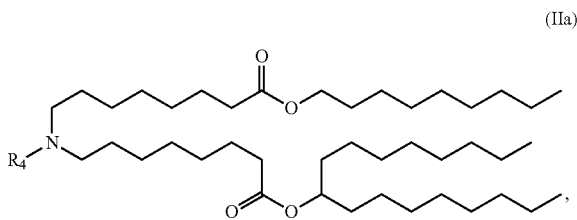

(IIa)

or salts or isomers thereof, wherein R$_4$ is as described herein.

In another embodiment, the compounds of Formula (I) are of Formula (IIb),

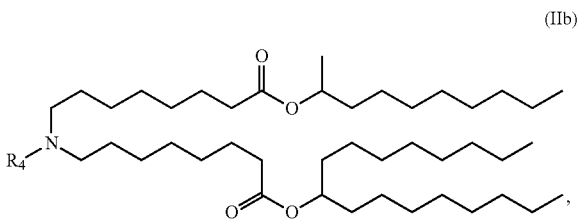

(IIb)

or salts or isomers thereof, wherein R$_4$ is as described herein.

In another embodiment, the compounds of Formula (I) are of Formula (IIc) or (IIe):

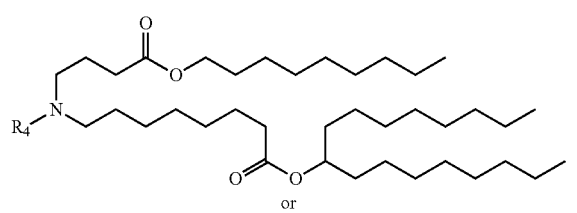

(IIc)

or

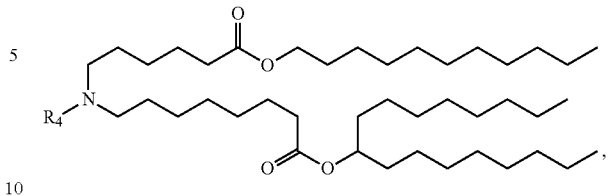

(IIe)

or salts or isomers thereof, wherein R$_4$ is as described herein.

In a further embodiment, the compounds of Formula (I) are of Formula (IId),

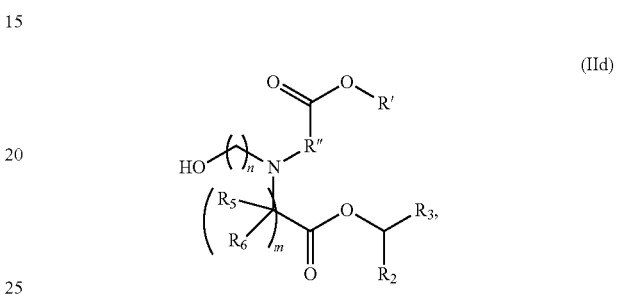

(IId)

or salts or isomers thereof, wherein n is 2, 3, or 4; and m, R', R", and R$_2$ through R$_6$ are as described herein. For example, each of R$_2$ and R$_3$ may be independently selected from the group consisting of C$_{5-14}$ alkyl and C$_{5-14}$ alkenyl.

The compounds of any one of formulae (I), (IA), (II), (IIa), (IIb), (IIc), (IId), and (IIe) include one or more of the following features when applicable.

In some embodiments, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, 5- to 14-membered aromatic or non-aromatic heterocycle having one or more heteroatoms selected from N, O, S, and P, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (=O), OH, amino, and C$_{1-3}$ alkyl, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, R$_4$ is unsubstituted C$_{1-4}$ alkyl, e.g., unsubstituted methyl.

In certain embodiments, the disclosure provides a compound having the Formula (I), wherein R$_4$ is —(CH$_2$)$_n$Q or —(CH$_2$)$_n$CHQR, where Q is —N(R)$_2$, and n is selected from 3, 4, and 5.

In certain embodiments, the disclosure provides a compound having the Formula (I), wherein R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5.

In certain embodiments, the disclosure provides a compound having the Formula (I), wherein R$_2$ and R$_3$ are independently selected from the group consisting of C$_{2-14}$ alkyl, C$_{2-14}$ alkenyl, —R*YR″, —YR″, and —R*OR″, or R$_2$ and R$_3$, together with the atom to which they are attached, form a heterocycle or carbocycle, and R$_4$ is —(CH$_2$)$_n$Q or —(CH$_2$)$_n$CHQR, where Q is —N(R)$_2$, and n is selected from 3, 4, and 5.

In certain embodiments, R$_2$ and R$_3$ are independently selected from the group consisting of C$_{2-14}$ alkyl, C$_{2-14}$ alkenyl, —R*YR″, —YR″, and —R*OR″, or R$_2$ and R$_3$, together with the atom to which they are attached, form a heterocycle or carbocycle.

In some embodiments, R$_1$ is selected from the group consisting of C$_{5-20}$ alkyl and C$_{5-20}$ alkenyl.

In other embodiments, R$_1$ is selected from the group consisting of —R*YR″, —YR″, and —R″M′R′.

In certain embodiments, R$_1$ is selected from —R*YR″ and —YR″. In some embodiments, Y is a cyclopropyl group. In some embodiments, R* is C$_8$ alkyl or C$_8$ alkenyl. In certain embodiments, R″ is C$_{3-12}$ alkyl. For example, R″ may be C$_3$ alkyl. For example, R″ may be C$_{4-8}$ alkyl (e.g., C$_4$, C$_5$, C$_6$, C$_7$, or C$_8$ alkyl).

In some embodiments, R$_1$ is C$_{5-20}$ alkyl. In some embodiments, R$_1$ is C$_6$ alkyl. In some embodiments, R$_1$ is C$_8$ alkyl. In other embodiments, R$_1$ is C$_9$ alkyl. In certain embodiments, R$_1$ is C$_{14}$ alkyl. In other embodiments, R$_1$ is C$_{18}$ alkyl.

In some embodiments, R$_1$ is C$_{21-30}$ alkyl. In some embodiments, R$_1$ is C$_{26}$ alkyl. In some embodiments, R$_1$ is C$_{28}$ alkyl. In certain embodiments, R$_1$ is

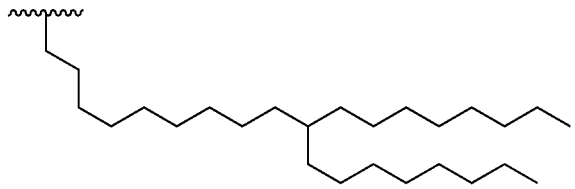 [SMILES: *CCCCCCCCCC(CCCCCCCC)CCCCCCCC]

In some embodiments, R$_1$ is C$_{5-20}$ alkenyl. In certain embodiments, R$_1$ is C$_{18}$ alkenyl. In some embodiments, R$_1$ is linoleyl.

In certain embodiments, R$_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, R$_1$ is

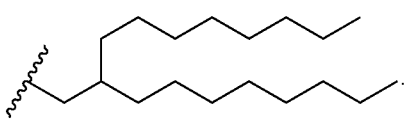 [SMILES: *CC(CCCCCCCC)CCCCCCCC]

In certain embodiments, R$_1$ is unsubstituted C$_{5-20}$ alkyl or C$_{5-20}$ alkenyl. In certain embodiments, R' is substituted C$_{5-20}$ alkyl or C$_{5-20}$ alkenyl (e.g., substituted with a C$_{3-6}$ carbocycle such as 1-cyclopropylnonyl or substituted with OH or alkoxy). For example, R$_1$ is

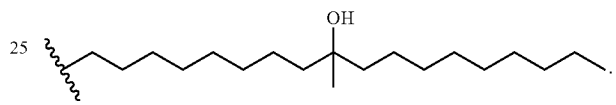

In other embodiments, R$_1$ is —R″M′R′.

In some embodiments, R' is selected from —R*YR″ and —YR″. In some embodiments, Y is C$_{3-8}$ cycloalkyl. In some embodiments, Y is C$_{6-10}$ aryl. In some embodiments, Y is a cyclopropyl group. In some embodiments, Y is a cyclohexyl group. In certain embodiments, R* is C$_1$ alkyl.

In some embodiments, R″ is selected from the group consisting of C$_{3-12}$ alkyl and C$_{3-12}$ alkenyl. In some embodiments, R″ adjacent to Y is C$_1$ alkyl. In some embodiments, R″ adjacent to Y is C$_{4-9}$ alkyl (e.g., C$_4$, C$_5$, C$_6$, C$_7$ or C$_8$ or C$_9$ alkyl).

In some embodiments, R' is selected from C$_4$ alkyl and C$_4$ alkenyl. In certain embodiments, R' is selected from C$_5$ alkyl and C$_5$ alkenyl. In certain embodiments, R' is selected from C$_6$ alkyl and C$_6$ alkenyl. In certain embodiments, R' is selected from C$_7$ alkyl and C$_7$ alkenyl. In certain embodiments, R' is selected from C$_9$ alkyl and C$_9$ alkenyl.

In other embodiments, R' is selected from C$_{11}$ alkyl and C$_{11}$ alkenyl. In other embodiments, R' is selected from C$_{12}$ alkyl, C$_{12}$ alkenyl, C$_{13}$ alkyl, C$_{13}$ alkenyl, C$_{14}$ alkyl, C$_{14}$ alkenyl, C$_{15}$ alkyl, C$_{15}$ alkenyl, C$_{16}$ alkyl, C$_{16}$ alkenyl, C$_{17}$ alkyl, C$_{17}$ alkenyl, C$_{18}$ alkyl, and C$_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

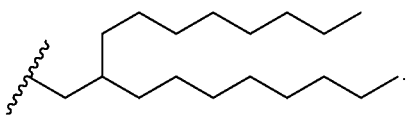 [SMILES: *CC(CCCCCCCC)CCCCCCCC]

In certain embodiments, R' is unsubstituted C$_{1-8}$ alkyl. In certain embodiments, R' is substituted C$_{1-18}$ alkyl (e.g., C$_{1-15}$ alkyl substituted with, e.g., an alkoxy such as methoxy, or a $C_{3-6}$ carbocycle such as 1-cyclopropylnonyl, or C(O)O-alkyl or OC(O)-alkyl such as $C(O)OCH_3$ or $OC(O)CH_3$). For example, R' is

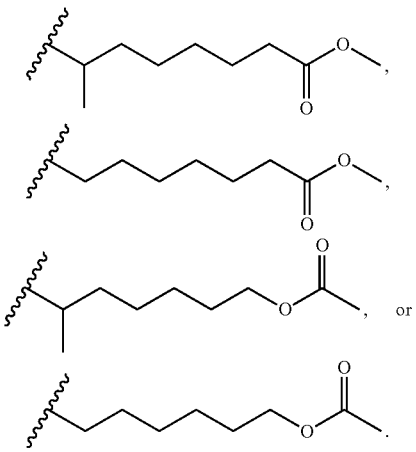

or

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' may be selected from the group consisting of phenyl, oxazole, and thiazole.

In some embodiments, M is —C(O)O—. In some embodiments, M is —OC(O)—. In some embodiments, M is —C(O)N(R')—. In some embodiments, M is —P(O)(OR')O—.

In other embodiments, M is an aryl group or heteroaryl group. For example, M may be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_nQ$ and —$(CH_2)_nCHQR$.

In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), —C(R)N(R)$_2$C(O)OR, a carbocycle, and a heterocycle.

In certain embodiments, Q is —N(R)$R_8$, —$O(CH_2)_nOR$, —N(R)C(=$NR_9$)N(R)$_2$, —N(R)C(=$CHR_9$)N(R)$_2$, —OC(O)N(R)$_2$, or —N(R)C(O)OR.

In certain embodiments, Q is —N(OR)C(O)R, —N(OR)S(O)$_2$R, —N(OR)C(O)OR, —N(OR)C(O)N(R)$_2$, —N(OR)C(S)N(R)$_2$, —N(OR)C(=$NR_9$)N(R)$_2$, or —N(OR)C(=$CHR_9$)N(R)$_2$.

In certain embodiments, Q is thiourea or an isostere thereof, e.g.,

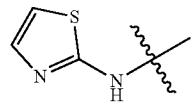 [SMILES: *Nc1nccs1]

or —NHC(=$NR_9$)N(R)$_2$.

In certain embodiments, Q is —C(=$NR_9$)N(R)$_2$. For example, when Q is —C(=$NR_9$)N(R)$_2$, n is 4 or 5. For example, $R_9$ is —S(O)$_2$N(R)$_2$.

In certain embodiments, Q is —C(=$NR_9$)R or —C(O)N(R)OR, e.g., —CH(=N—$OCH_3$), —C(O)NH—OH, —C(O)NH—$OCH_3$, —C(O)N($CH_3$)—OH, or —C(O)N($CH_3$)—$OCH_3$.

In certain embodiments, Q is —OH.

In certain embodiments, Q is a substituted or unsubstituted 5- to 10-membered heteroaryl, e.g., Q is a triazole, an imidazole, a pyrimidine, a purine, 2-amino-1,9-dihydro-6H-purin-6-one-9-yl (or guanin-9-yl), adenin-9-yl, cytosin-1-yl, or uracil-1-yl, each of which is optionally substituted with one or more substituents selected from alkyl, OH, alkoxy, -alkyl-OH, -alkyl-O-alkyl, and the substituent can be further substituted. In certain embodiments, Q is a substituted 5- to 14-membered heterocycloalkyl, e.g., substituted with one or more substituents selected from oxo (=O), OH, amino, mono- or di-alkylamino, and $C_{1-3}$ alkyl. For example, Q is 4-methylpiperazinyl, 4-(4-methoxybenzyl)piperazinyl, isoindolin-2-yl-1,3-dione, pyrrolidin-1-yl-2,5-dione, or imidazolidin-3-yl-2,4-dione.

In certain embodiments, Q is —$NHR_8$, in which $R_8$ is a $C_{3-6}$ cycloalkyl optionally substituted with one or more substituents selected from oxo (=O), amino (NH$_2$), mono- or di-alkylamino, $C_{1-3}$ alkyl and halo. For example, $R_8$ is cyclobutenyl, e.g., 3-(dimethylamino)-cyclobut-3-ene-4-yl-1,2-dione.

In certain embodiments, Q is —$NHR_8$, in which $R_8$ is a heteroaryl optionally substituted with one or more substituents selected from amino (NH$_2$), mono- or di-alkylamino, $C_{1-3}$ alkyl and halo. For example, $R_8$ is thiazole or imidazole.

In certain embodiments, Q is —NHC(=$NR_9$)N(R)$_2$ in which $R_9$ is CN, $C_{1-6}$ alkyl, NO$_2$, —S(O)$_2$N(R)$_2$, —OR, —S(O)$_2$R, or H. For example, Q is —NHC(=$NR_9$)N($CH_3$)$_2$, —NHC(=$NR_9$)NHCH$_3$, —NHC(=$NR_9$)NH$_2$.

In certain embodiments, Q is —NHC(=$CHR_9$)N(R)$_2$, in which $R_9$ is NO$_2$, CN, $C_{1-6}$ alkyl, —S(O)$_2$N(R)$_2$, —OR, —S(O)$_2$R, or H. For example, Q is —NHC(=$CHR_9$)N($CH_3$)$_2$, —NHC(=$CHR_9$)NHCH$_3$, or —NHC(=$CHR_9$)NH$_2$.

In certain embodiments, Q is —OC(O)N(R)$_2$, —N(R)C(O)OR, —N(OR)C(O)OR, such as —OC(O)NHCH$_3$, —N(OH)C(O)OCH$_3$, —N(OH)C(O)CH$_3$, —N(OCH$_3$)C(O)OCH$_3$, —N(OCH$_3$)C(O)CH$_3$, —N(OH)S(O)$_2$CH$_3$, or —NHC(O)OCH$_3$.

In certain embodiments, Q is an unsubstituted or substituted C$_{6-10}$ aryl (such as phenyl) or C$_{3-6}$ cycloalkyl.

In some embodiments, n is 1. In other embodiments, n is 2. In further embodiments, n is 3. In certain other embodiments, n is 4. For example, R$_4$ may be —(CH$_2$)$_2$OH. For example, R$_4$ may be —(CH$_2$)$_{30}$H. For example, R$_4$ may be —(CH$_2$)$_{40}$H. For example, R$_4$ may be benzyl. For example, R$_4$ may be 4-methoxybenzyl.

In some embodiments, R$_4$ is a C$_{3-6}$ carbocycle. In some embodiments, R$_4$ is a C$_{3-6}$ cycloalkyl. For example, R$_4$ may be cyclohexyl optionally substituted with e.g., OH, halo, C$_{1-6}$ alkyl, etc. For example, R$_4$ may be 2-hydroxycyclohexyl.

In some embodiments, R is H.

In some embodiments, R is unsubstituted C$_{1-3}$ alkyl or unsubstituted C$_{2-3}$ alkenyl. For example, R$_4$ may be —CH$_2$CH(OH)CH$_3$, —CH(CH$_3$)CH$_2$OH, or —CH$_2$CH(OH)CH$_2$CH$_3$.

In some embodiments, R is substituted C$_{1-3}$ alkyl, e.g., CH$_2$OH. For example, R$_4$ may be —CH$_2$CH(OH)CH$_2$OH, —(CH$_2$)$_3$NHC(O)CH$_2$OH, —(CH$_2$)$_3$NHC(O)CH$_2$OBn, —(CH$_2$)$_2$O(CH$_2$)$_2$OH, or —CH(CH$_2$OH)$_2$.

In some embodiments, R$_4$ is selected from any of the following groups:

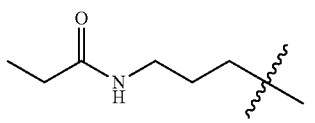

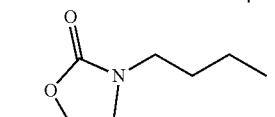

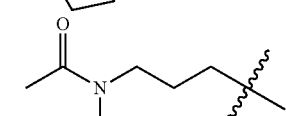

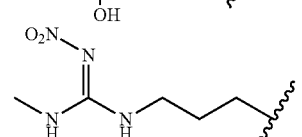

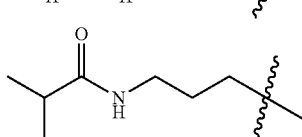

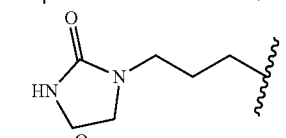

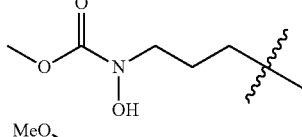

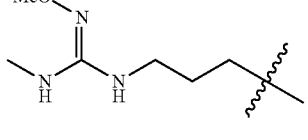

-continued

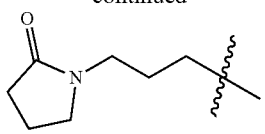

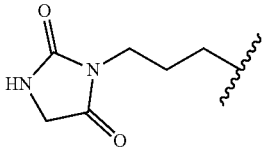

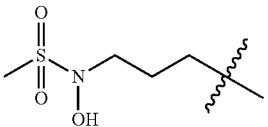

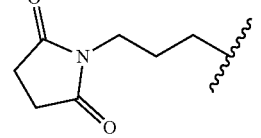

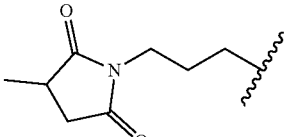

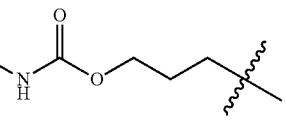

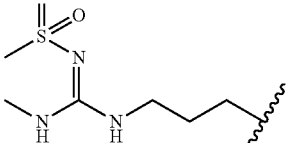

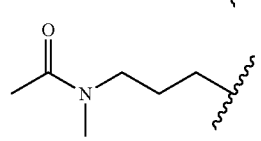

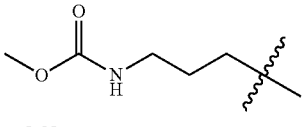

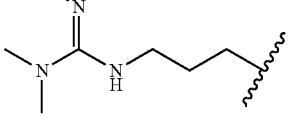

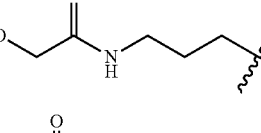

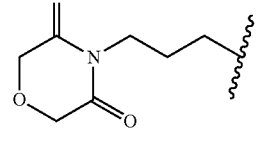

-continued
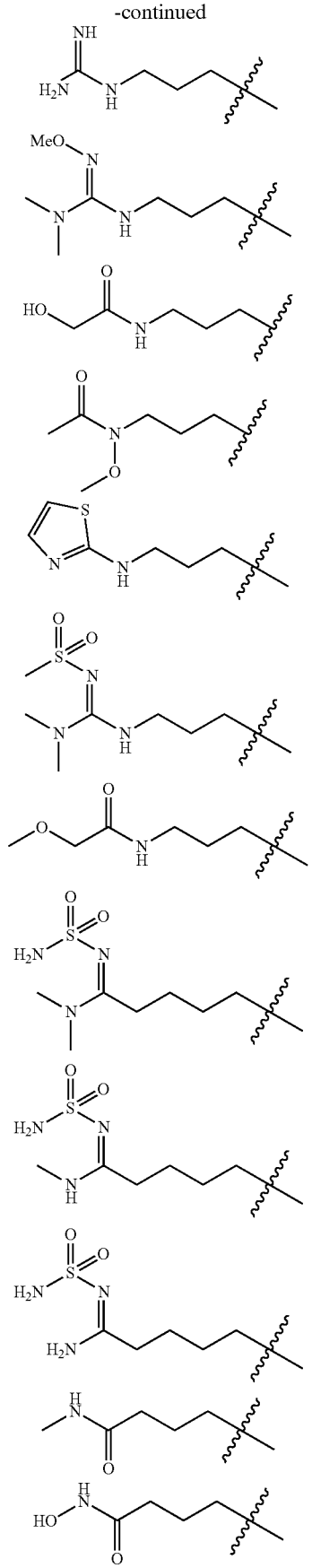
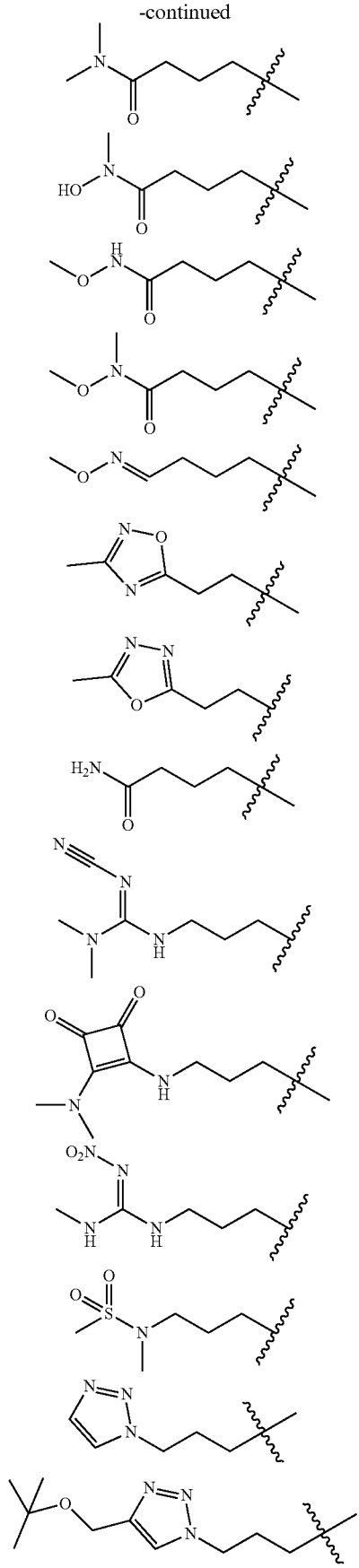

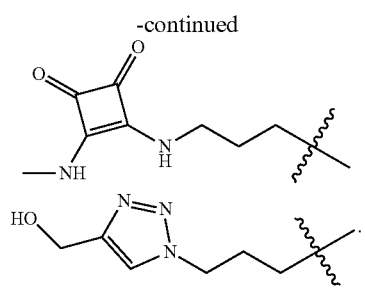
In some embodiments, $R_4$ is selected from any of the following groups:
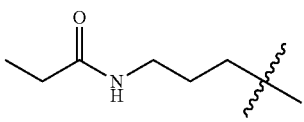
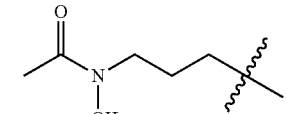
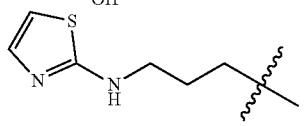
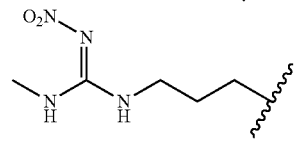
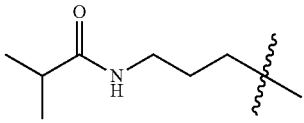
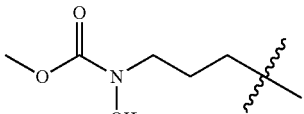
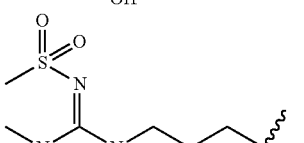
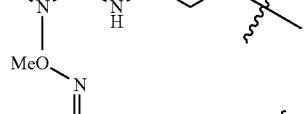
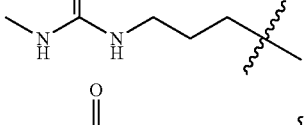
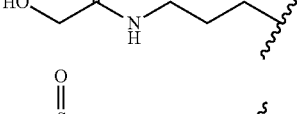
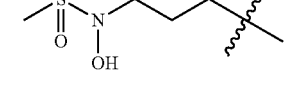
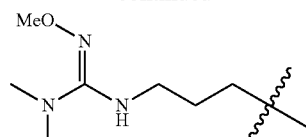
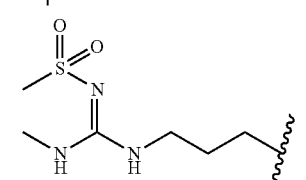
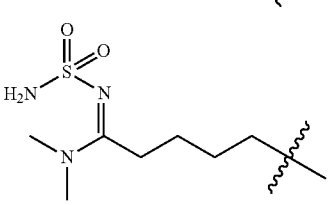
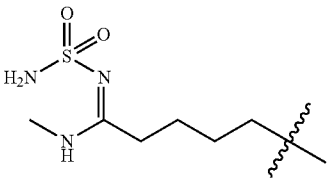
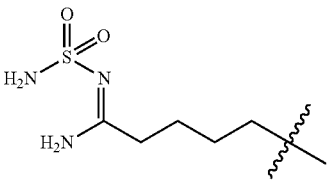
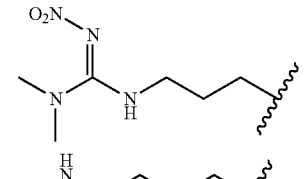
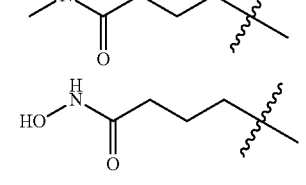
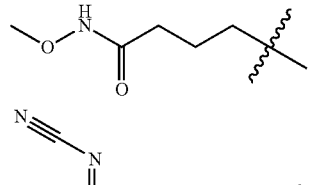
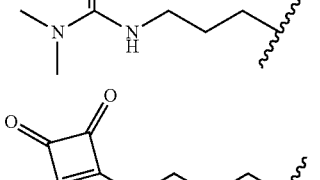
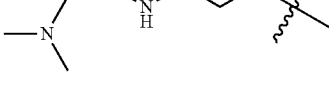

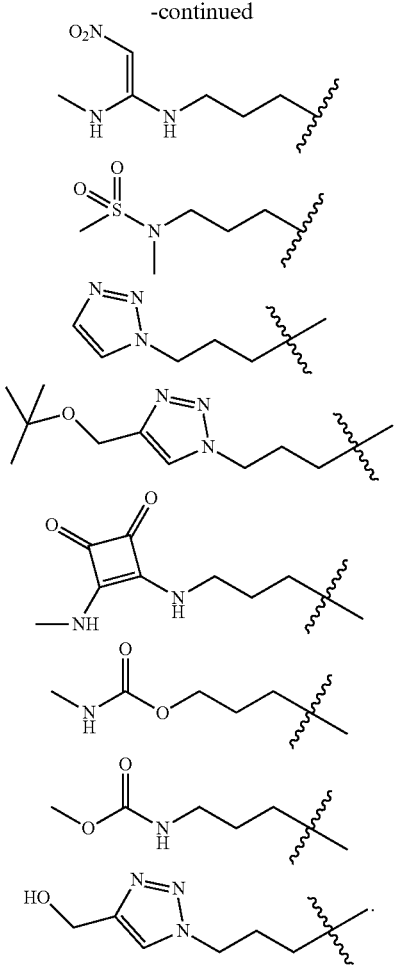

In some embodiments the compound of any of the formulae described herein is suitable for making a nanoparticle composition for intramuscular administration.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, may form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, may form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from $—(CH_2)_nQ$ and $—(CH_2)_nCHQR$. In some embodiments, Q is selected from the group consisting of $—OR$, $—OH$, $—O(CH_2)_nN(R)_2$, $—OC(O)R$, $—CX_3$, $—CN$, $—N(R)C(O)R$, $—N(H)C(O)R$, $—N(R)S(O)_2R$, $—N(H)S(O)_2R$, $—N(R)C(O)N(R)_2$, $—N(H)C(O)$ $N(R)_2$, $—N(H)C(O)N(H)(R)$, $—N(R)C(S)N(R)_2$, $—N(H)C(S)N(R)_2$, $—N(H)C(S)N(H)(R)$, and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, may form a phenyl group bearing one or more $C_5$ alkyl substitutions.

In some embodiments, the compound of Formula (I) is selected from the group consisting of:

(Compound 1)

(Compound 2)

-continued
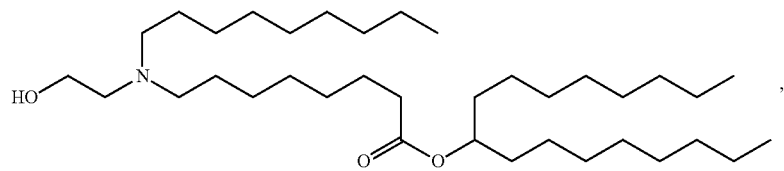
(Compound 3)
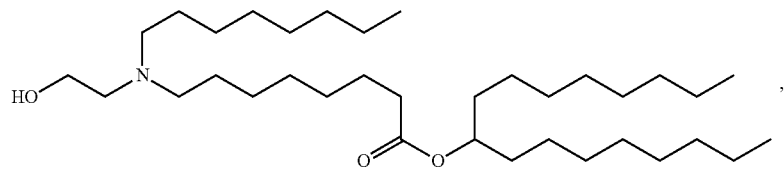
(Compound 4)
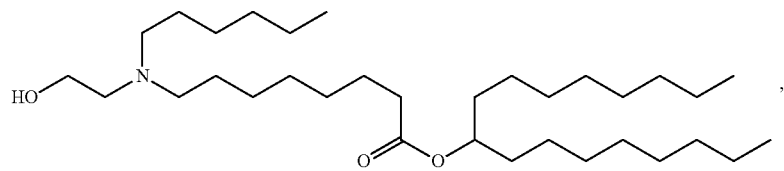
(Compound 5)
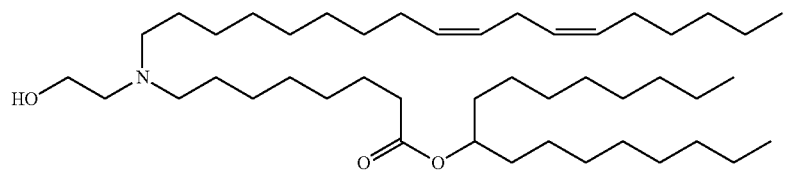
(Compound 6)
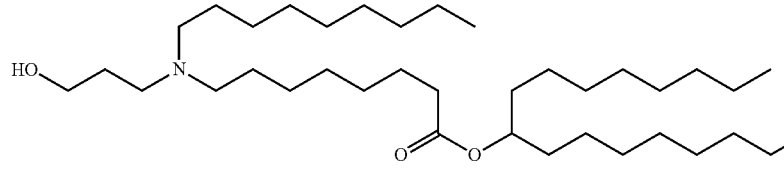
(Compound 7)
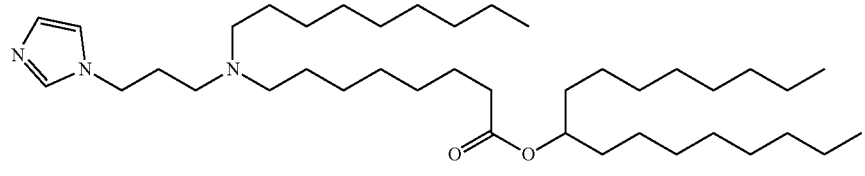
(Compound 8)
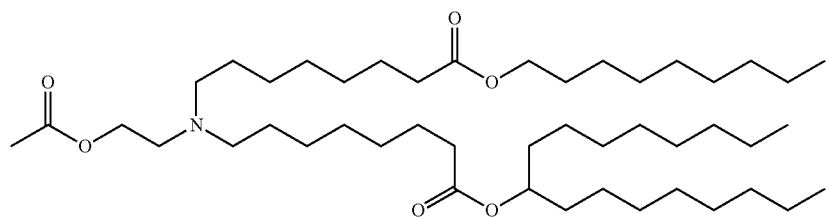
(Compound 9)
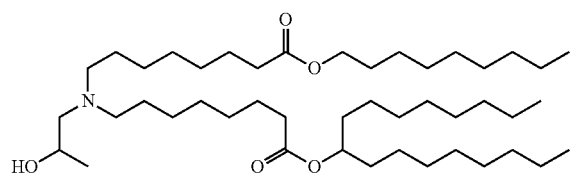
(Compound 10)
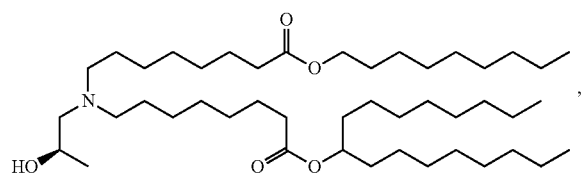
(Compound 11)

(Compound 12)
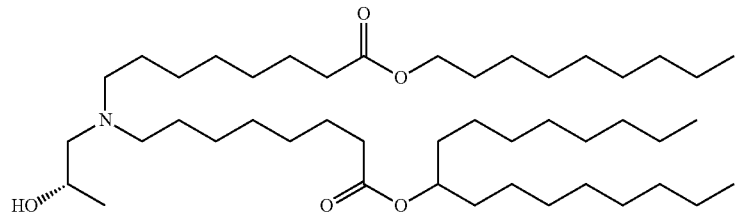
(Compound 13)
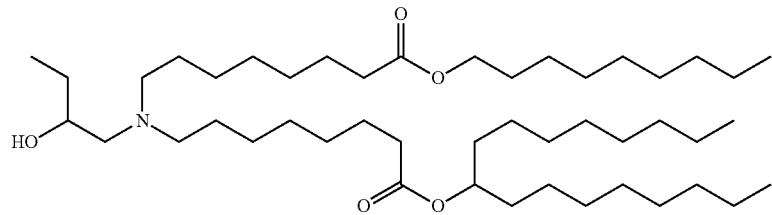
(Compound 14)
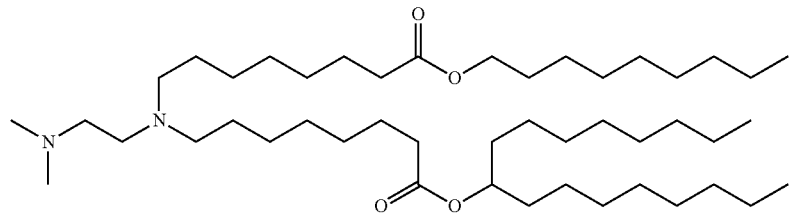
(Compound 15)
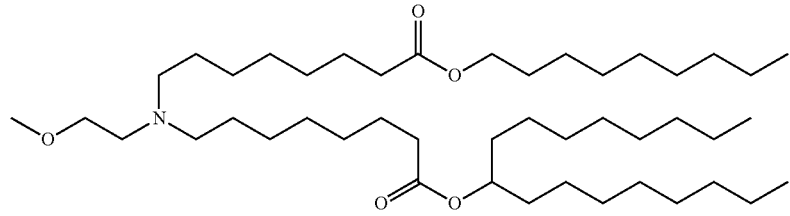
(Compound 16)
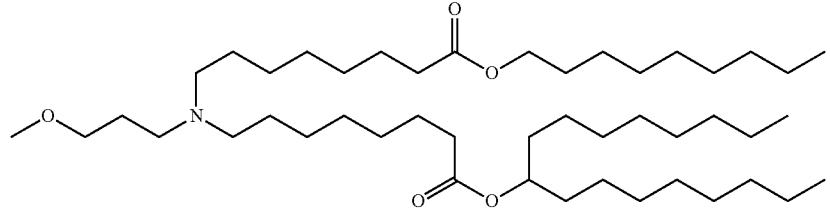
(Compound 17)
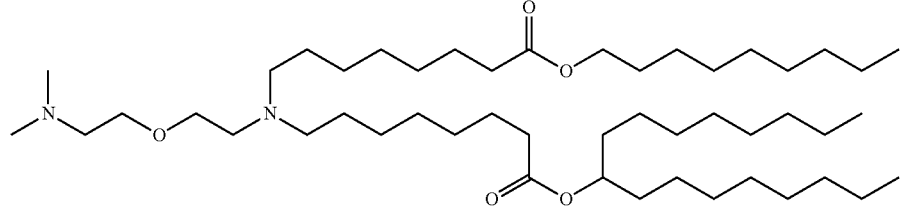
(Compound 18)
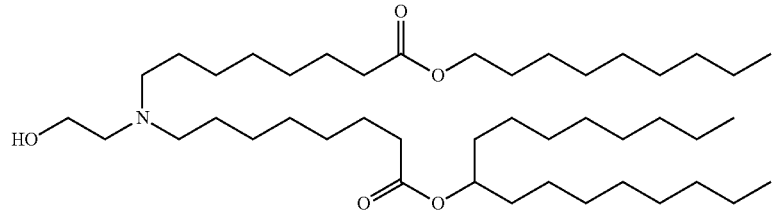

-continued
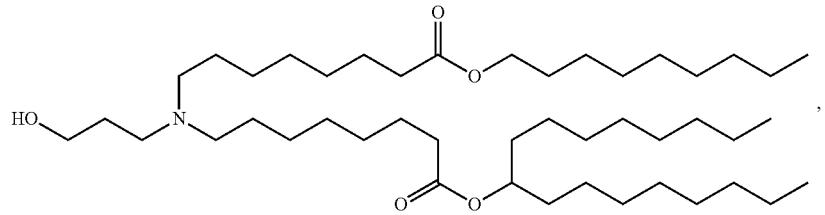
(Compound 19)
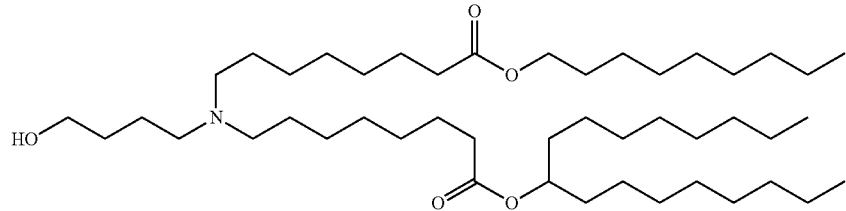
(Compound 20)
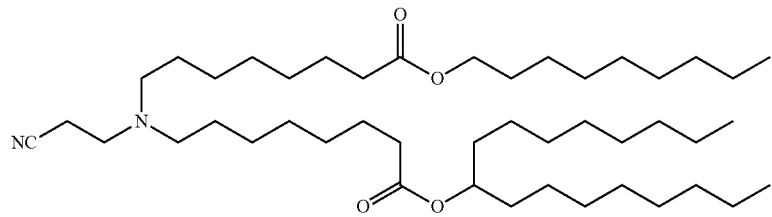
(Compound 21)
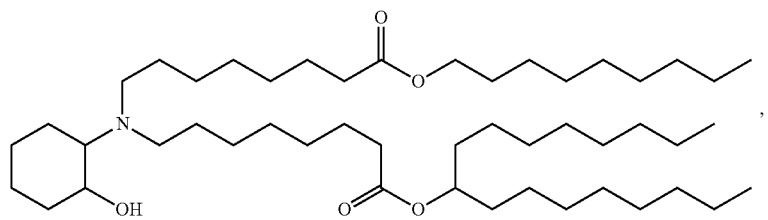
(Compound 22)
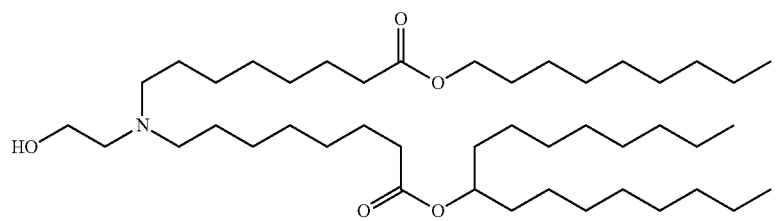
(Compound 23)
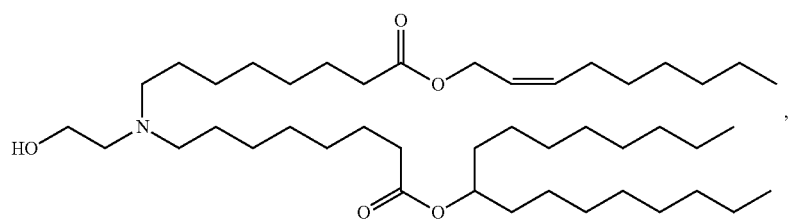
(Compound 24)
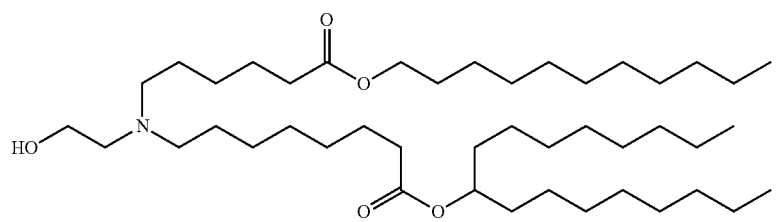
(Compound 25)

-continued
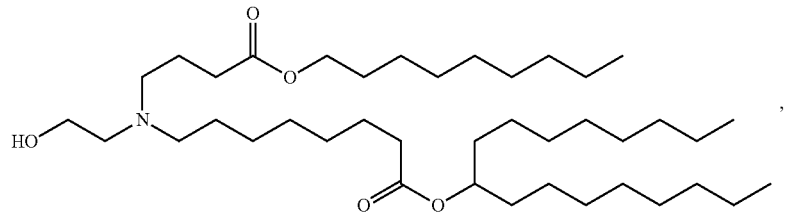
(Compound 26)
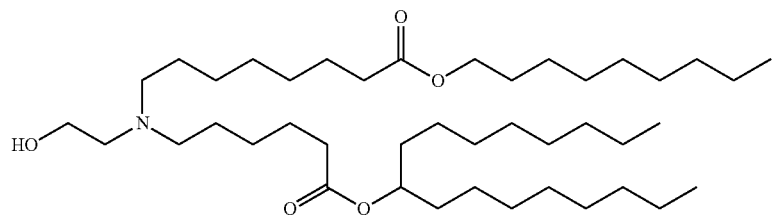
(Compound 27)
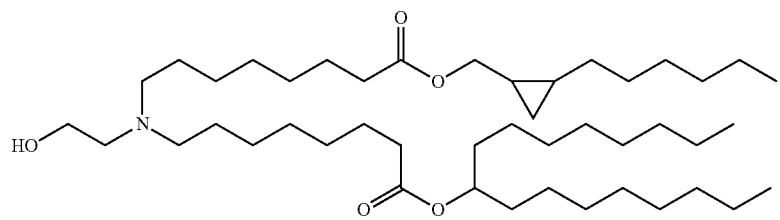
(Compound 28)
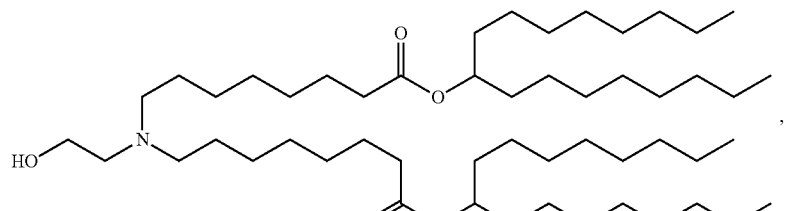
(Compound 29)
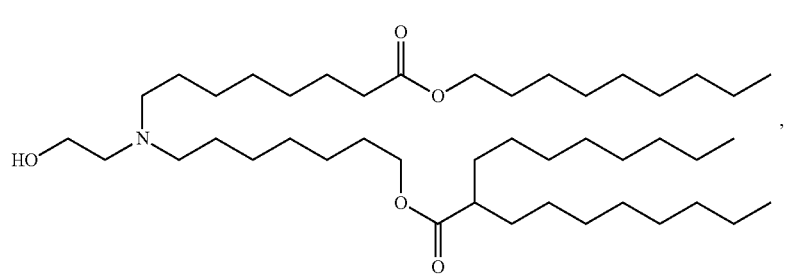
(Compound 30)
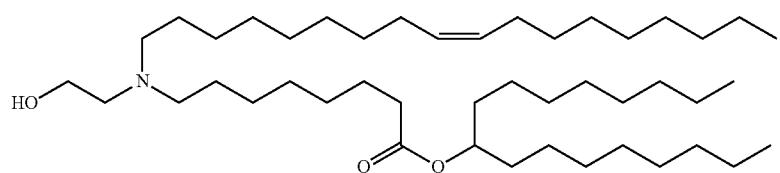
(Compound 31)
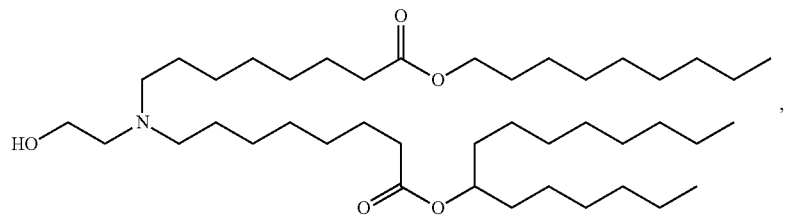
(Compound 32)

-continued
(Compound 33)
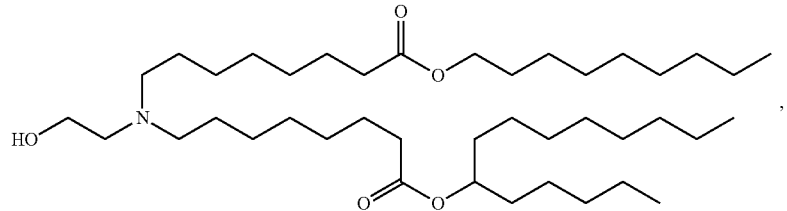
(Compound 34)
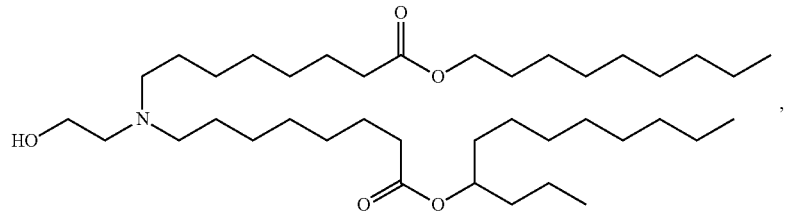
(Compound 35)
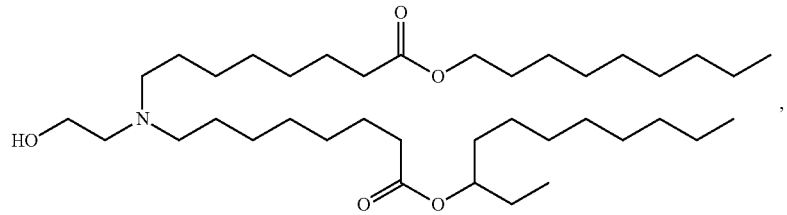
(Compound 36)
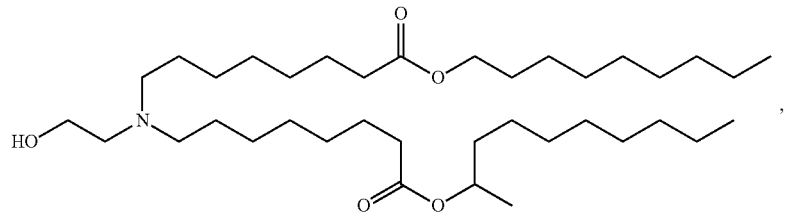
(Compound 37)
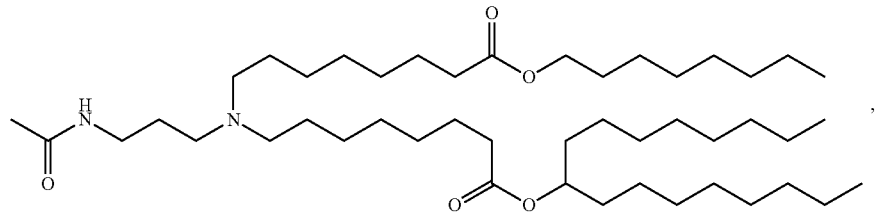
(Compound 38)
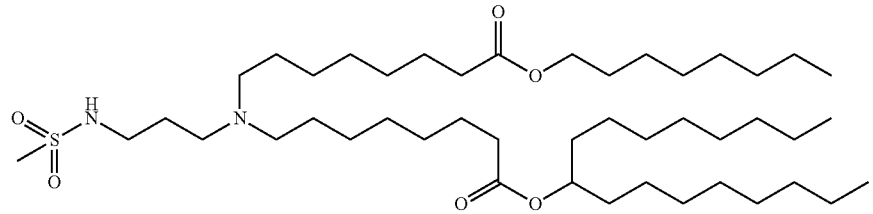
(Compound 39)
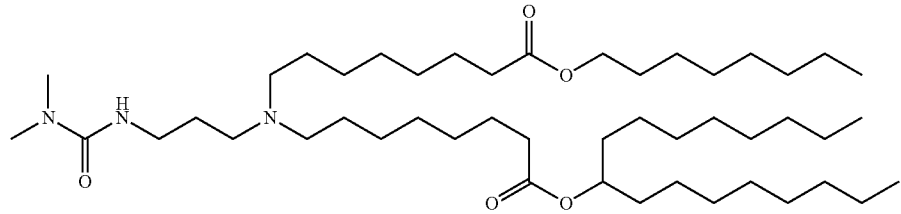

(Compound 40)
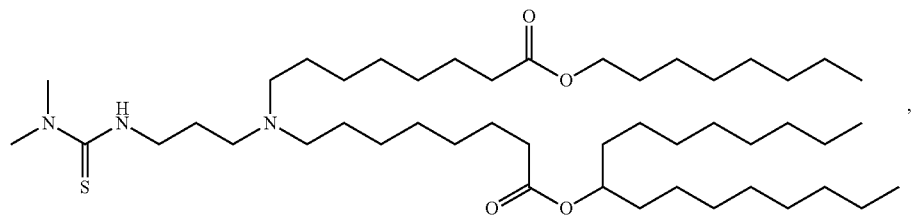
(Compound 41)
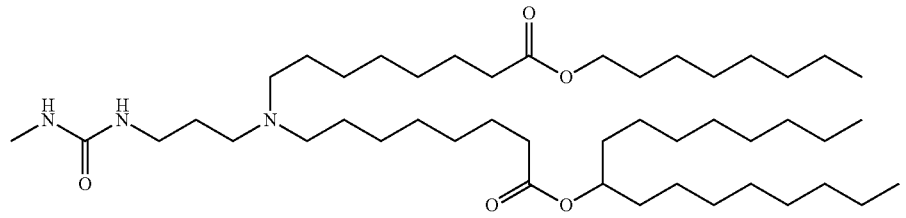
(Compound 42)
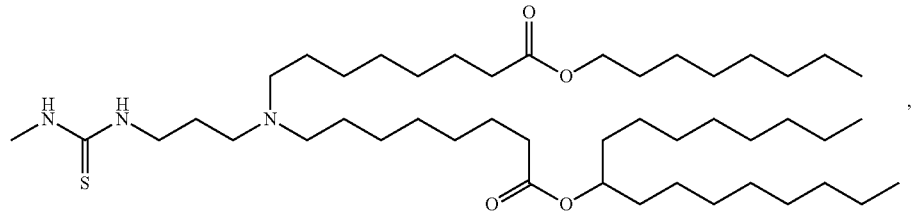
(Compound 43)
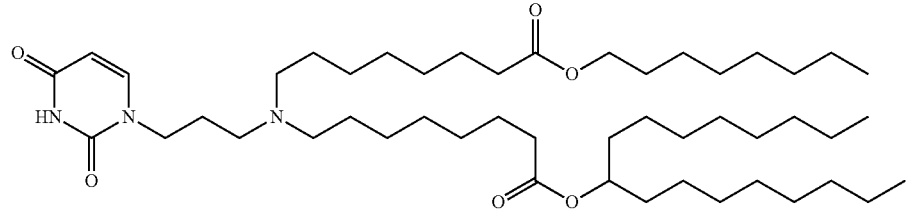
(Compound 44)
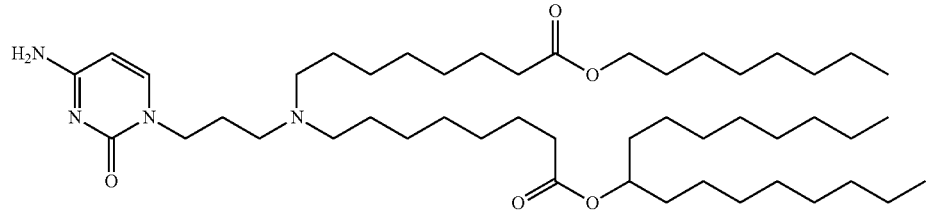
(Compound 45)
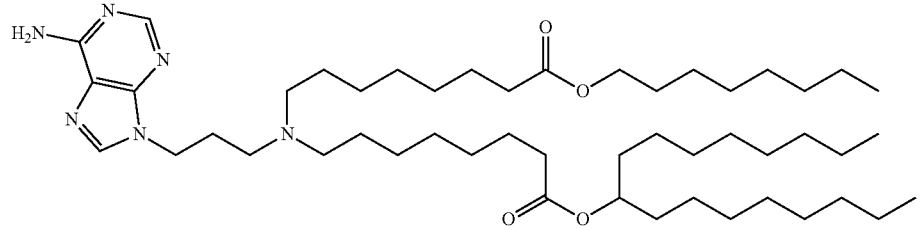
(Compound 46)
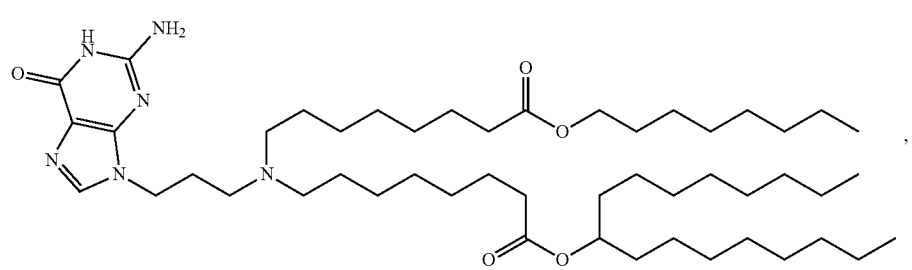

(Compound 47)
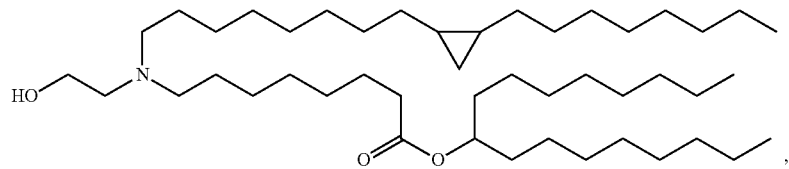
(Compound 48)
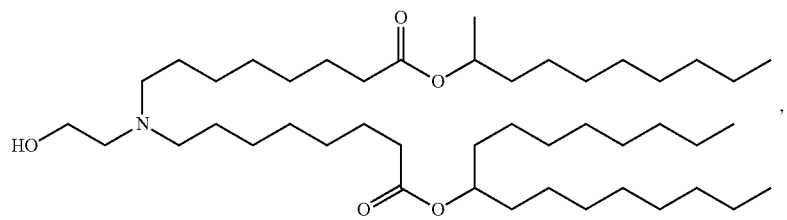
(Compound 49)
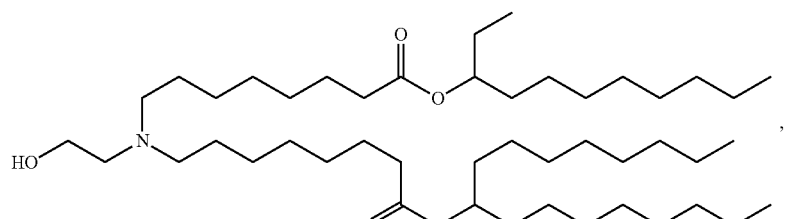
(Compound 50)
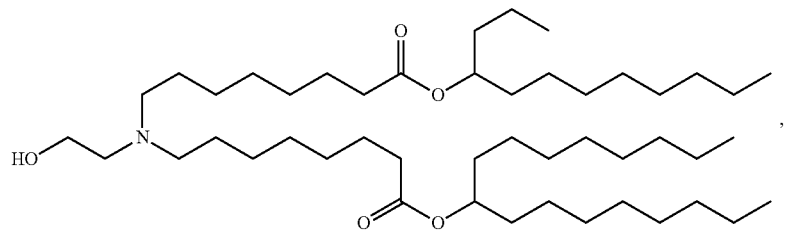
(Compound 51)
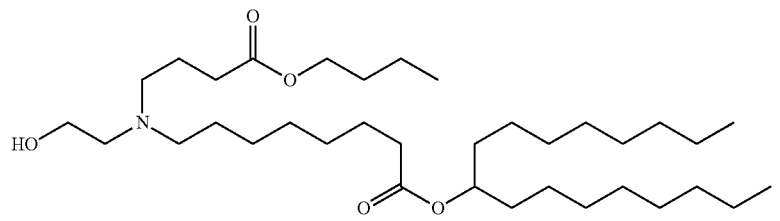
(Compound 52)
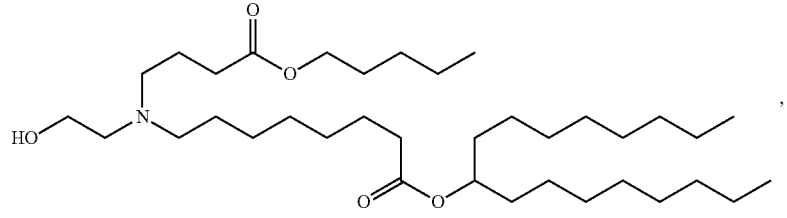
(Compound 53)
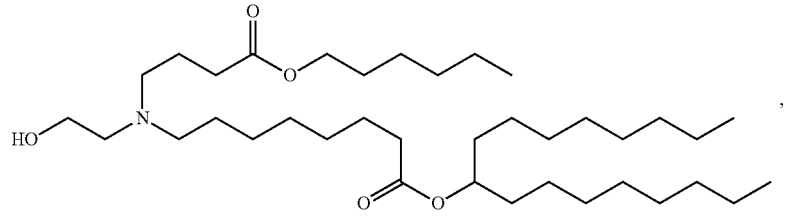

-continued
(Compound 54)
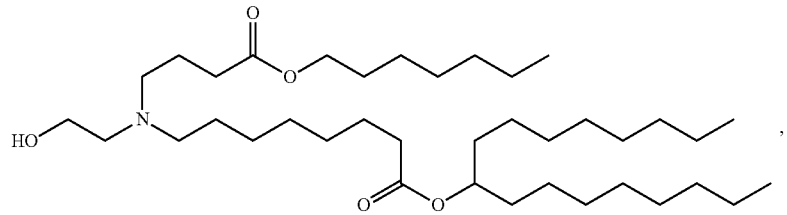
(Compound 55)
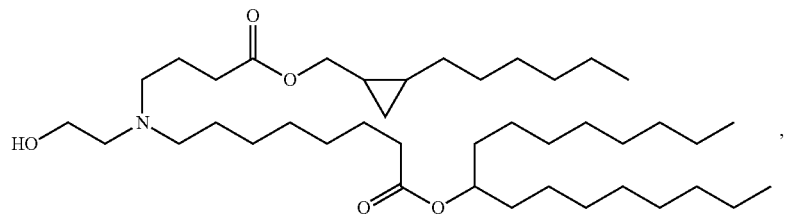
(Compound 56)
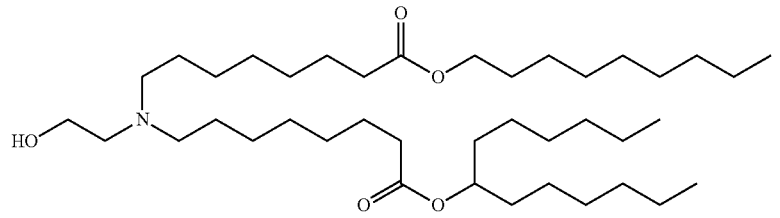
(Compound 57)
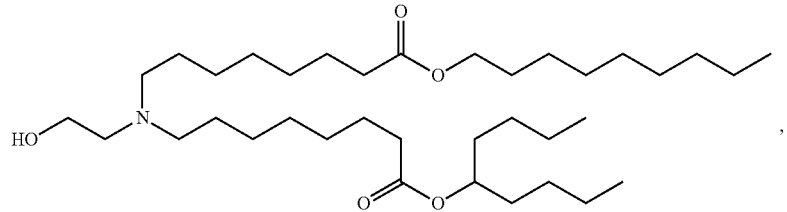
(Compound 58)
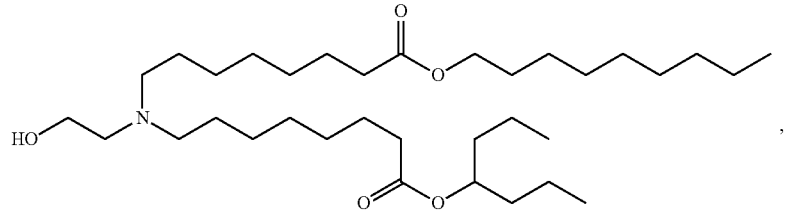
(Compound 59)
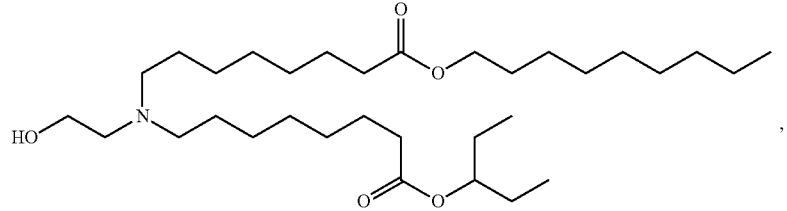
(Compound 60)
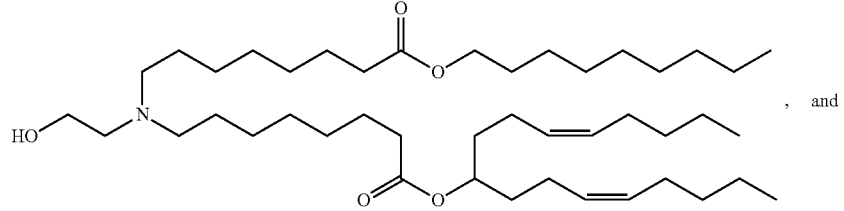
, and

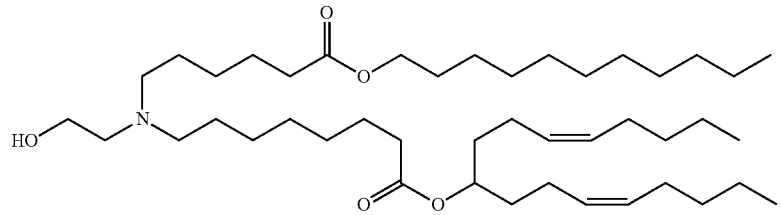
(Compound 61)
In further embodiments, the compound of Formula (I) is selected from the group consisting of:
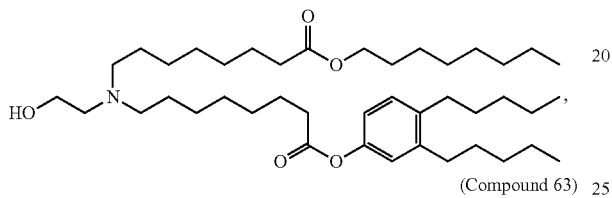
(Compound 62)
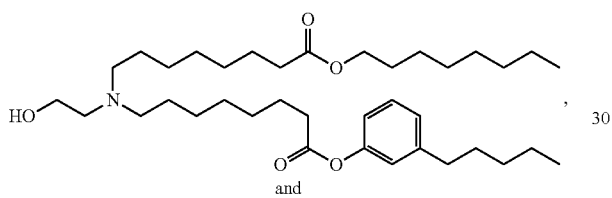
(Compound 63)
and
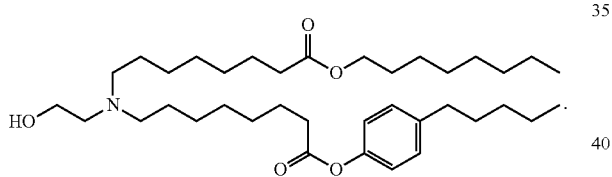
(Compound 64)
In some embodiments, the compound of Formula (I) is selected from the group consisting of:
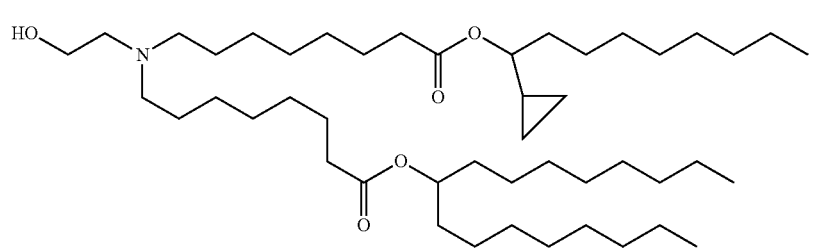
(Compoound 65)
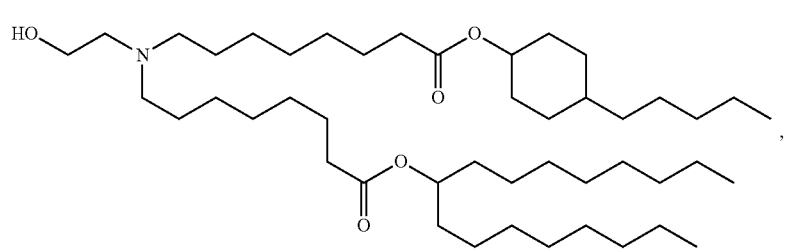
(Compound 66)

(Compound 67)
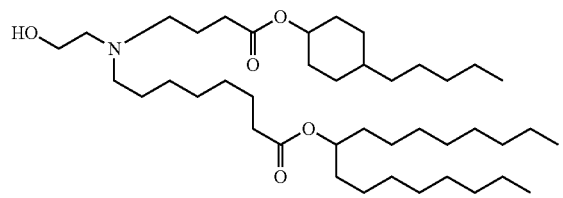
(Compound 68)
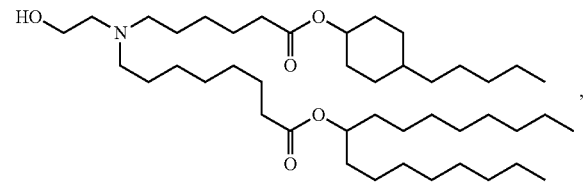
(Compound 69)
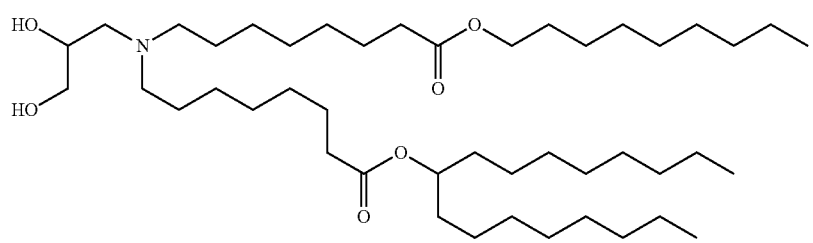
(Compound 70)
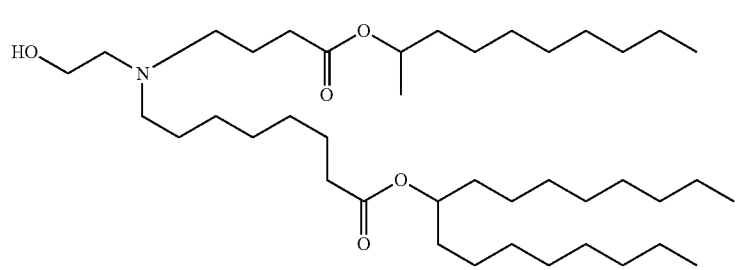
(Compound 71)
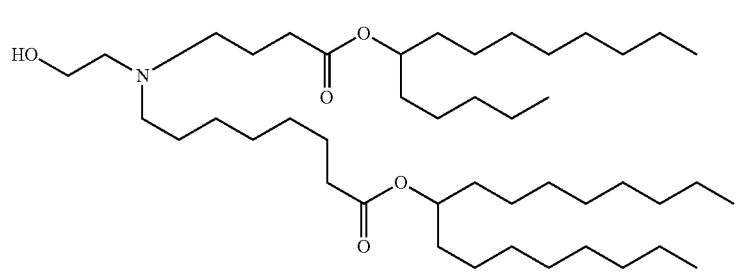
(Compound 72)
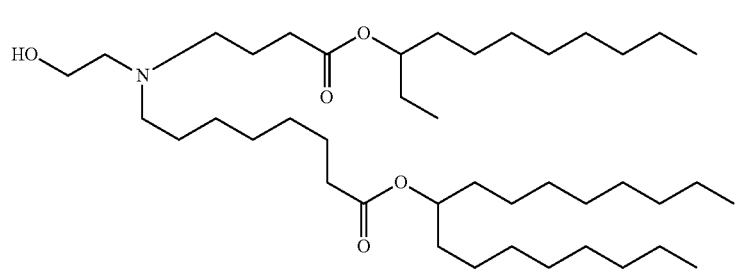
(Compound 73)
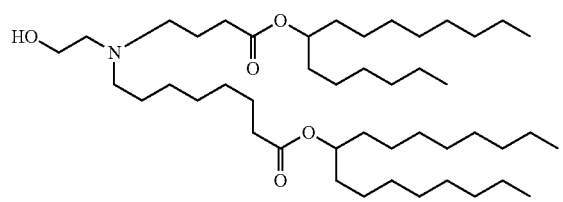
(Compound 74)
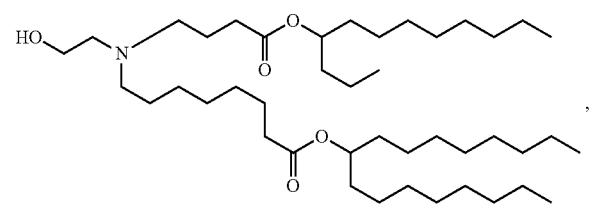

-continued
(Compound 75)
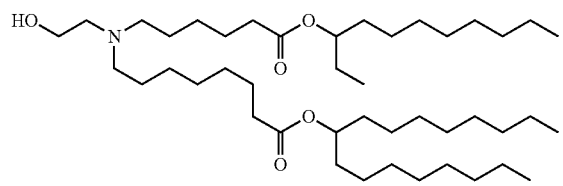
(Compound 76)
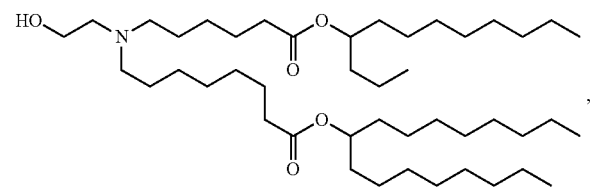
(Compound 77)
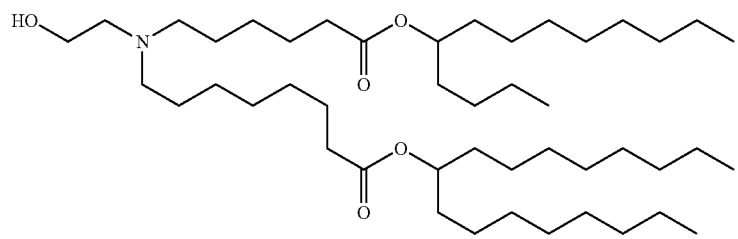
(Compound 78)
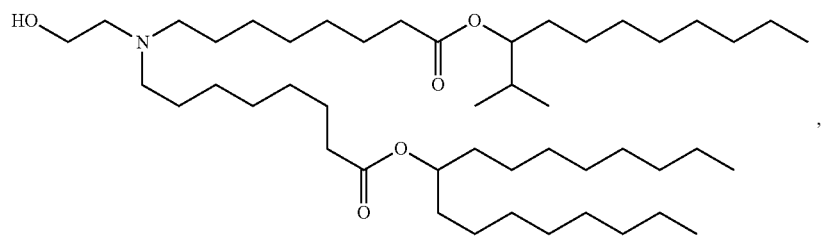
(Compound 79)
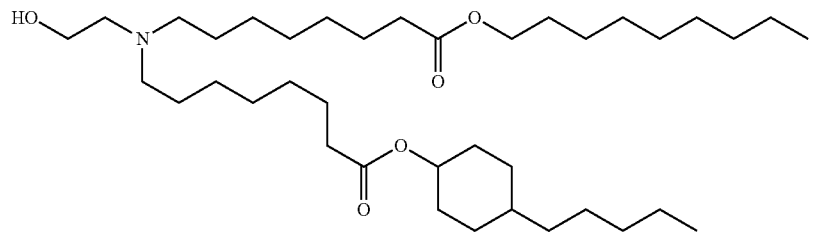
(Compound 80)
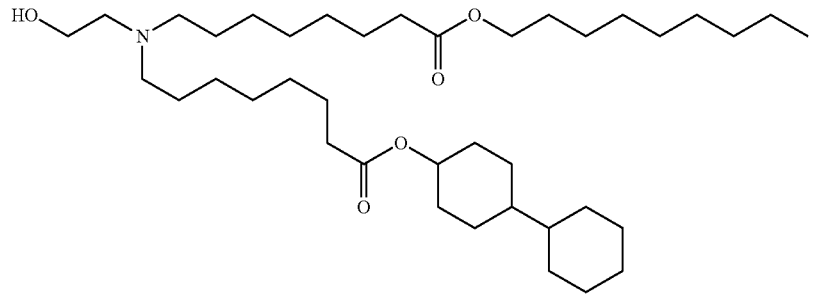
(Compound 81)
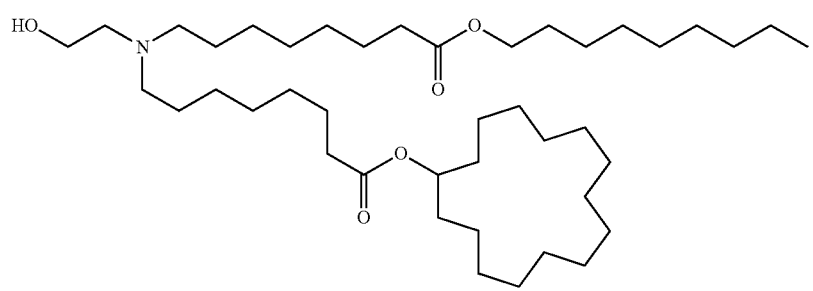

-continued
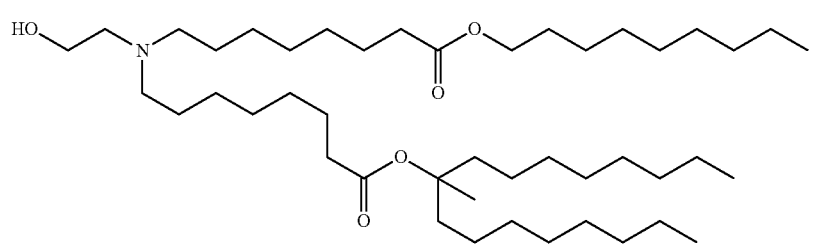
(Compound 82)
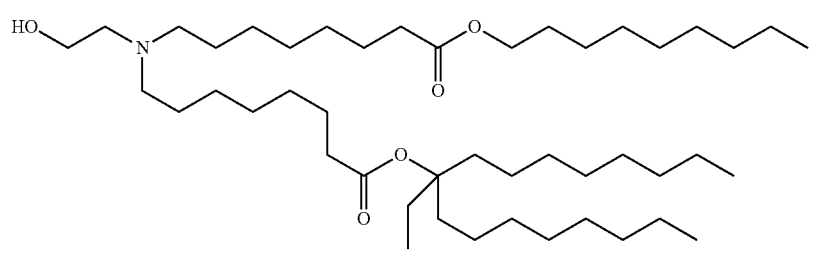
(Compound 83)
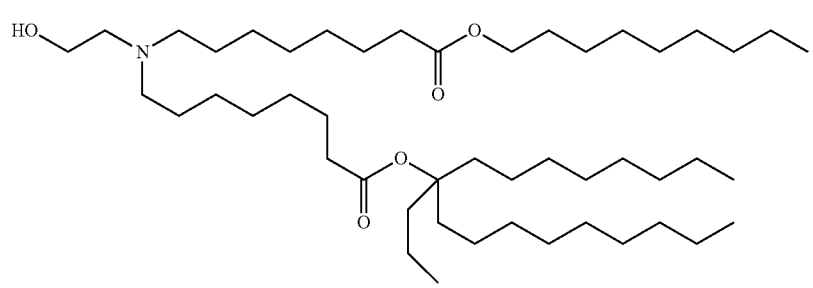
(Compound 84)
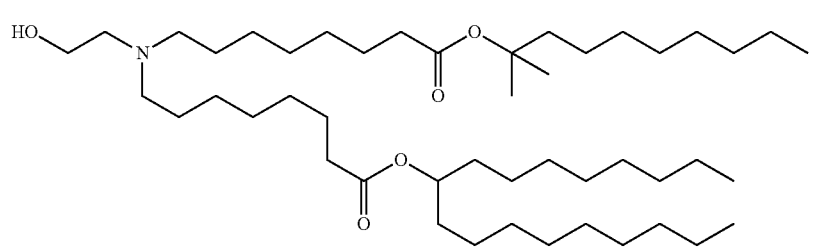
(Compound 85)
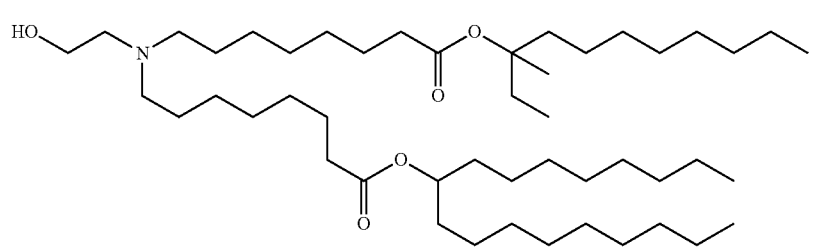
(Compound 86)

(Compound 87)

-continued
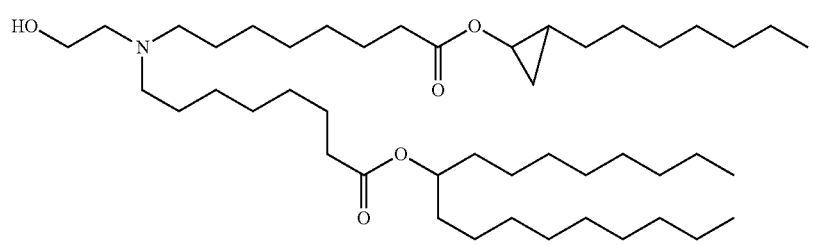
(Compound 88)
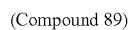
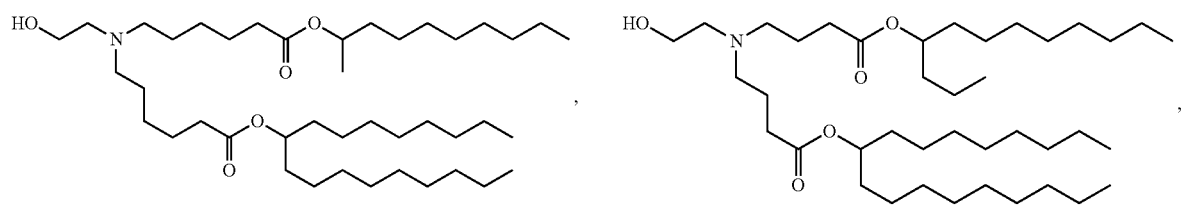
(Compound 89) (Compound 90)
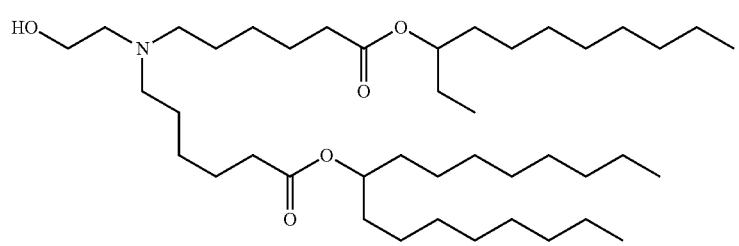
(Compound 91)
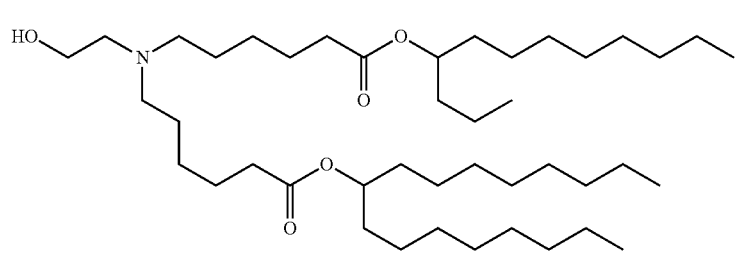
(Compound 92)
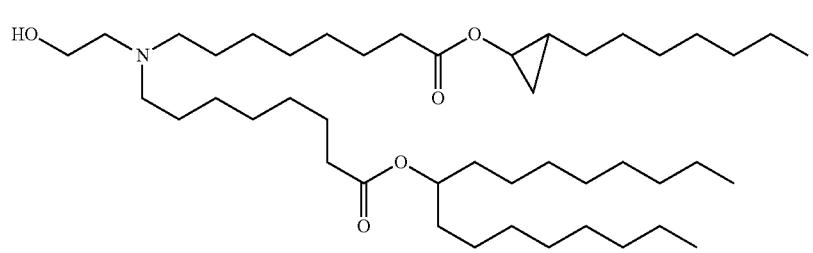
(Compound 93)
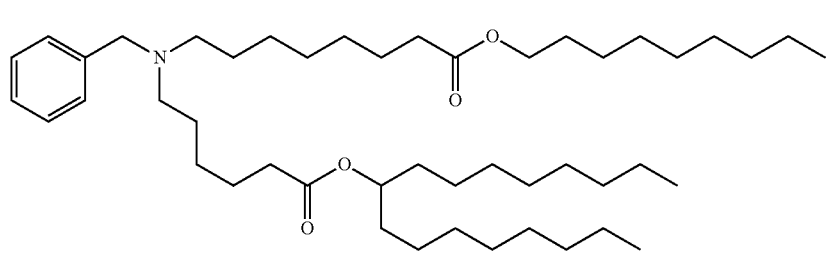
(Compound 94)

(Compound 95)
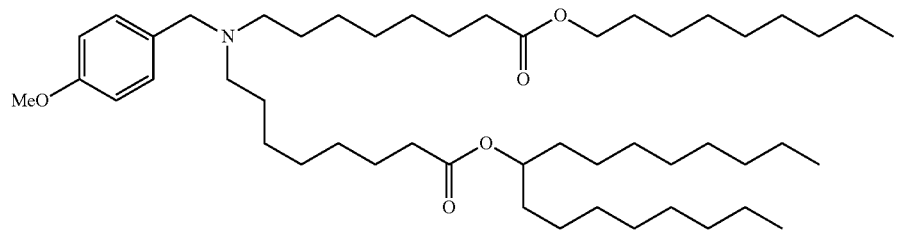
(Compound 96)
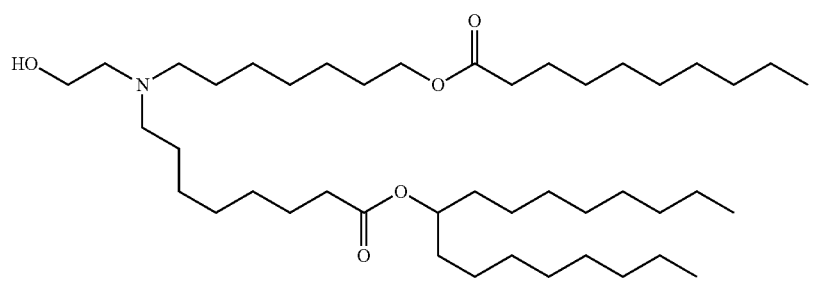
(Compound 97)
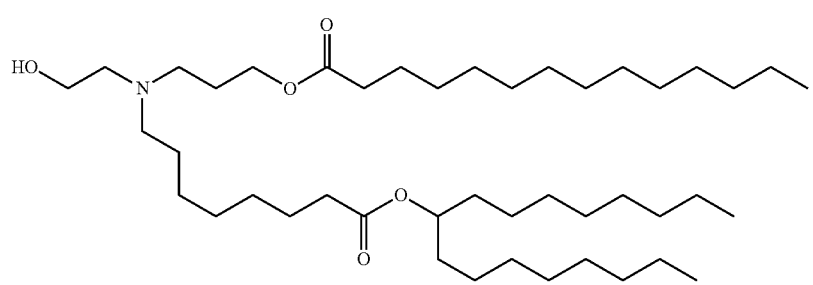
(Compound 98)
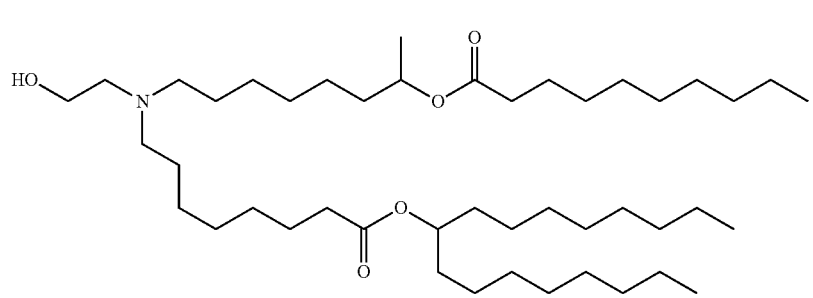
(Compound 99)
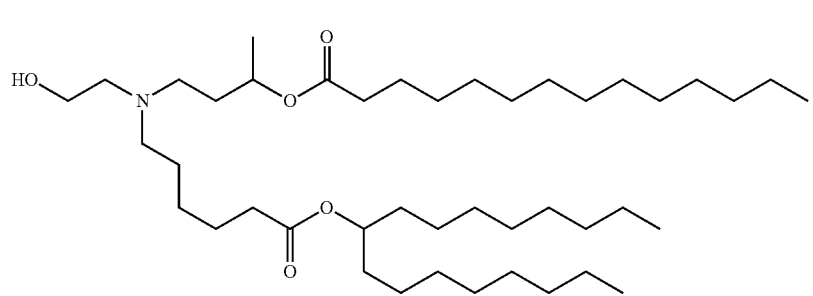

(Compound 100)
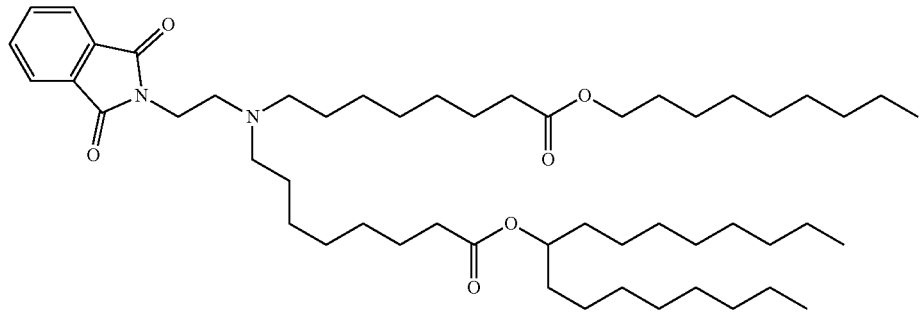
(Compound 101)
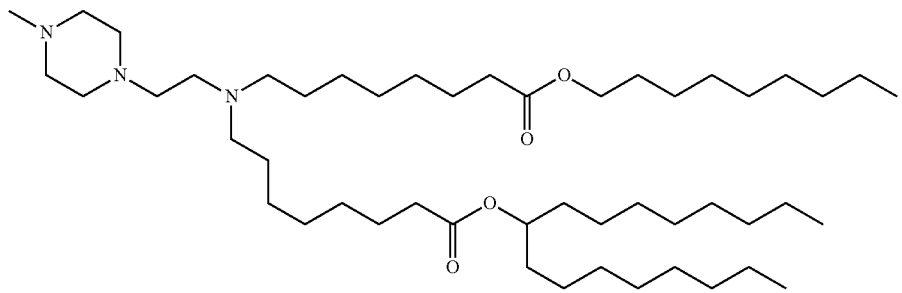
(Compound 102)
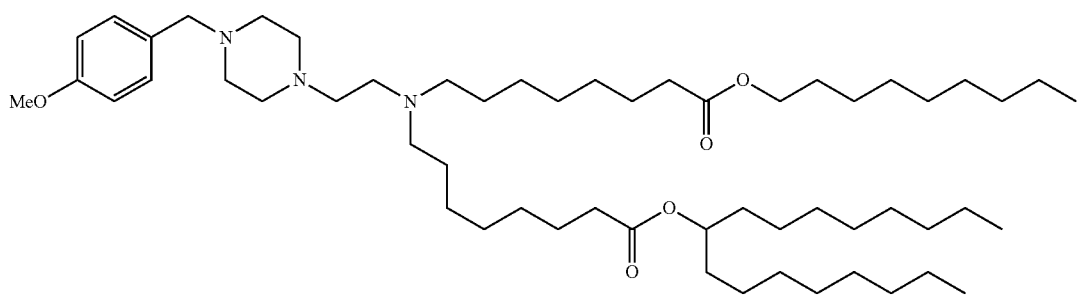
(Compound 103)
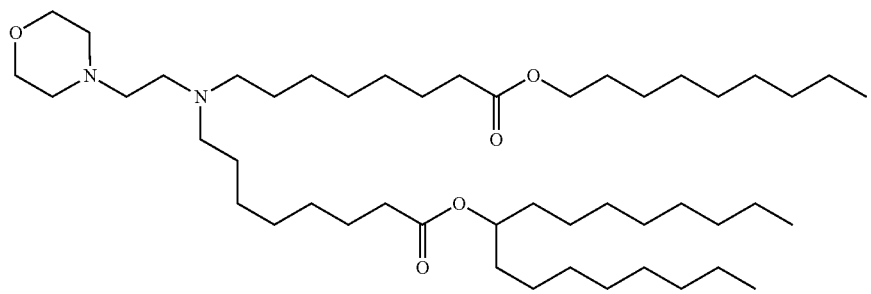
(Compound 104)
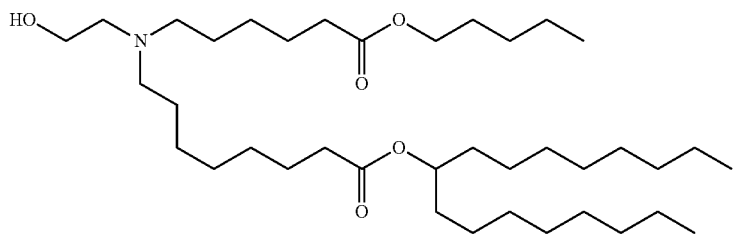

(Compound 105)
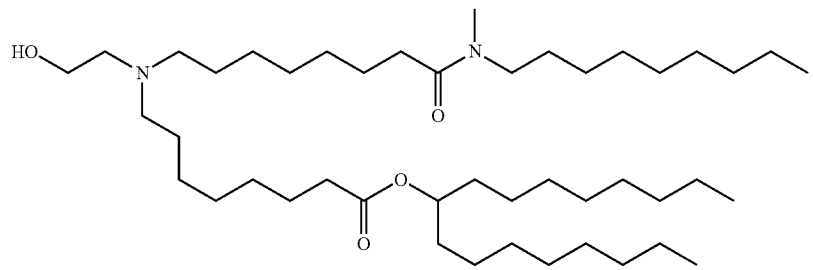,
(Compound 106)
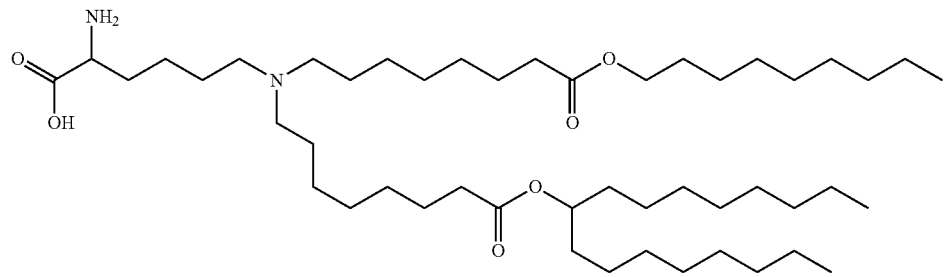,
(Compound 107)
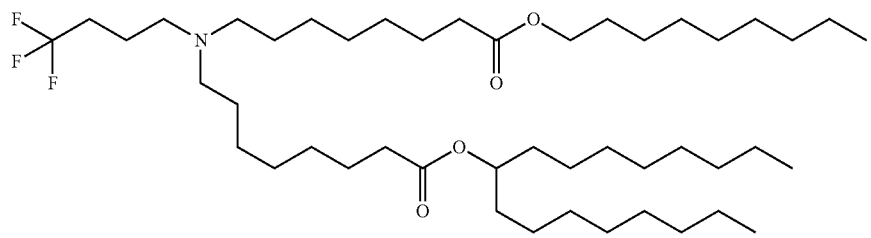,
(Compound 108)
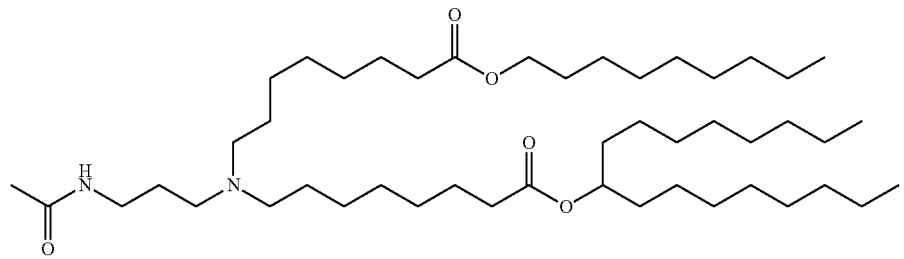,
(Compound 109)
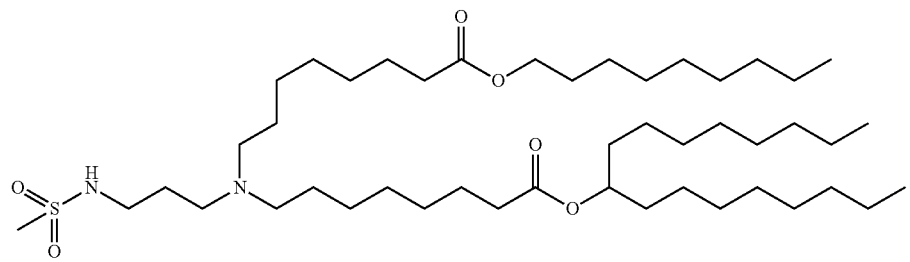,
(Compound 110)
, (Compound 111)
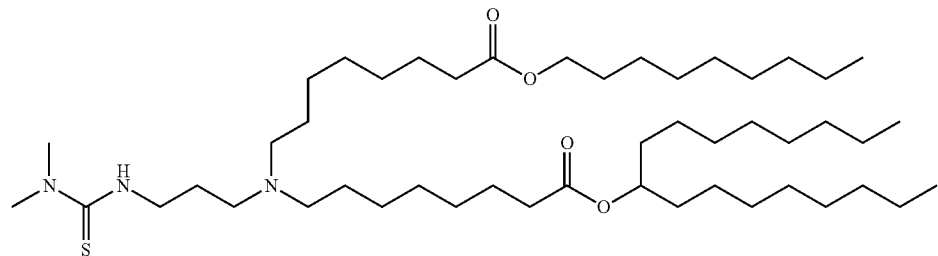
(Compound 112)
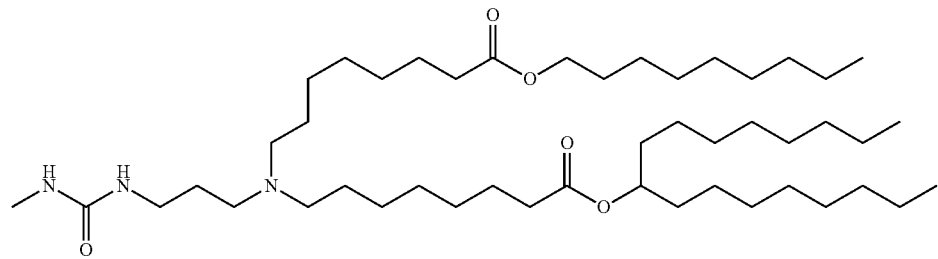
(Compound 113)
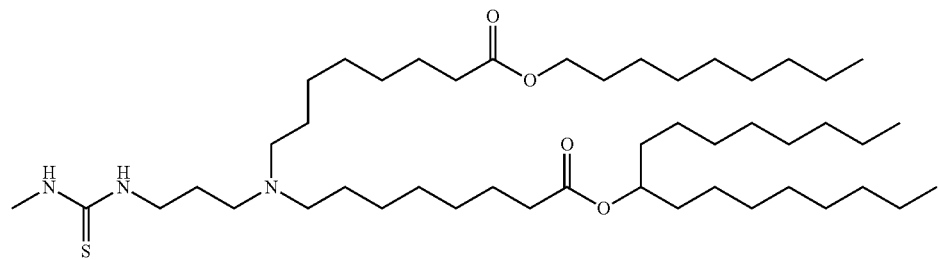
(Compound 114)
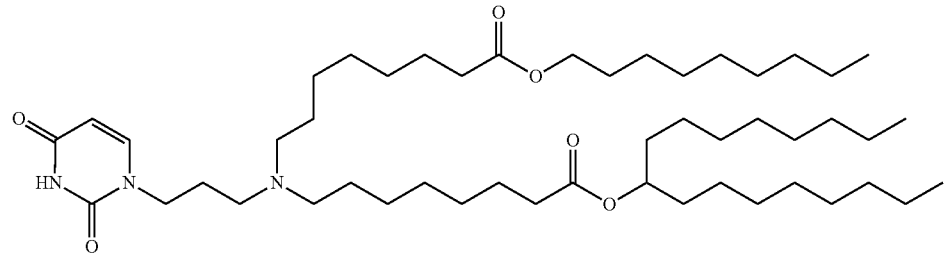
(Compound 115)
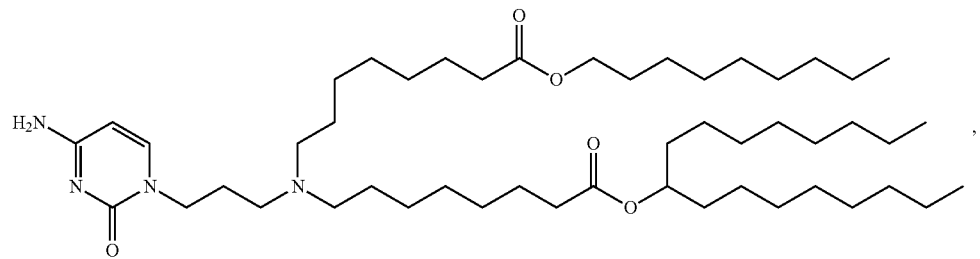
(Compound 116)
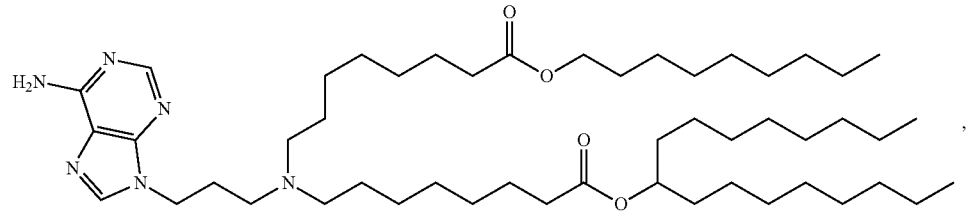

(Compound 117)
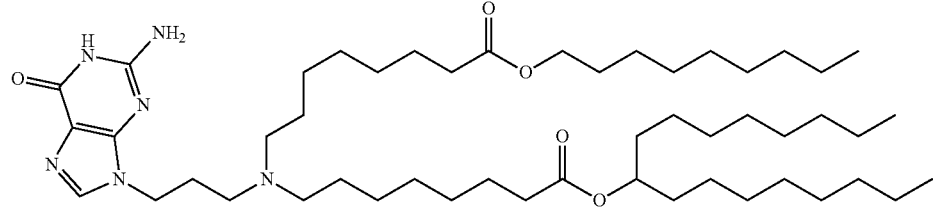
(Compound 118)
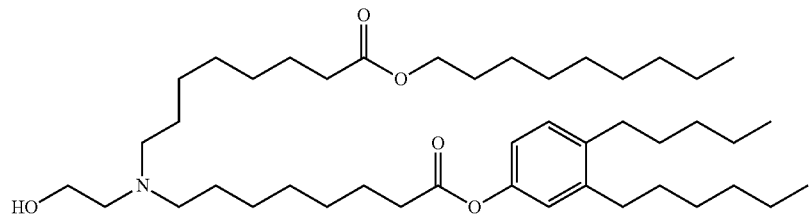
(Compound 119)
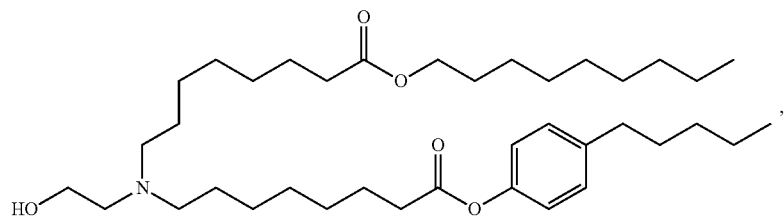
(Compound 120)
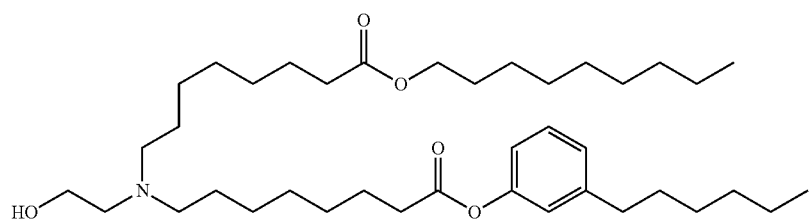
(Compound 121)
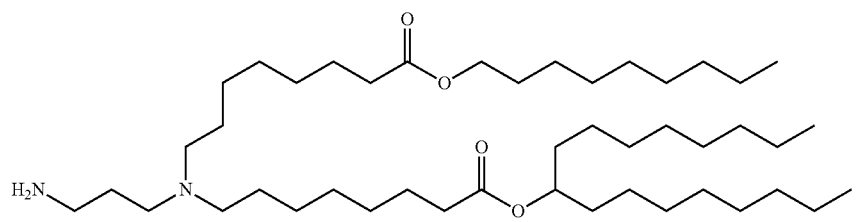
(Compound 122)
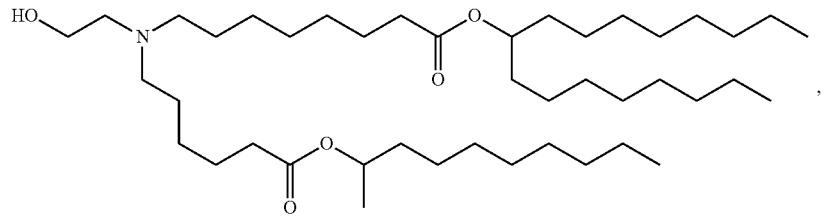
(Compound 123)
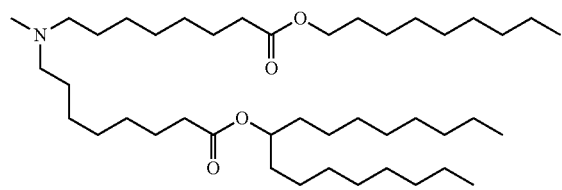
(Compound 124)
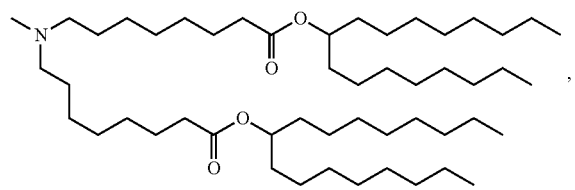

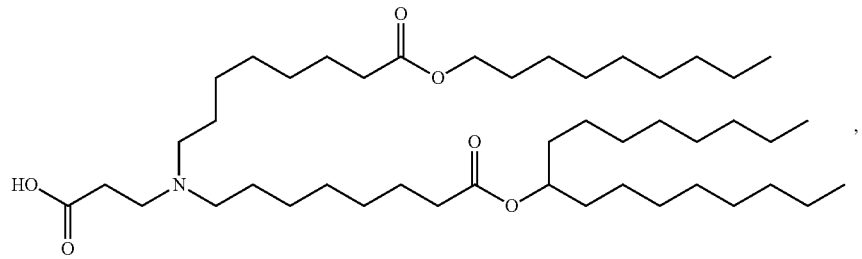
(Compound 125)
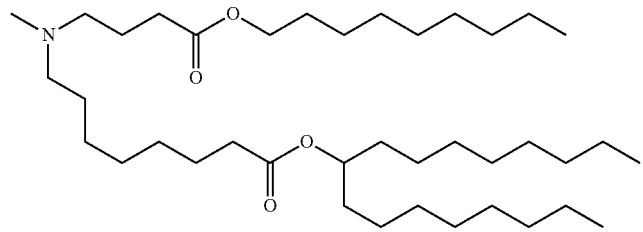
(Compound 126)
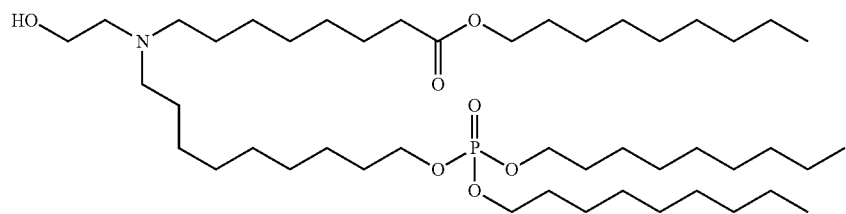
(Compound 127)
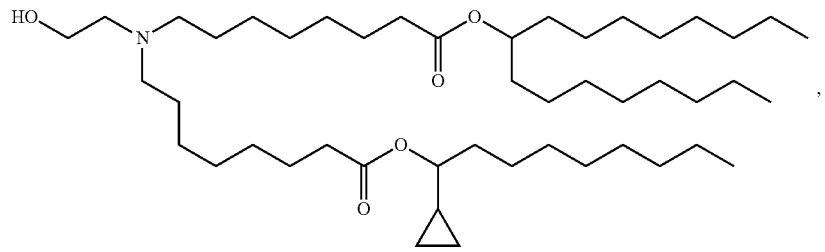
(Compound 128)
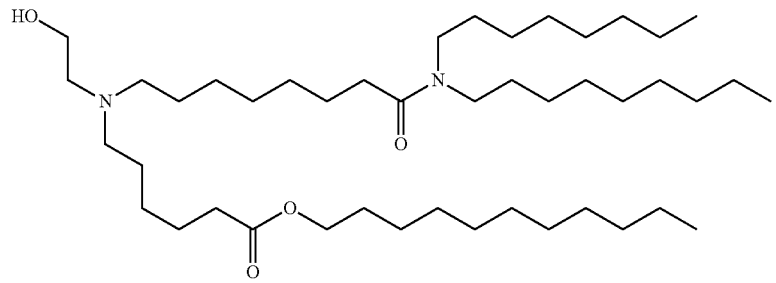
(Compound 129)
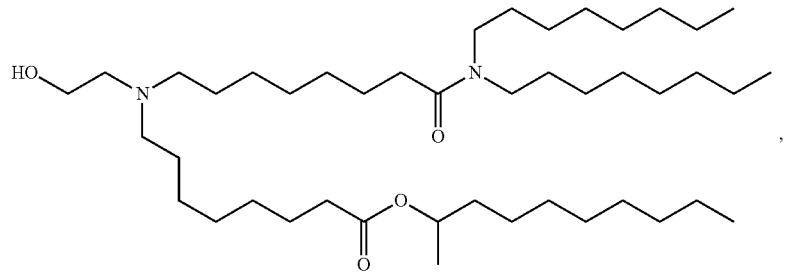
(Compound 130)

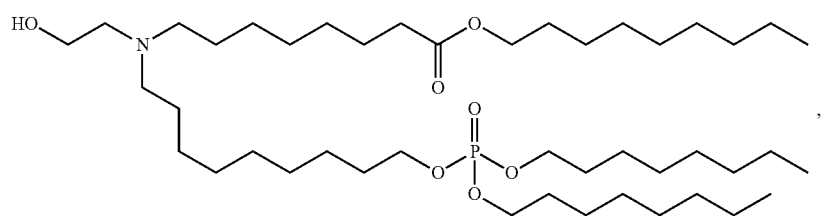
(Compound 131)
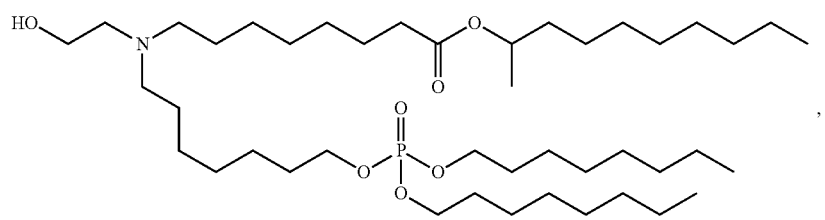
(Compound 132)
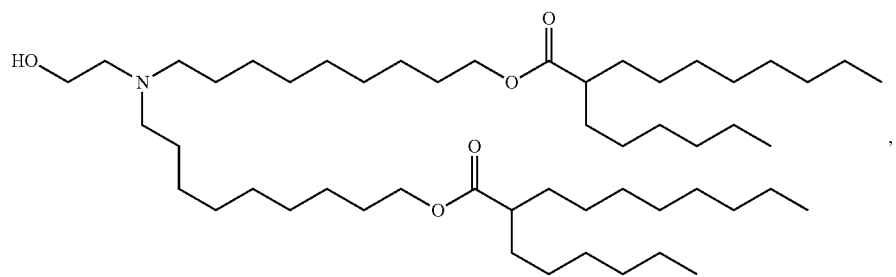
(Compound 133)
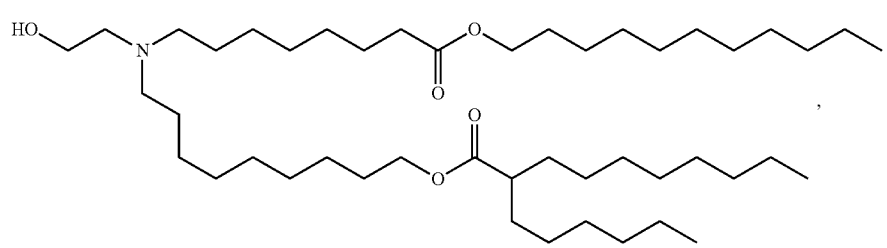
(Compound 134)
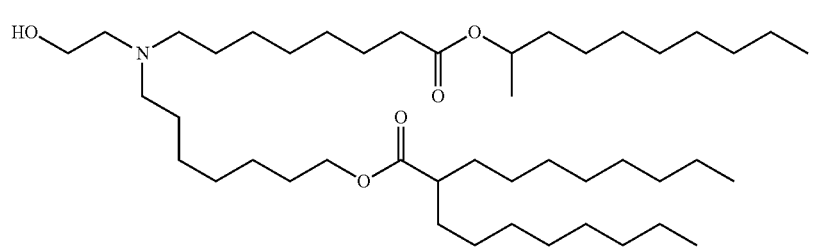
(Compound 135)
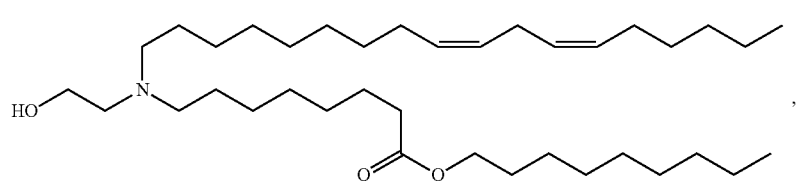
(Compound 136)
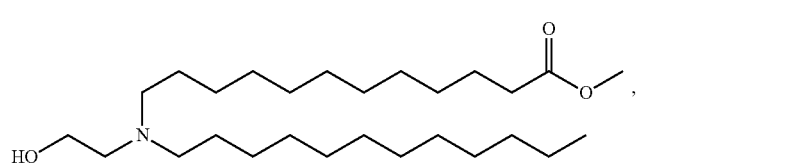
(Compound 137)

-continued
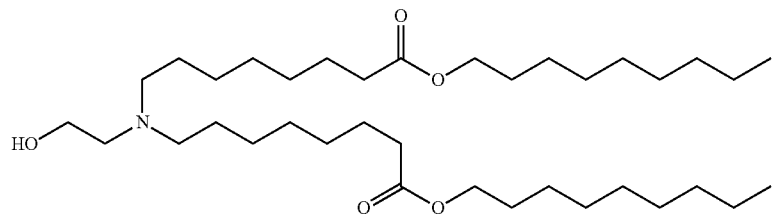
(Compound 138)
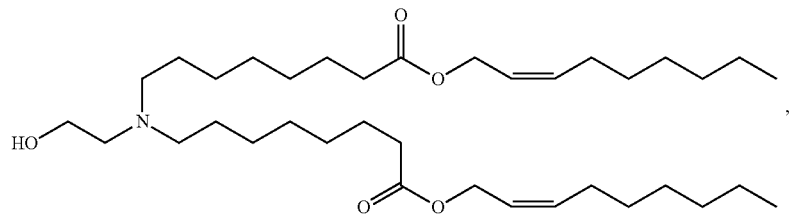
(Compound 139)
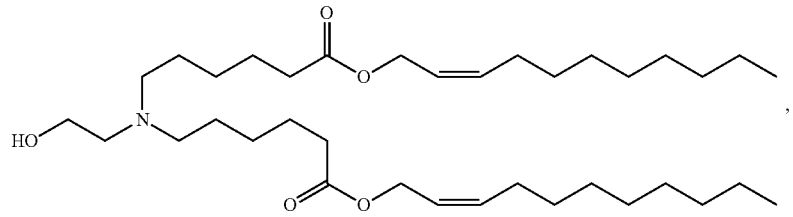
(Compound 140)
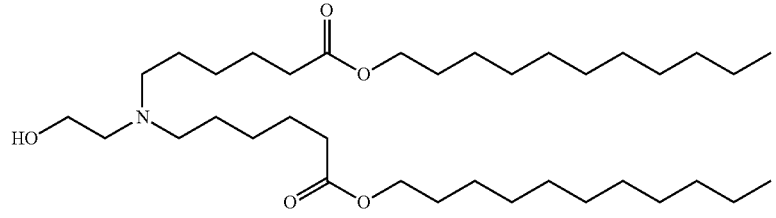
(Compound 141)
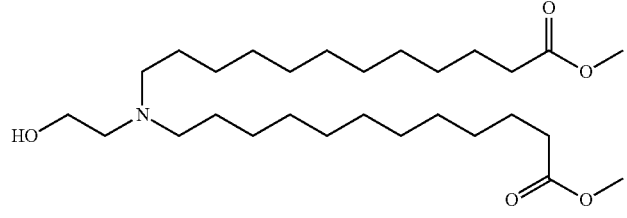
(Compound 142)
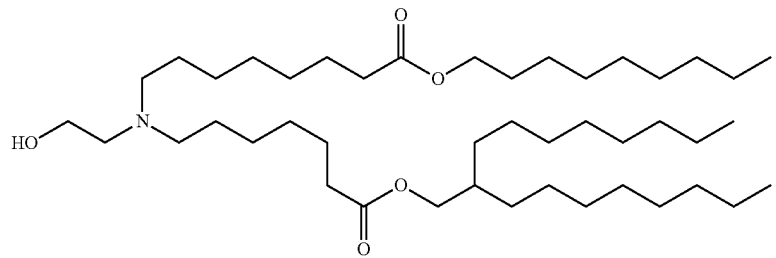
(Compound 143)

(Compound 144)
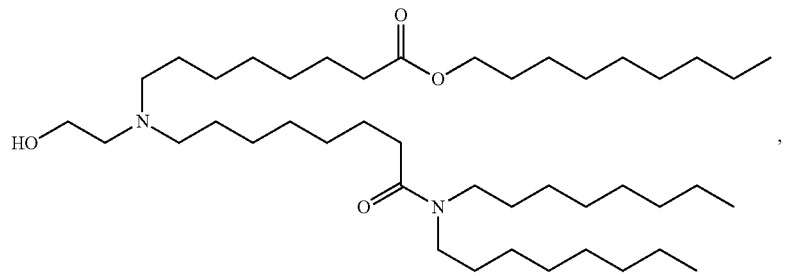
(Compound 145)
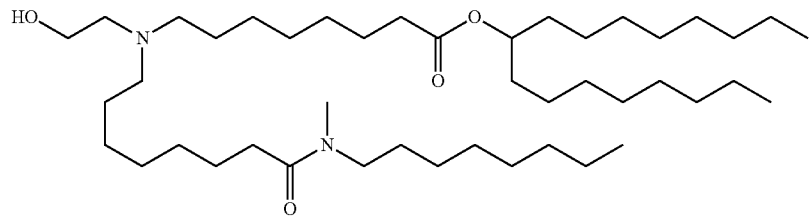
(Compound 146)
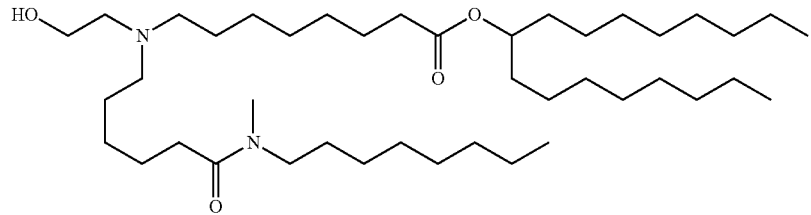
(Compound 147)
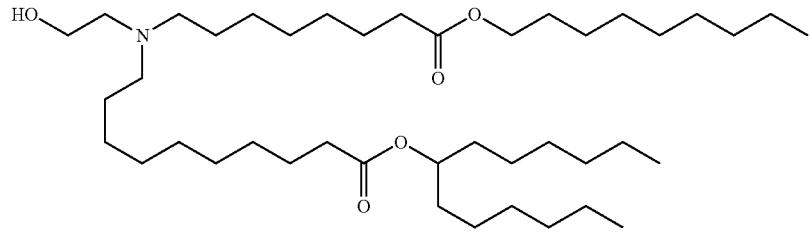
(Compound 148)
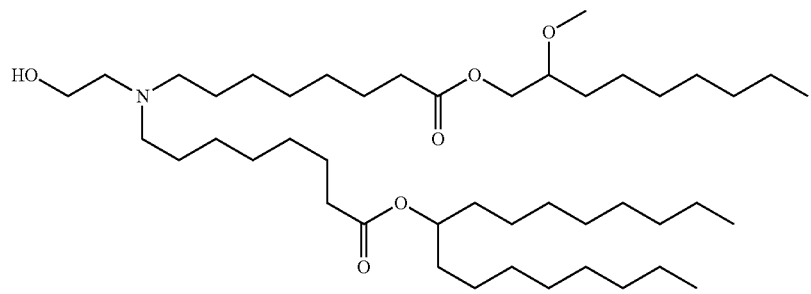
(Compound 149)
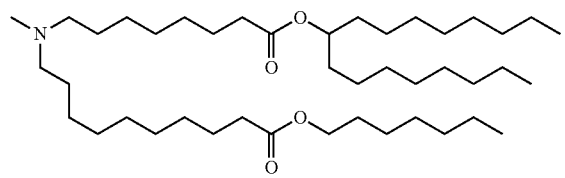
(Compound 150)
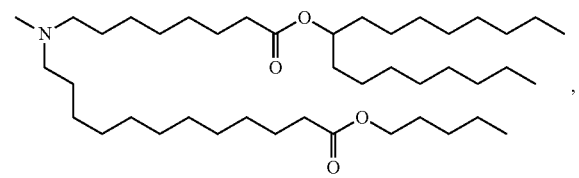

-continued
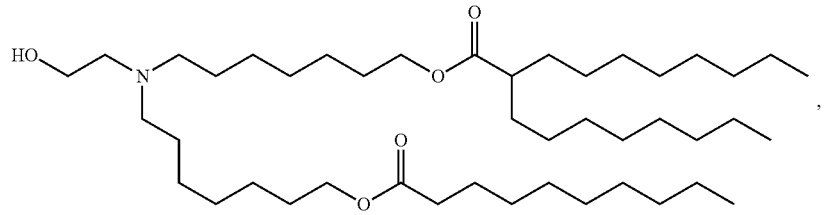
(Compound 151)
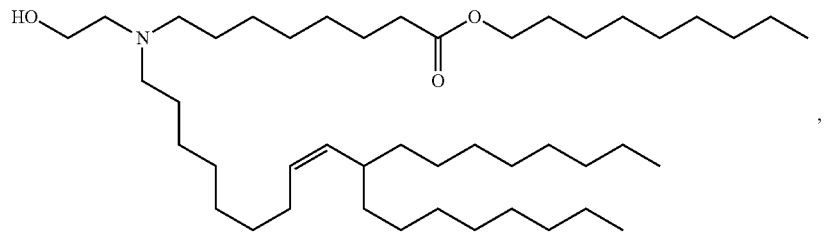
(Compound 152)
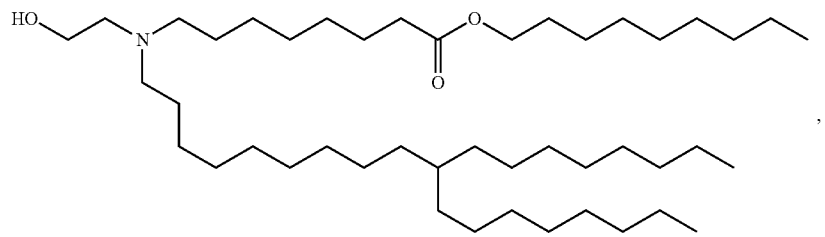
(Compound 153)
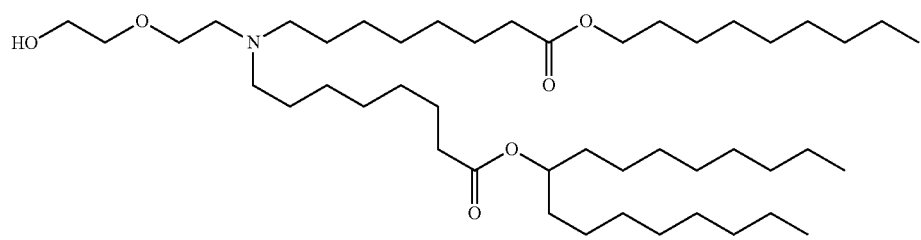
(Compound 154)
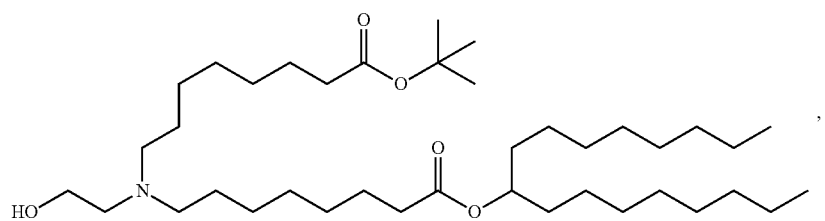
(Compound 155)
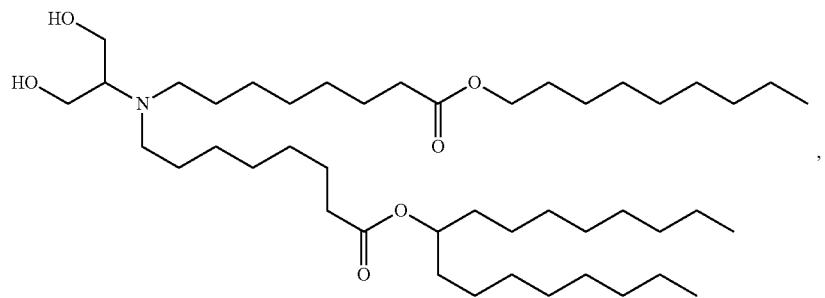
(Compound 156)

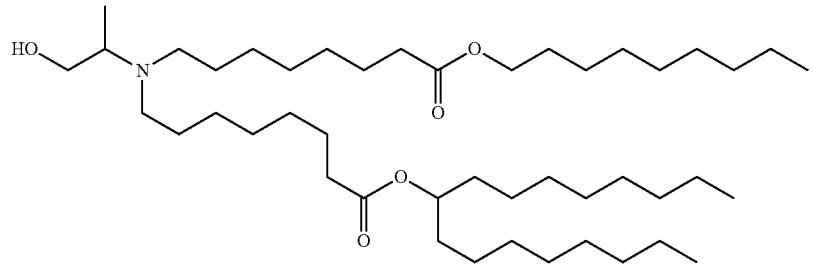
(Compound 157)
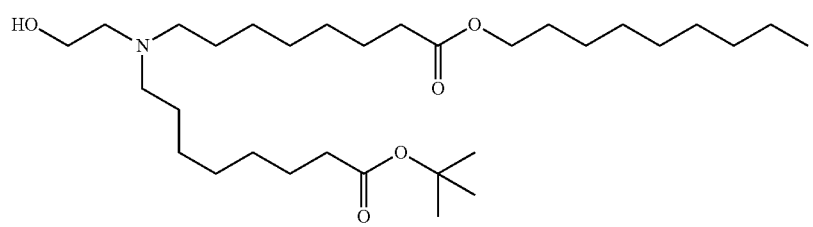
(Compound 158)
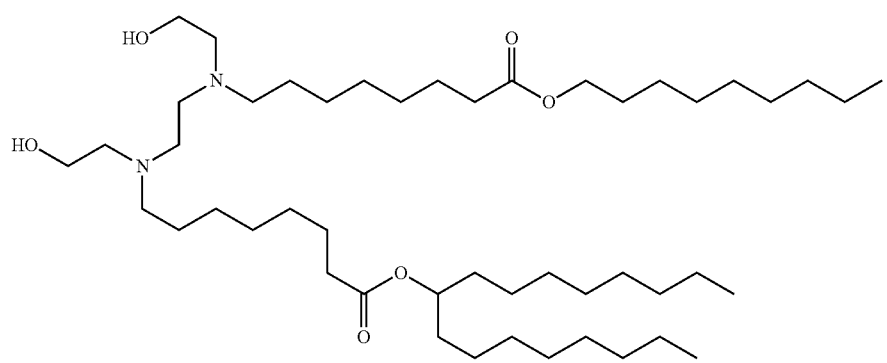
(Compound 159)
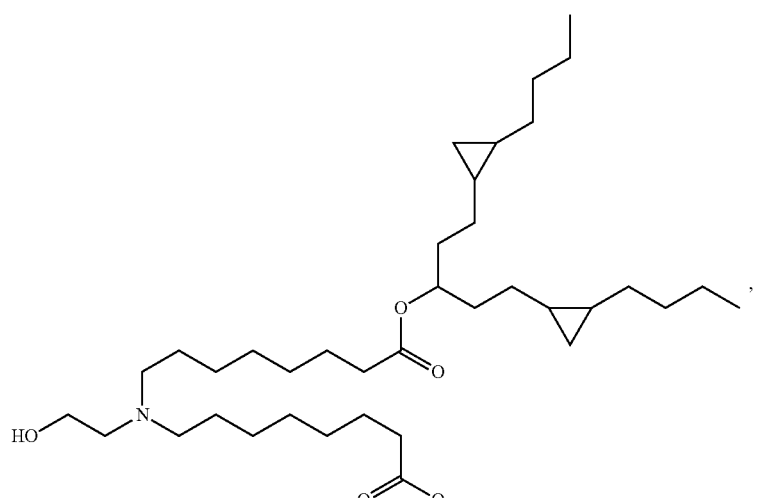
(Compound 160)
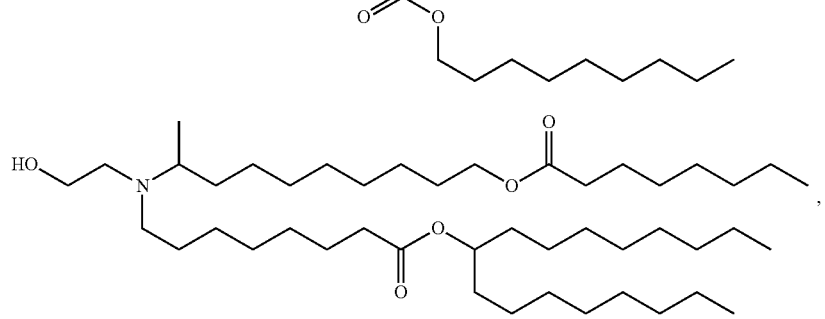
(Compound 161)

(Compound 162)
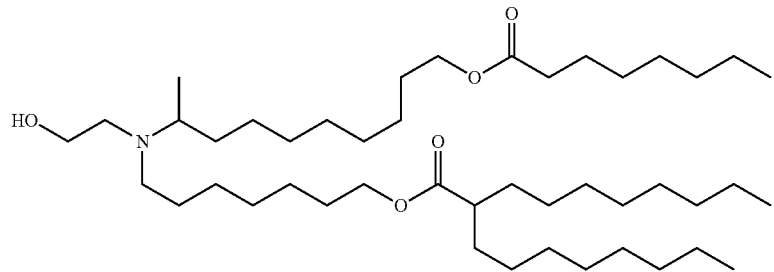
(Compound 163)
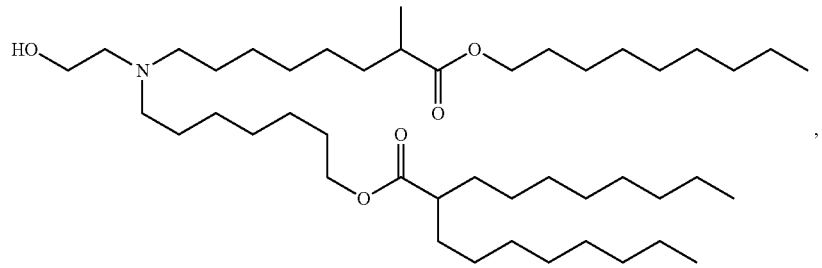
(Compound 164)
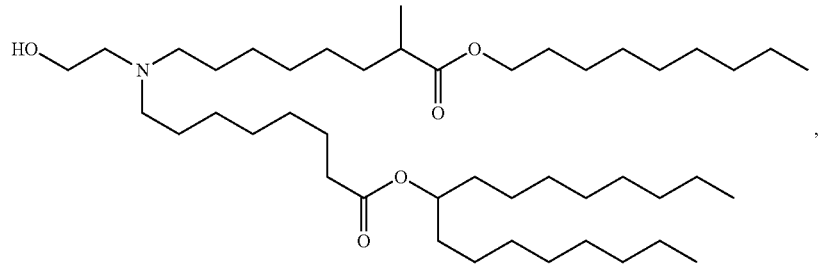
(Compound 165)
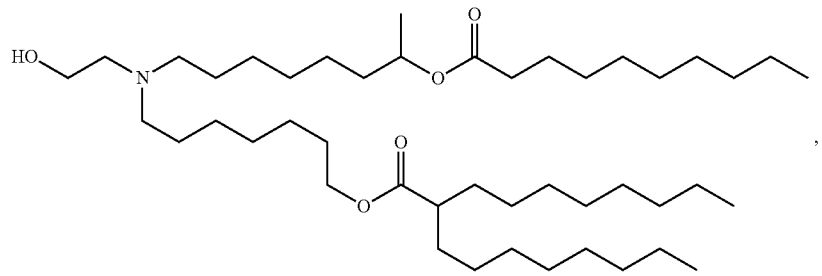
(Compound 166)
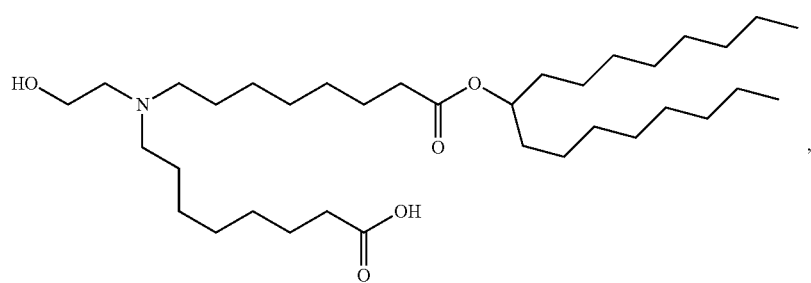

(Compound 167)
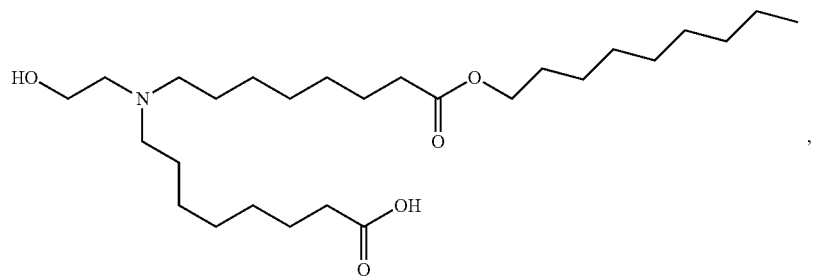
(Compound 168)
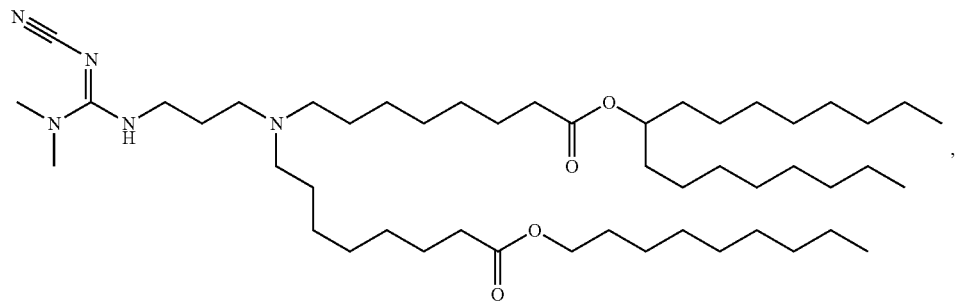
(Compound 169)
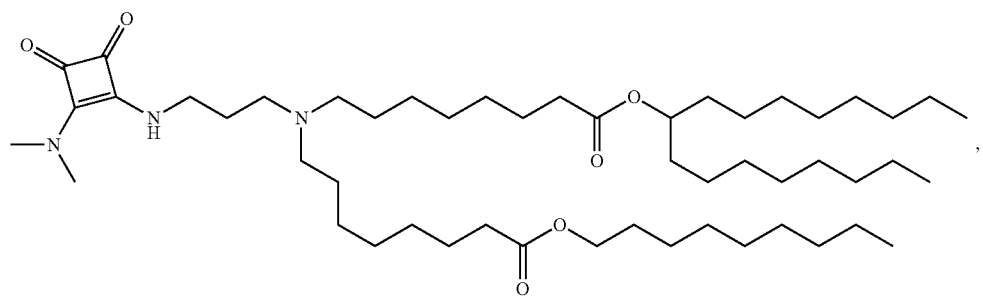
(Compound 170)
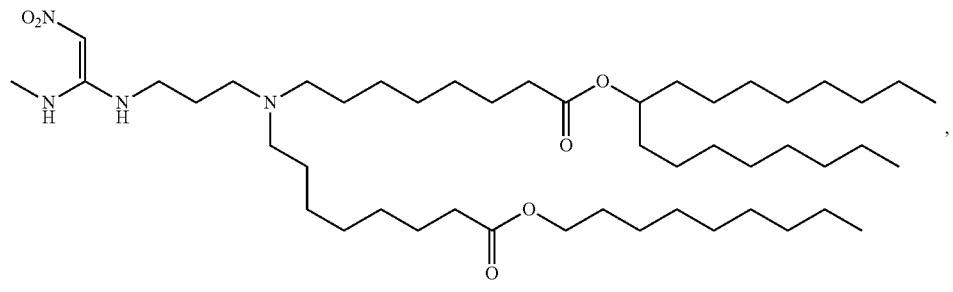
(Compound 171)
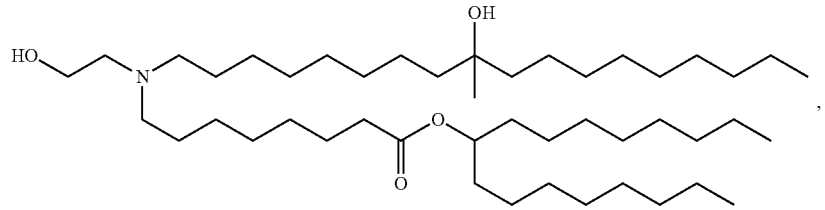
(Compound 172)
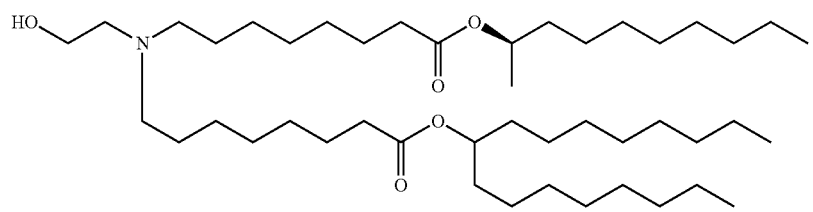

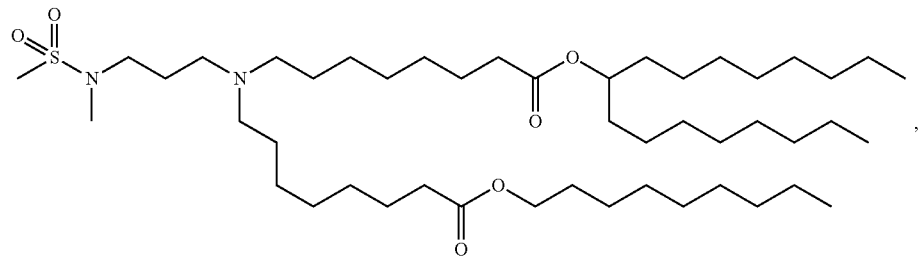
(Compound 173)
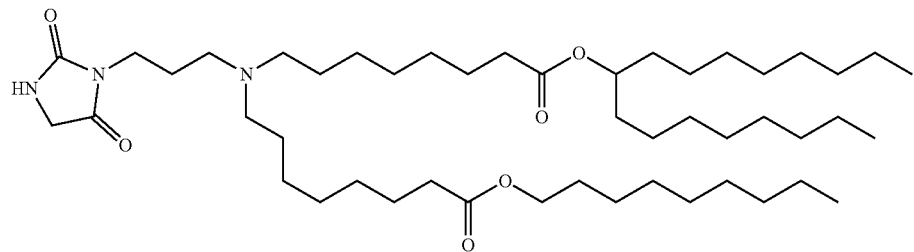
(Compound 174)
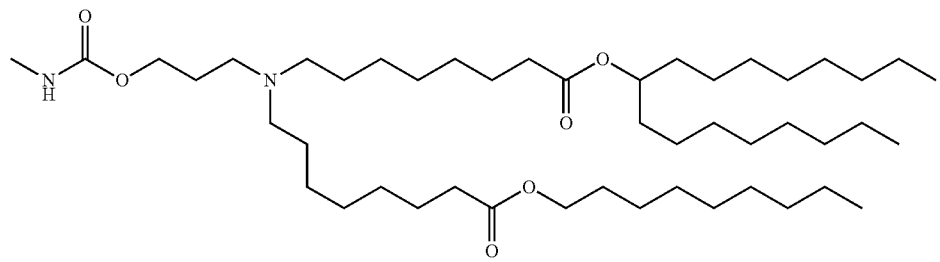
(Compound 175)
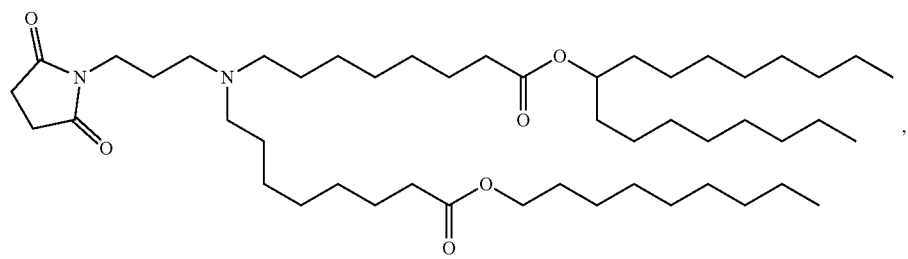
(Compound 176)
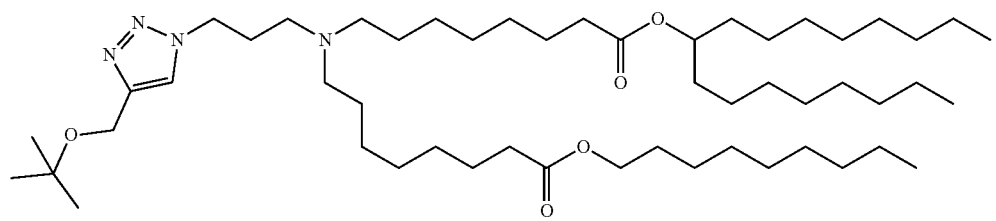
(Compound 177)
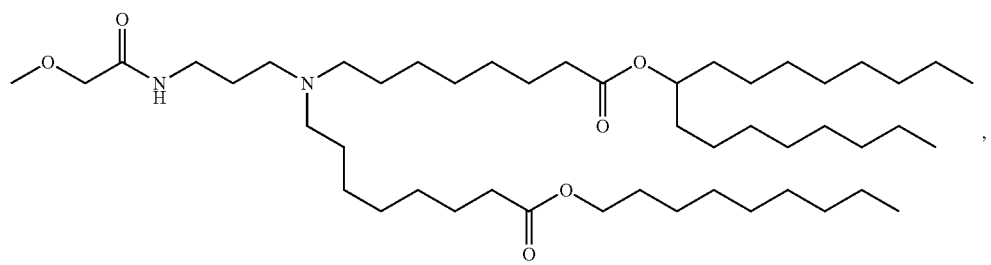
(Compound 178)

-continued
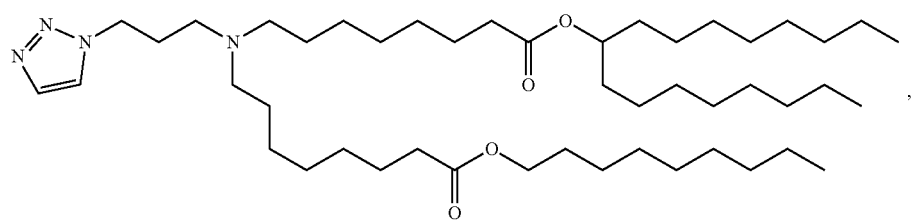
(Compound 179)
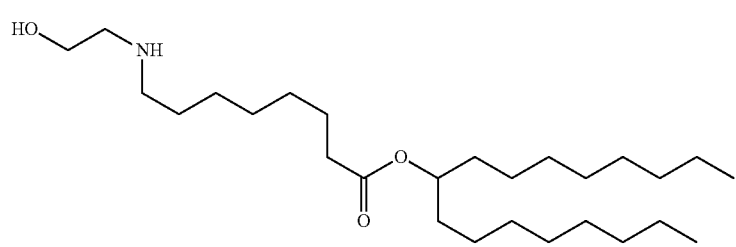
(Compound 180)
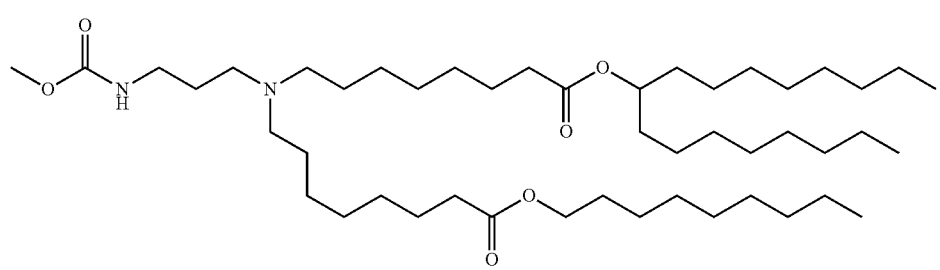
(Compound 181)
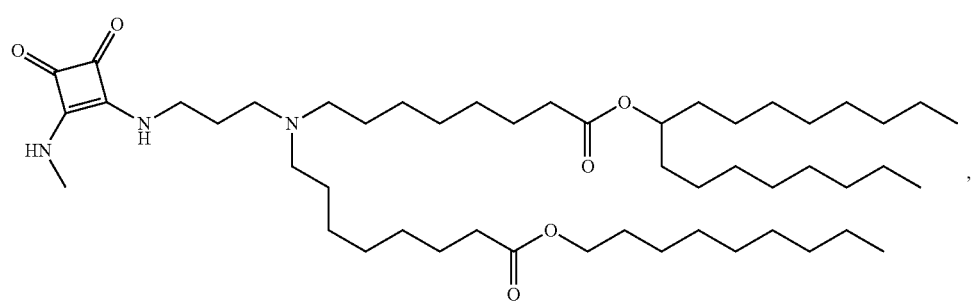
(Compound 182)
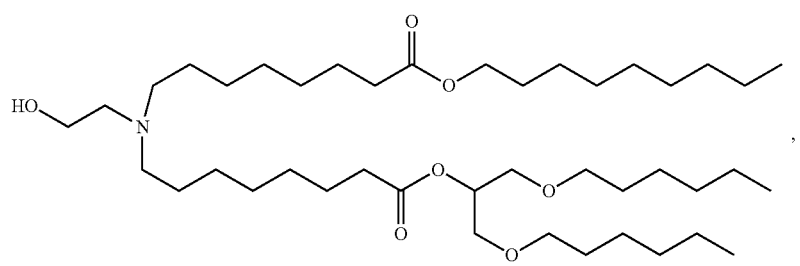
(Compound 183)
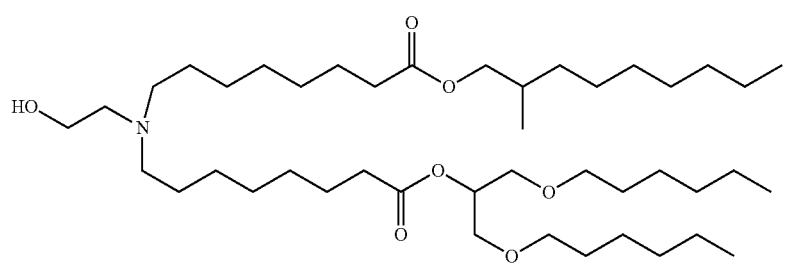
(Compound 184)

-continued
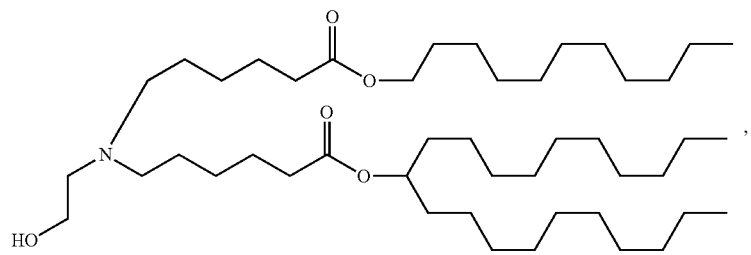
(Compound 185)
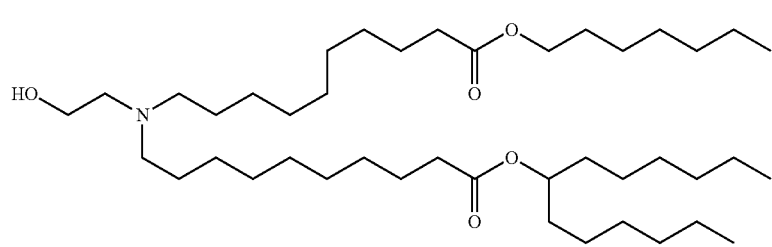
(Compound 186)
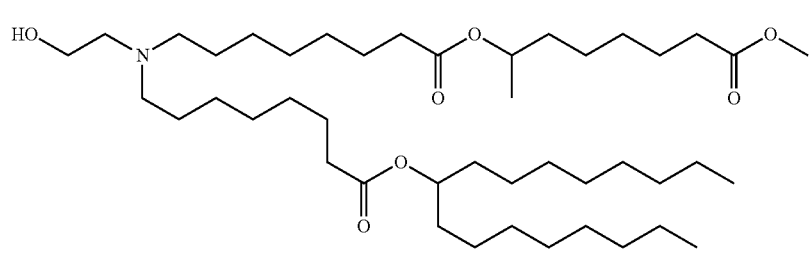
(Compound 187)
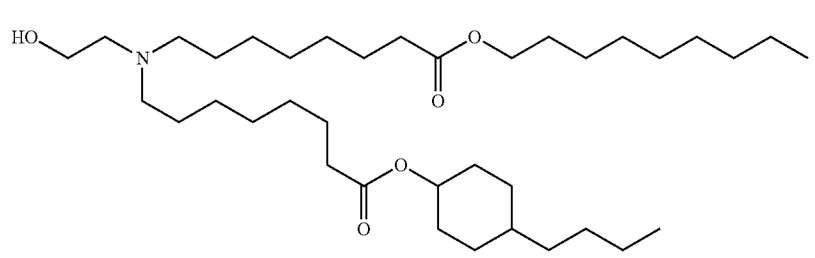
(Compound 188)
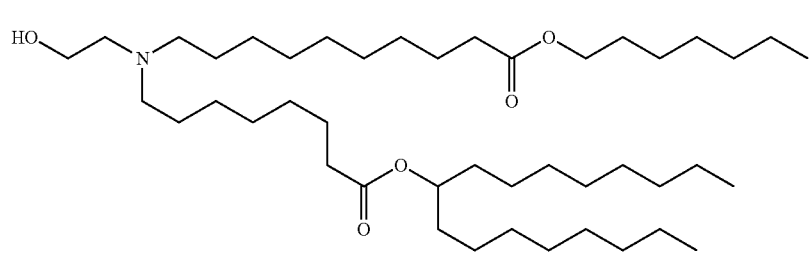
(Compound 189)
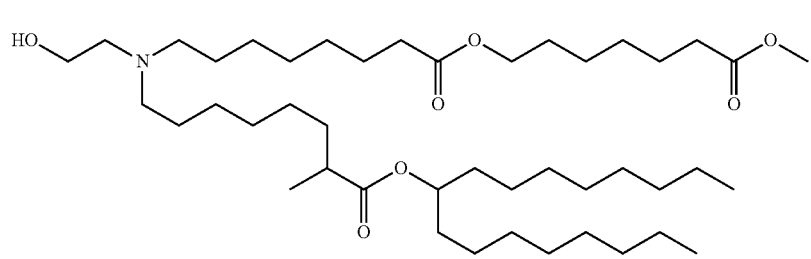
(Compound 190)

-continued
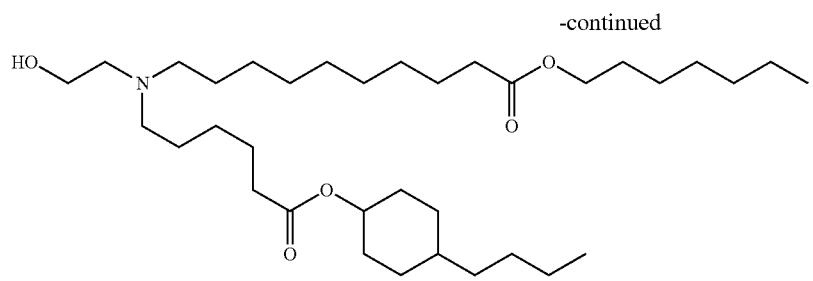
(Compound 191)
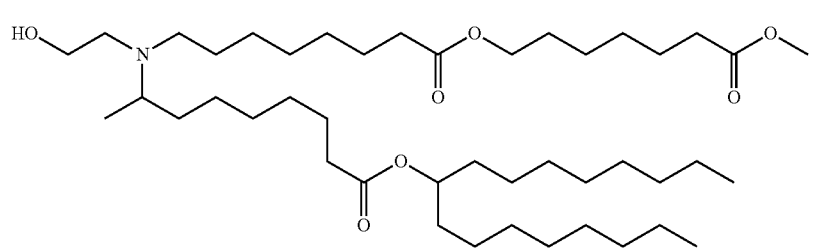
(Compound 192)
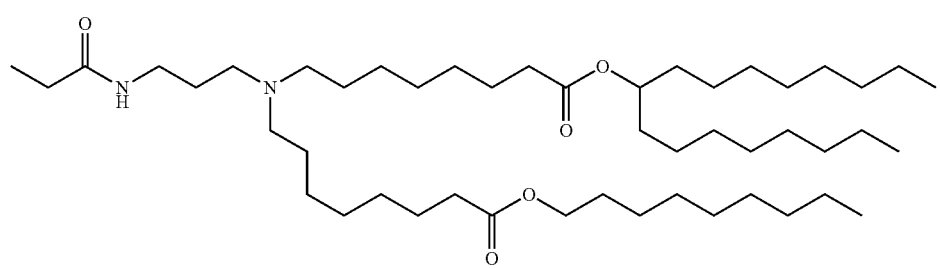
(Compound 193)
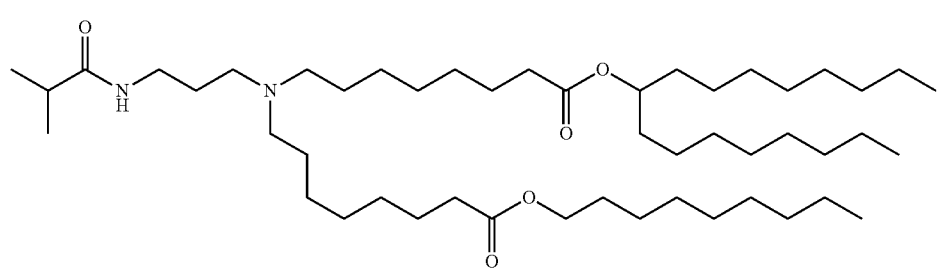
(Compound 194)
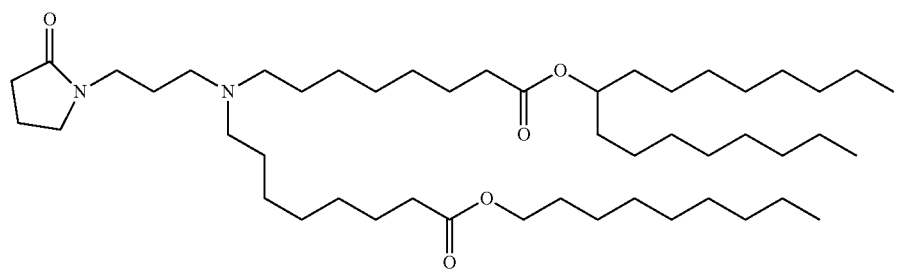
(Compound 195)
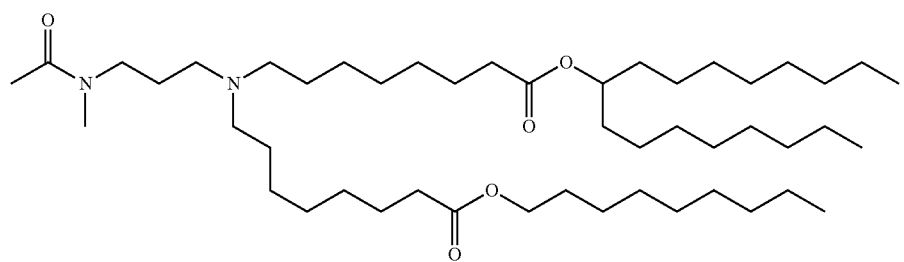
(Compound 196)

(Compound 197)
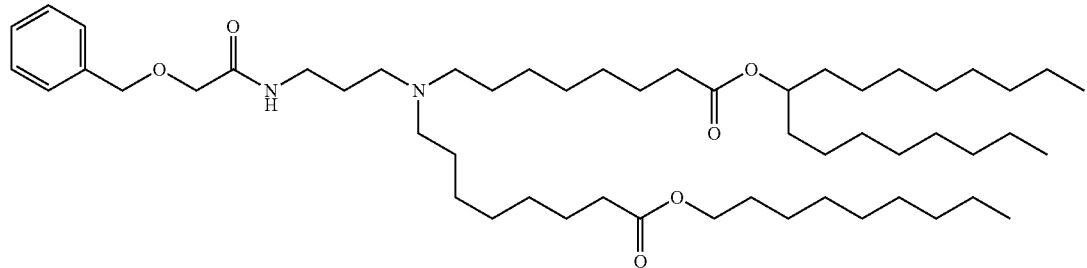
(Compound 198)
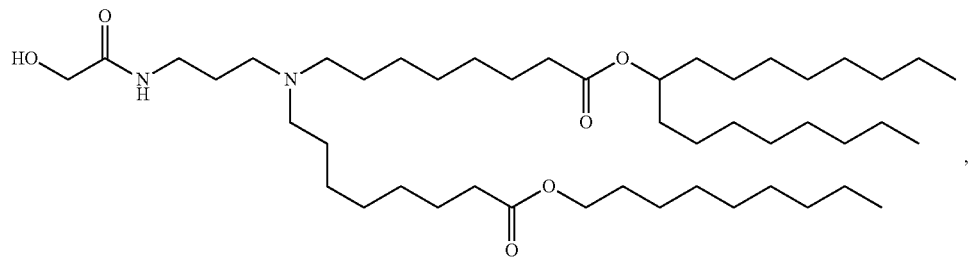
(Compound 199)
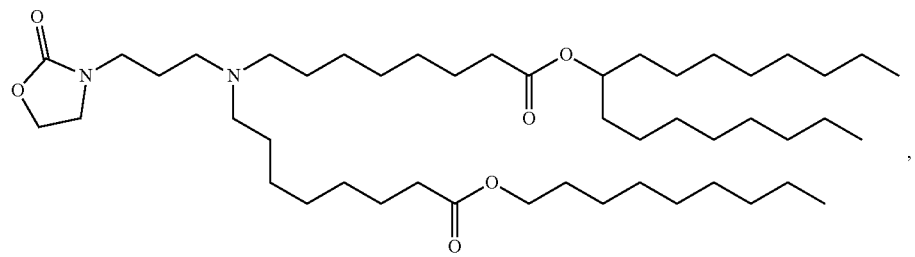
(Compound 200)
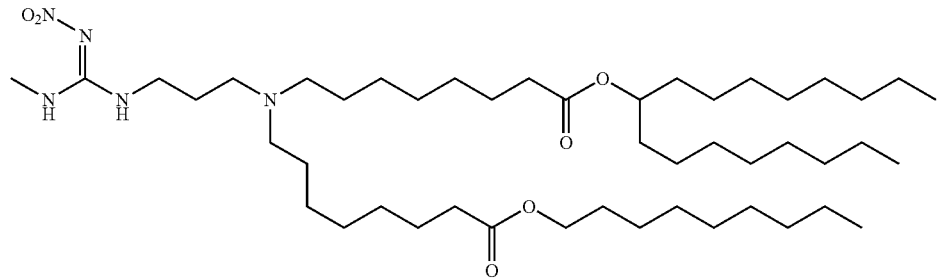
(Compound 201)
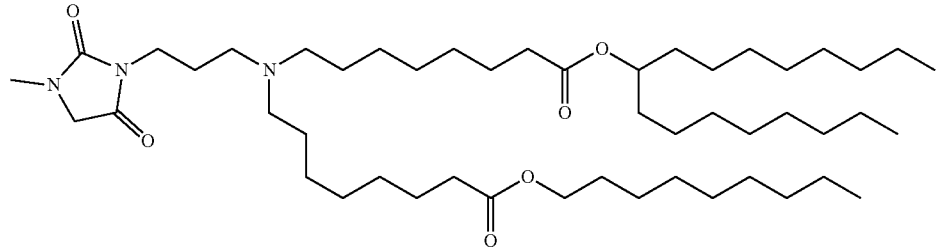
(Compound 202)
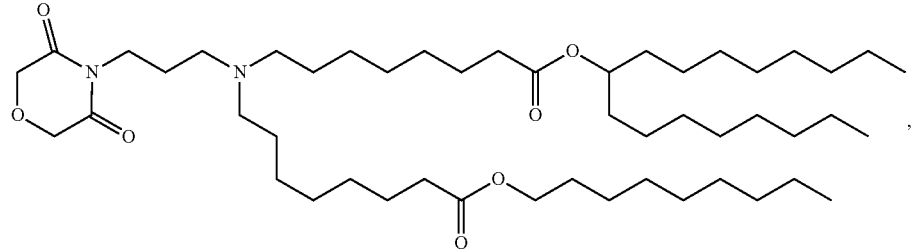

-continued
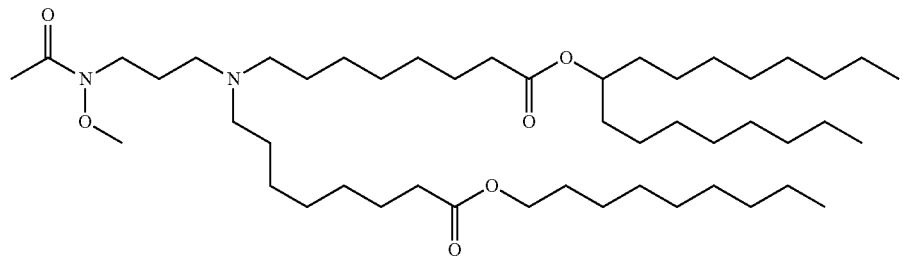
(Compound 203)
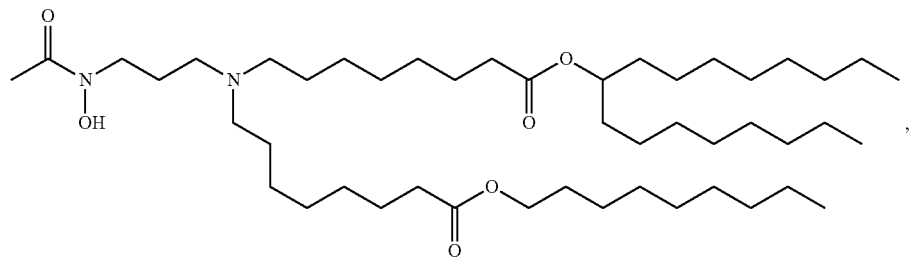
(Compound 204)
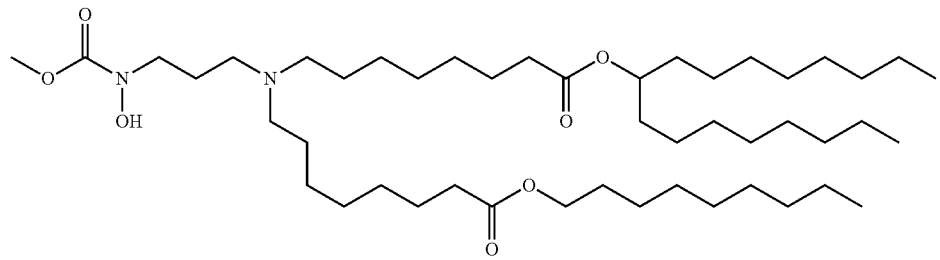
(Compound 205)
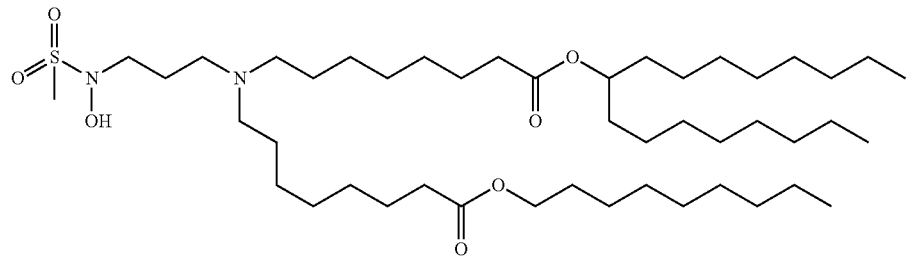
(Compound 206)
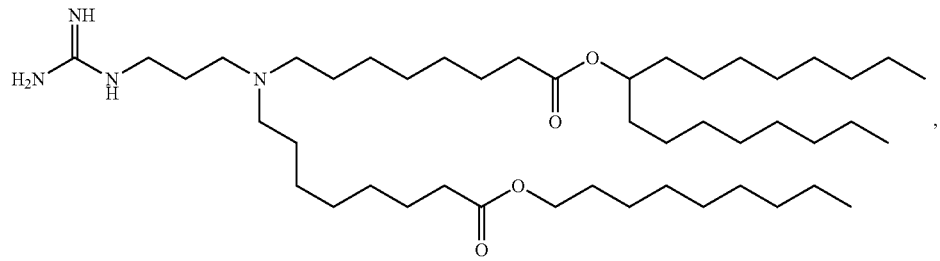
(Compound 207)
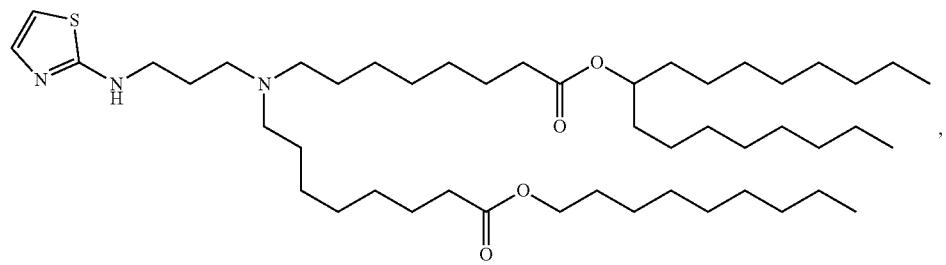
(Compound 208)

(Compound 209)
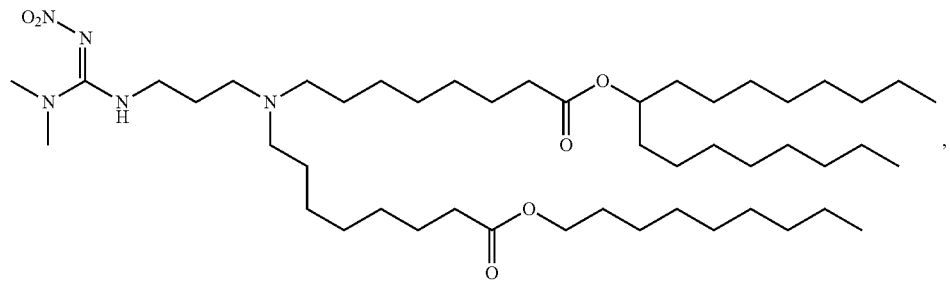
(Compound 210)
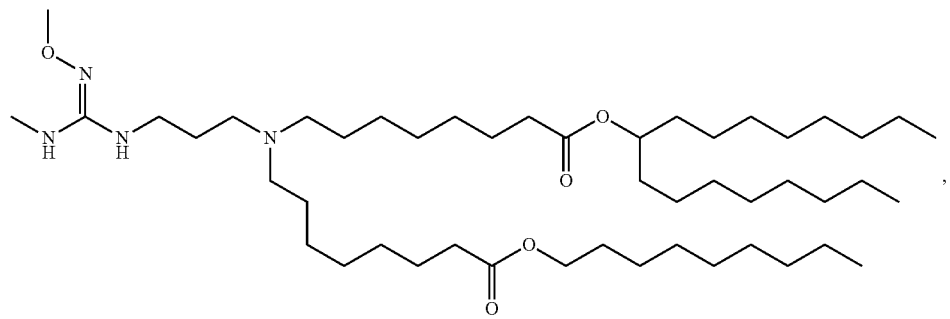
(Compound 211)
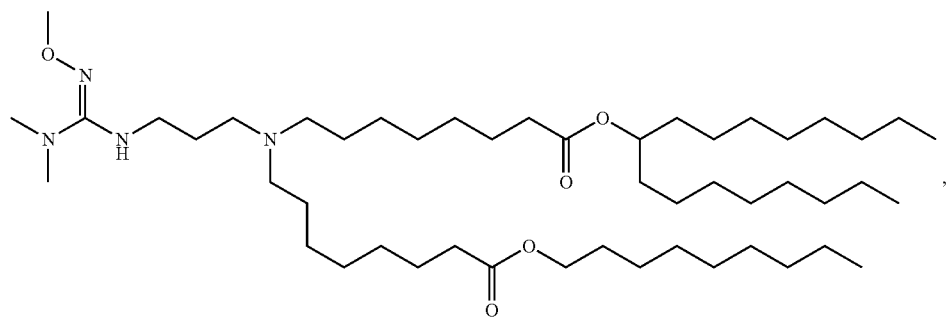
(Compound 212)
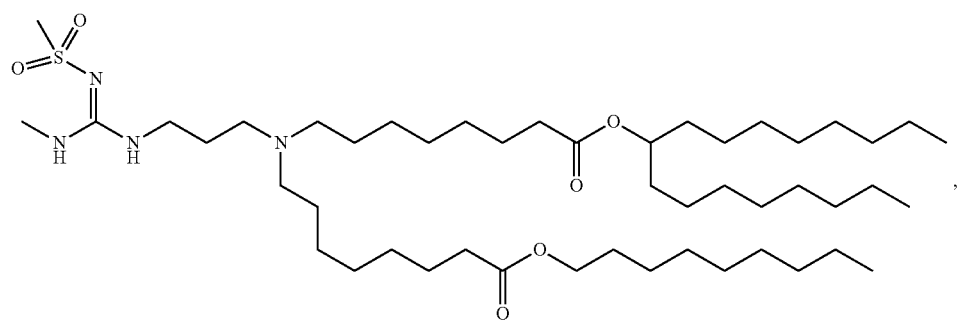
(Compound 213)
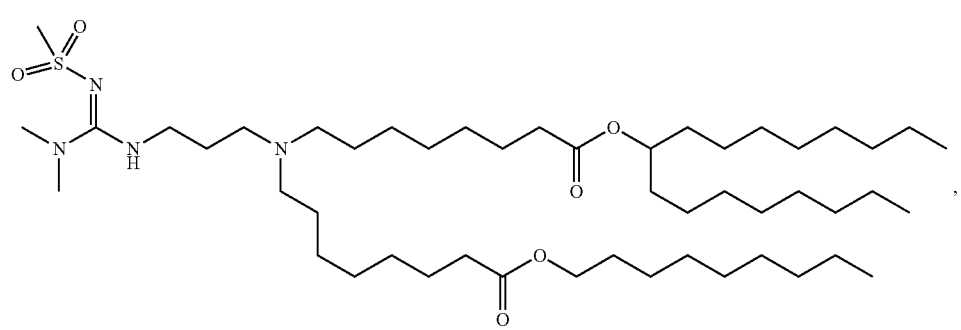

-continued
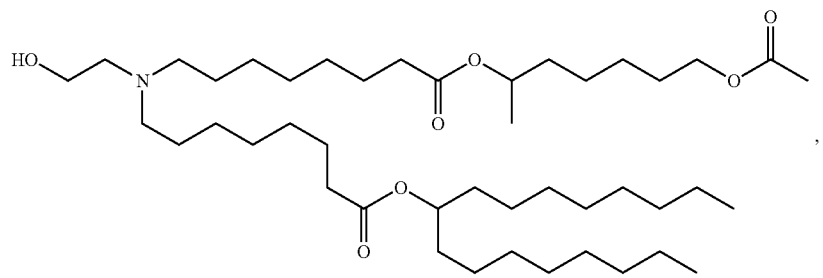
(Compound 214)
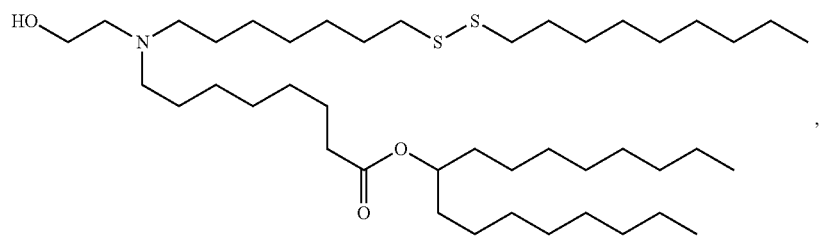
(Compound 215)
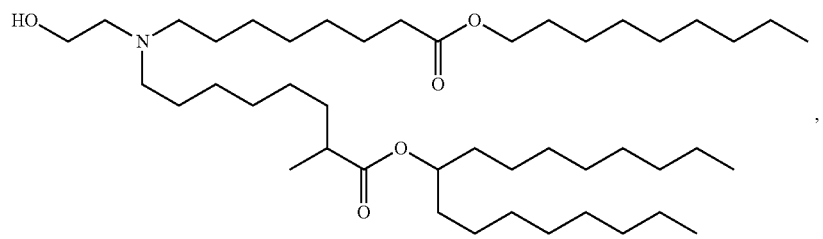
(Compound 216)
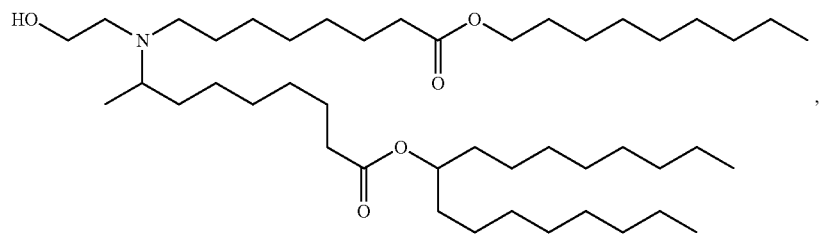
(Compound 217)
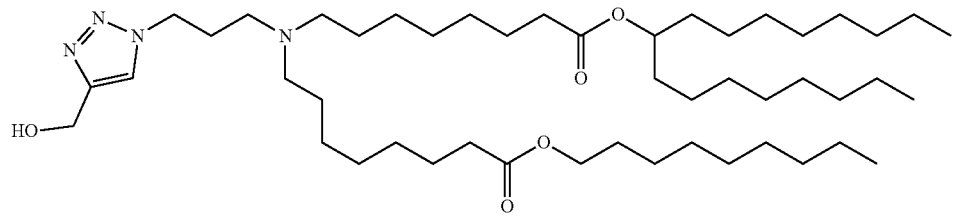
(Compound 218)
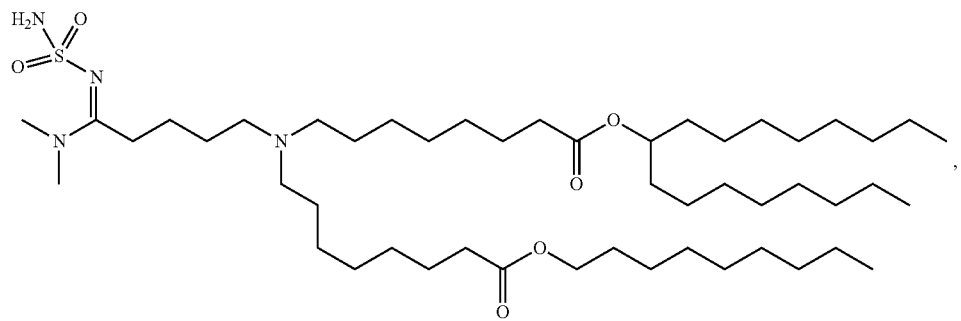
(Compound 219)

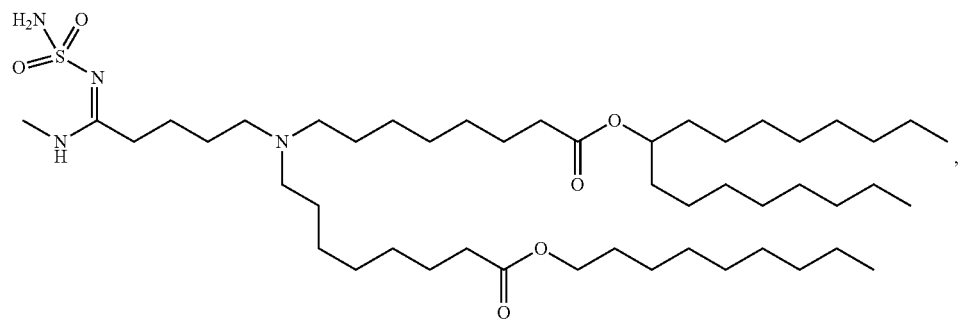
(Compound 220)
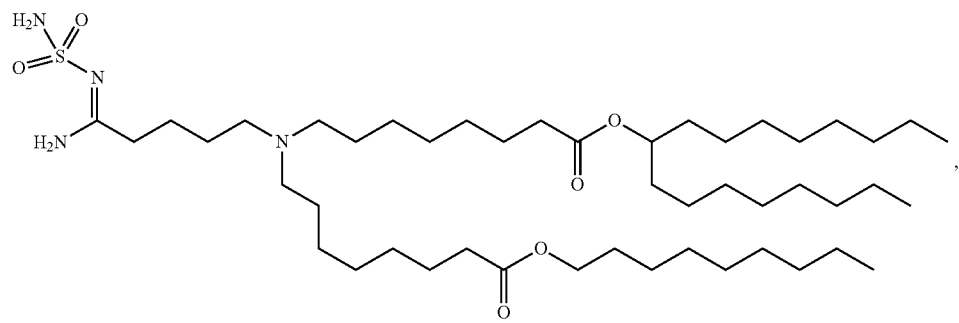
(Compound 221)
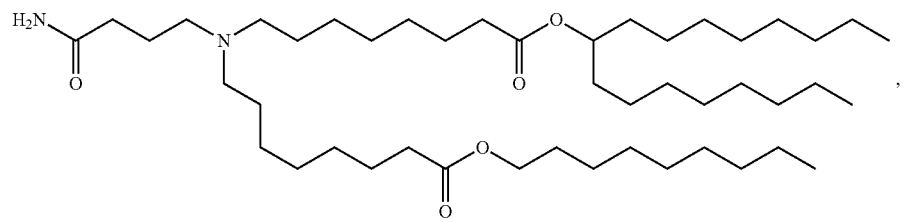
(Compound 222)
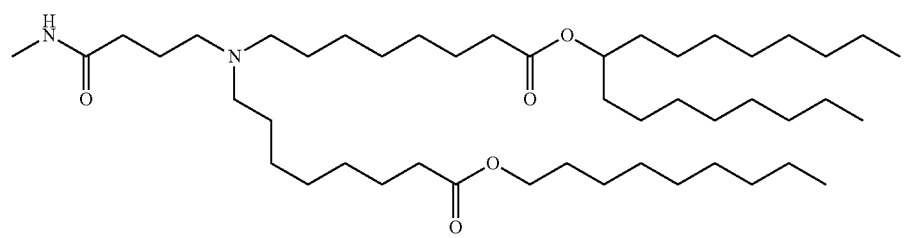
(Compound 223)
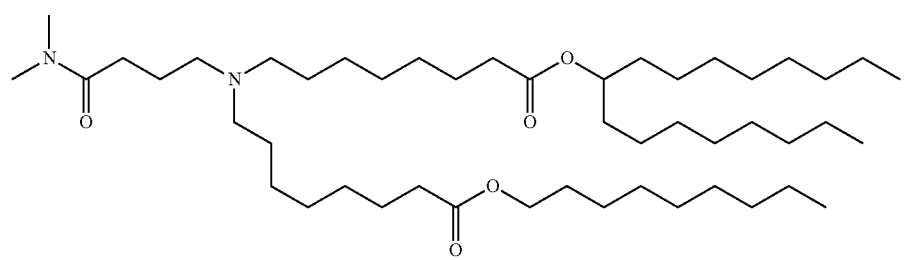
(Compound 224)
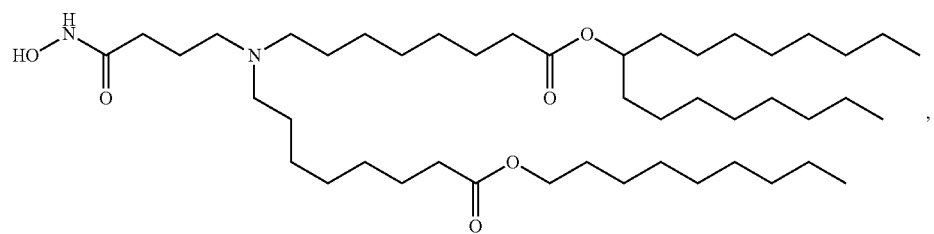
(Compound 225)

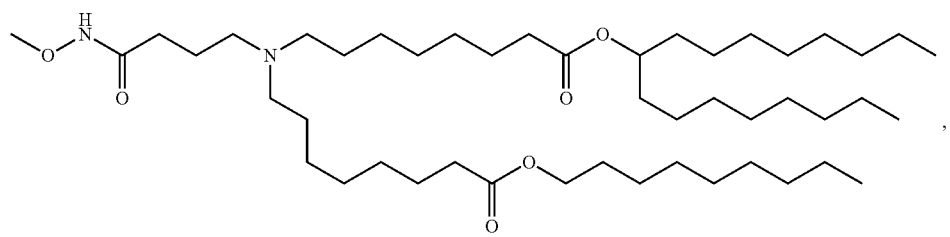
(Compound 226)
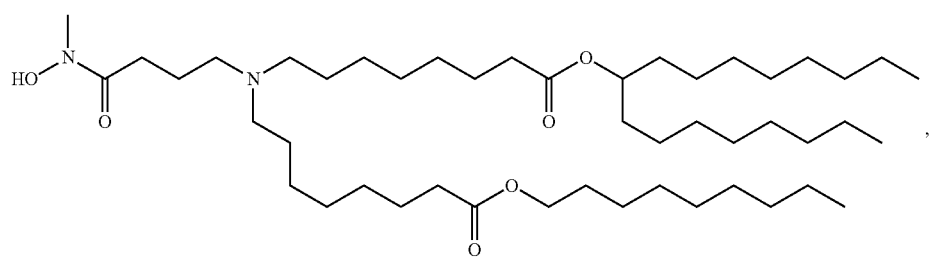
(Compound 227)
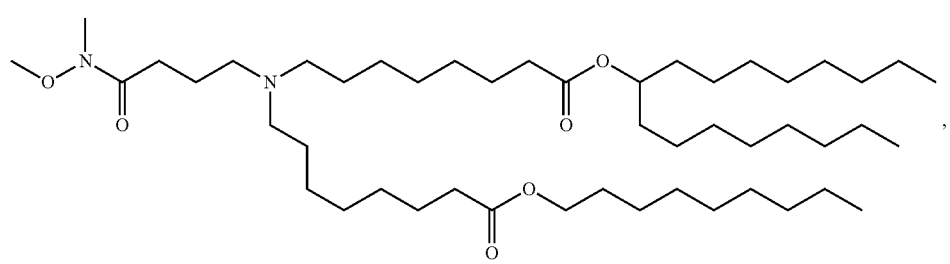
(Compound 228)
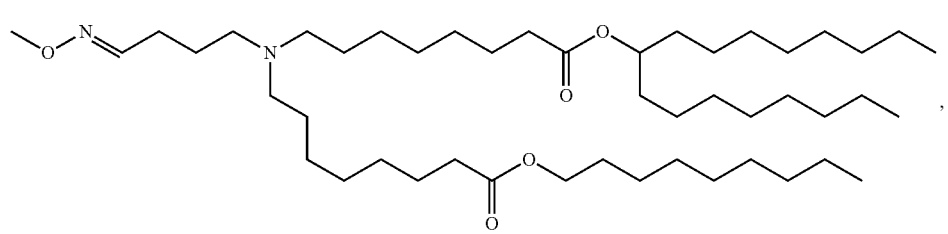
(Compound 229)
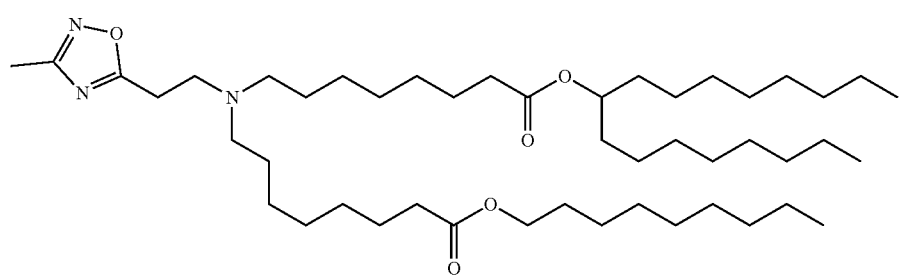
(Compound 230)
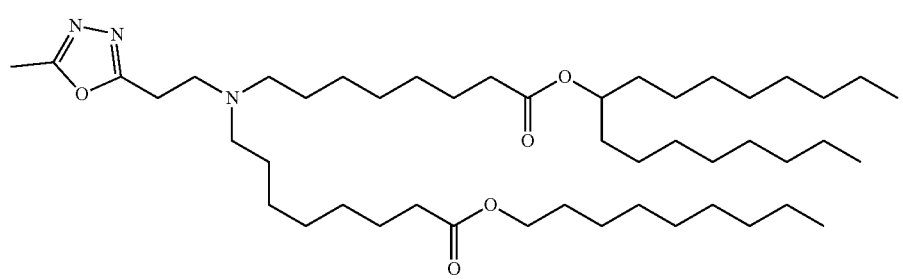
(Compound 231)

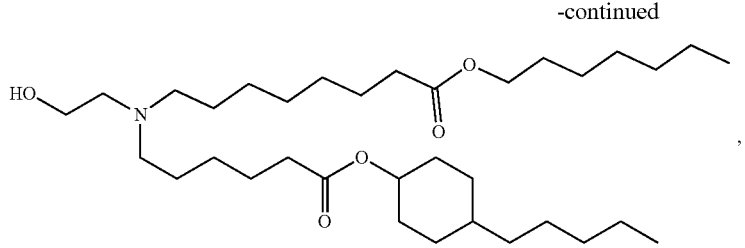

(Compound 232)

and salts and isomers thereof.

The central amine moiety of a lipid according to Formula (I), (IA), (II), (IIa), (IIb), (IIc), (IId) or (IIe) may be protonated at a physiological pH. Thus, a lipid may have a positive or partial positive charge at physiological pH. Such lipids may be referred to as cationic or ionizable (amino) lipids. Lipids may also be zwitterionic, i.e., neutral molecules having both a positive and a negative charge.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_2$-14 alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, $C_{18}$ alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multicyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multicyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R''', in which each OR are alkoxy groups that can be the same or different and R''' is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C$_{1-6}$ alkyl group may be further substituted with one, two, three, four, five, or six substituents as described herein.

About, Approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

As used herein, the term "delivering" means providing an entity to a destination. For example, delivering a therapeutic and/or prophylactic to a subject may involve administering a nanoparticle composition including the therapeutic and/or prophylactic to the subject (e.g., by an intravenous, intramuscular, intradermal, or subcutaneous route). Administration of a nanoparticle composition to a mammal or mammalian cell may involve contacting one or more cells with the nanoparticle composition.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model). In certain embodiments, a nanoparticle composition including a compound according to Formula (I), (IA), (II), (IIa), (IIb), (IIc), (IId) or (IIe) has substantively the same level of delivery enhancement regardless of administration routes. For example, certain compounds disclosed herein exhibit similar delivery enhancement when they are used for delivering a therapeutic and/or prophylactic either intravenously or intramuscularly. In other embodiments, certain compounds disclosed herein (e.g., a compound of Formula (IA) or (II), such as Compound 18, 25, 30, 60, 108-112, or 122) exhibit a higher level of delivery enhancement when they are used for delivering a therapeutic and/or prophylactic intramuscularly than intravenously.

As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. For example, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereometric mixtures of compounds and means of resolving them into their component enantiomers or stereoisomers are well-known.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a nanoparticle composition including a lipid component and an RNA.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the "polydispersity index" is a ratio that describes the homogeneity of the particle size distribution of a system. A small value, e.g., less than 0.3, indicates a narrow particle size distribution.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, and mixtures thereof.

As used herein, a "single unit dose" is a dose of any therapeutic administered in one dose/at one time/single route/single point of contact, i.e., single administration event.

As used herein, a "split dose" is the division of single unit dose or total daily dose into two or more doses.

As used herein, a "total daily dose" is an amount given or prescribed in 24 hour period. It may be administered as a single unit dose.

As used herein, "size" or "mean size" in the context of nanoparticle compositions refers to the mean diameter of a nanoparticle composition.

As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

As used herein "target tissue" refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The term "therapeutic agent" or "prophylactic agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "transfection" refers to the introduction of a species (e.g., an RNA) into a cell. Transfection may occur, for example, in vitro, ex vivo, or in vivo.

As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the "zeta potential" is the electrokinetic potential of a lipid, e.g., in a particle composition.

Nanoparticle Compositions

The disclosure also features nanoparticle compositions comprising a lipid component comprising a compound according to Formula (I), (IA), (II), (IIa), (IIb), (IIc), (IId) or (IIe) as described herein.

In some embodiments, the largest dimension of a nanoparticle composition is 1 µm or shorter (e.g., 1 µm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

Nanoparticle compositions comprise a lipid component including at least one compound according to Formula (I), (IA), (II), (IIa), (IIb), (IIc), (IId) or (IIe). For example, the lipid component of a nanoparticle composition may include one or more of Compounds 1-147. Nanoparticle compositions may also include a variety of other components. For example, the lipid component of a nanoparticle composition may include one or more other lipids in addition to a lipid according to Formula (I), (IA), (II), (IIa), (IIb), (IIc), (IId) or (IIe).

Cationic/Ionizable Lipids

A nanoparticle composition may include one or more cationic and/or ionizable lipids (e.g., lipids that may have a positive or partial positive charge at physiological pH) in addition to a lipid according to Formula (I), (IA), (II), (IIa), (IIb), (IIc), (IId) or (IIe). Cationic and/or ionizable lipids may be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, a cationic lipid may also be a lipid including a cyclic amine group.

PEG Lipids

The lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

Structural Lipids

The lipid component of a nanoparticle composition may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the structural lipid includes cholesterol and a corticosteroid (such as prednisolone, dexamethasone, prednisone, and hydrocortisone), or a combination thereof.

Phospholipids

The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. For example, a phospholipid may be a lipid according to Formula (III):

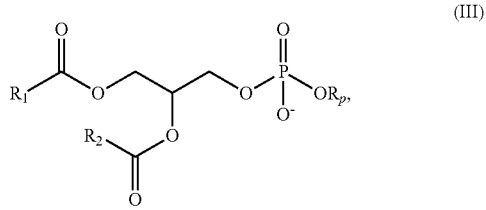

in which $R_p$ represents a phospholipid moiety and $R_1$ and $R_2$ represent fatty acid moieties with or without unsaturation that may be the same or different. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some embodiments, a nanoparticle composition includes DSPC. In certain embodiments, a nanoparticle composition includes DOPE. In some embodiments, a nanoparticle composition includes both DSPC and DOPE.

Adjuvants

In some embodiments, a nanoparticle composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Therapeutic Agents

Nanoparticle compositions may include one or more therapeutic and/or prophylactics. The disclosure features methods of delivering a therapeutic and/or prophylactic to a mammalian cell or organ, producing a polypeptide of interest in a mammalian cell, and treating a disease or disorder in a mammal in need thereof comprising administering to a mammal and/or contacting a mammalian cell with a nanoparticle composition including a therapeutic and/or prophylactic.

Therapeutic and/or prophylactics include biologically active substances and are alternately referred to as "active agents." A therapeutic and/or prophylactic may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic is a small molecule drug useful in the treatment of a particular disease, disorder, or condition. Examples of drugs useful in the nanoparticle compositions include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cystine arabinoside, anthracyclines, alkylative agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetolol), antihypertensive agents (e.g., clonidine and hydralazine), anti-depressants (e.g., imipramine, amitriptyline, and doxepim), anti-conversants (e.g., phenytoin), antihistamines (e.g., diphenhydramine, chlorphenirimine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

In some embodiments, a therapeutic and/or prophylactic is a cytotoxin, a radioactive ion, a chemotherapeutic, a vaccine, a compound that elicits an immune response, and/or another therapeutic and/or prophylactic. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol, rachelmycin (CC-1065), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Vaccines include compounds and preparations that are capable of providing immunity against one or more conditions related to infectious diseases such as influenza, measles, human papillomavirus (HPV), rabies, meningitis, whooping cough, tetanus, plague, hepatitis, and tuberculosis and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. Compounds eliciting immune responses may include vaccines, corticosteroids (e.g., dexamethasone), and other species. In some embodiments, a vaccine and/or a compound capable of eliciting an immune response is administered intramuscularly via a composition including a compound according to Formula (I), (IA), (II), (IIa), (IIb), (IIc), (IId) or (IIe) (e.g., Compound 3, 18, 20, 25, 26, 29, 30, 60, 108-112, or 122). Other therapeutic and/or prophylactics include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In other embodiments, a therapeutic and/or prophylactic is a protein. Therapeutic proteins useful in the nanoparticles in the disclosure include, but are not limited to, gentamycin, amikacin, insulin, erythropoietin (EPO), granulocyte-colony stimulating factor (G-CSF), granulocyte-macrophage colony stimulating factor (GM-CSF), Factor VIR, luteinizing hormone-releasing hormone (LHRH) analogs, interferons, heparin, Hepatitis B surface antigen, typhoid vaccine, and cholera vaccine.

Polynucleotides and Nucleic Acids

In some embodiments, a therapeutic agent is a polynucleotide or nucleic acid (e.g., ribonucleic acid or deoxyribonucleic acid). The term "polynucleotide," in its broadest sense, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In some embodiments, a therapeutic and/or prophylactic is an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and mixtures thereof. In certain embodiments, the RNA is an mRNA.

In certain embodiments, a therapeutic and/or prophylactic is an mRNA. An mRNA may encode any polypeptide of interest, including any naturally or non-naturally occurring or otherwise modified polypeptide. A polypeptide encoded by an mRNA may be of any size and may have any secondary structure or activity. In some embodiments, a polypeptide encoded by an mRNA may have a therapeutic effect when expressed in a cell.

In other embodiments, a therapeutic and/or prophylactic is an siRNA. An siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. An siRNA may comprise a sequence that is complementary to an mRNA sequence that encodes a gene or protein of interest. In some embodiments, the siRNA may be an immunomodulatory siRNA.

In some embodiments, a therapeutic and/or prophylactic is an shRNA or a vector or plasmid encoding the same. An shRNA may be produced inside a target cell upon delivery of an appropriate construct to the nucleus. Constructs and mechanisms relating to shRNA are well known in the relevant arts.

Nucleic acids and polynucleotides useful in the disclosure typically include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some embodiments, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide or nucleic acid (e.g., an mRNA) may include a 5' cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methylpseudouridine or 1-ethyl-pseudouridine), and/or a 5-substituted cytidine (e.g., 5-methyl-cytidine).

Generally, the shortest length of a polynucleotide can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In some cases, a polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

Nucleic acids and polynucleotides may include one or more naturally occurring components, including any of the canonical nucleotides A (adenosine), G (guanosine), C (cytosine), U (uridine), or T (thymidine). In one embodiment, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

Nucleic acids and polynucleotides may include one or more alternative components, as described herein, which impart useful properties including increased stability and/or the lack of a substantial induction of the innate immune response of a cell into which the polynucleotide is introduced. For example, an alternative polynucleotide or nucleic acid exhibits reduced degradation in a cell into which the polynucleotide or nucleic acid is introduced, relative to a corresponding unaltered polynucleotide or nucleic acid. These alternative species may enhance the efficiency of protein production, intracellular retention of the polynucleotides, and/or viability of contacted cells, as well as possess reduced immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides useful in a nanoparticle composition can include any useful modification or alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

Polynucleotides and nucleic acids may or may not be uniformly altered along the entire length of the molecule. For example, one or more or all types of nucleotide (e.g., purine or pyrimidine, or any one or more or all of A, G, U, C) may or may not be uniformly altered in a polynucleotide or nucleic acid, or in a given predetermined sequence region thereof. In some instances, all nucleotides X in a polynucleotide (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of a canonical nucleotide (e.g., A, G, U, or C).

Polynucleotides may contain at a minimum zero and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, polynucleotides may contain an alternative pyrimidine such as an alternative uracil or cytosine. In some embodiments, at least 5%, at least 10%, at least 25%, at least 50%, at least 80%, at least 90% or 100% of the uracil in a polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some instances, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

In some instances, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc., and/or 3) termination or reduction in protein translation.

The nucleic acids can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors). In some embodiments, the nucleic acids may include one or more messenger RNAs (mRNAs) having one or more alternative nucleoside or nucleotides (i.e., alternative mRNA molecules).

In some embodiments, a nucleic acid (e.g. mRNA) molecule, formula, composition or method associated therewith comprises one or more polynucleotides comprising features as described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, all of which are incorporated by reference herein.

Nucleobase Alternatives

The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including but not limited to alkyl, aryl, halo, oxo, hydroxyl, alkyloxy, and/or thio substitutions; one or more fused or open rings; oxidation; and/or reduction.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include pseudouridine ($\psi$), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5 s^2U$), 5-methylaminomethyl-uracil ($mnm^5U$), 5-methylaminomethyl-2-thio-uracil ($mnm^5 s^2U$), 5-methylaminomethyl-2-seleno-uracil ($mnm^5 se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5 s^2U$), 5-propynyl-uracil, 1-propynyl-pseudouracil, 5-taurinomethyl-uracil ($\tau m^5U$), 1-taurinomethyl-pseudouridine, 5-taurinomethyl-2-thio-uracil($\tau m^5 s^2U$), 1-taurinomethyl-4-thio-pseudouridine, 5-methyl-uracil ($m^5U$, i.e., having the nucleobase deoxythymine), 1-methyl-pseudouridine ($m^1\psi$), 1-ethyl-pseudouridine ($Et^1\psi$), 5-methyl-2-thio-uracil ($m^5s^2U$), 1-methyl-4-thio-pseudouridine ($m^1s^4$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil ($acp^3U$), 1-methyl-3-(3-amino-3-carboxypropyl)pseudouridine ($acp^3\psi$), 5-(isopentenylaminomethyl)uracil ($inm^5U$), 5-(isopentenylaminomethyl)-2-thio-uracil ($inm^5 s^2U$), 5,2'-O-dimethyl-uridine ($m^5Um$), 2-thio-2'-O_methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2 g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1 Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

Nucleosides include a sugar molecule (e.g., a 5-carbon or 6-carbon sugar, such as pentose, ribose, arabinose, xylose, glucose, galactose, or a deoxy derivative thereof) in combination with a nucleobase, while nucleotides are nucleosides containing a nucleoside and a phosphate group or alternative group (e.g., boranophosphate, thiophosphate, selenophosphate, phosphonate, alkyl group, amidate, and glycerol). A nucleoside or nucleotide may be a canonical species, e.g., a nucleoside or nucleotide including a canonical nucleobase, sugar, and, in the case of nucleotides, a phosphate group, or may be an alternative nucleoside or nucleotide including one or more alternative components. For example, alternative nucleosides and nucleotides can be altered on the sugar of the nucleoside or nucleotide. In some embodiments, the alternative nucleosides or nucleotides include the structure:

Formula IV

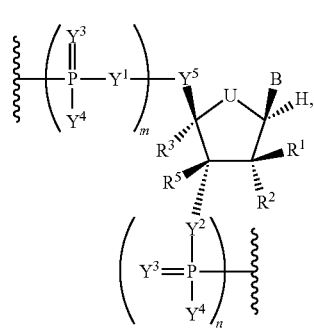

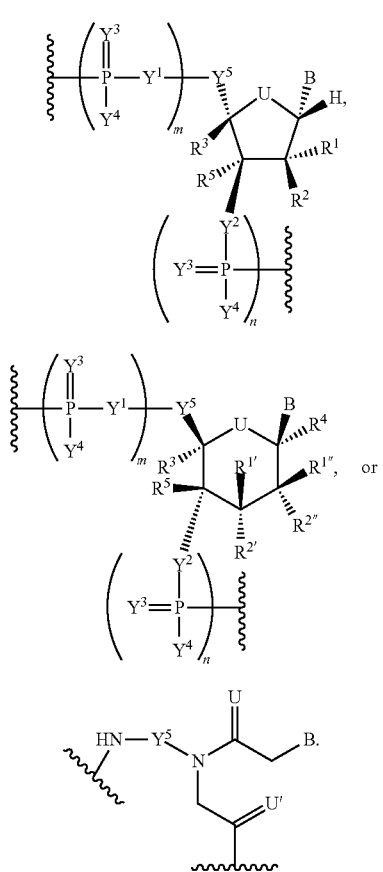

Formula V

Formula VI

Formula VII

In each of the Formulae IV, V, VI and VII, each of m and n is independently, an integer from 0 to 5, each of U and U' independently, is O, S, $N(R^U)_{nu}$, or $C(R^U)_{nu}$, wherein nu is an integer from 0 to 2 and each $R^U$ is, independently, H, halo, or optionally substituted alkyl;

each of $R^{1'}$, $R^{2'}$, $R^{1''}$, $R^{2''}$, $R^1$, $R^2$, $R^3$, $R^4$, and $R^5$ is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R^3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of $R^4$ and one or more of $R^{1'}$, $R^{1''}$, $R^{2'}$, $R^{2''}$, $R^3$, or $R^5$ can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m'' is, independently, an integer from 0 to 3 (e.g., from 0 to 2, from 0 to 1, from 1 to 3, or from 1 to 2);

each of $Y^1$, $Y^2$, and $Y^3$, is, independently, O, S, Se, $-NR^{N1}-$, optionally substituted alkylene, or optionally substituted heteroalkylene, wherein $R^{N1}$ is H, optionally substituted alkyl, optionally substituted alkenyl, optionally substituted alkynyl, optionally substituted aryl, or absent;

each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each $Y^5$ is, independently, O, S, Se, optionally substituted alkylene (e.g., methylene), or optionally substituted heteroalkylene; and B is a nucleobase, either modified or unmodified. In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $-O(CH_2CH_2O)_n CH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

Alternative nucleotides can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha ($\alpha$), beta ($\beta$) or gamma ($\gamma$) position) can be replaced with a sulfur (thio) and a methoxy.

The replacement of one or more of the oxygen atoms at the a position of the phosphate moiety (e.g., $\alpha$-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Internal Ribosome Entry Sites

Polynucleotides may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

5'-Cap Structure

A polynucleotide (e.g., an mRNA) may include a 5'-cap structure. The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The cap further assists the removal of 5'-proximal introns removal during mRNA splicing.

Endogenous polynucleotide molecules may be 5'-end capped generating a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a polynucleotide molecule, such as an mRNA molecule, for degradation.

Alterations to polynucleotides may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, Mass.) may be used with $\alpha$-thio-guanosine nucleotides according to the manufacturer's instructions to create a phosphorothioate linkage in the 5'-ppp-5' cap. Additional alternative guanosine nucleotides may be used such as $\alpha$-methyl-phosphonate and selenophosphate nucleotides.

Additional alterations include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule.

5'-Cap structures include those described in International Patent Publication Nos. WO2008127688, WO 2008016473, and WO 2011015347, the cap structures of each of which are incorporated herein by reference.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7$G-3'mppp-G, which may equivalently be designated 3' O-Me-$m^7$G(5')ppp (5')G). The 3'-0 atom of the other, unaltered, guanosine becomes linked to the 5'-terminal nucleotide of the capped polynucleotide (e.g., an mRNA). The N7- and 3'-O-methlyated guanosine provides the terminal moiety of the capped polynucleotide (e.g., mRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

A cap may be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the cap structures of which are herein incorporated by reference.

Alternatively, a cap analog may be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the cap structures of which are herein incorporated by reference). In other instances, a cap analog useful in the polynucleotides of the present disclosure is a 4-chloro/bromophenoxyethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in the polynucleotides of the present disclosure are those which, among other things, have enhanced binding of cap binding proteins, increased half life, reduced susceptibility to 5'-endonucleases, and/or reduced 5'-decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5'cap analog structures known in the art. Other exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2')Up (Cap 4).

Because the alternative polynucleotides may be capped post-transcriptionally, and because this process is more efficient, nearly 100% of the alternative polynucleotides may be capped. This is in contrast to ~80% when a cap analog is linked to an polynucleotide in the course of an in vitro transcription reaction.

5'-terminal caps may include endogenous caps or cap analogs. A 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine.

In some cases, a polynucleotide contains a modified 5'-cap. A modification on the 5'-cap may increase the stability of polynucleotide, increase the half-life of the polynucleotide, and could increase the polynucleotide translational efficiency. The modified 5'-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

5'-UTRs

A 5'-UTR may be provided as a flanking region to polynucleotides (e.g., mRNAs). A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA). In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of a polynucleotide (e.g., mRNA), 5'-UTRs which are heterologous to the coding region of an alternative polynucleotide (e.g., mRNA) may be engineered. The polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA). Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and Translation Enhancer Elements (TEEs)

The 5'-UTR of a polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In one aspect, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed as SEQ ID NOs: 1-35 in US Patent Publication No. 2009/0226470, SEQ ID NOs: 1-35 in US Patent Publication No. 2013/0177581, SEQ ID NOs: 1-35 in International Patent Publication No. WO2009/075886, SEQ ID NOs: 1-5, and 7-645 in International Patent Publication No. WO2012/009644, SEQ ID NO: 1 in International Patent Publication No. WO1999/024595, SEQ ID NO: 1 in U.S. Pat. No. 6,310,197, and SEQ ID NO: 1 in U.S. Pat. No. 6,849,405, the TEE sequences of each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371 WO1999/024595, and European Patent Nos. 2610341 and 2610340; the TEE sequences of each of which are incorporated herein by reference) or their variants, homologs or functional derivatives. One or multiple copies of a specific TEE can be present in a polynucleotide (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

A polynucleotide (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310,197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

A polynucleotide (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

The 5'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of a polynucleotide (e.g., mRNA) may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In some cases, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In other instances, the spacer separating two TEE sequences may include other sequences known in the art which may regulate the translation of the polynucleotides (e.g., mRNA) of the present disclosure such as, but not limited to, miR sequences (e.g., miR binding sites and miR seeds). As a non-limiting example, each spacer used to separate two TEE sequences may include a different miR sequence or component of a miR sequence (e.g., miR seed sequence).

In some instances, the TEE in the 5'-UTR of a polynucleotide (e.g., mRNA) may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO 1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395 the TEE sequences of each of which are incorporated herein by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In certain cases, the TEE in the 5'-UTR of the polynucleotides (e.g., mRNA) of the present disclosure may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/ NMETH.2522); the TEE sequences of each of which are herein incorporated by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522); the TEE sequences of each of which is incorporated herein by reference.

In some cases, the TEE used in the 5'-UTR of a polynucleotide (e.g., mRNA) is an IRES sequence such as, but not limited to, those described in U.S. Pat. No. 7,468,275 and International Patent Publication No. WO2001/055369, the TEE sequences of each of which are incorporated herein by reference.

In some instances, the TEEs used in the 5'-UTR of a polynucleotide (e.g., mRNA) may be identified by the methods described in US Patent Publication Nos. 2007/ 0048776 and 2011/0124100 and International Patent Publication Nos. WO2007/025008 and WO2012/009644, the methods of each of which are incorporated herein by reference.

In some cases, the TEEs used in the 5'-UTR of a polynucleotide (e.g., mRNA) of the present disclosure may be a transcription regulatory element described in U.S. Pat. Nos. 7,456,273 and 7,183,395, US Patent Publication No. 2009/ 0093049, and International Publication No. WO2001/ 055371, the TEE sequences of each of which is incorporated herein by reference. The transcription regulatory elements may be identified by methods known in the art, such as, but not limited to, the methods described in U.S. Pat. Nos. 7,456,273 and 7,183,395, US Patent Publication No. 2009/ 0093049, and International Publication No. WO2001/ 055371, the methods of each of which is incorporated herein by reference.

In yet other instances, the TEE used in the 5'-UTR of a polynucleotide (e.g., mRNA) is a polynucleotide or portion thereof as described in U.S. Pat. Nos. 7,456,273 and 7,183, 395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

The TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In some cases, the 3'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present disclosure may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one instance, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In other cases, the spacer separating two TEE sequences may include other sequences known in the art which may regulate the translation of the polynucleotides (e.g., mRNA) of the present disclosure such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In yet other cases, the incorporation of a miR sequence and/or a TEE sequence changes the shape of the stem loop region which may increase and/or decrease translation. (see e.g., Kedde et al. A Pumilio-induced RNA structure switch in p27-3'UTR controls miR-221 and miR-22 accessibility. Nature Cell Biology. 2010).

Stem Loops

Polynucleotides (e.g., mRNAs) may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013/103659, of which SEQ ID NOs: 7-17 are incorporated herein by reference. The histone stem loop may be located 3'-relative to the coding region (e.g., at the 3'-terminus of the coding region). As a non-limiting example, the stem loop may be located at the 3'-end of a polynucleotide described herein. In some cases, a polynucleotide (e.g., an mRNA) includes more than one stem loop (e.g., two stem loops). Examples of stem loop sequences are described in International Patent Publication Nos. WO2012/ 019780 and WO201502667, the stem loop sequences of which are herein incorporated by reference. In some instances, a polynucleotide includes the stem loop sequence CAAAGGCTCTTTTCAGAGCCACCA (SEQ ID NO: 5). In others, a polynucleotide includes the stem loop sequence CAAAGGCUCUUUUCAGAGCCACCA (SEQ ID NO: 6).

A stem loop may be located in a second terminal region of a polynucleotide. As a non-limiting example, the stem loop may be located within an untranslated region (e.g., 3'-UTR) in a second terminal region.

In some cases, a polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In other cases, a polynucleotide such as, but not limited to mRNA, which includes the histone stem loop may be stabilized by an alteration to the 3'-region of the polynucleotide that can prevent and/or inhibit the addition of oligio(U) (see e.g., International Patent Publication No. WO2013/103659).

In yet other cases, a polynucleotide such as, but not limited to mRNA, which includes the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In some instances, the polynucleotides of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In other instances, the polynucleotides of the present disclosure may include a histone stem loop and a 5'-cap structure. The 5'-cap structure may include, but is not limited to, those described herein and/or known in the art.

In some cases, the conserved stem loop region may include a miR sequence described herein. As a non-limiting example, the stem loop region may include the seed sequence of a miR sequence described herein. In another non-limiting example, the stem loop region may include a miR-122 seed sequence.

In certain instances, the conserved stem loop region may include a miR sequence described herein and may also include a TEE sequence.

In some cases, the incorporation of a miR sequence and/or a TEE sequence changes the shape of the stem loop region which may increase and/or decrease translation. (See, e.g., Kedde et al. A Pumilio-induced RNA structure switch in p27-3'UTR controls miR-221 and miR-22 accessibility. Nature Cell Biology. 2010, herein incorporated by reference in its entirety).

Polynucleotides may include at least one histone stem-loop and a poly-A region or polyadenylation signal. Non-limiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In certain cases, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In other cases, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In some cases, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In other cases, the polynucleotide encoding for a histone stem loop and a poly-A region or a polyadenylation signal may code for a allergenic antigen or an autoimmune self-antigen such as the polynucleotide sequences described in International Patent Publication No WO2013/120498 and WO2013/120626, the sequences of both of which are incorporated herein by reference.

Poly-A Regions

A polynucleotide or nucleic acid (e.g., an mRNA) may include a polyA sequence and/or polyadenylation signal. A polyA sequence may be comprised entirely or mostly of adenine nucleotides or analogs or derivatives thereof. A polyA sequence may be a tail located adjacent to a 3' untranslated region of a nucleic acid.

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long.

Unique poly-A region lengths may provide certain advantages to the alternative polynucleotides of the present disclosure.

Generally, the length of a poly-A region of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some instances, the poly-A region may be 80 nucleotides, 120 nucleotides, 160 nucleotides in length on an alternative polynucleotide molecule described herein.

In other instances, the poly-A region may be 20, 40, 80, 100, 120, 140 or 160 nucleotides in length on an alternative polynucleotide molecule described herein.

In some cases, the poly-A region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In certain cases, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In certain cases, a poly-A region may be used to modulate translation initiation. While not wishing to be bound by theory, the poly-A region recruits PABP which in turn can interact with translation initiation complex and thus may be essential for protein synthesis.

In some cases, a poly-A region may also be used in the present disclosure to protect against 3'-5'-exonuclease digestion.

In some instances, a polynucleotide (e.g., mRNA) may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet results in protein production equivalent to at least 75% of that seen using a poly-A region of 120 nucleotides alone.

In some cases, a polynucleotide (e.g., mRNA) may include a poly-A region and may be stabilized by the addition of a 3'-stabilizing region. The polynucleotides (e.g., mRNA) with a poly-A region may further include a 5'-cap structure.

In other cases, a polynucleotide (e.g., mRNA) may include a poly-A-G Quartet. The polynucleotides (e.g., mRNA) with a poly-A-G Quartet may further include a 5'-cap structure.

In some cases, the 3'-stabilizing region which may be used to stabilize a polynucleotide (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In other cases, the 3'-stabilizing region which may be used with the present disclosure include a chain termination nucleoside such as 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside.

In other cases, a polynucleotide such as, but not limited to mRNA, which includes a polyA region or a poly-A-G Quartet may be stabilized by an alteration to the 3'-region of the polynucleotide that can prevent and/or inhibit the addition of oligio(U) (see e.g., International Patent Publication No. WO2013/103659).

In yet other instances, a polynucleotide such as, but not limited to mRNA, which includes a poly-A region or a poly-A-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Chain Terminating Nucleosides

A nucleic acid may include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine.

Other Components

A nanoparticle composition may include one or more components in addition to those described in the preceding sections. For example, a nanoparticle composition may include one or more small hydrophobic molecules such as a vitamin (e.g., vitamin A or vitamin E) or a sterol.

Nanoparticle compositions may also include one or more permeability enhancer molecules, carbohydrates, polymers, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone (PVP), polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly(ortho)esters, poly(butyric acid), poly (valeric acid), poly(lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface altering agent may be disposed within a nanoparticle and/or on the surface of a nanoparticle composition (e.g., by coating, adsorption, covalent linkage, or other process).

A nanoparticle composition may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a nanoparticle composition may also be conjugated with one or more useful antibodies. Functional groups and conjugates useful in targeted cell delivery, imaging, and membrane permeation are well known in the art.

In addition to these components, nanoparticle compositions may include any substance useful in pharmaceutical compositions. For example, the nanoparticle composition may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy*, 21$^{st}$ Edition, A. R. Gennaro; Lippincott, Williams & Wilkins, Baltimore, Md., 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®

45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Formulations

Nanoparticle compositions may include a lipid component and one or more additional components, such as a therapeutic and/or prophylactic. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to Formula (I), (IA), (II), (IIa), (IIb), (IIc), (IId) or (IIe), a phospholipid (such as an unsaturated lipid, e.g., DOPE or DSPC), a PEG lipid, and a structural lipid. The elements of the lipid component may be provided in specific fractions.

In some embodiments, the lipid component of a nanoparticle composition includes a lipid according to Formula (I), (IA), (II), (IIa), (IIb), (IIc), (IId) or (IIe), a phospholipid, a PEG lipid, and a structural lipid. In certain embodiments, the lipid component of the nanoparticle composition includes about 30 mol % to about 60 mol % compound of Formula (I), (IA), (II), (IIa), (IIb), (IIc), (IId) or (IIe), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % compound of Formula (I), (IA), (II), (IIa), (IIb), (IIc), (IId) or (IIe), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-DMG and/or the structural lipid may be cholesterol.

Nanoparticle compositions may be designed for one or more specific applications or targets. For example, a nanoparticle composition may be designed to deliver a therapeutic and/or prophylactic such as an RNA to a particular cell, tissue, organ, or system or group thereof in a mammal's body. Physiochemical properties of nanoparticle compositions may be altered in order to increase selectivity for particular bodily targets. For instance, particle sizes may be adjusted based on the fenestration sizes of different organs. The therapeutic and/or prophylactic included in a nanoparticle composition may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

The amount of a therapeutic and/or prophylactic in a nanoparticle composition may depend on the size, composition, desired target and/or application, or other properties of the nanoparticle composition as well as on the properties of the therapeutic and/or prophylactic. For example, the amount of an RNA useful in a nanoparticle composition may depend on the size, sequence, and other characteristics of the RNA. The relative amounts of a therapeutic and/or prophylactic and other elements (e.g., lipids) in a nanoparticle composition may also vary. In some embodiments, the wt/wt ratio of the lipid component to a therapeutic and/or prophylactic in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In certain embodiments, the wt/wt ratio is about 20:1. The amount of a therapeutic and/or prophylactic in a nanoparticle composition may, for example, be measured using absorption spectroscopy (e.g., ultraviolet-visible spectroscopy).

In some embodiments, a nanoparticle composition includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

Physical Properties

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The mean size of a nanoparticle composition may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition may be from about 70 nm to about 100 nm. In a particular embodiment, the mean size may be about 80 nm. In other embodiments, the mean size may be about 100 nm.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic describes the amount of therapeutic and/or prophylactic that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic and/or prophylactic in a solution containing the nanoparticle composition before and after breaking up the nanoparticle composition with one or more organic solvents or detergents. Fluorescence may be used to measure the amount of free therapeutic and/or prophylactic (e.g., RNA) in a solution. For the nanoparticle compositions described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

Pharmaceutical Compositions

Nanoparticle compositions may be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's The Science and Practice of Pharmacy, 21$^{st}$ Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a nanoparticle composition if its combination with the component may result in any undesirable biological effect or otherwise deleterious effect.

In some embodiments, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more nanoparticle compositions.

In certain embodiments, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (I), (IA), (II), and (IIa)-(IIe) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the nanoparticle compositions and/or pharmaceutical compositions comprising a compound of any of Formulae (I), (IA), (II), and (IIa)-(IIe) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one embodiment, the formulation is stabilized for at least 4 weeks at about 4° C. In certain embodiments, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. "Stability," "stabilized," and "stable" in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Nanoparticle compositions and/or pharmaceutical compositions including one or more nanoparticle compositions may be administered to any patient or subject, including those patients or subjects that may benefit from a therapeutic effect provided by the delivery of a therapeutic and/or prophylactic to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more nanoparticle compositions may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactics, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay, silicates), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

Methods of Producing Polypeptides in Cells

The present disclosure provides methods of producing a polypeptide of interest in a mammalian cell. Methods of producing polypeptides involve contacting a cell with a nanoparticle composition including an mRNA encoding the polypeptide of interest. Upon contacting the cell with the nanoparticle composition, the mRNA may be taken up and translated in the cell to produce the polypeptide of interest.

In general, the step of contacting a mammalian cell with a nanoparticle composition including an mRNA encoding a polypeptide of interest may be performed in vivo, ex vivo, in culture, or in vitro. The amount of nanoparticle composition contacted with a cell, and/or the amount of mRNA therein, may depend on the type of cell or tissue being contacted, the means of administration, the physiochemical characteristics of the nanoparticle composition and the mRNA (e.g., size, charge, and chemical composition) therein, and other factors. In general, an effective amount of the nanoparticle composition will allow for efficient polypeptide production in the cell. Metrics for efficiency may include polypeptide translation (indicated by polypeptide expression), level of mRNA degradation, and immune response indicators.

The step of contacting a nanoparticle composition including an mRNA with a cell may involve or cause transfection. A phospholipid including in the lipid component of a nanoparticle composition may facilitate transfection and/or increase transfection efficiency, for example, by interacting and/or fusing with a cellular or intracellular membrane. Transfection may allow for the translation of the mRNA within the cell.

In some embodiments, the nanoparticle compositions described herein may be used therapeutically. For example, an mRNA included in a nanoparticle composition may encode a therapeutic polypeptide (e.g., in a translatable region) and produce the therapeutic polypeptide upon contacting and/or entry (e.g., transfection) into a cell. In other embodiments, an mRNA included in a nanoparticle composition may encode a polypeptide that may improve or increase the immunity of a subject. For example, an mRNA may encode a granulocyte-colony stimulating factor or trastuzumab.

In certain embodiments, an mRNA included in a nanoparticle composition may encode a recombinant polypeptide that may replace one or more polypeptides that may be substantially absent in a cell contacted with the nanoparticle composition. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a nanoparticle composition including an mRNA may reduce the innate immune response of a cell to an exogenous nucleic acid. A cell may be contacted with a first nanoparticle composition including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

The present disclosure provides methods of delivering a therapeutic and/or prophylactic to a mammalian cell or organ. Delivery of a therapeutic and/or prophylactic to a cell involves administering a nanoparticle composition including the therapeutic and/or prophylactic to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a nanoparticle composition may target a particular type or class of cells (e.g., cells of a particular organ or system thereof). For example, a nanoparticle composition including a therapeutic and/or prophylactic of interest may be specifically delivered to a mammalian liver, kidney, spleen, femur, or lung. Specific delivery to a particular class of cells, an organ, or a system or group thereof implies that a higher proportion of nanoparticle compositions including a therapeutic and/or prophylactic are delivered to the destination (e.g., tissue) of interest relative to other destinations, e.g., upon administration of a nanoparticle composition to a mammal. In some embodiments, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some embodiments, the tissue of interest is selected from the group consisting of a liver, kidney, a lung, a spleen, a femur, an ocular tissue (e.g., via intraocular, subretinal, or intravitreal injection), vascular endothelium in vessels (e.g., intracoronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other therapeutic and/or prophylactics or elements (e.g., lipids or ligands) of a nanoparticle composition may be selected based on their affinity for particular receptors (e.g., low density lipoprotein receptors) such that a nanoparticle composition may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')$_2$ fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell. For example an estrogen receptor ligand, such as tamoxifen, can target cells to estrogen-dependent breast cancer cells that have an increased number of estrogen receptors on the cell surface. Other non-limiting examples of ligand/receptor interactions include CCR1 (e.g., for treatment of inflamed joint tissues or brain in rheumatoid arthritis, and/or multiple sclerosis), CCR7, CCR8 (e.g., targeting to lymph node tissue), CCR6, CCR9,CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), and VLA-4NCAM-1 (e.g., targeting to endothelium). In general, any receptor involved in targeting (e.g., cancer metastasis) can be harnessed for use in the methods and compositions described herein.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, a nanoparticle composition may target hepatocytes. Apolipoprotiens such as apolipoprotein E (apoE) have been shown to associate with neutral or near neutral lipid-containing nanoparticle compositions in the body, and are known to associate with receptors such as low-density lipoprotein receptors (LDLRs) found on the surface of hepatocytes. Thus, a nanoparticle composition including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Nanoparticle compositions may be useful for treating a disease, disorder, or condition. In particular, such compositions may be useful in treating a disease, disorder, or condition characterized by missing or aberrant protein or polypeptide activity. For example, a nanoparticle composition comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a nanoparticle composition may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a nanoparticle composition including an RNA and a lipid component including a lipid according to Formula (I), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

The disclosure provides methods involving administering nanoparticle compositions including one or more therapeutic and/or prophylactic agents and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutic and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A nanoparticle composition including one or more therapeutic and/or prophylactics may be administered by any route. In some embodiments, compositions, including prophylactic, diagnostic, or imaging compositions including one or more nanoparticle compositions described herein, are administered by one or more of a variety of routes, including oral, intravenous, intramuscular, intra-arterial, intramedullary, intrathecal, subcutaneous, intraventricular, trans- or intra-dermal, interdermal, rectal, intravaginal, intraperitoneal, intraocular, subretinal, intravitreal, topical (e.g. by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, intraocularly, subretinally, intravitreally, or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the nanoparticle composition including one or more therapeutic and/or prophylactics (e.g., its stability in various bodily environments such as the bloodstream and gastrointestinal tract), the condition of the patient (e.g., whether the patient is able to tolerate particular routes of administration), etc.

In certain embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some embodiments, a dose of about 0.001 mg/kg to about 10 mg/kg of a therapeutic and/or prophylactic (e.g., mRNA) of a nanoparticle composition may be administered. In other embodiments, a dose of about 0.005 mg/kg to about 2.5 mg/kg of a therapeutic and/or prophylactic may be administered. In certain embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Nanoparticle compositions including one or more therapeutic and/or prophylactics may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more nanoparticle compositions including one or more different therapeutic and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A nanoparticle composition may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, a nanoparticle composition may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a nanoparticle composition. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the nanoparticle composition and may occur one, two, or more times in, for example, increasing dosage amounts.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5th edition, John Wiley & Sons: New York, 2001; Greene, T. W., Wuts, P. G. M., *Protective Groups in Organic Synthesis*, 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the formulae described herein may be prepared according to the procedures illustrated in Schemes 1 and 2 below, from commercially available starting materials or starting materials which can be prepared using literature procedures. The variables in the schemes (e.g., $R_1$, $R_2$, and $R_3$ etc. are as defined herein). One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3rd edition, John Wiley & Sons: New York, 1999.

Preferred protecting groups include, but are not limited to:
For a hydroxyl moiety: TBS, benzyl, THP, Ac;
For carboxylic acids: benzyl ester, methyl ester, ethyl ester, allyl ester;
For amines: Fmoc, Cbz, BOC, DMB, Ac, Bn, Tr, Ts, trifluoroacetyl, phthalimide, benzylideneamine;
For diols: Ac (×2) TBS (×2), or when taken together acetonides;
For thiols: Ac;
For benzimidazoles: SEM, benzyl, PMB, DMB;
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

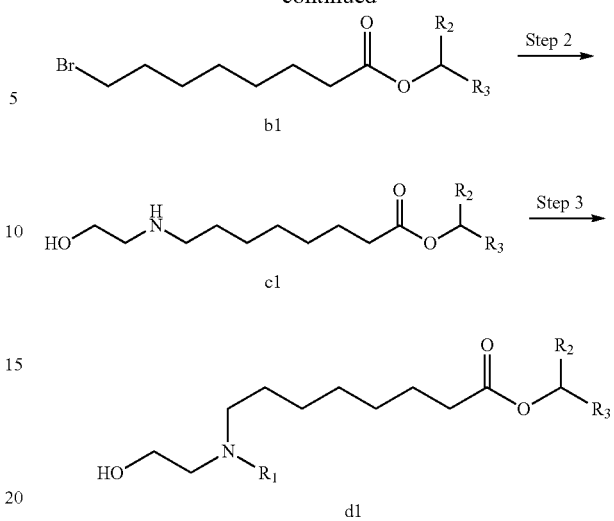

As illustrated in Scheme 1 above, 8-bromooctanoic acid reacts with an alcohol a1 (e.g., heptadecan-9-ol) to afford an ester b1 (e.g., heptadecan-9-yl 8-bromooctanoate). Step 1 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Step 1 can take place at room temperature for 18 h. Next, ester b1 reacts with 2-aminoethan-1-ol to afford amine c1 (e.g., heptadecan-9-yl 8-((2-hydroxyethyl)amino)octanoate). Step 2 can take place in ethanol at, e.g., a temperature of about 60° C. Then amine c1 reacts with an bromoallyl $R_1$—Br (e.g., 1-bromotetradecane) to afford compound d1 (e.g., heptadecan-9-yl 8-((2-hydroxyethyl)(tetradecyl)amino)octanoate). Step 3 can take place in ethanol in the presence of N,N-diisopropylethylamine.

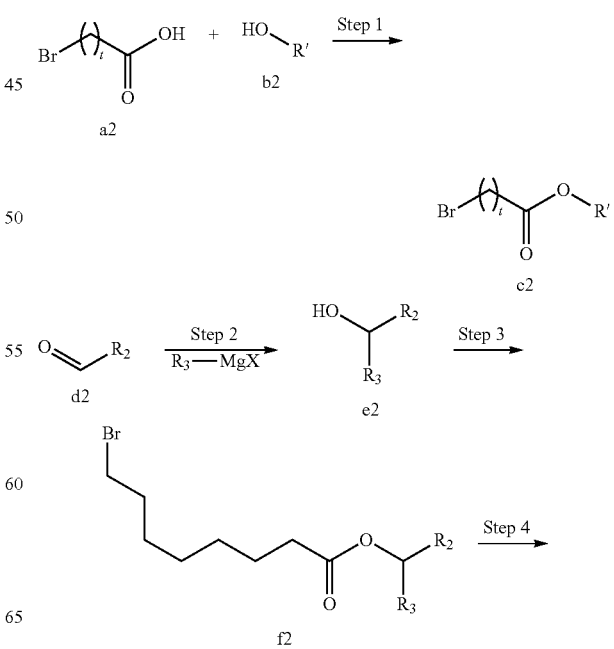

-continued

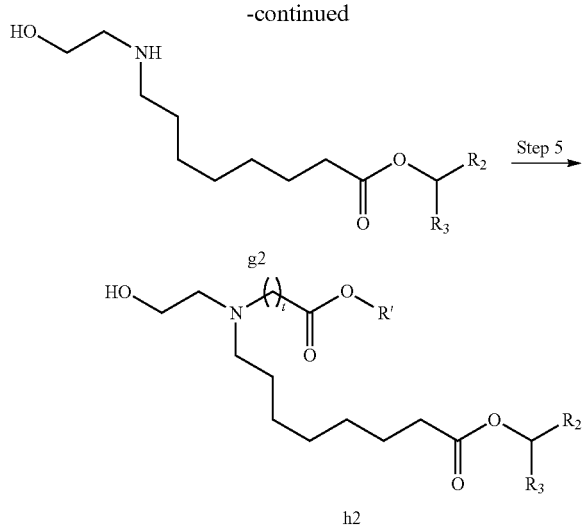

As illustrated in Scheme 2 above, an acid a2 (t is an integer between 1 and 7; e.g., 8-bromooctanoic acid) reacts with an alcohol b2 (e.g., nonan-1-ol) to afford an ester c2 (e.g., nonyl-8-bromooctanoate). Step 1 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Alcohol e2 (e.g., heptadecan-9-ol) can be obtained from reacting aldehyde d2 (e.g., nonanal) with a Grignard reagent $R_3$—MgX (e.g., n-$C_8H_{17}$MgBr) via Step 2. Next, 8-bromooctanoic acid reacts with an alcohol e2 (e.g., heptadecan-9-ol) to afford an ester f2 (e.g., heptadecan-9-yl 8-bromooctanoate). Step 3 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Next, ester f2 reacts with 2-aminoethan-1-ol to afford amine g2 (e.g., heptadecan-9-yl 8-((2-hydroxyethyl)amino)octanoate). Step 4 can take place in ethanol in the presence of i-$Pr_2$EtN. Then amine g2 reacts with ester c2 (e.g., nonyl-8-bromooctanoate) to afford compound h2 (e.g., heptadecan-9-yl 8-((2-hydroxyethyl)(8-(nonyloxy)-8-oxooctyl)amino)octanoate). Step 5 can take place in an organic solvent (e.g., a mixture of CPME and MeCN), in the presence of a base (such as an inorganic base (e.g., $K_2CO_3$) or non-nucleophilic organic base (e.g., i-$Pr_2$EtN)) and a catalyst (e.g., an iodide such as KI or NaI) at, e.g., an elevated temperature (such as at about 70-90° C., e.g., about 80° C.).

A person of ordinary skill in the art will recognize that in the above schemes the order of certain steps may be interchangeable.

In certain aspects, the disclosure also includes methods of synthesizing a compound of any of Formulae (I), (IA), (II), (IIa), (IIb), (IIc), (IId) or (IIe) and intermediate(s) for synthesizing the compound.

In some embodiments, the method of synthesizing a compound of Formula (I) includes reacting a compound of Formula (X2):

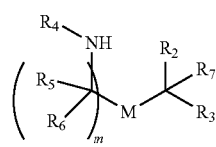

with $R_1$—Br to afford the compound of Formula (I), wherein each variables are as defined herein. For example, m is 5, 6, 7, 8, or 9, preferably 5, 7, or 9. For example, each of $R_5$, $R_6$, and $R_7$ is H. For example, M is —C(O)O— or —OC(O)—. For example, $R_4$ is unsubstituted $C_{1-3}$ alkyl, or —$(CH_2)_nQ$, in which n is 2, 3, or 4 and Q is OH, —NHC(S)N(R)$_2$, —NHC(O)N(R)$_2$, —N(R)C(O)R, or —N(R)S(O)$_2$R. For example, the reaction of the compound of Formula (X2) with $R_1$—Br takes place in the presence of a base (such as an inorganic base (e.g., $K_2CO_3$) or non-nucleophilic organic base (e.g., i-$Pr_2$EtN)). For example, the reaction takes place in the presence of an inorganic base (e.g., $K_2CO_3$) and a catalyst (e.g., an iodide such as KI or NaI). For example, the reaction takes place at an elevated temperature, e.g., about 50-100° C., 70-90° C., or about 80° C.).

The method may also include reacting a compound of Formula (X1):

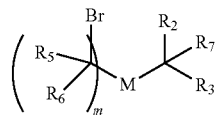

with $R_4NH_2$ to afford a compound of Formula (X2), wherein each variables are as defined herein.

In some embodiments, the intermediate(s) include those having any of Formulae (X1) and (X2):

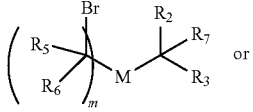 (X1)

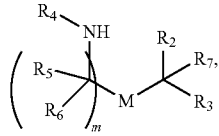 (X2)

wherein each variables are as defined herein. For example, the intermediate includes heptadecan-9-yl 8-bromooctanoate, and heptadecan-9-yl 8-((2-hydroxyethyl)amino)octanoate, and morphic forms thereof (e.g., a crystalline form).

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1: Synthesis of Compounds According to Formula (I), (IA), (II), (IIa), (IIb), (IIc), (IId) or (IIe)

A. General Considerations

All solvents and reagents used were obtained commercially and used as such unless noted otherwise. $^1$H NMR spectra were recorded in CDCl$_3$, at 300 K using a Bruker Ultrashield 300 MHz instrument. Chemical shifts are reported as parts per million (ppm) relative to TMS (0.00) for $^1$H. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 μm, and a gradient of 65 to 100% acetonitrile in water with 0.1% TFA over 5 minutes at 1.2 mL/min. Injection volume was 5 μL and the column temperature was 80° C. Detection was based on electrospray ionization (ESI) in positive mode using Waters SQD mass spectrometer (Milford, Mass., USA) and evaporative light scattering detector.

The procedures described below are useful in the synthesis of Compounds 1-147.

The following abbreviations are employed herein:
THF: Tetrahydrofuran
MeCN: Acetonitrile
LAH: Lithium Aluminum Hydride
DCM: Dichloromethane
DMAP: 4-Dimethylaminopyridine
LDA: Lithium Diisopropylamide
rt: Room Temperature
DME: 1,2-Dimethoxyethane
n-BuLi: n-Butyllithium
CPME: Cyclopentyl methyl ether
i-Pr$_2$EtN: N,N-Diisopropylethylamine B. Compound 2: Heptadecan-9-yl 8-((2-hydroxyethyl)(tetradecyl)amino)octanoate Representative Procedure 1

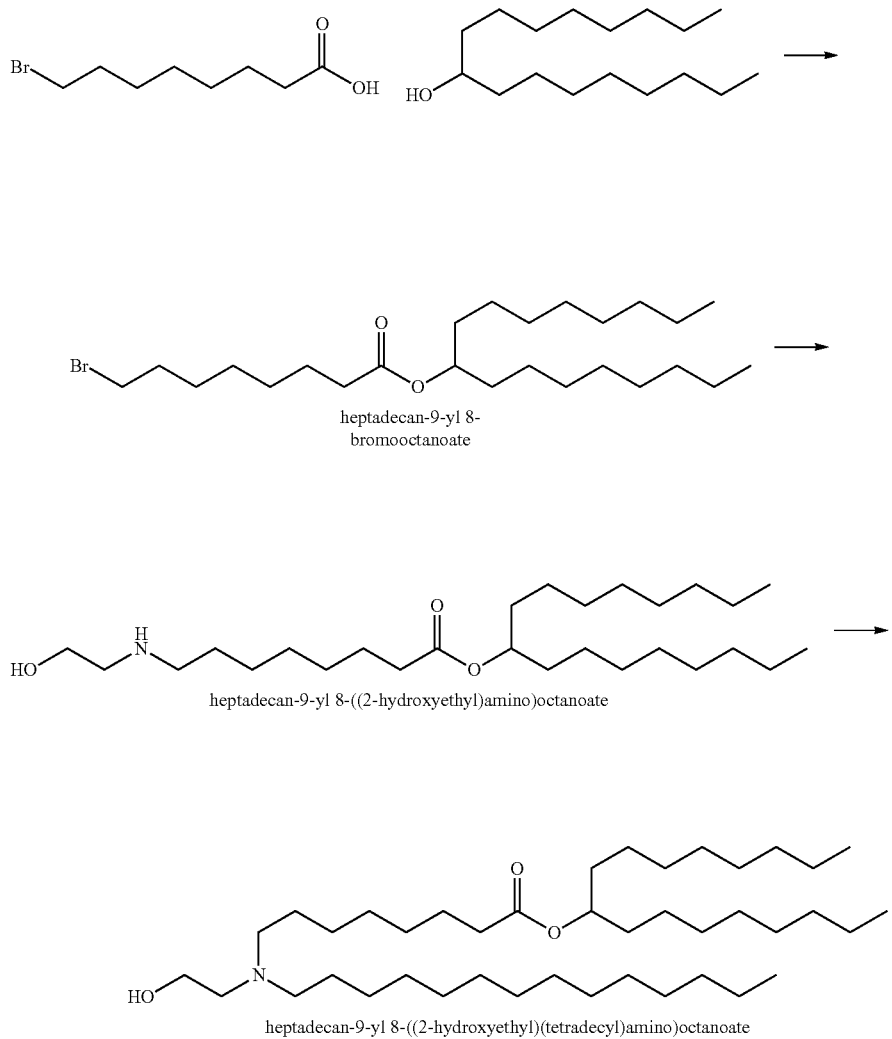

Heptadecan-9-yl 8-bromooctanoate (Method A)

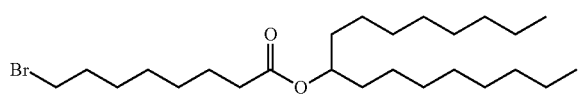 [SMILES: CCCCCCCCC(CCCCCCCC)OC(=O)CCCCCCCBr]

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at rt for 18 h. The reaction was diluted with dichloromethane and washed with saturated sodium bicarbonate. The organic layer was separated and washed with brine, and dried over $MgSO_4$. The organic layer was filtered and evaporated in vacuo. The residue was purified by silica gel chromatography (0-10% ethyl acetate in hexanes) to obtain heptadecan-9-yl 8-bromooctanoate (875 mg, 1.9 mmol, 41%). $^1$H NMR (300 MHz, $CDCl_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Heptadecan-9-yl 8-((2-hydroxyethyl)amino)octanoate (Method B)

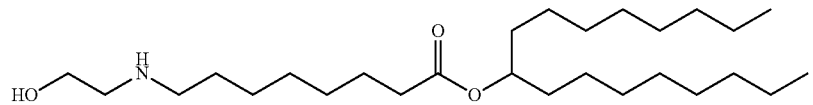 [SMILES: CCCCCCCCC(CCCCCCCC)OC(=O)CCCCCCCNCCO]

A solution of heptadecan-9-yl 8-bromooctanoate (3.8 g, 8.2 mmol) and 2-aminoethan-1-ol (15 mL, 248 mmol) in ethanol (3 mL) was allowed to stir at 62° C. for 18 h. The reaction mixture was concentrated in vacuo and the residue was taken-up in ethyl acetate and water. The organic layer was separated and washed with water, brine and dried over $Na_2SO_4$. The mixture was filtered and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)amino)octanoate (3.1 g, 7 mmol, 85%). UPLC/ELSD: RT=2.67 min. MS (ES): m/z (MH$^+$) 442.68 for $C_{27}H_{55}NO_3$ $^1$H NMR (300 MHz, $CDCl_3$) δ: ppm 4.89 (p, 1H); 3.67 (t, 2H); 2.81 (t, 2H); 2.65 (t, 2H); 2.30 (t, 2H); 2.05 (br. m, 2H); 1.72-1.41 (br. m, 8H); 1.40-1.20 (br. m, 30H); 0.88 (m, 6H).

Heptadecan-9-yl 8-((2-hydroxyethyl)(tetradecyl)amino)octanoate (Method C)

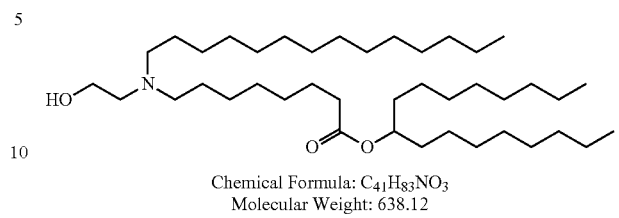

Chemical Formula: $C_{41}H_{83}NO_3$
Molecular Weight: 638.12

A solution of heptadecan-9-yl 8-((2-hydroxyethyl)amino) octanoate (125 mg, 0.28 mmol), 1-bromotetradecane (94 mg, 0.34 mmol) and N,N-diisopropylethylamine (44 mg, 0.34 mmol) in ethanol was allowed to stir at 65° C. for 18 h. The reaction was cooled to rt and solvents were evaporated in vacuo. The residue was taken-up in ethyl acetate and saturated sodium bicarbonate. The organic layer was separated, dried over $Na_2SO_4$ and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)(tetradecyl)amino)octanoate (89 mg, 0.14 mmol, 50%). UPLC/ELSD: RT=3.61 min. MS (ES): m/z (MH$^+$) 638.91 for $C_{41}H_{83}NO_3$. $^1$H NMR (300 MHz, $CDCl_3$) δ: ppm 4.86 (p, 1H); 3.72-3.47 (br. m, 2H); 2.78-2.40 (br. m, 5H); 2.28 (t, 2H); 1.70-1.40 (m, 10H); 1.38-1.17 (br. m, 54H); 0.88 (m, 9H).

Synthesis of Intermediates

Intermediate A: 2-Octyldecanoic Acid

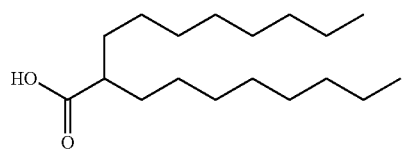 [SMILES: CCCCCCCCC(CCCCCCCC)C(=O)O]

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at rt for 30 min. After this time 1-iodooctane (5 g, 20.8 mmol) was added and the reaction mixture was heated at 45° C. for 6 h. The reaction was quenched with 1N HCl (10 mL). The organic layer was dried over $MgSO_4$, filtered and evaporated in vacuo. The residue was purified by silica gel chromatography (0-20% ethyl acetate in hexanes) to yield 2-octyldecanoic acid (1.9 g, 6.6 mmol, 38%). $^1$H NMR (300 MHz, $CDCl_3$) δ: ppm 2.38 (br. m, 1H); 1.74-1.03 (br. m, 28H); 0.91 (m, 6H).

Intermediate B: 7-Bromoheptyl 2-octyldecanoate

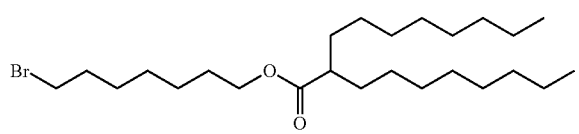 [SMILES: CCCCCCCCC(CCCCCCCC)C(=O)OCCCCCCCBr]

7-bromoheptyl 2-octyldecanoate was synthesized using Method A from 2-octyldecanoic acid and 7-bromoheptan-1-ol. $^1$H NMR (300 MHz, CDCl$_3$) δ: ppm 4.09 (br. m, 2H); 3.43 (br. m, 2H); 2.48-2.25 (br. m, 1H); 1.89 (br. m, 2H); 1.74-1.16 (br. m, 36H); 0.90 (m, 6H).

Intermediate C: (2-Hexylcyclopropyl)methanol

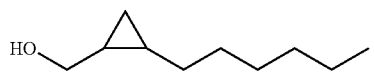

A solution of diethyl zinc (20 mL, 20 mmol, 1 M in hexanes), in dichloromethane (20 mL) was allowed to cool to −40° C. for 5 min. Then a solution of diiodomethane (3.22 mL, 40 mmol) in dichloromethane (10 mL) was added dropwise. After the reaction was allowed to stir for 1 h at −40° C., a solution of trichloro-acetic acid (327 mg, 2 mmol) and DME (1 mL, 9.6 mmol) in dichloromethane (10 mL) was added. The reaction was allowed to warm to −15° C. and stir at this temperature for 1 h. A solution of (Z)-non-2-en-1-ol (1.42 g, 10 mmol) in dichloromethane (10 mL) was then added to the −15° C. solution. The reaction was then slowly allowed to warm to rt and stir for 18 h. After this time saturated NH$_4$C$_1$ (200 mL) was added and the reaction was extracted with dichloromethane (3×), washed with brine, and dried over Na$_2$SO$_4$. The organic layer was filtered, evaporated in vacuo and the residue was purified by silica gel chromatography (0-50% ethyl acetate in hexanes) to yield (2-hexylcyclopropyl)methanol (1.43 g, 9.2 mmol, 92%). $^1$H NMR (300 MHz, CDCl$_3$) δ: ppm 3.64 (m, 2H); 1.57-1.02 (m, 12H); 0.99-0.80 (m, 4H); 0.72 (m, 1H), 0.00 (m, 1H).

C. Compound 1: Heptadecan-9-yl 8-((2-hydroxyethyl)(octadecyl)amino)octanoate

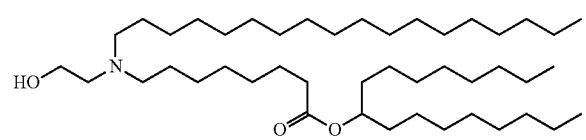

Chemical Formula: C$_{45}$H$_{91}$NO$_3$
Molecular Weight: 694.23

Compound 1 was synthesized according to the general procedure and Representative Procedure 1 described above. UPLC/ELSD: RT=3.86 min. MS (ES): m/z (MH$^+$) 694.93 for C$_{45}$H$_{91}$NO$_3$. $^1$H NMR (300 MHz, CDCl$_3$) δ: ppm 4.86 (m, 1H); 3.77-3.47 (br. m, 2H); 2.78-2.37 (br. m, 5H); 2.28 (t, 2H); 1.73-1.40 (br. m, 10H); 1.38-1.18 (br. m, 62H); 0.88 (m, 9H).

D. Compound 3: Heptadecan-9-yl 8-((2-hydroxyethyl)(nonyl)amino)octanoate

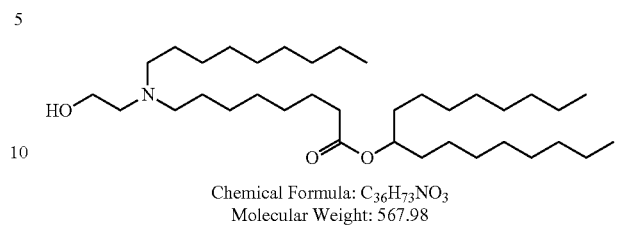

Chemical Formula: C$_{36}$H$_{73}$NO$_3$
Molecular Weight: 567.98

Compound 3 was synthesized according to the general procedure and Representative Procedure 1 and Representative Procedure 1 described above. UPLC/ELSD: RT=3.36 min. MS (ES): m/z (MH$^+$) 568.80 for C$_{36}$H73NO$_3$. $^1$H NMR (300 MHz, CDCl$_3$) δ: ppm 4.86 (p, 1H); 3.72-3.45 (br. m, 2H); 2.79-2.34 (br. m, 5H); 2.28 (t, 2H); 1.70-1.38 (m, 10H); 1.38-1.16 (br. m, 44H); 0.88 (m, 9H).

E. Compound 4: Heptadecan-9-yl 8-((2-hydroxyethyl)(octyl)amino)octanoate

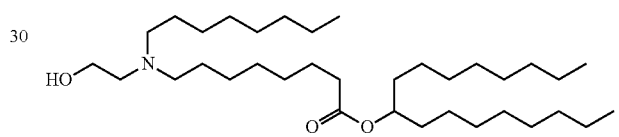

Chemical Formula: C$_{35}$H$_{71}$NO$_3$
Molecular Weight: 553.96

Compound 4 was synthesized according to the general procedure and Representative Procedure 1 described above. UPLC/ELSD: RT=2.99 min. MS (ES): m/z (MH$^+$) 554.777 for C$_{35}$H$_{71}$NO$_3$. $^1$H NMR (300 MHz, CDCl$_3$) δ: ppm 4.86 (p, 1H); 3.71 (br. s, 2H); 2.70 (br. s, 5H); 2.26 (t, 2H); 1.48-1.59 (br. m., 10H); 1.24 (m, 42H); 0.86 (t, 9H).

F. Compound 5: Heptadecan-9-yl 8-(hexyl(2-hydroxyethyl)amino)octanoate

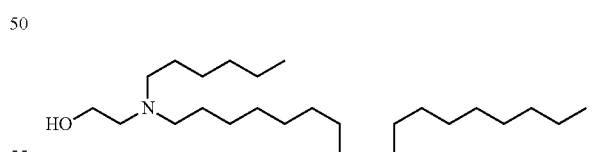

Chemical Formula: C$_{33}$H$_{67}$NO$_3$
Molecular Weight: 525.90

Compound 5 was synthesized according to the general procedure and Representative Procedure 1 described above. UPLC/ELSD: RT=3.10 min. MS (ES): m/z (MH$^+$) 526.73 for C$_{33}$H$_{67}$NO$_3$. $^1$H NMR (300 MHz, CDCl$_3$) δ: ppm 4.86 (p, 1H); 3.67-3.48 (br. m, 2H); 2.74-2.39 (br. m, 5H); 2.28 (t, 2H); 1.68-1.39 (br. m, 10H); 1.38-1.16 (br. m, 38H); 0.88 (m, 9H).

G. Compound 6: Heptadecan-9-yl 8-((2-hydroxyethyl)((9Z,12Z)-octadeca-9,12-dien-1-yl)amino)octanoate

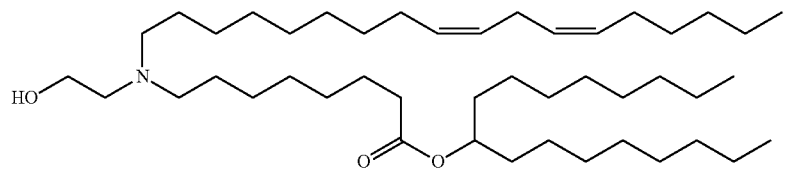

Chemical Formula: $C_{45}H_{87}NO_3$
Molecular Weight: 690.20

Compound 6 was synthesized according to the general procedure and Representative Procedure 1 described above. UPLC/ELSD: RT=3.77 min. MS (ES): m/z (MH$^+$) 690.84 for $C_{45}H_{87}NO_3$. $^1$H NMR (300 MHz, CDCl$_3$) δ: ppm 5.37 (m, 4H); 4.86 (br. m, 1H); 3.53 (br. m; 2H); 2.78 (br. m, 2H); 2.58 (br. m, 2H); 2.45 (br. m, 4H); 2.28 (m, 2H); 2.05 (m, 4H); 1.68-1.15 (br. m, 57H); 0.89 (m, 9H).

H. Compound 7: Heptadecan-9-yl 8-((3-hydroxypropyl)(nonyl)amino)octanoate

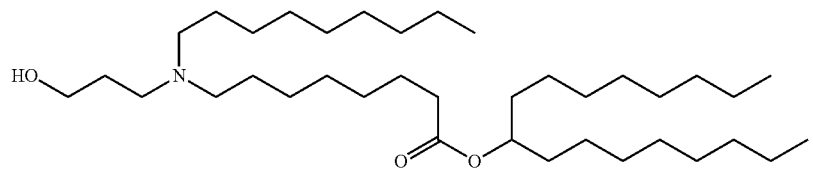

Chemical Formula: $C_{37}H_{75}NO_3$
Molecular Weight: 582.01

Compound 7 was synthesized according to the general procedure and Representative Procedure 1 described above. UPLC/ELSD: RT=3.24 min. MS (ES): m/z (MH$^+$) 582.987 for $C_{37}H_{75}NO_3$. $^1$H NMR (300 MHz, CDCl$_3$) δ: ppm 4.84 (p, 1H); 3.76 (t, 2H); 2.42-2.66 (br. s, 5H); 2.25 (t, 2H); 1.47-1.68 (br. m, 12H); 1.24 (m, 42H); 0.86 (t, 9H).

I. Compound 8: Heptadecan-9-yl 8-((3-(1H-imidazol-1-yl)propyl)(nonyl)amino)octanoate

Step 1: Heptadecan-9-yl 8-((3-chloropropyl)(nonyl)amino)octanoate

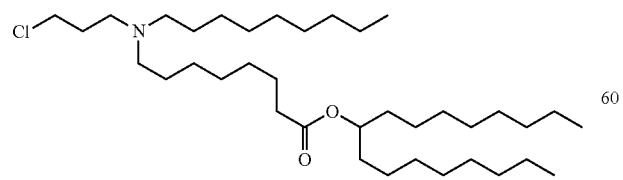

Chemical Formula: $C_{37}H_{74}ClNO_2$
Molecular Weight: 600.45

To a 0° C. solution of heptadecan-9-yl 8-((3-hydroxypropyl)(nonyl)amino)octanoate (0.53 g, 0.91 mmol) in 4 mL of DCM was added mesyl chloride (0.070 mL, 0.91 mmol) followed by triethylamine (0.13 mL, 0.91 mmol). The reaction was allowed to slowly warm to rt and stir overnight. The reaction was quenched by the addition of water (~10 mL). The mixture was extracted with DCM three times and the pooled organics were washed with brine, dried over $MgSO_4$, filtered and concentrated in vacuo. The crude oil was purified by silica gel chromatography to afford heptadecan-9-yl 8-((3-chloropropyl)(nonyl)amino)octanoate (0.23 g, 42%). $^1H$ NMR (300 MHz, $CDCl_3$) δ: ppm 4.84 (p, 1H); 3.58 (t, 2H); 2.51 (br. s, 2H); 2.35 (br. s, 2H); 2.26 (2, 2H); 1.86 (br. s, 2H); 1.40-1.60 (br. m, 12H); 1.24 (br. m, 42H); 0.86 (t, 9H).

Step 2. Heptadecan-9-yl 8-((3-(1H-imidazol-1-yl)propyl)(nonyl)amino)octanoate

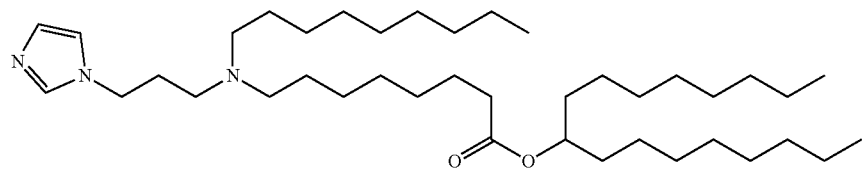

Chemical Formula: $C_{40}H_{77}N_3O_2$
Molecular Weight: 632.08

In a round bottom flask, heptadecan-9-yl 8-((3-chloropropyl)(nonyl)amino)octanoate (50 mg, 0.083 mmol) was combined with imidazole (17 mg, 0.25 mmol), $K_2CO_3$ (35 mg, 0.25 mmol) in MeCN (0.5 mL). The flask was fitted with a condenser and placed in an 82° C. heating mantle and was allowed to stir for 24 h. After this time, the reaction was allowed to cool to rt, was filtered and the filtrate was concentrated in vacuo. The crude oil was purified by silica gel chromatography (0-100% [DCM, 20% MeOH, 1% $NH_4OH$]/MeOH) to afford the desired product as a clear oil (39 mg, 74%). UPLC/ELSD: RT=2.92 min. MS (ES): m/z ($MH^+$) 633.994 for $C_{40}H_{77}N_3O_2$. $^1H$ NMR (300 MHz, $CDCl_3$) δ: ppm 7.46 (s, 1H); 7.05 (s, 1H); 6.91 (s, 1H); 4.84 (dt, 1H); 4.02 (br. s, 2H); 2.47 (br. s, 4H); 2.26 (t, 2H); 2.00 (br. s, 2H); 1.47-1.59 (br. m, 10H); 1.24 (br. m, 44H); 0.86 (t, 9H).

J. Compound 9: Heptadecan-9-yl 8-((2-acetoxyethyl)(8-(nonyloxy)-8-oxooctyl)amino) octanoate

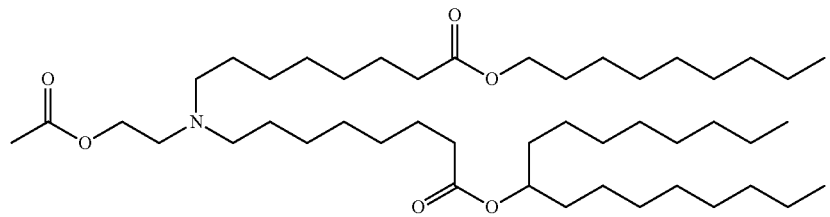

Chemical Formula: $C_{46}H_{89}NO_6$
Molecular Weight: 752.22

To a solution of heptadecan-9-yl 8-((2-hydroxyethyl)(8-(nonyloxy)-8-oxooctyl)amino)octanoate (100 mg, 0.14 mmol) and acetic acid (8 mg, 0.13 mmol) in dichloromethane (1 mL) were added N-(3-Dimethylaminopropyl)-N'-ethylcarbodiimide hydrochloride (31 mg, 0.16 mmol), N,N-diisopropylethylamine (73 mg, 0.56 mmol) and DMAP (3 mg, 0.02 mmol). The reaction was allowed to stir at rt for 18 h. The reaction was diluted with dichloromethane and washed with saturated sodium bicarbonate. The organic layer was separated and washed with brine and dried over $MgSO_4$. The organic layer was filtered and evaporated in vacuo. The residue was purified by silica gel chromatography (0-100% (mixture of 1% $NH_4OH$, 20% MeOH in dichloromethane) in dichloromethane) to yield heptadecan-9-yl 8-((2-acetoxyethyl)(8-(nonyloxy)-8-oxooctyl)amino) octanoate (63 mg, 0.08 mmol). UPLC/ELSD: RT=3.63 min.

MS (ES): m/z (MH⁺) 753.07 for $C_{46}H_{89}NO_6$. ¹H NMR (300 MHz, CDCl₃) δ: ppm 4.87 (p, 1H); 4.17-3.99 (m, 4H); 2.67 (m, 2H); 2.43 (m, 3H); 2.29 (m, 4H); 2.05 (s, 3H); 1.71-1.17 (br. m, 63H); 0.88 (m, 9H).

K. Compound 10: Heptadecan-9-yl 8-((2-hydroxypropyl)(8-(nonyloxy)-8-oxooctyl)amino) octanoate

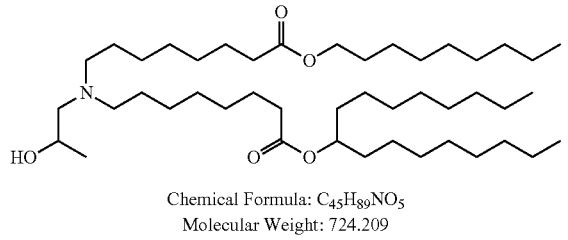 [SMILES: CCCCCCCCCOC(=O)CCCCCCCN(CCCCCCCC(=O)OC(CCCCCCCC)CCCCCCCC)CC(C)O]

Chemical Formula: $C_{45}H_{89}NO_5$
Molecular Weight: 724.209

Compound 10 was synthesized according to the general procedure and Representative Procedure 1 described above. UPLC/ELSD: RT=3.73 min. MS (ES): m/z (MH⁺) 725.10 for $C_{45}H_{89}NO_5$. ¹H NMR (300 MHz, CDCl₃) δ: ppm 4.86 (p, 1H); 4.05 (t, 2H); 3.80-3.54 (br. m, 1H); 2.61-2.13 (br. m, 9H); 1.69-1.03 (br. m, 67H); 0.88 (m, 9H).

L. Compound 11: Heptadecan-9-yl (R)-8-((2-hydroxypropyl)(8-(nonyloxy)-8-oxooctyl) amino)octanoate

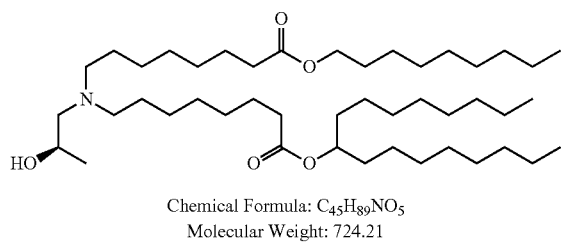 [SMILES: CCCCCCCCCOC(=O)CCCCCCCN(CCCCCCCC(=O)OC(CCCCCCCC)CCCCCCCC)C[C@@H](C)O]

Chemical Formula: $C_{45}H_{89}NO_5$
Molecular Weight: 724.21

Compound 11 was synthesized according to the general procedure and Representative Procedure 1 described above. UPLC/ELSD: RT=5.21 min. MS (ES): m/z (MH⁺) 725.02 for $C_{45}H_{89}NO_5$. ¹H NMR (300 MHz, CDCl₃) δ: ppm 4.86 (p, 1H); 4.05 (t, 2H); 3.72 (br. m, 1H); 2.65-2.10 (br. m, 8H); 1.71-0.99 (br. m, 68H); 0.88 (m, 9H).

M. Compound 12: Heptadecan-9-yl (S)-8-((2-hydroxypropyl)(8-(nonyloxy)-8-oxooctyl) amino)octanoate

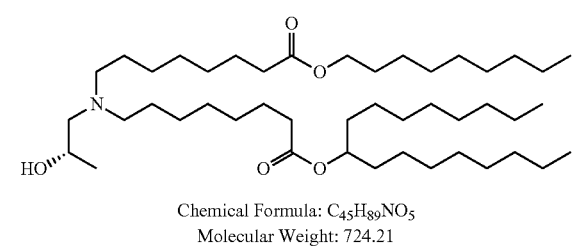 [SMILES: CCCCCCCCCOC(=O)CCCCCCCN(CCCCCCCC(=O)OC(CCCCCCCC)CCCCCCCC)C[C@H](C)O]

Chemical Formula: $C_{45}H_{89}NO_5$
Molecular Weight: 724.21

Compound 12 was synthesized according to the general procedure and Representative Procedure 1 described above. UPLC/ELSD: RT=5.30 min. MS (ES): m/z (MH⁺) 725.10 for $C_{45}H_{89}NO_5$. ¹H NMR (300 MHz, CDCl₃) δ: ppm 4.86 (p, 1H); 4.05 (t, 2H); 3.71 (br. m, 1H); 2.64-2.10 (br. m, 8H); 1.71-1.03 (br. m, 68H); 0.88 (m, 9H).

N. Compound 13: Heptadecan-9-yl 8-((2-hydroxybutyl)(8-(nonyloxy)-8-oxooctyl)amino) octanoate

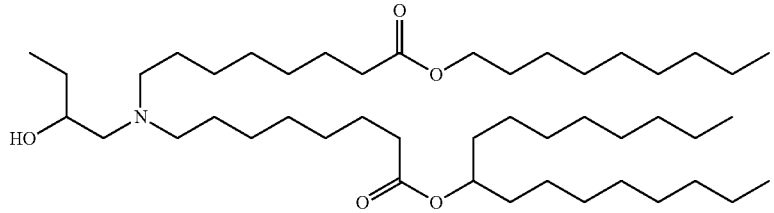

Chemical Formula: $C_{46}H_{91}NO_5$
Molecular Weight: 738.24

Compound 13 was synthesized according to the general procedure and Representative Procedure 1 described above. UPLC/ELSD: RT=3.89 min. MS (ES): m/z (MH$^+$) 739.21 for $C_{46}H_{91}NO_5$. $^1$H NMR (300 MHz, CDCl$_3$) δ: ppm 4.86 (p, 1H); 4.05 (t, 2H); 3.58-3.38 (br. m, 1H); 2.65-2.15 (br. m, 9H); 1.72-1.12 (br. m, 66H); 0.98 (t, 3H); 0.88 (m, 9H).

O. Compound 14: Heptadecan-9-yl 8-((2-(dimethylamino)ethyl)(8-(nonyloxy)-8-oxooctyl)amino)octanoate

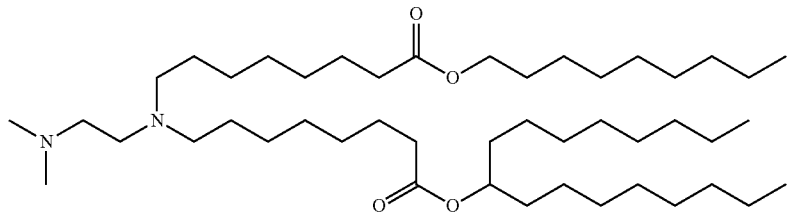

Chemical Formula: $C_{46}H_{92}N_2O_4$
Molecular Weight: 737.252

Compound 14 was synthesized according to the general procedure and Representative Procedure 1 described above. UPLC/ELSD: RT=3.51 min. MS (ES): m/z (MH$^+$) 738.23 for $C_{46}H_{92}N_2O_4$. $^1$H NMR (300 MHz, CDCl$_3$) δ: ppm 4.84 (p, 1H); 4.04 (t, 2H); 2.95 (m, 2H); 2.78 (m, 6H); 2.44 (s, 6H); 2.28 (m, 4H); 1.70-1.41 (br. m, 14H); 1.41-1.14 (br. m, 48H); 0.87 (m, 9H).

P. Compound 15: Heptadecan-9-yl 8-((2-methoxyethyl)(8-(nonyloxy)-8-oxooctyl)amino)octanoate

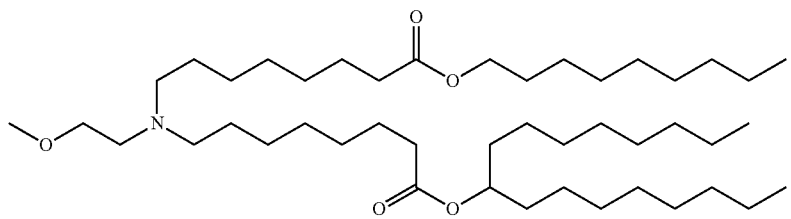

Chemical Formula: $C_{45}H_{89}NO_5$
Molecular Weight: 724.21

Compound 15 was synthesized according to the general procedure and Representative Procedure 1 described above. UPLC/ELSD: RT=3.90 min. MS (ES): m/z (MH$^+$) 725.19 for $C_{45}H_{89}NO_5$. $^1$H NMR (300 MHz, CDCl$_3$) δ: ppm 4.86 (p, 1H); 4.05 (t, 2H); 3.43 (m, 2H); 3.34 (s, 3H); 2.61 (m, 2H); 2.43 (m, 3H); 2.29 (m, 4H); 1.70-1.15 (br. m, 63H); 0.88 (m, 9H).

Q. Compound 16: Heptadecan-9-yl 8-((3-methoxypropyl)(8-(nonyloxy)-8-oxooctyl)amino) octanoate

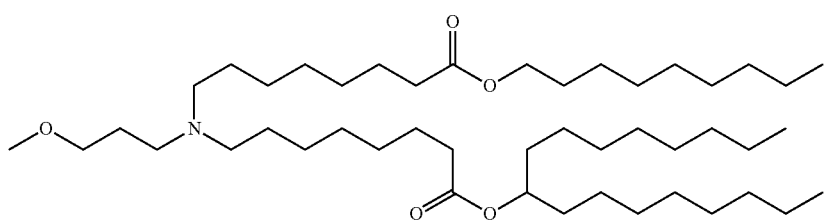

Chemical Formula: $C_{46}H_{91}NO_5$
Molecular Weight: 738.236

Compound 16 was synthesized according to the general procedure and Representative Procedure 1 described above. UPLC/ELSD: RT=3.90 min. MS (ES): m/z (MH⁺) 739.13 for $C_{46}H_{91}NO_5$. $^1$H NMR (300 MHz, CDCl$_3$) δ: ppm 4.89 (p, 1H); 4.08 (t, 2H); 3.42 (m, 2H); 3.35 (s, 3H); 2.55-2.21 (m, 9H); 1.81-1.18 (br. m, 65H); 0.88 (m, 9H).

R. Compound 17: Heptadecan-9-yl 8-((2-(2-(dimethylamino)ethoxy)ethyl) (8-(nonyloxy)-8-oxooctyl)amino)octanoate

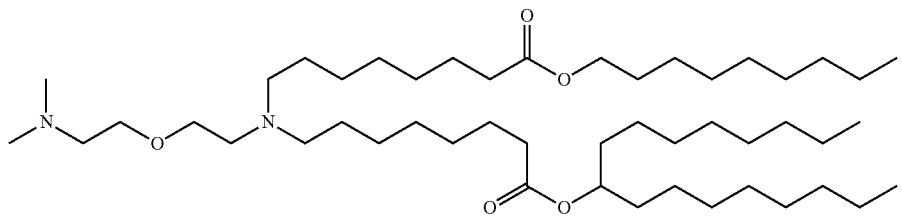

Chemical Formula: $C_{48}H_{96}N_2O_5$
Molecular Weight: 781.305

Compound 17 was synthesized according to the general procedure and Representative Procedure 1 described above. UPLC/ELSD: RT=3.72 min. MS (ES): m/z (MH⁺) 782.27 for $C_{48}H_{96}N_2O_5$. $^1$H NMR (300 MHz, CDCl$_3$) δ: ppm 4.88 (p, 1H); 4.08 (t, 2H); 3.57 (m, 4H); 2.72 (m, 2H); 2.52 (m, 5H); 2.38-2.13 (br. m, 12H); 1.73-1.19 (br. m, 61H); 0.90 (m, 9H).

S. Compound 18: Heptadecan-9-yl 8-((2-hydroxyethyl)(8-(nonyloxy)-8-oxooctyl)amino)octanoate

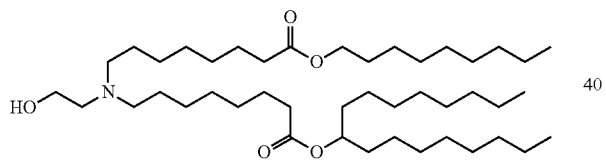

Chemical Formula: $C_{44}H_{87}NO_5$
Molecular Weight: 710.18

Compound 18 was synthesized according to the general procedure and Representative Procedure 1 described above or according to the scheme below:

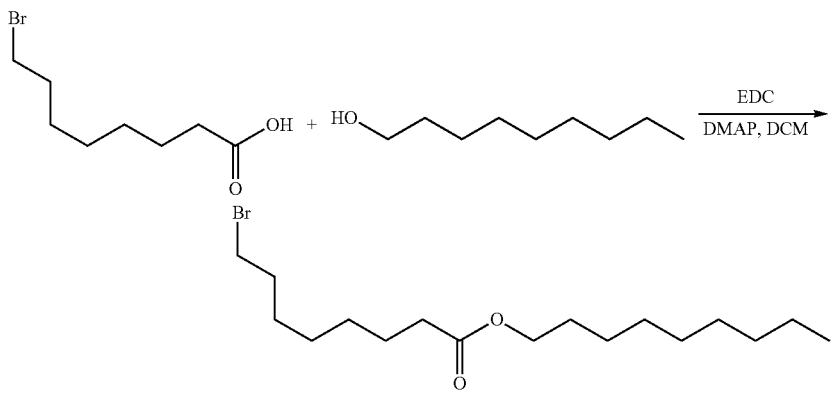

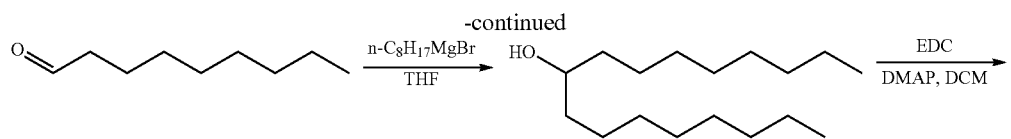
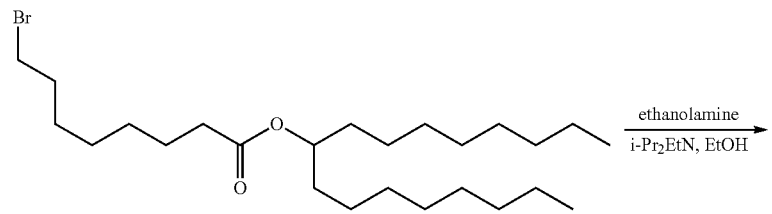
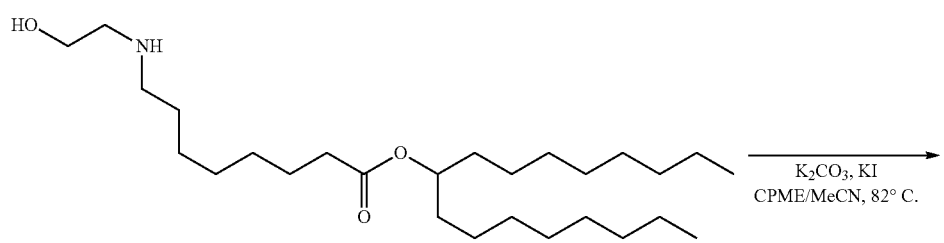
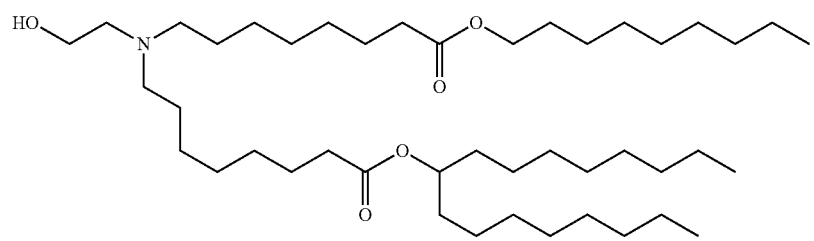
UPLC/ELSD: RT=3.59 min. MS (ES): m/z (MH$^+$) 710.89 for $C_{44}H_{87}NO_5$. $^1$H NMR (300 MHz, CDCl$_3$) δ: ppm 4.86 (m, 1H); 4.05 (t, 2H); 3.53 (br. m, 2H); 2.83-2.36 (br. m, 5H); 2.29 (m, 4H); 0.96-1.71 (m, 64H); 0.88 (m, 9H).
T. Compound 19: Heptadecan-9-yl 8-((3-hydroxypropyl)(8-(nonyloxy)-8-oxooctyl)amino) octanoate
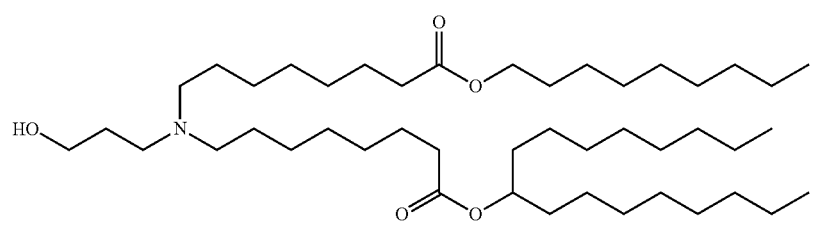
Chemical Formula: $C_{45}H_{89}NO_5$
Molecular Weight: 724.21

Compound 19 was synthesized according to the general procedure and Representative Procedure 1 described above. UPLC/ELSD: RT=4.51 min. MS (ES): m/z (MH$^+$) 725.19 for C$_{45}$H$_{89}$NO$_5$. $^1$H NMR (300 MHz, CDCl$_3$) δ: ppm 4.86 (p, 1H); 4.05 (t, 2H); 3.80 (m, 2H); 2.92-2.36 (br. m, 5H); 2.29 (m, 4H); 1.89-1.42 (br. m, 16H); 1.42-1.02 (br. m, 50H); 0.88 (m, 9H).

U. Compound 20: Heptadecan-9-yl 8-((4-hydroxybutyl)(8-(nonyloxy)-8-oxooctyl)amino) octanoate

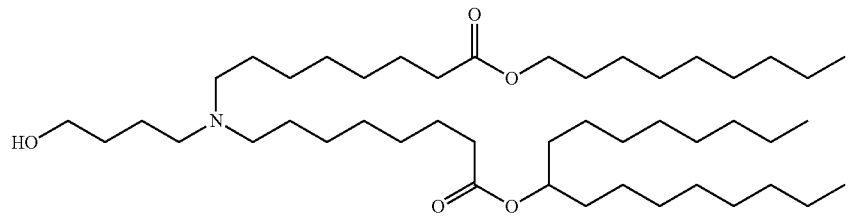

Chemical Formula: C$_{46}$H$_{91}$NO$_5$
Molecular Weight: 738.24

Compound 20 was synthesized according to the general procedure and Representative Procedure 1 described above. UPLC/ELSD: RT=3.84 min. MS (ES): m/z (MH$^+$) 739.21 for C$_{46}$H$_{91}$NO$_5$. $^1$H NMR (300 MHz, CDCl$_3$) δ: ppm 4.86 (p, 1H); 4.05 (t, 2H); 3.77-3.45 (br. m, 2H); 2.63-2.20 (br. m, 8H); 1.82-1.40 (br. m, 18H); 1.40-1.15 (br. m, 51H); 0.88 (m, 9H).

V. Compound 21: Heptadecan-9-yl 8-((2-cyanoethyl)(8-(nonyloxy)-8-oxooctyl)amino) octanoate

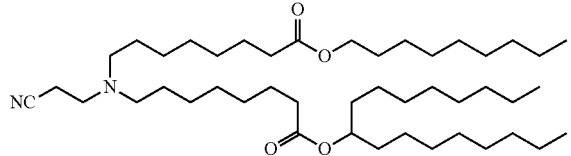

Chemical Formula: C$_{45}$H$_{86}$N$_2$O$_4$
Molecular Weight: 719.19

Compound 21 was synthesized according to the general procedure and Representative Procedure 1 described above. UPLC/ELSD: RT=4.04 min. MS (ES): m/z (MH$^+$) 720.18 for C$_{45}$H$_{86}$N$_2$O$_4$. $^1$H NMR (300 MHz, CDCl$_3$) δ: ppm 4.88 (p, 1H); 4.07 (t, 2H); 2.81 (m, 2H); 2.44 (m, 5H); 2.30 (m, 4H); 1.73-1.18 (br. m, 63H); 0.89 (m, 9H).

W. Compound 22: Heptadecan-9-yl 8-((2-hydroxycyclohexyl)(8-(nonyloxy)-8-oxooctyl)amino)octanoate

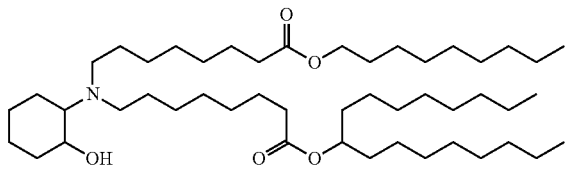

Chemical Formula: C$_{48}$H$_{93}$NO$_5$
Molecular Weight: 764.27

Compound 22 was synthesized according to the general procedure and Representative Procedure 1 described above. UPLC/ELSD: RT=4.54 min. MS (ES): m/z (MH$^+$) 765.21 for C$_{48}$H$_{93}$NO$_5$. $^1$H NMR (300 MHz, CDCl$_3$) δ: ppm 4.86 (p, 1H); 4.05 (t, 2H); 2.89-2.34 (br. m, 4H); 2.28 (m, 4H); 2.00 (m, 1H); 1.86-0.99 (br. m, 72H); 0.88 (m, 9H).

X. Compound 23: Heptadecan-9-yl 10-((2-hydroxyethyl)(8-(nonyloxy)-8-oxooctyl)amino) decanoate

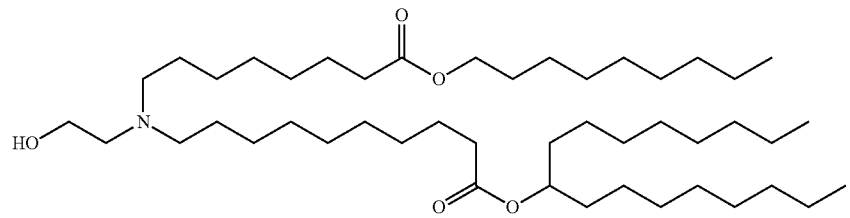

Chemical Formula: C$_{46}$H$_{91}$NO$_5$
Molecular Weight: 738.24

Compound 23 was synthesized according to the general procedure and Representative Procedure 1 described above. UPLC/ELSD: RT=3.75 min. MS (ES): m/z (MH$^+$) 739.13 for $C_{46}H_{91}NO_5$. $^1$H NMR (300 MHz, CDCl$_3$) δ: ppm 4.86 (m, 1H); 4.05 (m, 2H); 3.72-3.46 (br. m, 2H); 2.81-2.35 (br. m, 5H); 2.29 (m, 4H); 1.71-1.40 (br. m, 13H); 1.40-1.15 (br. m, 55H); 0.88 (m, 9H).

Y. Compound 24: Heptadecan-9-yl (Z)-8-((2-hydroxyethyl) (8-(non-2-en-1-yloxy)-8-oxooctyl) amino)octanoate

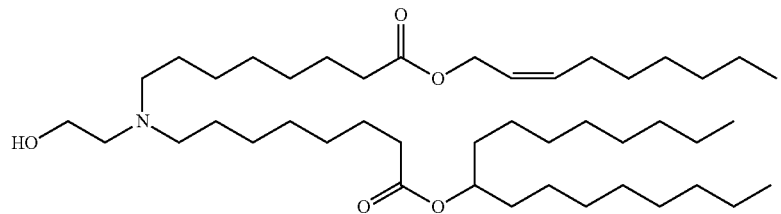

Chemical Formula: $C_{44}H_{85}NO_5$
Molecular Weight: 708.17

Compound 24 was synthesized according to the general procedure and Representative Procedure 1 described above. UPLC/ELSD: RT=3.54 min. MS (ES): m/z (MH$^+$) 708.95 for $C_{44}H_{85}NO_5$. $^1$H NMR (300 MHz, CDCl$_3$) δ: ppm 5.74-5.44 (br. m, 2H); 4.86 (m, 1H); 4.62 (m, 2H); 3.71-3.40 (br. m, 2H); 2.81-2.37 (br. m, 5H); 2.29 (m, 4H); 2.09 (m, 2H); 1.70-1.14 (br. m, 58H); 0.88 (m, 9H).

Z. Compound 25: Heptadecan-9-yl 8-((2-hydroxyethyl)(6-oxo-6-(undecyloxy)hexyl)amino)octanoate

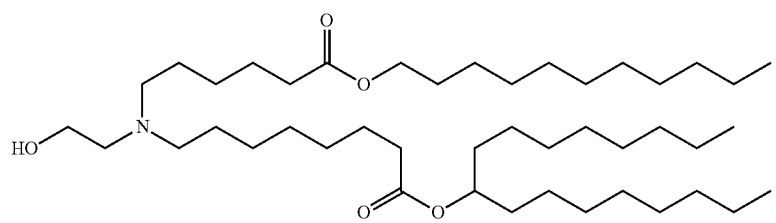

Chemical Formula: $C_{44}H_{87}NO_5$
Molecular Weight: 710.182

Compound 25 was synthesized according to the general procedure and Representative Procedure 1 described above. UPLC/ELSD: RT=3.66 min. MS (ES): m/z (MH$^+$) 711.00 for $C_{44}H_{87}NO_5$. $^1$H NMR (300 MHz, CDCl$_3$) δ: ppm 4.86 (m, 1H); 4.05 (t, 2H); 3.68-3.46 (br. m, 2H); 2.77-2.37 (br. m, 5H); 2.29 (m, 4H); 1.74-1.41 (br. m, 14H); 1.39-1.18 (m, 50H); 0.88 (m, 9H).

AA. Compound 26: Heptadecan-9-yl 8-((2-hydroxyethyl)(4-(nonyloxy)-4-oxobutyl)amino) octanoate

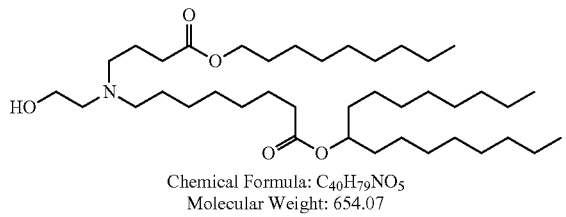 [SMILES: CCCCCCCCCOC(=O)CCCN(CCO)CCCCCCCC(=O)OC(CCCCCCCC)CCCCCCCC]

Chemical Formula: $C_{40}H_{79}NO_5$
Molecular Weight: 654.07

Compound 26 was synthesized according to the general procedure and Representative Procedure 1 described above. UPLC/ELSD: RT=4.29 min. MS (ES): m/z (MH$^+$) 655.07 for $C_{40}H_{79}NO_5$. $^1$H NMR (300 MHz, CDCl$_3$) δ: ppm 4.86 (p, 1H); 4.06 (t, 2H); 3.79 (br. m, 2H); 2.91-2.20 (br. m, 10H); 1.98-1.03 (br. m, 55H); 0.88 (m, 9H).

AB. Compound 27: Nonyl 8-((6-(heptadecan-9-yloxy)-6-oxohexyl)(2-hydroxyethyl)amino) octanoate

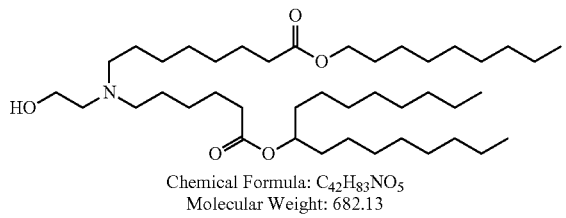 [SMILES: CCCCCCCCCOC(=O)CCCCCCCN(CCO)CCCCCC(=O)OC(CCCCCCCC)CCCCCCCC]

Chemical Formula: $C_{42}H_{83}NO_5$
Molecular Weight: 682.13

Compound 27 was synthesized according to the general procedure and Representative Procedure 1 described above. UPLC/ELSD: RT=3.57 min. MS (ES): m/z (MH$^+$) 683.12 for $C_{42}H_{83}NO_5$. $^1$H NMR (300 MHz, CDCl$_3$) δ: ppm 4.86 (m, 1H); 4.05 (m, 2H); 3.70-3.45 (br. m, 2H); 2.78-2.35 (br. m, 5H); 2.29 (m, 4H); 1.73-1.41 (m, 13H); 1.41-1.16 (m, 47H); 0.88 (m, 9H).

AC. Compound 28: Heptadecan-9-yl 8-((8-((2-hexylcyclopropyl)methoxy)-8-oxooctyl)(2-hydroxyethyl)amino)octanoate

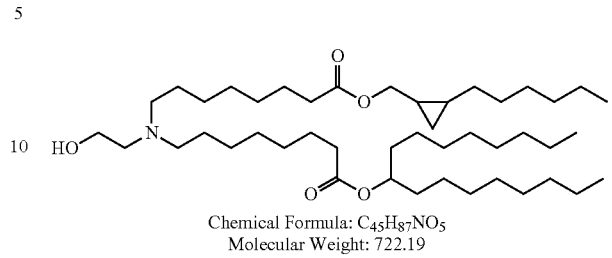

Chemical Formula: $C_{45}H_{87}NO_5$
Molecular Weight: 722.19

Compound 28 was synthesized according to the general procedure and Representative Procedure 1 described above using Intermediate C. UPLC/ELSD: RT=5.17 min. MS (ES): m/z (MH$^+$) 722.97 for $C_{45}H_{87}NO_5$. $^1$H NMR (300 MHz, CDCl$_3$) δ: ppm 4.86 (p, 1H); 4.17 (m, 1H); 3.93 (m, 1H); 3.61 (br. m, 2H); 2.97-2.37 (br. m, 6H); 2.35-2.21 (m, 4H); 1.74-0.97 (br. m, 60H); 0.94-0.79 (m, 10H); 0.74 (m, 1H); 0.01 (m, 1H).

AD. Compound 29: Di(heptadecan-9-yl) 8,8'-((2-hydroxyethyl)azanediyl)dioctanoate

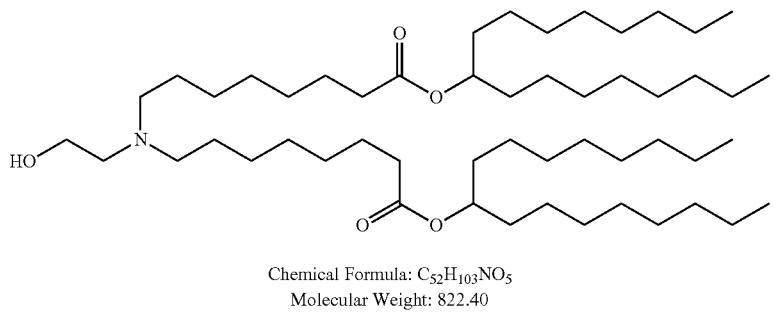 [SMILES: CCCCCCCCC(CCCCCCCC)OC(=O)CCCCCCCN(CCO)CCCCCCCC(=O)OC(CCCCCCCC)CCCCCCCC]

Chemical Formula: $C_{52}H_{103}NO_5$
Molecular Weight: 822.40

Compound 29 was synthesized according to the general procedure and Representative Procedure 1 described above. UPLC/ELSD: RT=3.98 min. MS (ES): m/z (MH$^+$) 823.19 for $C_{52}H_{103}NO_5$. $^1$H NMR (300 MHz, CDCl$_3$) δ: ppm 4.86 (m, 2H); 3.72-3.44 (br. m, 2H); 2.83-2.34 (br. m, 5H); 2.28 (m, 4H); 1.69-1.39 (br. m, 16H); 1.39-1.16 (br. m, 62H); 0.88 (m, 12H).

AE. Compound 30: 7-((2-Hydroxyethyl)(8-(nonyloxy)-8-oxooctyl)amino)heptyl 2-octyldecanoate

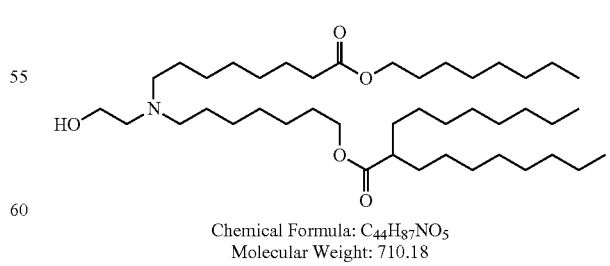

Chemical Formula: $C_{44}H_{87}NO_5$
Molecular Weight: 710.18

Compound 30 was synthesized according to the general procedure and Representative Procedure 1 described above using Intermediate B. UPLC/ELSD: RT=3.55 min. MS (ES): m/z (MH$^+$) 711.16 for $C_{44}H_{87}NO_5$. $^1$H NMR (300

MHz, CDCl$_3$) δ: ppm 4.06 (m, 4H); 3.69-3.44 (br. m, 2H); 2.71-2.39 (br. m, 5H); 2.29 (m, 3H); 1.70-1.16 (br. m, 64H); 0.88 (m, 9H).

AF. Compound 31: heptadecan-9-yl (Z)-8-((2-hydroxyethyl)(octadec-9-en-1-yl)amino) octanoate

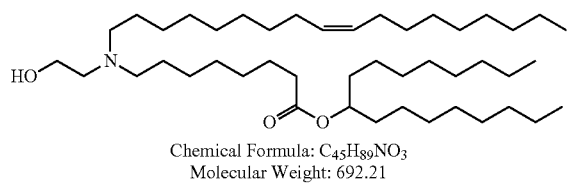 [SMILES: CCCCCCCC/C=C\CCCCCCCCN(CCO)CCCCCCCC(=O)OC(CCCCCCCC)CCCCCCCC]

Chemical Formula: C$_{45}$H$_{89}$NO$_3$
Molecular Weight: 692.21

Compound 31 was synthesized according to the general procedure and Representative Procedure 1 described above. UPLC/ELSD: RT=3.83 min. MS (ES): m/z (MH$^+$) 693.20 for C$_{45}$H$_{89}$NO$_3$. $^1$H NMR (300 MHz, CDCl$_3$) δ: ppm 5.37 (m, 2H); 4.89 (p, 1H); 3.58 (br. m, 2H); 2.72-2.43 (br. m, 5H); 2.30 (m, 2H), 2.05 (m, 4H); 1.71-1.03 (br. m, 63H), 0.90 (m, 9H).

AG. Compound 32: nonyl 8-((2-hydroxyethyl)(8-oxo-8-(pentadecan-7-yloxy)octyl)amino) octanoate

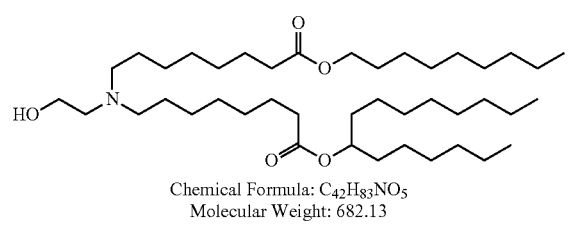 [SMILES: CCCCCCCCCOC(=O)CCCCCCCN(CCO)CCCCCCCC(=O)OC(CCCCCC)CCCCCCCC]

Chemical Formula: C$_{42}$H$_{83}$NO$_5$
Molecular Weight: 682.13

Compound 32 was synthesized according to the general procedure and Representative Procedure 1 described above. UPLC/ELSD: RT=3.45 min. MS (ES): m/z (MH$^+$) 683.20 for C$_{42}$H$_{83}$NO$_5$. $^1$H NMR (300 MHz, CDCl$_3$) δ: ppm 4.89 (p, 1H); 4.08 (t, 2H); 3.60 (br. m, 2H); 2.85-2.40 (br. m, 5H); 2.31 (m, 4H), 1.78-1.01 (m, 59H), 0.90 (m, 9H).

AH. Compound 33: nonyl 8-((2-hydroxyethyl)(8-oxo-8-(tetradecan-6-yloxy)octyl)amino) octanoate

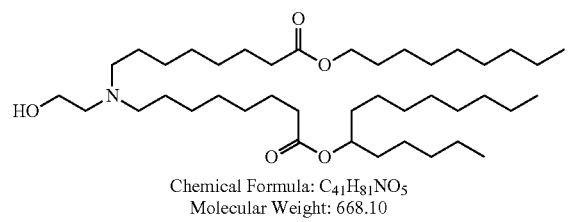 [SMILES: CCCCCCCCCOC(=O)CCCCCCCN(CCO)CCCCCCCC(=O)OC(CCCCC)CCCCCCCC]

Chemical Formula: C$_{41}$H$_{81}$NO$_5$
Molecular Weight: 668.10

Compound 33 was synthesized according to the general procedure and Representative Procedure 1 described above. UPLC/ELSD: RT=3.39 min. MS (ES): m/z (MH$^+$) 669.09 for C$_{41}$H$_{81}$NO$_5$. $^1$H NMR (300 MHz, CDCl$_3$) δ: ppm 4.89 (p, 1H); 4.08 (t, 2H); 3.84-3.54 (br. m, 2H); 2.99-2.41 (br. m, 5H); 2.31 (m, 4H), 1.76-1.02 (br. m, 57H), 0.90 (m, 9H).

AI. Compound 34: dodecan-4-yl 8-((2-hydroxyethyl)(8-(nonyloxy)-8-oxooctyl)amino) octanoate

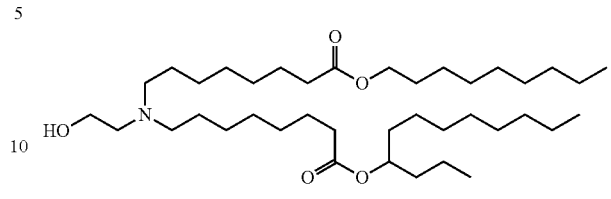

Chemical Formula: C$_{39}$H$_{77}$NO$_5$
Molecular Weight: 640.05

Compound 34 was synthesized according to the general procedure and Representative Procedure 1 described above. UPLC/ELSD: RT=3.21 min. MS (ES): m/z (MH$^+$) 641.05 for C$_{39}$H$_{77}$NO$_5$. $^1$H NMR (300 MHz, CDCl$_3$) δ: ppm 4.91 (p, 1H); 4.08 (t, 2H); 3.67 (br. m, 2H); 3.03-2.44 (br. m, 5H); 2.30 (m, 4H), 1.75-1.00 (br. m, 53H), 0.90 (m, 9H).

AJ. Compound 35: nonyl 8-((2-hydroxyethyl)(8-oxo-8-(undecan-3-yloxy)octyl)amino) octanoate

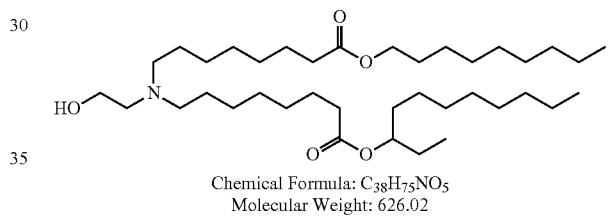

Chemical Formula: C$_{38}$H$_{75}$NO$_5$
Molecular Weight: 626.02

Compound 35 was synthesized according to the general procedure and Representative Procedure 1 described above. UPLC/ELSD: RT=3.16 min. MS (ES): m/z (MH$^+$) 627.11 for C$_{38}$H$_{75}$NO$_5$. $^1$H NMR (300 MHz, CDCl$_3$) δ: ppm 4.83 (p, 1H); 4.08 (t, 2H); 3.63 (br. m, 2H); 2.81-2.39 (br. m, 5H); 2.31 (m, 4H), 1.74-1.01 (br. m, 51H), 0.90 (m, 9H).

AK. Compound 36: decan-2-yl 8-((2-hydroxyethyl)(8-(nonyloxy)-8-oxooctyl)amino) octanoate

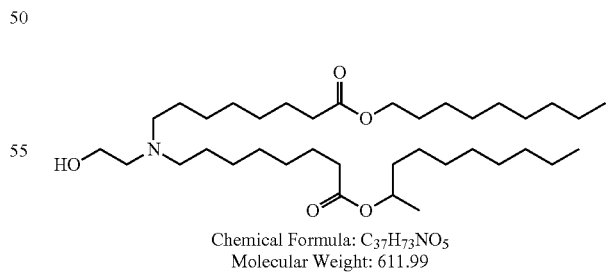

Chemical Formula: C$_{37}$H$_{73}$NO$_5$
Molecular Weight: 611.99

Compound 36 was synthesized according to the general procedure and Representative Procedure 1 described above. UPLC/ELSD: RT=3.05 min. MS (ES): m/z (MH$^+$) 613.00 for C$_{37}$H$_{73}$NO$_5$. $^1$H NMR (300 MHz, CDCl$_3$) δ: ppm 4.91 (p, 1H); 4.08 (t, 2H); 3.55 (m, 2H); 2.60 (m, 2H); 2.47 (m, 4H); 2.29 (m, 4H), 1.731-1.01 (m, 51H), 0.90 (m, 6H).

AL. Compound 47: heptadecan-9-yl 8-((2-hydroxy-ethyl)(8-(2-octylcyclopropyl)octyl) amino)octanoate

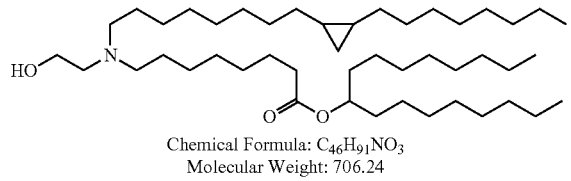 [SMILES: CCCCCCCCC(CCCCCCCC)OC(=O)CCCCCCCN(CCO)CCCCCCCCC1CC1CCCCCCCC]

Chemical Formula: C$_{46}$H$_{91}$NO$_3$
Molecular Weight: 706.24

Compound 47 was synthesized according to the general procedure and Representative Procedure 1 described above. UPLC/ELSD: RT=3.92 min. MS (ES): m/z (MH$^+$) 707.39 for C$_{46}$H$_{91}$NO$_3$. $^1$H NMR (300 MHz, CDCl$_3$) δ: ppm 4.86 (p, 1H); 3.56 (br. m, 2H); 2.72-2.38 (br. m, 5H); 2.28 (t, 2H); 1.70-1.02 (br. m, 67H), 0.88 (m, 9H); 0.71-0.49 (m, 4H); −0.33 (m, 1H).

AM. Compound 48: decan-2-yl 8-((8-(heptadecan-9-yloxy)-8-oxooctyl)(2-hydroxyethyl) amino)octanoate

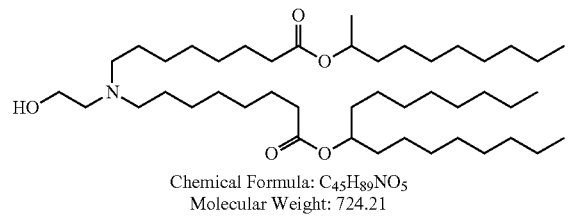 [SMILES: CCCCCCCCC(C)OC(=O)CCCCCCCN(CCO)CCCCCCCC(=O)OC(CCCCCCCC)CCCCCCCC]

Chemical Formula: C$_{45}$H$_{89}$NO$_5$
Molecular Weight: 724.21

Compound 48 was synthesized according to the general procedure and Representative Procedure 1 described above. UPLC/ELSD: RT=3.60 min. MS (ES): m/z (MH$^+$) 725.10 for C$_{45}$H$_{89}$NO$_5$. $^1$H NMR (300 MHz, CDCl$_3$) δ: ppm 4.91 (m, 2H); 3.59 (br. m, 2H); 2.79-2.37 (br. m, 5H); 2.29 (m, 4H); 1.74-1.13 (m, 66H); 0.90 (m, 9H).

AN. Compound 49: heptadecan-9-yl 8-((2-hydroxy-ethyl)(8-oxo-8-(undecan-3-yloxy)octyl) amino)octanoate

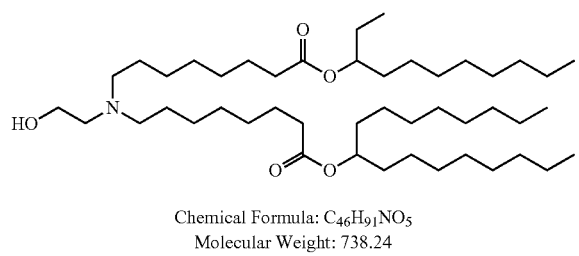 [SMILES: CCCCCCCCC(CC)OC(=O)CCCCCCCN(CCO)CCCCCCCC(=O)OC(CCCCCCCC)CCCCCCCC]

Chemical Formula: C$_{46}$H$_{91}$NO$_5$
Molecular Weight: 738.24

Compound 49 was synthesized according to the general procedure and Representative Procedure 1 described above. UPLC/ELSD: RT=3.68 min. MS (ES): m/z (MH$^+$) 739.21 for C$_{46}$H$_{91}$NO$_5$. $^1$H NMR (300 MHz, CDCl$_3$) δ: ppm 4.89 (m, 2H); 3.56 (br. m, 2H); 2.68-2.39 (br. m, 5H); 2.30 (m, 4H); 1.71-1.19 (m, 66H); 0.90 (m, 12H).

AO. Compound 50: dodecan-4-yl 8-((8-(heptadecan-9-yloxy)-8-oxooctyl)(2-hydroxyethyl) amino) octanoate

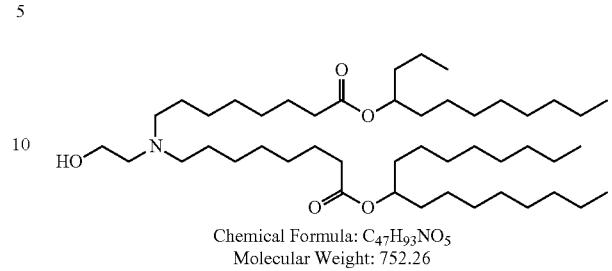

Chemical Formula: C$_{47}$H$_{93}$NO$_5$
Molecular Weight: 752.26

Compound 50 was synthesized according to the general procedure and Representative Procedure 1 described above. UPLC/ELSD: RT=3.73 min. MS (ES): m/z (MH$^+$) 753.23 for C$_{47}$H$_{93}$NO$_5$. $^1$H NMR (300 MHz, CDCl$_3$) δ: ppm 4.89 (m, 2H); 3.60 (br. m, 2H); 2.75-2.43 (br. m, 5H); 2.30 (m, 4H); 1.71-1.44 (m, 16H); 1.28 (m, 51H); 0.90 (m, 12H).

AP. Compound 51: heptadecan-9-yl 8-((4-butoxy-4-oxobutyl)(2-hydroxyethyl)amino) octanoate

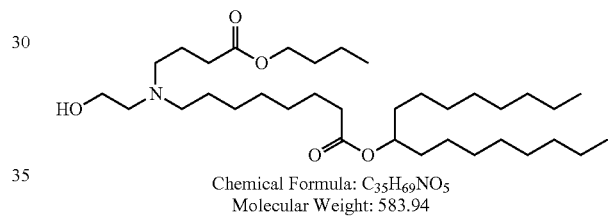

Chemical Formula: C$_{35}$H$_{69}$NO$_5$
Molecular Weight: 583.94

Compound 51 was synthesized according to the general procedure and Representative Procedure 1 described above. UPLC/ELSD: RT=3.05 min. MS (ES): m/z (MH$^+$) 584.87 for C$_{35}$H$_{69}$NO$_5$. $^1$H NMR (300 MHz, CDCl$_3$) δ: ppm 4.89 (p, 1H); 4.10 (t, 2H); 3.61 (br. m, 2H); 2.81-2.21 (br. m, 9H); 1.87 (br. m, 2H), 1.70-1.04 (m, 43H), 0.98-0.82 (m, 9H).

AQ. Compound 52: heptadecan-9-yl 8-((2-hydroxy-ethyl)(4-oxo-4-(pentyloxy)butyl)amino) octanoate

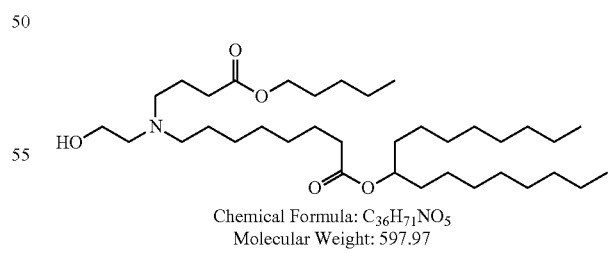

Chemical Formula: C$_{36}$H$_{71}$NO$_5$
Molecular Weight: 597.97

Compound 52 was synthesized according to the general procedure and Representative Procedure 1 described above. UPLC/ELSD: RT=3.11 min. MS (ES): m/z (MH$^+$) 598.90 for C$_{36}$H$_{71}$NO$_5$. $^1$H NMR (300 MHz, CDCl$_3$) δ: ppm 4.89 (p, 1H); 4.09 (t, 2H); 3.61 (br. m, 2H); 2.89-2.22 (br. m, 9H); 1.87 (br. m, 2H), 1.73-1.43 (m, 11H), 1.28 (m, 34H); 0.90 (m, 9H).

AR. Compound 53: heptadecan-9-yl 8-((4-(hexyloxy)-4-oxobutyl)(2-hydroxyethyl)amino) octanoate

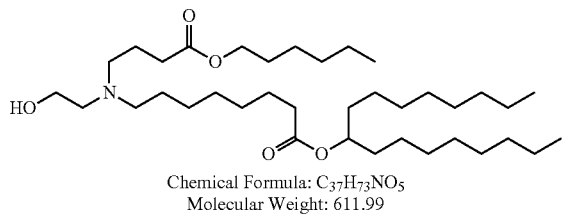 [SMILES: CCCCCCCCC(CCCCCCCC)OC(=O)CCCCCCCN(CCO)CCCC(=O)OCCCCCC]

Chemical Formula: C₃₇H₇₃NO₅
Molecular Weight: 611.99

Compound 53 was synthesized according to the general procedure and Representative Procedure 1 described above. UPLC/ELSD: RT=3.22 min. MS (ES): m/z (MH⁺) 612.92 for C₃₇H₇₃NO₅. ¹H NMR (300 MHz, CDCl₃) δ: ppm 4.86 (p, 1H); 4.06 (t, 2H); 3.55 (br. m, 2H); 2.68-2.38 (br. m, 5H); 2.28 (m, 4H); 1.79 (br. m, 2H); 1.71-0.96 (m, 48H); 0.88 (m, 9H).

AS. Compound 54: heptadecan-9-yl 8-((4-(heptyloxy)-4-oxobutyl)(2-hydroxyethyl)amino) octanoate

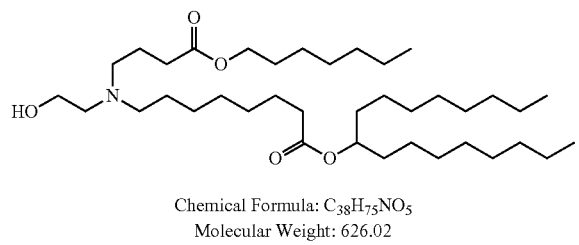 [SMILES: CCCCCCCCC(CCCCCCCC)OC(=O)CCCCCCCN(CCO)CCCC(=O)OCCCCCCC]

Chemical Formula: C₃₈H₇₅NO₅
Molecular Weight: 626.02

Compound 54 was synthesized according to the general procedure and Representative Procedure 1 described above. UPLC/ELSD: RT=3.28 min. MS (ES): m/z (MH⁺) 626.94 for C₃₈H₇₅NO₅. ¹H NMR (300 MHz, CDCl₃) δ: ppm 4.89 (p, 1H); 4.09 (t, 2H); 3.60 (br. m, 2H); 2.77-2.42 (br. m, 5H); 2.32 (m, 4H); 1.84 (br. m, 2H); 1.75-1.03 (m, 49H); 0.90 (m, 9H).

AT. Compound 55: heptadecan-9-yl 8-((4-((2-hexyl-cyclopropyl)methoxy)-4-oxobutyl)(2-hydroxyethyl) amino)octanoate

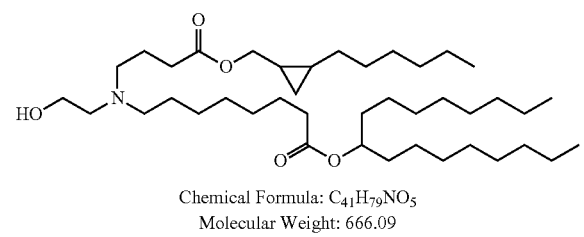 [SMILES: CCCCCCCCC(CCCCCCCC)OC(=O)CCCCCCCN(CCO)CCCC(=O)OCC1CC1CCCCCC]

Chemical Formula: C₄₁H₇₉NO₅
Molecular Weight: 666.09

Compound 55 was synthesized according to the general procedure and Representative Procedure 1 described above. UPLC/ELSD: RT=3.37 min. MS (ES): m/z (MH⁺) 667.04 for C₄₁H₇₉NO₅. ¹H NMR (300 MHz, CDCl₃) δ: ppm 4.83 (p, 1H); 4.15 (m, 1H); 3.95 (m, 1H); 3.53 (br. m, 2H); 2.66-2.39 (br. m, 5H); 2.34-2.19 (m, 4H); 1.78 (br. m, 2H); 1.66-0.98 (m, 50H); 0.85 (m, 10H); 0.70 (m, 1H); 0.00 (m, 1H).

AU. Compound 56: nonyl 8-((2-hydroxyethyl)(8-oxo-8-(tridecan-7-yloxy)octyl)amino) octanoate

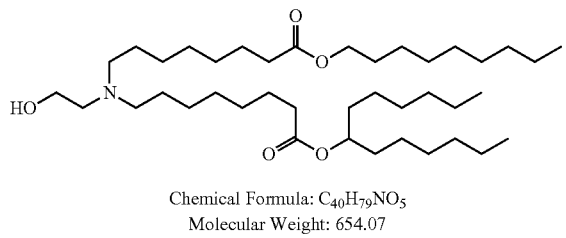 [SMILES: CCCCCCCCCOC(=O)CCCCCCCN(CCO)CCCCCCCC(=O)OC(CCCCCC)CCCCCC]

Chemical Formula: C₄₀H₇₉NO₅
Molecular Weight: 654.07

Compound 56 was synthesized according to the general procedure and Representative Procedure 1 described above. UPLC/ELSD: RT=3.28 min. MS (ES): m/z (MH⁺) 654.99 for C₄₀H₇₉NO₅. ¹H NMR (300 MHz, CDCl₃) δ: ppm 4.89 (p, 1H); 4.08 (t, 2H); 3.60 (br. m, 2H); 2.77-2.40 (br. m, 5H); 2.30 (m, 4H); 1.78-0.99 (m, 55H); 0.90 (m, 9H).

AV. Compound 57: nonan-5-yl 8-((2-hydroxyethyl)(8-(nonyloxy)-8-oxooctyl)amino) octanoate

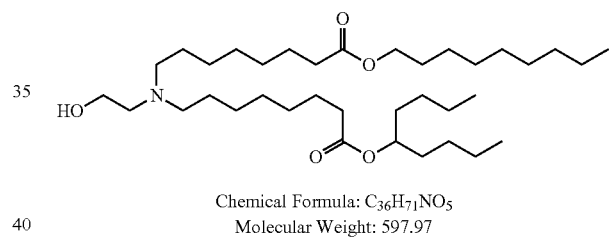

Chemical Formula: C₃₆H₇₁NO₅
Molecular Weight: 597.97

Compound 57 was synthesized according to the general procedure and Representative Procedure 1 described above. UPLC/ELSD: RT=2.88 min. MS (ES): m/z (MH⁺) 598.98 for C₃₆H₇₁NO₅. ¹H NMR (300 MHz, CDCl₃) δ: ppm 4.89 (p, 1H); 4.08 (t, 2H); 3.59 (br. m, 2H); 2.82-2.37 (br. m, 5H); 2.31 (m, 4H); 1.73-1.03 (m, 47H); 0.91 (m, 9H).

AW. Compound 58: heptan-4-yl 8-((2-hydroxy-ethyl)(8-(nonyloxy)-8-oxooctyl)amino) octanoate

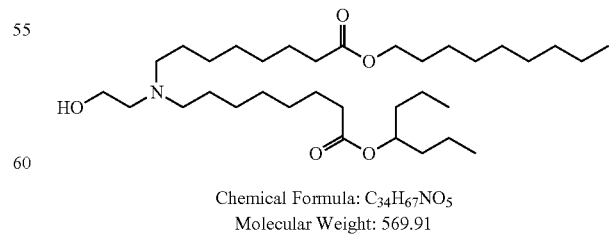

Chemical Formula: C₃₄H₆₇NO₅
Molecular Weight: 569.91

Compound 58 was synthesized according to the general procedure and Representative Procedure 1 described above. UPLC/ELSD: RT=2.67 min. MS (ES): m/z (MH⁺) 570.93 for $C_{34}H_{67}NO_5$. $^1H$ NMR (300 MHz, $CDCl_3$) δ: ppm 4.93 (p, 1H); 4.08 (t, 2H); 3.57 (br. m, 2H); 2.69-2.42 (br. m, 5H); 2.30 (m, 4H); 1.72-1.04 (m, 43H); 0.93 (m, 9H).

AX. Compound 59: nonyl 8-((2-hydroxyethyl)(8-oxo-8-(pentan-3-yloxy)octyl)amino) octanoate

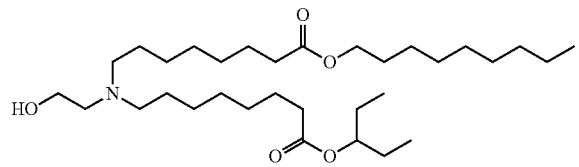

Chemical Formula: $C_{32}H_{63}NO_5$
Molecular Weight: 541.86

Compound 59 was synthesized according to the general procedure and Representative Procedure 1 described above. UPLC/ELSD: RT=2.39 min. MS (ES): m/z (MH$^+$) 542.80 for $C_{32}H_{63}NO_5$. $^1H$ NMR (300 MHz, $CDCl_3$) δ: ppm 4.78 (p, 1H); 4.08 (t, 2H); 3.57 (br. m, 2H); 2.71-2.39 (br. m, 5H); 2.31 (m, 4H); 1.77-1.05 (m, 39H); 0.90 (m, 9H).

AY. Compound 60: (5Z,12Z)-Heptadeca-5,12-dien-9-yl 8-((2-hydroxyethyl)(8-(nonyloxy)-8-oxooctyl)amino)octanoate (5Z,12Z)-Heptadeca-5,12-dien-9-ol

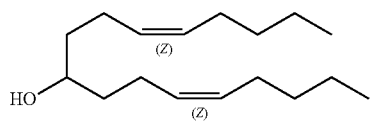

Chemical Formula: $C_{17}H_{32}O$
Molecular Weight: 252.44

To a solution of (Z)-1-bromooct-3-ene (6.2 g, 32.4 mmol) in THF (45 mL) Mg turnings were added (0.843 g, 34.7 mmol). The reaction was heated to 45° C. for 3 h. The reaction was cooled to 0° C. and ethyl formate (2.4 g, 32.4 mmol) in THF (5 mL) was added dropwise. The reaction was allowed to warm to rt and stir for 30 min. The reaction was cooled to 0° C. and quenched with water (15 mL) and 6N HCl (15 mL). The reaction was stirred until all the Mg was dissolved. Water (25 mL) was added and the mixture was extracted with hexanes (3×25 mL). The combined organic layer was washed with brine, separated, dried over $Na_2SO_4$, filtered, and evaporated under vacuum. The residue was dissolved in EtOH (20 mL), a solution of KOH in water (1.76 g in 8 mL of water) was added and allowed to stir for 15 min. EtOH was evaporated under vacuum. The residue was diluted with water (20 mL), acidified with 6N HCl (20 mL) and extracted with hexanes (3×). The combined organic layers were washed with brine, separated, dried over $Na_2SO_4$, filtered, and evaporated under vacuum. The residue was purified by silica gel chromatography with (0-5%) EtOAc in hexanes to obtain (5Z,12Z)-heptadeca-5,12-dien-9-ol (2.3 g, 9.1 mmol, 28%). $^1H$ NMR (300 MHz, $CDCl_3$) δ: ppm 5.41 (m, 4); 3.66 (m, 1H); 2.13 (m, 8H); 1.51 (m, 5H); 1.36 (m, 8H); 0.92 (m, 6H).

(5Z,12Z)-Heptadeca-5,12-dien-9-yl 8-((2-hydroxyethyl)(8-(nonyloxy)-8-oxooctyl)amino)octanoate

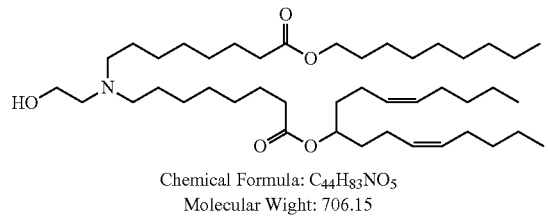 [SMILES: CCCC/C=C\CCC(CC/C=C\CCCC)OC(=O)CCCCCCCN(CCO)CCCCCCCC(=O)OCCCCCCCCC]

Chemical Formula: $C_{44}H_{83}NO_5$
Molecular Wight: 706.15

Compound 60 was synthesized according to the general procedure and Representative Procedure 1 described above. UPLC/ELSD: RT=3.36 min. MS (ES): m/z (MH$^+$) 707.10 for $C_{44}H_{83}NO_5$. $^1H$ NMR (300 MHz, $CDCl_3$) δ: ppm 5.37 (m, 4H); 4.92 (p, 1H); 4.08 (t, 2H); 3.57 (br. m, 2H); 2.73-2.38 (br. m, 5H); 2.31 (m, 4H); 2.04 (m, 8H); 1.73-1.01 (m, 47H); 0.92 (m, 9H).

AZ. Compound 61: (5Z,12Z)-heptadeca-5,12-dien-9-yl 8-((2-hydroxyethyl)(6-oxo-6-(undecyloxy)hexyl)amino)octanoate

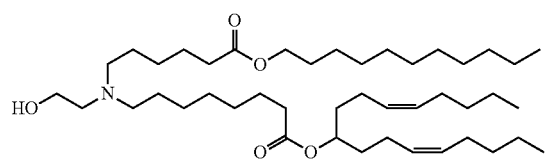

Chemical Formula: $C_{44}H_{83}NO_5$
Molecular Wight: 706.15

Compound 61 was synthesized according to the general procedure and Representative Procedure 1 described above. UPLC/ELSD: RT=3.39 min. MS (ES): m/z (MH$^+$) 707.10 for $C_{44}H_{83}NO_5$. $^1H$ NMR (300 MHz, $CDCl_3$) δ: ppm 5.37 (m, 4H); 4.92 (p, 1H); 4.08 (t, 2H); 3.58 (br. m, 2H); 2.70-2.41 (br. m, 5H); 2.32 (m, 4H); 2.04 (m, 8H); 1.77-1.03 (m, 47H); 0.92 (m, 9H).

X1. Compound 65: 1-Cyclopropylnonyl 8-((8-(heptadecan-9-yloxy)-8-oxooctyl)(2-hydroxyethyl)amino)octanoate

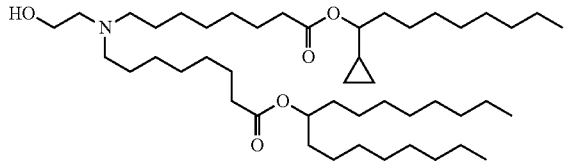

Chemical Formula: $C_{47}H_{91}NO_5$
Molecular Weight: 750.247

Compound 65 was synthesized according to the general procedure and Representative Procedure 1 described above. UPLC/ELSD: RT=3.72 min. MS (ES): m/z (MH$^+$) 750.9 for $C_{47}H_{91}NO_5$. $^1H$ NMR (300 MHz, $CDCl_3$) δ: ppm 4.89 (m, 1H); 4.28 (m, 1H); 3.54 (m, 2H); 2.59 (m, 2H); 2.46 (m, 4H); 2.29 (m, 4H), 1.73-1.18 (m, 61H); 0.90 (m, 10H); 0.62-0.33 (m, 3H); 0.28 (m, 1H).

X2. Compound 66: Heptadecan-9-yl 8-((2-hydroxyethyl)(8-oxo-8-((4-pentylcyclohexyl)oxy)octyl)amino)octanoate

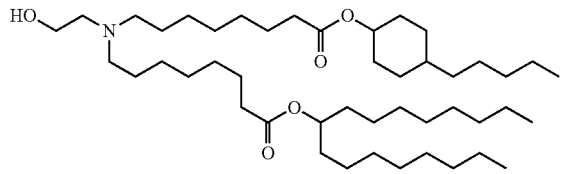

Chemical Formula: $C_{46}H_{89}NO_5$
Molecular Weight: 736.220

Compound 66 was synthesized according to the general procedure and Representative Procedure 1 described above. UPLC/ELSD: RT=3.72 min. MS (ES): m/z (MH$^+$) 736.9 for $C_{46}H_{89}NO_5$. $^1$H NMR (300 MHz, CDCl$_3$) δ: ppm 5.00 (m, 0.5H); 4.89 (m, 1H); 4.68 (m, 0.6H); 3.56 (m, 2H), 2.61 (br. m, 2H); 2.48 (m, 4H); 2.30 (m, 4H); 1.98 (m, 1H); 1.82 (m, 2H); 1.73-1.14 (m, 61H); 1.04 (m, 1H); 0.90 (m, 9H).

X3. Compound 67: Heptadecan-9-yl 8-((2-hydroxyethyl)(4-oxo-4-((4-pentylcyclohexyl)oxy)butyl)amino)octanoate

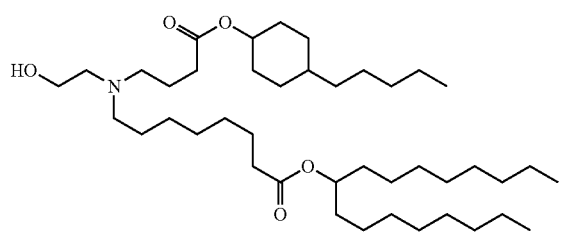

Chemical Formula: $C_{42}H_{81}NO_5$
Molecular Weight: 680.112

Compound 67 was synthesized according to the general procedure and Representative Procedure 1 described above. UPLC/ELSD: RT=3.56 min. MS (ES): m/z (MH$^+$) 680.8 for $C_{42}H_{81}NO_5$. $^1$H NMR (300 MHz, CDCl$_3$) δ: ppm 5.01 (m, 0.4H); 4.89 (m, 1H); 4.68 (m, 0.6H); 3.59 (m, 2H), 2.72-2.43 (br. m, 6H); 2.30 (m, 4H); 1.98 (m, 1H); 1.83 (m, 4H); 1.69-1.44 (m, 10H); 1.28 (m, 41H); 1.03 (m, 1H); 0.90 (m, 9H).

X4. Compound 68: Heptadecan-9-yl 8-((2-hydroxyethyl)(6-oxo-6-((4-pentylcyclohexyl)oxy)hexyl)amino)octanoate

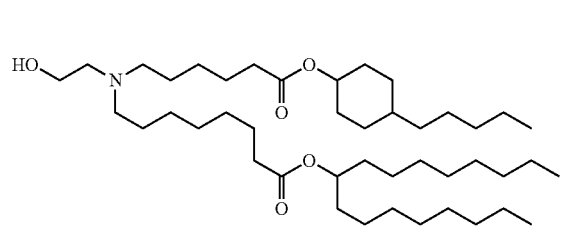

Chemical Formula: $C_{44}H_{85}NO_5$
Molecular Weight: 708.166

Compound 68 was synthesized according to the general procedure and Representative Procedure 1 described above. UPLC/ELSD: RT=3.66 min. MS (ES): m/z (MH$^+$) 708.9 for $C_{44}H_{85}NO_5$. $^1$H NMR (300 MHz, CDCl$_3$) δ: ppm 5.00 (m, 0.5H); 4.89 (m, 1H); 4.68 (m, 0.6H); 3.55 (m, 2H), 2.66-2.39 (br. m, 6H); 2.30 (m, 4H); 1.97 (m, 1H); 1.83 (m, 2H); 1.73-1.41 (m, 15H); 1.41-1.17 (m, 42H); 1.04 (m, 1H); 0.90 (m, 9H).

XX1. Compound 69: Heptadecan-9-yl 8-((2,3-dihydroxypropyl)(8-(nonyloxy)-8-oxooctyl)amino)octanoate

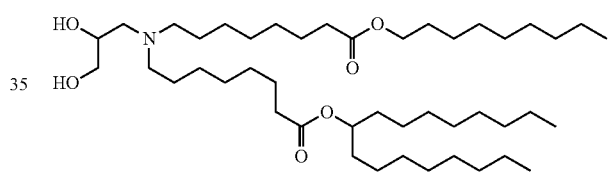

Chemical Formula: $C_{45}H_{89}NO_6$
Molecular Weight: 740.21

Compound 69 was synthesized according to the general procedure and Representative Procedure 1 described above. UPLC/ELSD: RT=3.60 min. MS (ES): m/z (MH$^+$) 741.0 for $C_{45}H_{89}NO_6$. $^1$H NMR (300 MHz, CDCl$_3$) δ: ppm 4.89 (p, 1H); 4.08 (t, 2H); 3.76 (br. m, 2H); 3.51 (m, 1H); 2.57 (m, 6H); 2.31 (m, 4H); 1.71-1.41 (m, 14H); 1.41-1.12 (m, 48H); 0.90 (m, 9H).

XX2. Compound 70: Heptadecan-9-yl 8-((4-(decan-2-yloxy)-4-oxobutyl)(2-hydroxyethyl)amino)octanoate

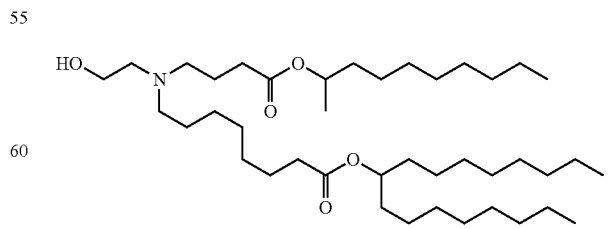

Chemical Formula: $C_{41}H_{81}NO_5$
Molecular Weight: 667.61

Compound 70 was synthesized according to the general procedure and Representative Procedure 1 described above. UPLC/ELSD: RT=3.44 min. MS (ES): m/z (MH+) 668.9 for $C_{41}H_{81}NO_5$. $^1$H NMR (300 MHz, $CDCl_3$) δ: ppm 4.91 (m, 2H); 3.57 (m, 2H); 2.71-2.40 (m, 5H); 2.30 (m, 4H), 1.80 (m, 2H); 1.71-1.40 (m, 11H); 1.39-1.05 (m, 45H); 0.90 (m, 9H).

X5. Compound 71: Heptadecan-9-yl 8-((2-hydroxyethyl)(4-oxo-4-(tetradecan-6-yloxy)butyl)amino)octanoate

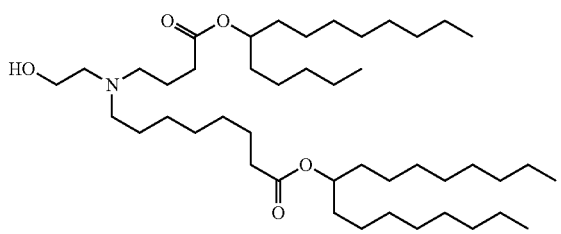

Chemical Formula: $C_{45}H_{89}NO_5$
Molecular Weight: 724.209

Compound 71 was synthesized according to the general procedure and Representative Procedure 1 described above. UPLC/ELSD: RT=3.72 min. MS (ES): m/z (MH+) 724.9 for $C_{45}H_{89}NO_5$. $^1$H NMR (300 MHz, $CDCl_3$) δ: ppm 4.89 (m, 2H); 3.56 (m, 2H); 2.70-2.41 (m, 6H); 2.33 (m, 4H), 1.80 (m, 2H); 1.69-1.41 (m, 13H); 1.28 (m, 48H); 0.90 (m, 12H).

XX3. Compound 72: Heptadecan-9-yl 8-((2-hydroxyethyl)(4-oxo-4-(undecan-3-yloxy)butyl)amino)octanoate

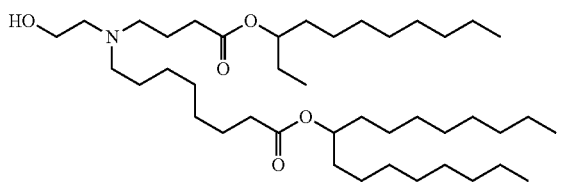

Chemical Formula: $C_{42}H_{83}NO_5$
Molecular Weight: 682.13

Compound 72 was synthesized according to the general procedure and Representative Procedure 1 described above. UPLC/ELSD: RT=3.57 min. MS (ES): m/z (MH+) 683.0 for $C_{42}H_{83}NO_5$. $^1$H NMR (300 MHz, $CDCl_3$) δ: ppm 4.86 (m, 2H); 3.58 (br. m, 2H); 2.75-2.41 (br. m, 5H); 2.30 (m, 4H), 1.81 (br. m, 2H); 1.70-1.42 (m, 13H); 1.40-1.18 (m, 42H); 0.90 (m, 12H).

X6. Compound 73: Heptadecan-9-yl 8-((2-hydroxyethyl)(4-oxo-4-(pentadecan-7-yloxy)butyl)amino)octanoate

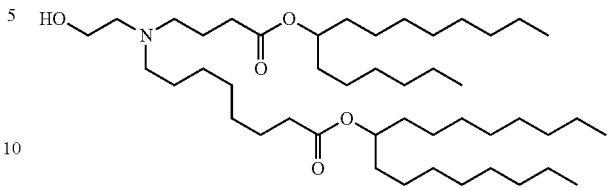

Chemical Formula: $C_{46}H_{91}NO_5$
Molecular Weight: 738.236

Compound 73 was synthesized according to the general procedure and Representative Procedure 1 described above. UPLC/ELSD: RT=3.80 min. MS (ES): m/z (MH+) 739.09 for $C_{46}H_{91}NO_5$. $^1$H NMR (300 MHz, $CDCl_3$) δ: ppm 4.89 (m, 2H); 3.59 (br. m, 2H); 2.81-2.43 (br. m, 6H); 2.31 (m, 4H); 1.83 (m, 2H); 1.69-1.42 (m, 12H); 1.28 (m, 50H); 0.90 (m, 12H).

X7. Compound 74: Heptadecan-9-yl 8-((4-(dodecan-4-yloxy)-4-oxobutyl)(2-hydroxyethyl)amino)octanoate

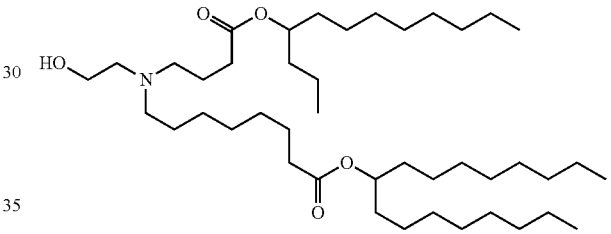

Chemical Formula: $C_{43}H_{85}NO_5$
Molecular Weight: 696.155

Compound 74 was synthesized according to the general procedure and Representative Procedure 1 described above. UPLC/ELSD: RT=3.68 min. MS (ES): m/z (MH+) 696.9 for $C_{43}H_{85}NO_5$. $^1$H NMR (300 MHz, $CDCl_3$) δ: ppm 4.89 (m, 2H); 3.56 (m, 2H); 2.70-2.41 (m, 6H); 2.30 (m, 4H), 1.80 (m, 2H); 1.70-1.40 (m, 12H); 1.28 (m, 44H); 0.90 (m, 12H).

XX4. Compound 75: Heptadecan-9-yl 8-((2-hydroxyethyl)(6-oxo-6-(undecan-3-yloxy)hexyl)amino)octanoate

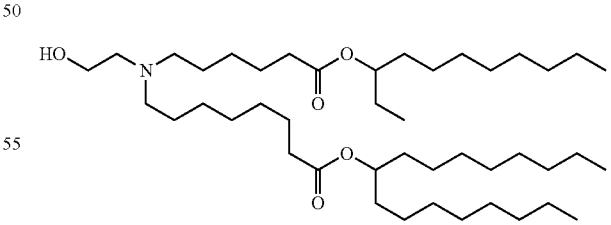

Chemical Formula: $C_{44}H_{87}NO_5$
Molecular Weight: 710.18

Compound 75 was synthesized according to the general procedure and Representative Procedure 1 described above. UPLC/ELSD: RT=3.67 min. MS (ES): m/z (MH+) 711.1 for $C_{44}H_{87}NO_5$. $^1$H NMR (300 MHz, $CDCl_3$) δ: ppm 4.86 (m, 2H); 3.57 (m, 2H); 2.72-2.40 (br. m, 5H); 2.30 (m, 4H); 1.70-1.42 (m, 16H); 1.28 (m, 45H); 0.90 (m, 12H).

XX5. Compound 79: Nonyl 8-((2-hydroxyethyl)(8-oxo-8-((4-pentylcyclohexyl)oxy)octyl)amino)octanoate

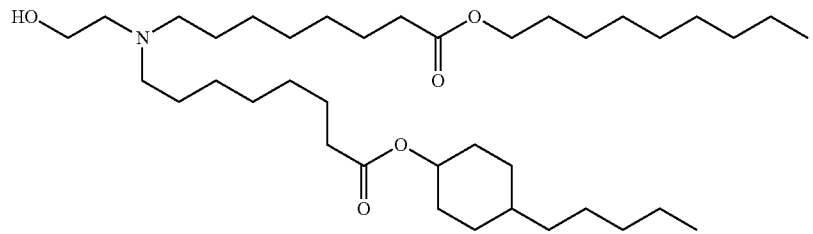

Chemical Formula: $C_{38}H_{73}NO_5$
Molecular Weight: 624.00

Compound 79 was synthesized according to the general procedure and Representative Procedure 1 described above. UPLC/ELSD: RT=3.10 min. MS (ES): m/z (MH$^+$) 624.8 for $C_{38}H_{73}NO_5$. $^1$H NMR (300 MHz, CDCl$_3$) δ: ppm 5.00 (br. m, 0.5H); 4.68 (m, 0.5H); 4.08 (t, 2H); 3.56 (m, 2H); 2.72-2.38 (m, 6H); 2.31 (m, 4H), 1.97 (m, 1H); 1.82 (m, 2H); 1.73-0.95 (m, 48H), 0.90 (m, 6H).

XX6. Compound 80: [1,1'-Bi(cyclohexan)]-4-yl 8-((2-hydroxyethyl)(8-(nonyloxy)-8-oxooctyl)amino)octanoate

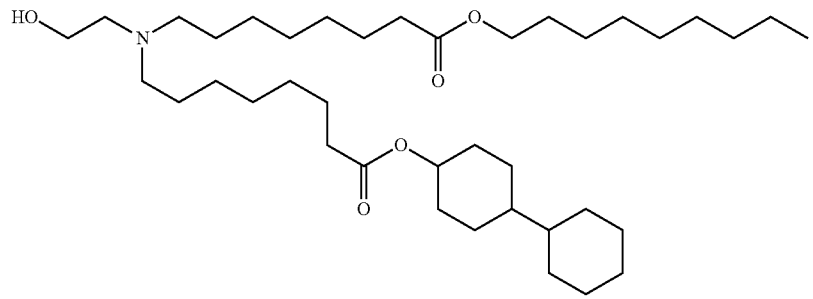

Chemical Formula: $C_{39}H_{73}NO_5$
Molecular Weight: 636.02

Compound 80 was synthesized according to the general procedure and Representative Procedure 1 described above. UPLC/ELSD: RT=3.10 min. MS (ES): m/z (MH$^+$) 636.9 for $C_{39}H_{73}NO_5$. $^1$H NMR (300 MHz, CDCl$_3$) δ: ppm 5.01 (br. m, 0.5H); 4.65 (m, 0.5H); 4.08 (t, 2H); 3.56 (m, 2H); 2.69-2.36 (m, 6H); 2.31 (m, 4H); 2.07-0.84 (m, 57H).

XX7. Compound 81: Cyclopentadecyl 8-((2-hydroxyethyl)(8-(nonyloxy)-8-oxooctyl)amino)octanoate

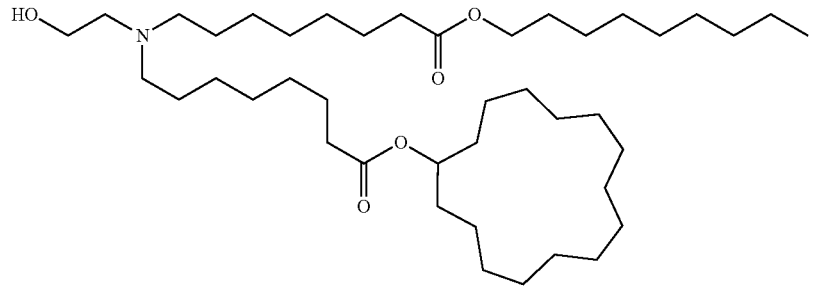

Chemical Formula: $C_{42}H_{81}NO_5$
Molecular Weight: 680.11

Compound 81 was synthesized according to the general procedure and Representative Procedure 1 described above. UPLC/ELSD: RT=3.36 min. MS (ES): m/z (MH$^+$) 681.0 for $C_{42}H_{81}NO_5$. $^1$H NMR (300 MHz, CDCl$_3$) δ: ppm 4.91 (p, 1H); 4.08 (t, 2H); 3.57 (br. m, 2H); 2.74-2.39 (m, 6H); 2.30 (m, 4H), 1.73-1.03 (m, 62H), 0.90 (m, 3H).

XX8. Compound 94: Heptadecan-9-yl) 8-(benzyl(8-nonyloxy)-8-oxooctyl)amino)octanoate Heptadecan-9-yl 8-(benzylamino)octanoate

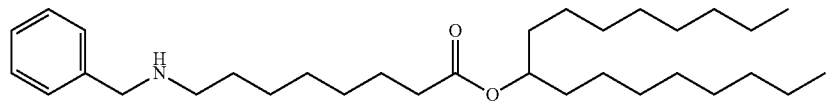

Chemical Formula: $C_{32}H_{57}NO_2$
Molecular Weight: 487.81

A solution of heptadecan-9-yl 8-bromooctanoate (250 mg, 0.542 mmol) in phenylmethanamine (1.2 mL, 10.83 mmol) was allowed to stir at rt for 6 h. The reaction was cooled to rt and solvents were evaporated in vacuo. The residue was taken-up in ethyl acetate and washed with saturated aqueous sodium bicarbonate. The organic layer was separated and washed with brine, dried over Na$_2$SO$_4$ and evaporated in vacuo. The residue was purified by silica gel chromatography (20-100% (mixture of 1% NH$_4$OH, 20% MeOH in dichloromethane) in dichloromethane) to obtain heptadecan-9-yl 8-(benzylamino)octanoate (200 mg, 0.41 mmol, 76%). UPLC/ELSD: RT=2.87 min. MS (ES): m/z (MH$^+$) 488.4 for $C_{32}H_{57}NO_2$. $^1$H NMR (300 MHz, CDCl$_3$) δ: ppm 7.35-7.25 (br. m, 5H); 4.89 (p, 1H); 3.81 (s, 2H); 2.65 (t, 2H); 2.29 (t, 2H); 1.65-1.51 (br. m, 8H); 1.28 (m, 30H); 0.90 (m, 6H).

Heptadecan-9-yl 8-(benzyl(8-(nonyloxy)-8-oxooctyl)amino)octanoate

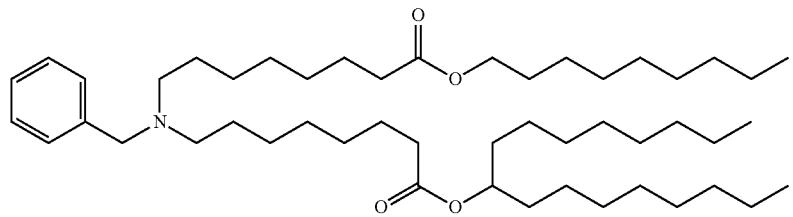

Chemical Formula: $C_{49}H_{89}NO_4$
Molecular Weight: 756.25

A solution of heptadecan-9-yl 8-(benzylamino)octanoate (200 mg, 0.41 mmol), nonyl 8-bromooctanoate (172 mg, 0.49 mmol) and N,N-diisopropylethylamine (100 μL, 0.57 mmol) were dissolved in ethanol and was allowed to stir at 62° C. for 48 h. The reaction was cooled to rt and solvents were evaporated in vacuo. The residue was taken-up in ethyl acetate and washed with saturated aqueous sodium bicarbonate. The organic layer was separated and washed with brine, dried over Na$_2$SO$_4$ and evaporated in vacuo. The residue was purified by silica gel chromatography (0-100% (mixture of 1% NH$_4$OH, 20% MeOH in dichloromethane) in dichloromethane) to obtain heptadecan-9-yl 8-(benzyl(8-(nonyloxy)-8-oxooctyl)amino)octanoate (138 mg, 0.18 mmol, 45%). UPLC/ELSD: RT=3.78 min. MS (ES): m/z (MH$^+$) 757.0 for $C_{49}H_{89}NO_4$. $^1$H NMR (300 MHz, CDCl$_3$) δ: ppm 7.33-7.23 (br. m, 5H); 4.89 (p, 1H); 4.08 (t, 2H); 3.55 (s, 2H); 2.40 (m, 4H); 2.30 (m, 4H); 1.64-1.28 (br. m, 62H); 0.90 (m, 9H).

X8. Compound 96: 7-((8-(Heptadecan-9-yloxy)-8-oxooctyl)(2-hydroxyethyl)amino)heptyl decanoate

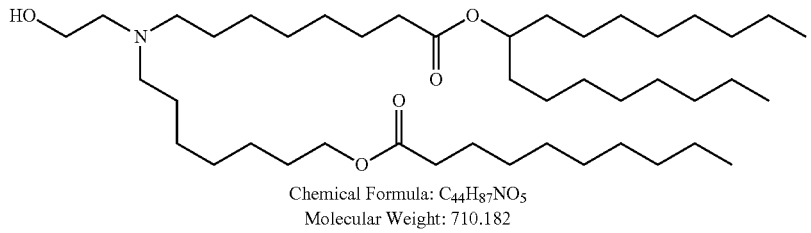 [SMILES: CCCCCCCCCC(=O)OCCCCCCCN(CCO)CCCCCCCC(=O)OC(CCCCCCCC)CCCCCCCC]

Chemical Formula: $C_{44}H_{87}NO_5$
Molecular Weight: 710.182

Compound 96 was synthesized according to the general procedure and Representative Procedure 1 described above. UPLC/ELSD: RT=2.74 min. MS (ES): m/z (MH$^+$) 711.0 for $C_{44}H_{87}NO_5$. $^1$H NMR (300 MHz, CDCl$_3$) δ: ppm 4.89 (m, 1H); 4.08 (t, 2H); 3.61 (m, 2H); 2.88-2.37 (br. m, 6H); 2.31 (m, 4H), 1.79-1.04 (m, 62H); 0.90 (m, 9H).

X9. Compound 98: 8-((8-(Heptadecan-9-yloxy)-8-oxooctyl)(2-hydroxyethyl)amino)octan-2-yl decanoate Octane-1,7-diol

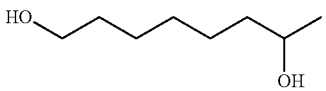

Chemical Formula: $C_8H_{18}O_2$
Molecular Weight: 146.230

A solution of 7-oxooctanoic acid (4 g, 25.29 mmol) in THF (10 mL) was added to a stirred solution of LAH in THF (70 mL) under N$_2$ at 0° C. The mixture was allowed to warm to rt and stir at rt for 4 h, after which time 10 mL of sat. Na$_2$SO$_4$.10H$_2$O (aq) was added to the solution slowly. White solid crashed out. Additional solid Na$_2$SO$_4$.10H$_2$O was added and the mixture was filtered through a plug of celite. The filtrate was diluted with EtOAc and washed with brine. The organic layer was separated, dried over Na$_2$SO$_4$, filtered, and evaporated under vacuum. The residue was purified by silica gel chromatography with (0-40%) EtOAc in hexanes to obtain octane-1,7-diol (2.97 g, 20.31 mmol, 80%). $^1$H NMR (300 MHz, CDCl$_3$) δ: ppm 3.81 (m, 1H); 3.66 (t, 2H); 1.66-1.31 (m, 12H); 1.22 (d, 3H).

8-((tert-Butyldiphenylsilyl)oxy)octan-2-ol

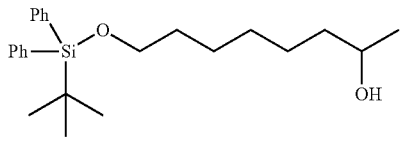

Chemical Formula: $C_{24}H_{36}O_2Si$
Molecular Weight: 384.635

To a solution of octane-1,7-diol (1 g, 6.84 mmol) in DCM (75 mL) at 0° C. imidazole (0.94 g, 13.81 mmol) was added followed by slow addition of a solution of tert-butyl(chloro)diphenylsilane (2.14 mL, 8.21 mmol) in DCM (using dropping funnel). The reaction allowed stir at 0° C. for 1.5 h. The reaction was quenched with saturated NH$_4$Cl$_{(aq)}$. The aqueous layer was extracted 3 times with a DCM (3×50 mL). The organic layer was dried over anhydrous MgSO$_4$ and filtered, and the solvent was evaporated. The crude product was purified by flash silica gel column chromatography 0-10% EtOAc in hexanes to obtain 8-((tert-butyldiphenylsilyl)oxy)octan-2-ol (2.29 g, 5.95 mmol, 87%). $^1$H NMR (300 MHz, CDCl$_3$) δ: ppm 7.69 (m, 4H); 7.42 (m, 6H); 3.80 (m, 1H); 3.68 (t, 2H); 1.59 (m, 2H); 1.50-1.26 (m, 9H); 1.21 (d, 3H); 1.07 (s, 9H).

8-((tert-Butyldiphenylsilyl)oxy)octan-2-yl decanoate

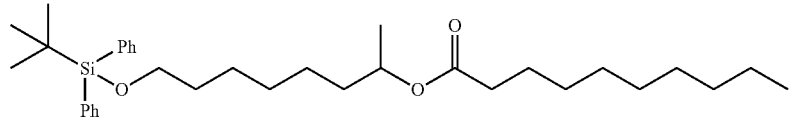

Chemical Formula: $C_{34}H_{54}O_3Si$
Molecular Weight: 538.888

8-((tert-Butyldiphenylsilyl)oxy)octan-2-yl decanoate was synthesized according to Method A. ¹H NMR (300 MHz, CDCl₃) δ: ppm 7.69 (m, 4H); 7.42 (m, 6H); 4.92 (m, 1H); 3.67 (t, 2H); 2.29 (t, 2H); 1.67-1.42 (m, 6H); 1.41-1.17 (m, 21H); 1.07 (s, 9H); 0.90 (m, 3H).

8-Hydroxyoctan-2-yl decanoate

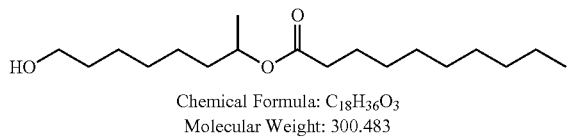 [SMILES: CCCCCCCCCC(=O)OC(C)CCCCCCO]

Chemical Formula: C₁₈H₃₆O₃
Molecular Weight: 300.483

To a solution of 8-[(tert-butyldiphenylsilyl)oxy]octan-2-yl decanoate (1.08 g, 2 mmol) in THF was added TBAF (8.02 mL 1 M solution in THF, 8.02 mmol) and the mixture was allowed to stir at rt for 3 h. The organic solvents were evaporated under vacuum. The residue was diluted with EtOAc and washed with sat. NaHCO₃, followed by brine. The organic layer was separated, dried over Na₂SO₄, filtered, and evaporated under vacuum. The residue was purified by silica gel chromatography with (0-40%) EtOAc in hexanes to obtain 8-hydroxyoctan-2-yl decanoate (0.55 g, 1.82 mmol, 91%). ¹H NMR (300 MHz, CDCl₃) δ: ppm 4.91 (m, 1H); 3.66 (t, 2H); 2.29 (t, 2H); 1.72-1.17 (m, 28H); 0.90 (m, 3H).

8-((8-(Heptadecan-9-yloxy)-8-oxooctyl)(2-hydroxyethyl)amino)octan-2-yl decanoate

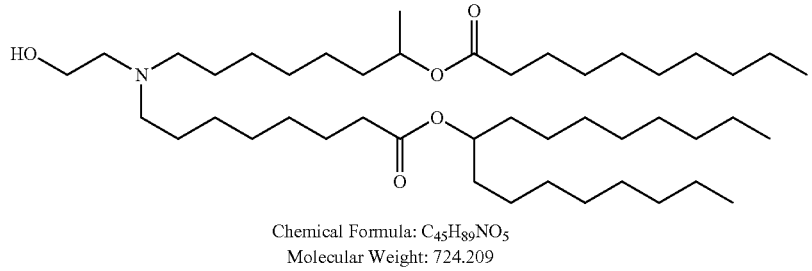 [SMILES: CCCCCCCCCC(=O)OC(C)CCCCCCN(CCO)CCCCCCCC(=O)OC(CCCCCCCC)CCCCCCCC]

Chemical Formula: C₄₅H₈₉NO₅
Molecular Weight: 724.209

Compound 98 was synthesized according to the general procedure and Representative Procedure 1 described above. UPLC/ELSD: RT=3.55 min. MS (ES): m/z (MH⁺) 725.0 for C₄₅H₈₉NO₅. ¹H NMR (300 MHz, CDCl₃) δ: ppm 4.89 (m, 2H); 3.58 (br. m, 2H); 2.77-2.40 (m, 6H); 2.29 (m, 4H); 1.72-1.41 (m, 14H); 1.28 (m, 51H); 0.90 (m, 9H).

X10. Compound 101: Heptadecan-9-yl 8-((2-(4-methylpiperazin-1-yl)ethyl)(8-(nonyloxy)-8-oxooctyl)amino)octanoate Heptadecan-9-yl 8-((2-chloroethyl)(8-(nonyloxy)-8-oxooctyl)amino)octanoate

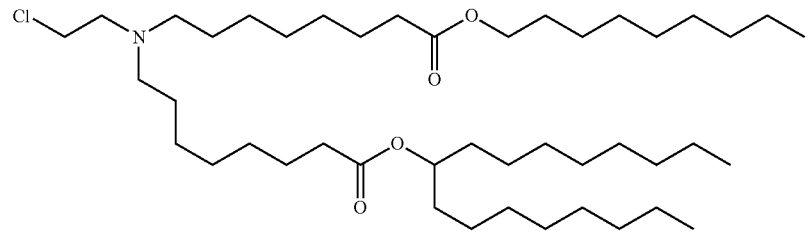

Chemical Formula: C₄₄H₈₆ClNO₄
Molecular Weight: 728.63

A solution of heptadecan-9-yl 8-((2-hydroxyethyl)(8-(nonyloxy)-8-oxooctyl)amino)octanoate (1100 mg, 1.55 mmol) in dichloromethane (25 mL) at 0° C. was added N-Chlorosuccinimide in one portion. The reaction was allowed to stir at 0° C. for 1 h followed by 1 h at room temperature. Added 90 mL of hexanes and allowed the reaction to stir at room temperature for 20 min. Filtered off white solid through a silica gel plug and washed three times with hexanes. Organic layers were concentrated in vacuo. $^1$H NMR (300 MHz, CDCl$_3$) δ: ppm 4.89 (p, 1H); 4.08 (t, 2H); 3.57 (m, 2H); 2.85 (m, 2H); 2.54 (m, 4H); 2.33-2.27 (m, 4H); 1.66-1.28 (br. m, 62H); 0.90 (m, 9H).

Heptadecan-9-yl 8-((2-(4-methylpiperazin-1-yl)ethyl)(8-(nonyloxy)-8-oxooctyl)amino)octanoate

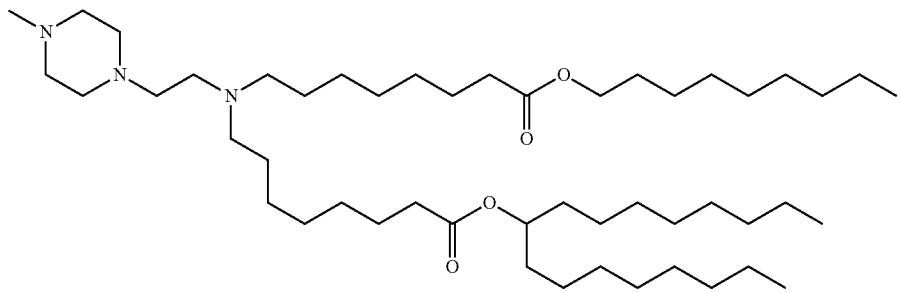

Chemical Formula: C$_{49}$H$_{97}$N$_3$O$_4$
Molecular Weight: 792.33

A solution of 1-methylpiperazine (15 mg, 0.151 mmol), heptadecan-9-yl 8-((2-chloroethyl)(8-(nonyloxy)-8-oxooctyl)amino)octanoate (110 mg, 0.151 mmol), K$_2$CO$_3$ (42 mg, 0.302 mmol) and KI (3 mg, 0.0151 mmol) were dissolved in 1:1 THF:MeCN (1 mL:1 mL). The reaction was allowed to stir at 65° C. for 18 hours. The reaction was cooled to room temperature, filtered and washed with hexanes and EtOAc. The organic filtrate was transferred to separatory funnel and washed with water and brine. Dried organic layers over Na$_2$SO$_4$, filtered and concentrated in vacuo. The residue was purified by silica gel chromatography [0-100% (mixture of 1% NH$_4$OH, 20% MeOH in dichloromethane) in dichloromethane] to obtain heptadecan-9-yl 8-((2-(4-methylpiperazin-1-yl)ethyl)(8-(nonyloxy)-8-oxooctyl)amino)octanoate (36 mg, 0.045 mmol, 30%). UPLC/ELSD: RT=3.25 min. MS (ES): m/z (MH$^+$) 792.8 for C$_{49}$H$_{97}$N$_3$O$_4$. $^1$H NMR (300 MHz, CDCl$_3$) δ: ppm 4.88 (p, 1H); 4.08 (t, 2H); 2.57-2.45 (br. m, 20H); 2.31 (m, 3H); 1.64-1.28 (br. m, 62H); 0.90 (m, 9H).

X11. Compound 103: Heptadecan-9-yl 8-((2-(4-methylpiperazin-1-yl)ethyl)(8-(nonyloxy)-8-oxooctyl)amino)octanoate Heptadecan-9-yl 8-((2-chloroethyl)(8-(nonyloxy)-8-oxooctyl)amino)octanoate

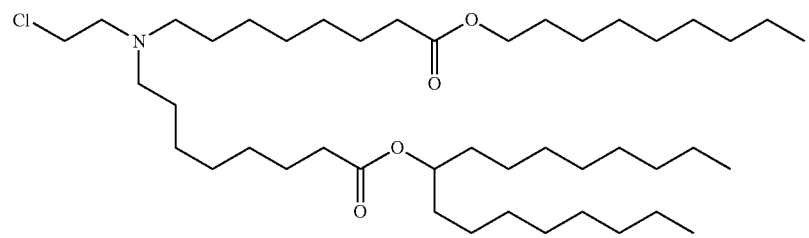

Chemical Formula: C$_{44}$H$_{86}$ClNO$_4$
Molecular Weight: 728.63

To a stirred solution of heptadecan-9-yl 8-((2-hydroxyethyl)(8-(nonyloxy)-8-oxooctyl)amino)octanoate (1100 mg, 1.55 mmol) in dichloromethane (25 mL) at 0° C. was added N-Chlorosuccinimide in one portion. The reaction was allowed to stir at 0° C. for 1 h followed by 1 h at room temperature. Added 90 mL of hexanes and allowed the reaction to stir at room temperature for 20 min. Filtered off white solid through a silica gel plug and washed three times with hexanes. Organic layers were concentrated in vacuo. $^1$H NMR (300 MHz, CDCl$_3$) δ: ppm 4.89 (p, 1H); 4.08 (t, 2H); 3.57 (m, 2H); 2.85 (m, 2H); 2.54 (m, 4H); 2.33-2.27 (m, 4H); 1.66-1.28 (br. m, 62H); 0.90 (m, 9H).

Heptadecan-9-yl 8-((2-morpholinoethyl)(8-(nonyloxy)-8-oxooctyl)amino)octanoate

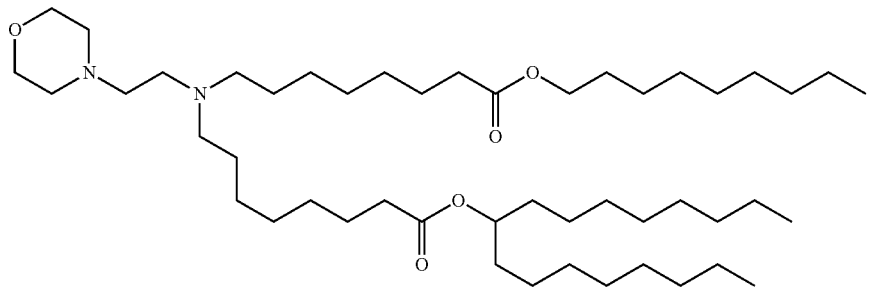

Chemical Formula: C$_{48}$H$_{94}$N$_2$O$_5$
Molecular Weight: 779.29

A solution of morpholine (13 mg, 0.151 mmol), heptadecan-9-yl 8-((2-chloroethyl)(8-(nonyloxy)-8-oxooctyl)amino)octanoate (110 mg, 0.151 mmol), K$_2$CO$_3$ (42 mg, 0.302 mmol) and KI (3 mg, 0.0151 mmol) were dissolved in 1:1 THF:MeCN (1 mL:1 mL). The reaction was allowed to stir at 65° C. for 18 hours. The reaction was cooled to room temperature, filtered and washed with hexanes and EtOAc. The organic filtrate was transferred to separatory funnel and washed with water and brine. Dried organic layers over Na$_2$SO$_4$, filtered and concentrated in vacuo. The residue was purified by silica gel chromatography [0-100% (mixture of 1% NH$_4$OH, 20% MeOH in dichloromethane) in dichloromethane] to obtain heptadecan-9-yl 8-((2-(4-methylpiperazin-1-yl)ethyl)(8-(nonyloxy)-8-oxooctyl)amino)octanoate (58 mg, 0.074 mmol, 49%). UPLC/ELSD: RT=3.53 min. MS (ES): m/z (MH$^+$) 779.8 for C$_{48}$H$_{94}$N$_2$O$_5$. $^1$H NMR (300 MHz, CDCl$_3$) δ: ppm 4.86 (p, 1H); 4.05 (t, 2H); 3.70 (m, 4H); 2.59-2.54 (m, 2H); 2.48-2.38 (m, 10H); 2.31-2.25 (m, 4H); 1.64-1.26 (br. m, 62H); 0.88 (m, 9H).

XX9. Compound 108: Heptadecan-9-yl 8-((3-acetamidopropyl)(8-(nonyloxy)-8-oxooctyl)amino)octanoate

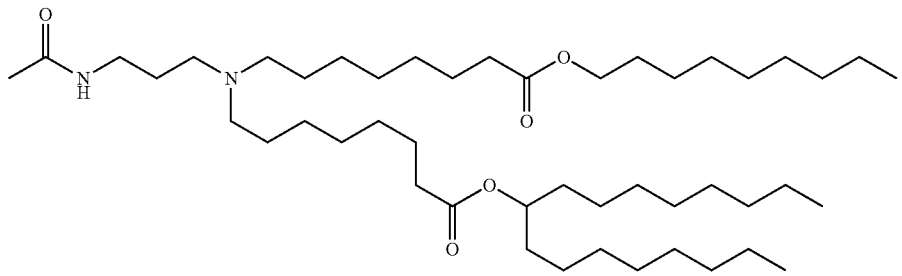

Chemical Formula: C$_{47}$H$_{92}$N$_2$O$_5$
Molecular Weight: 765.26

To a solution of heptadecan-9-yl 8-((3-aminopropyl)(8-(nonyloxy)-8-oxooctyl)amino)octanoate (400 mg, 0.553 mmol) and triethylamine (0.15 mL, 1.10 mmol) in 10 mL dichloromethane was added dropwise at 0° C. acetyl chloride (47 µL, 0.66 mmol), and the reaction mixture was allowed to warm to room temperature for 16 h. MS showed the product, and the mixture was diluted with dichloromethane and washed with saturated sodium bicarbonate and brine. After it was dried over sodium sulfate, the filtrate was concentrated and purified by ISCO (SiO$_2$: MeOH/CH$_2$Cl$_2$/ 1% NH$_4$OH 0 to 5%) to provide the product as a colorless oil (300 mg, 71%). LC/UV (202 nm): RT=9.14 min. MS (APCI): m/z (MH$^+$) 765.7. $^1$H NMR (300 MHz, CDCl$_3$) δ: ppm 7.41 (bs, 1H); 4.85 (p, 1H, J=6.0 Hz); 4.04 (t, 2H, J=6.6 Hz); 3.40-3.25 (m, 2H); 2.53-2.23 (m, 10H); 1.91 (s, 3H); 1.65-1.16 (m, 64H); 0.86 (m, 9H).

XX10. Compound 109: Heptadecan-9-yl 8-((3-(methylsulfonamido)propyl)(8-(nonyloxy)-8-oxooctyl)amino)octanoate

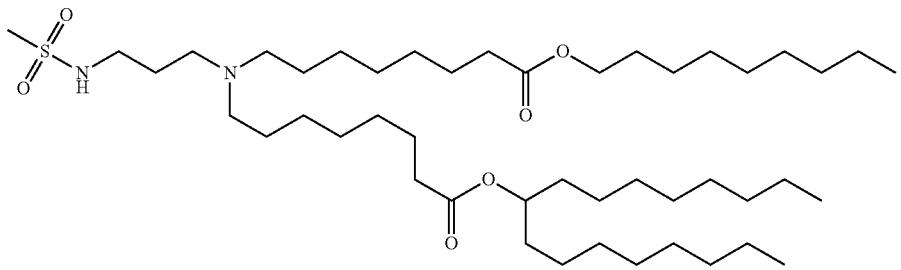

Chemical Formula: C$_{46}$H$_{92}$N$_2$O$_6$S
Molecular Weight: 801.31

Methanesulfonyl chloride (51 µL, 0.66 mmol) was added dropwise to a 0° C. solution of heptadecan-9-yl 8-((3-aminopropyl)(8-(nonyloxy)-8-oxooctyl)amino)octanoate (400 mg, 0.553 mmol) and triethylamine (0.15 mL, 1.10 mmol) in 10 mL dichloromethane, and the reaction mixture was allowed to warm to room temperature for 16 h. MS showed the product, and the mixture was diluted with dichloromethane and washed with saturated sodium bicarbonate and brine. After drying over sodium sulfate, the filtrate was concentrated and purified by ISCO (SiO$_2$: MeOH/CH$_2$Cl$_2$/1% NH$_4$OH 0 to 5%) to provide the product as a colorless oil (296 mg, 88%). LC/UV (214 nm): RT=11.51 min. MS (APCI): m/z (MH$^+$) 801.7. $^1$H NMR (300 MHz, CDCl$_3$) δ: ppm 4.85 (p, 1H, J=6.0 Hz); 4.04 (t, 2H, J=6.6 Hz); 3.22 (t, 2H, J=5.8 Hz); 2.88 (s, 3H); 2.53-2.23 (m, 10H); 1.73-1.16 (m, 64H); 0.87 (m, 9H).

XX11. Compound 110: Heptadecan-9-yl 8-((3-(3,3-dimethylureido)propyl)(8-(nonyloxy)-8-oxooctyl)amino)octanoate

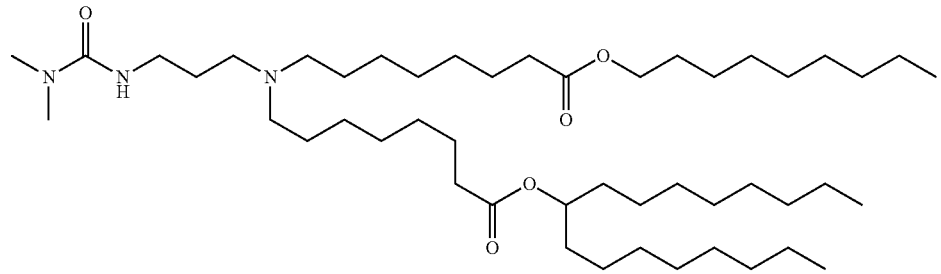

Chemical Formula: C$_{48}$H$_{95}$N$_3$O$_5$
Molecular Weight: 794.30

To a solution of heptadecan-9-yl 8-((3-aminopropyl)(8-(nonyloxy)-8-oxooctyl)amino)octanoate (400 mg, 0.553 mmol), dimethylaminopyridine (7 mg, 0.0553 mmol) and triethylamine (0.15 mL, 1.10 mmol) in 10 mL dichloromethane, dimethylcarbamic chloride (56 µL, 0.61 mmol) was added dropwise at 0° C., and the reaction mixture was allowed to stir at room temperature for 16 h. MS showed the product. The mixture was diluted with dichloromethane and washed with saturated sodium bicarbonate and brine. After it was dried over sodium sulfate, the filtrate was concentrated and purified by ISCO (SiO$_2$: MeOH/CH$_2$Cl$_2$/1% NH$_4$OH 0 to 5%) to afford the product as a colorless oil (267 mg, 60%). LC/UV (202 nm): RT=9.81 min. MS (APCI): m/z (MH$^+$) 794.7. $^1$H NMR (300 MHz, CDCl$_3$) δ: ppm 6.13 (t, 1H, J=4.5 Hz); 4.85 (p, 1H, J=6.0 Hz); 4.04 (t, 2H, J=6.6 Hz); 3.32-3.26 (m, 2H); 2.85 (s, 6H); 2.52-2.23 (m, 10H); 1.67-1.18 (m, 64H); 0.87 (m, 9H).

XX12. Compound 111: Heptadecan-9-yl 8-((3-(3,3-dimethylthioureido)propyl)(8-(nonyloxy)-8-oxooctyl)amino)octanoate

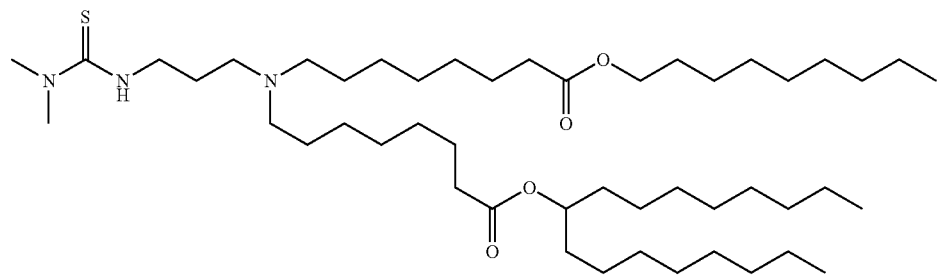

Chemical Formula: C$_{48}$H$_{95}$N$_3$O$_4$S
Molecular Weight: 810.37

To a solution of heptadecan-9-yl 8-((3-aminopropyl)(8-(nonyloxy)-8-oxooctyl)amino)octanoate (400 mg, 0.553 mmol) and triethylamine (0.15 mL, 1.10 mmol) in 10 mL dichloromethane was added dropwise at 0° C. thiophosgene (51 µL, 0.664 mmol), and the reaction mixture was allowed to stir at room temperature for 6 h. After this time, the reaction was cooled to 0° C., and a solution of dimethylamine in THF (2.0 M, 0.55 mL, 1.10 mmol) was added. The reaction was then allowed to stir at room temperature for 16 h. MS showed the product, and the mixture was diluted with dichloromethane and washed with saturated sodium bicarbonate and brine. After drying over sodium sulfate, the filtrate was concentrated and purified by ISCO (SiO$_2$: MeOH/CH$_2$Cl$_2$/1% NH$_4$OH 0 to 5%) to afford the product as a brown oil (346 mg, 77%). LC/UV (202 nm): RT=9.89 min. MS (APCI): m/z (MH$^+$) 810.7. $^1$H NMR (300 MHz, CDCl$_3$) δ: ppm 8.12 (bs, 1H); 4.85 (p, 1H, J=6.0 Hz); 4.04 (t, 2H, J=6.6 Hz); 3.74-3.64 (m, 2H); 3.20 (s, 6H); 2.62-2.23 (m, 10H); 1.77-1.17 (m, 64H); 0.87 (m, 9H).

XX13. Compound 112: Heptadecan-9-yl 8-((3-(3-methylureido)propyl)(8-(nonyloxy)-8-oxooctyl)amino)octanoate

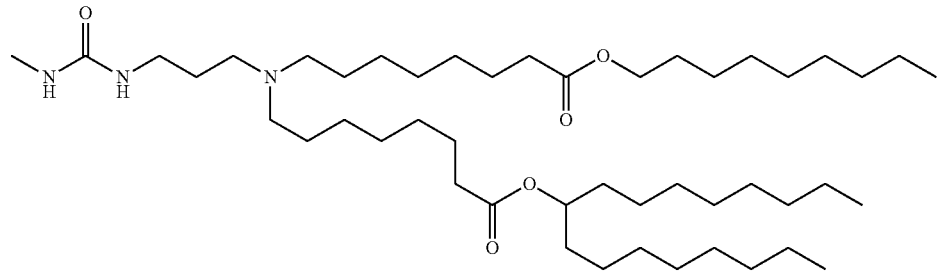

Chemical Formula: C$_{47}$H$_{93}$N$_3$O$_5$
Molecular Weight: 780.28

To a 0° C. solution of heptadecan-9-yl 8-((3-aminopropyl)(8-(nonyloxy)-8-oxooctyl)amino)octanoate (400 mg, 0.553 mmol) in 10 mL dichloromethane was methyl isocyanate (38 mg, 0.664 mmol), and the reaction mixture was allowed to stir at room temperature for 16 h. MS showed the product. The mixture was diluted with dichloromethane and washed with saturated sodium bicarbonate and brine. After it was dried over sodium sulfate, the filtrate was concentrated and purified by ISCO (SiO$_2$: MeOH/CH$_2$Cl$_2$/1% NH$_4$OH 0 to 5%) to afford the product as a colorless oil (320 mg, 70%).

LC/UV (202 nm): RT=9.63 min. MS (APCI): m/z (MH$^+$) 780.7. $^1$H NMR (300 MHz, CDCl$_3$) δ: ppm 5.54 (bs, 1H); 4.85 (p, 1H, J=6.0 Hz); 4.76 (bs, 1H); 4.04 (t, 2H, J=6.6 Hz); 3.23 (t, 2H, J=5.8 Hz); 2.74 (d, 3H, J=2.0 Hz); 2.47 (t, 2H, J=6.0 Hz); 2.37 (t, 4H, J=7.4 Hz); 2.31-2.23 (m, 4H); 1.68-1.17 (m, 64H); 0.87 (m, 9H).

XX14. Compound 113: Heptadecan-9-yl 8-((3-(3-methylthioureido)propyl)(8-(nonyloxy)-8-oxooctyl)amino)octanoate

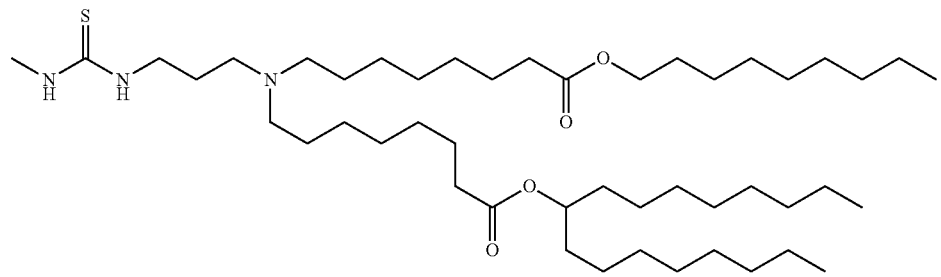

Chemical Formula: C$_{49}$H$_{93}$N$_3$O$_4$S
Molecular Weight: 795.69

To a 0° C. solution of heptadecan-9-yl 8-((3-aminopropyl)(8-(nonyloxy)-8-oxooctyl)amino)octanoate (400 mg, 0.553 mmol) in 10 mL dichloromethane was added methyl isothiocyanate (45 μL, 0.664 mmol), and the reaction mixture was allowed to stir at room temperature for 16 h. MS showed the product. The mixture was concentrated and purified by ISCO (SiO$_2$: MeOH/CH$_2$Cl$_2$/1% NH$_4$OH 0 to 5%) to afford the product as a colorless oil (312 mg, 70%). LC/UV (202 nm): RT=9.96 min. MS (APCI): m/z (MH$^+$) 796.7. $^1$H NMR (300 MHz, CDCl$_3$) δ: ppm 4.85 (p, 1H, J=6.0 Hz); 4.04 (t, 2H, J=6.6 Hz); 3.51 (bs, 2H); 2.93 (bs, 3H); 2.52 (t, 2H, J=6.0 Hz); 2.41 (t, 4H, J=7.8 Hz); 2.31-2.23 (m, 4H); 1.68-1.17 (m, 66H); 0.86 (m, 9H).

XX15. Compound 114: Heptadecan-9-yl 8-((3-(2,4-dioxo-3,4-dihydropyrimidin-1(2H)-yl)propyl)(8-(nonyloxy)-8-oxooctyl)amino)octanoate

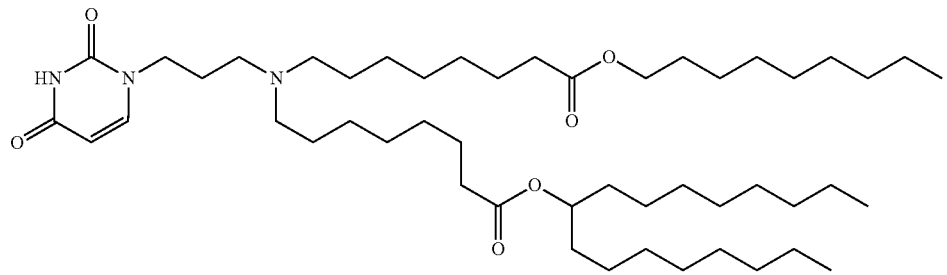

Chemical Formula: C$_{49}$H$_{91}$N$_3$O$_6$
Molecular Weight: 818.28

A mixture of heptadecan-9-yl 8-((3-chloropropyl)(8-(nonyloxy)-8-oxooctyl)amino)octanoate (500 mg, 0.67 mmol), uracil (300 mg, 2.67 mmol) and 1,8-diazabicycloundec-7-ene (150 µL, 1.07 mmol) in 3 mL DMF was heated at 100° C. in a sealed tube for 16 h. The reaction mixture was concentrated to dryness and partitioned between dichloromethane and water. The organic layer was washed with brine. After it was dried over sodium sulfate, the filtrate was concentrated and purified by ISCO (SiO$_2$: MeOH/CH$_2$Cl$_2$/1% NH$_4$OH 0 to 5%) to afford the product as a yellow oil (268 mg, 49%). LC/UV (202 nm): RT=8.91 min. MS (APCI): m/z (MH$^+$) 818.7. $^1$H NMR (300 MHz, CDCl$_3$) δ: ppm 8.19 (bs, 1H); 7.24 (d, 1H, J=7.7 Hz); 5.64 (d, 1H, J=7.7 Hz); 4.85 (p, 1H, J=6.0 Hz); 4.04 (t, 2H, J=6.6 Hz); 3.76 (t, 2H, J=7.0 Hz); 2.45-2.24 (m, 10H); 1.81 (p, 2H, J=6.6 Hz); 1.68-1.17 (m, 62H); 0.87 (m, 9H).

XX16. Compound 115: Heptadecan-9-yl 8-((3-(4-amino-2-oxopyrimidin-1(2H)-yl)propyl)(8-(nonyloxy)-8-oxooctyl)amino)octanoate

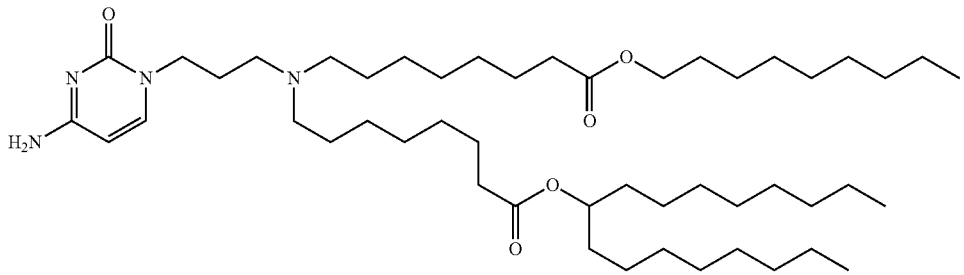

Chemical Formula: C$_{49}$H$_{92}$N$_4$O$_5$
Molecular Weight: 817.30

To a suspension of cytosine (82 mg, 0.74 mmol) in 1 mL DMF was added NaH (30 mg, 0.74 mmol) and the reaction mixture was stirred at room temperature for 30 min. A solution of heptadecan-9-yl 8-((3-chloropropyl)(8-(nonyloxy)-8-oxooctyl)amino)octanoate (500 mg, 0.67 mmol) in 2 mL DMF was then added and the mixture was heated at 100° C. in a sealed tube for 16 h. MS showed product. The reaction was quenched with saturated sodium bicarbonate and extracted with hexanes (2×). The combined organic layer was washed with water and brine. After it was dried over sodium sulfate, the filtrate was concentrated and purified by ISCO (SiO$_2$: MeOH/CH$_2$Cl$_2$/1% NH$_4$OH 0 to 5%) to afford the product as a yellow oil (310 mg, 56%). LC/UV (202 nm): RT=8.32 min. MS (APCI): m/z (MH$^+$) 817.7. $^1$H NMR (300 MHz, CDCl$_3$) δ: ppm 7.34 (d, 1H, J=7.1 Hz); 5.61 (d, 1H, J=7.1 Hz); 5.44 (bs, 2H); 4.85 (p, 1H, J=6.0 Hz); 4.04 (t, 2H, J=6.6 Hz); 3.79 (t, 2H, J=7.0 Hz); 2.42-2.22 (m, 9H); 1.84 (t, 2H, J=6.6 Hz); 1.68-1.17 (m, 63H); 0.86 (m, 9H).

XX17. Compound 116: Heptadecan-9-yl 8-((3-(6-amino-9H-purin-9-yl)propyl)(8-(nonyloxy)-8-oxooctyl)amino)octanoate

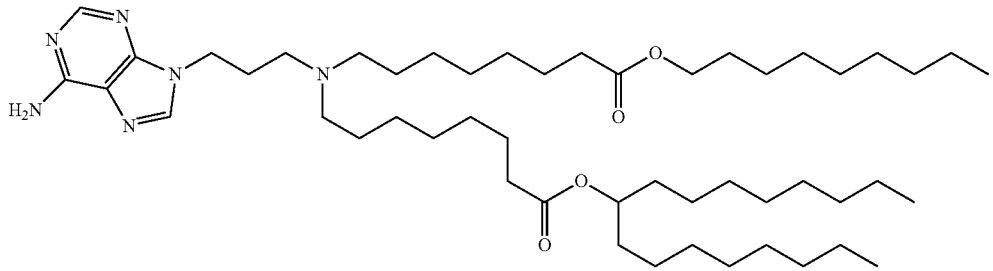

Chemical Formula: C$_{50}$H$_{92}$N$_6$O$_4$
Molecular Weight: 841.32

A mixture of heptadecan-9-yl 8-((3-chloropropyl)(8-(nonyloxy)-8-oxooctyl)amino)octanoate (500 mg, 0.67 mmol), adenine (135 mg, 1.0 mmol) and 1,8-diazabicycloundec-7-ene (137 μL, 1.0 mmol) in 2 mL DMF was heated at 90° C. in a sealed tube for 16 h. The reaction mixture was concentrated to dryness and partitioned between dichloromethane and water. The organic layer was washed with brine. After it was dried over sodium sulfate, the filtrate was concentrated and purified by ISCO (SiO$_2$: MeOH/CH$_2$Cl$_2$/1% NH$_4$OH 0 to 5%) to afford the product as a yellow oil (325 mg, 57%). LC/UV (202 nm): RT=8.47 min. MS (APCI): m/z (MH$^+$) 841.7. $^1$H NMR (300 MHz, CDCl$_3$) δ: ppm 8.36 (s, 1H); 7.80 (s, 1H); 5.51 (bs, 2H); 4.85 (p, 1H, J=6.0 Hz); 4.24 (t, 2H, J=7.0 Hz); 4.04 (t, 2H, J=6.6 Hz); 2.45-2.24 (m, 10H); 2.01 (p, 2H, J=6.9 Hz); 1.68-1.17 (m, 62H); 0.86 (m, 9H).

XX18. Compound 118: 3,4-Dipentylphenyl 8-((2-hydroxyethyl)(8-(nonyloxy)-8-oxooctyl)amino)octanoate 5-Methoxy-2-(pent-1-yn-1-yl)benzaldehyde (see e.g., *Bioorg. Med. Chem. Lett.* 2013, 23, 1365)

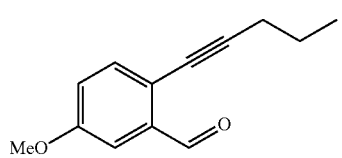

Chemical Formula: C$_{13}$H$_{14}$O$_2$
Molecular Weight: 202.25

A mixture of 2-bromo-5-methoxybenzaldehyde (4.30 g, 20 mmol), 1-pentyne (3.0 mL, 30 mmol), bis(triphenylphosphino)palladium chloride (702 mg, 1 mmol), CuI (380 mg, 2.0 mmol) and triethylamine (5.6 mL, 40 mmol) in 60 mL THF was heated to 50° C. for 16 h under nitrogen. TLC showed the disappearance of starting material. The reaction mixture was concentrated to dryness. The residue was dissolved in dichloromethane and washed with water and brine. After drying over sodium sulfate, the filtrate was concentrated and the residue was purified by ISCO (SiO$_2$: EtOAc/Hexanes 0 to 5%) to afford the product as a dark brown oil (3.00 g, 74%). $^1$H NMR (300 MHz, CDCl$_3$) δ: ppm 10.49 (s, 1H); 7.42 (d, 1H, J=8.5 Hz); 7.36 (d, 1H, J=2.8 Hz); 7.07 (dd, 1H, J=8.5 Hz, 2.8 Hz); 3.84 (s, 3H); 2.44 (t, 2H, J=7.0 Hz); 1.62 (m, 2H); 1.05 (t, 3H, J=7.2 Hz).

4-Methoxy-2-(pent-1-en-1-yl)-1-(pent-1-yn-1-yl)benzene

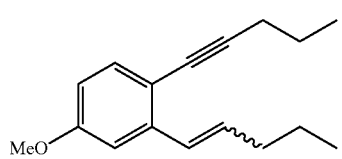

Chemical Formula: C$_{17}$H$_{22}$O
Molecular Weight: 242.36

To a suspension of butyl triphenylphosphonium bromide (8.88 g, 22.2 mmol) in 75 mL THF was added at 0° C. potassium tert-butoxide (2.50 g, 22.2 mmol). After 30 min, a solution of 5-methoxy-2-(pent-1-yn-1-yl)benzaldehyde (3.00 g, 14.8 mmol) in 25 mL THF was then added slowly into the orange suspension. The reaction mixture was allowed to warm up to room temperature and stir for 60 h. Saturated ammonium chloride solution was added and the mixture was extracted with ether (2×), and the combined organic layer was washed with brine. After drying over sodium sulfate, the filtrate was concentrated and the residue was purified by ISCO (SiO$_2$: EtOAc/Hexanes 0 to 5%) to afford the product as a brown oil (3.46 g, 96%). $^1$H NMR (300 MHz, CDCl$_3$) δ: ppm 7.33 (d, 0.5H, J=8.5 Hz); 7.26 (d, 0.5H, J=8.5 Hz); 6.99 (d, 0.5H, J=2.8 Hz); 6.88-6.80 (m, 1H); 6.73-6.61 (m, 1.5H); 6.25 (dt, 0.5H, J=15.9 Hz, 6.9 Hz); 5.73 (dt, 0.5H, J=11.5 Hz, 7.4 Hz); 3.80 (s, 3H); 2.45-2.37 (m, 2H); 2.31-2.18 (m, 2H); 1.71-1.41 (m, 4H); 1.09-0.90 (m, 6H).

4-Methoxy-1,2-dipentylbenzene

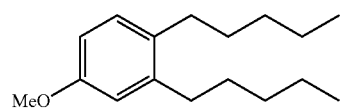

Chemical Formula: C$_{17}$H$_{28}$O
Molecular Weight: 248.41

A mixture of 4-methoxy-2-(pent-1-en-1-yl)-1-(pent-1-yn-1-yl)benzene (3.46 g, 14.3 mmol) and Pd/C (10%, 300 mg) in 60 mL EtOH was stirred for 60 h under a hydrogen balloon. TLC showed complete reaction. The reaction mixture was filtered through Celite and concentrated to afford the product as a yellow oil (3.70 g, quant.), which was used for the next step without purification. $^1$H NMR (300 MHz, CDCl$_3$) δ: ppm 7.05 (d, 1H, J=8.2 Hz); 6.72-6.55 (m, 2H); 3.78 (s, 3H); 2.59-2.50 (m, 4H); 1.62-1.48 (m, 4H); 1.39-1.28 (m, 8H); 0.93-0.86 (m, 6H).

3,4-Dipentylphenol

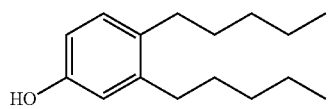

Chemical Formula: C$_{16}$H$_{26}$O
Molecular Weight: 234.38

To a solution of 4-methoxy-1,2-dipentylbenzene (3.40 g, 13.7 mmol) in 75 mL dichloromethane was added dropwise at −78° C. BBr$_3$ (1.65 mL, 17.1 mmol), and then the reaction was allowed to warm to room temperature over 3 h. TLC showed complete reaction. The reaction was quenched by addition of saturated sodium bicarbonate, and then it was extracted with dichloromethane (2×). The combined organic layer was washed with brine and dried over sodium sulfate. After concentration, the residue was purified by ISCO (SiO$_2$: EtOAc/Hexanes 0 to 30%) to afford the product as a brown oil (3.35 g, 97%). $^1$H NMR (300 MHz, CDCl$_3$) δ: ppm 6.99 (d, 1H, J=8.0 Hz); 6.64-6.59 (m, 2H); 4.45 (bs, 1H); 2.55-2.47 (m, 4H); 1.66-1.43 (m, 4H); 1.39-1.28 (m, 8H); 0.93-0.86 (m, 6H).

3,4-Dipentylphenyl 8-bromooctanoate

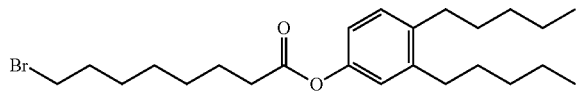

Chemical Formula: C₂₄H₃₉BrO₂
Molecular Weight: 439.48

To a solution of 8-bromooctanoic acid (2.23 g, 10 mmol) and 3,4-dipentylphenol (2.34 g, 10 mmol) in dichloromethane (50 mL) were added N-(3-Dimethylaminopropyl)-N'-ethylcarbodiimide hydrochloride (1.92 g, 10 mmol) and DMAP (244 mg, 2 mmol). The reaction was allowed to stir at room temperature for 18 h. The reaction was diluted with dichloromethane and extracted with saturated sodium bicarbonate. The organic layer was separated and washed with brine, dried over sodium sulfate. The organic layer was filtered and evaporated under vacuum. The residue was purified by ISCO (SiO₂: EtOAc/Hexanes 0 to 10%) to afford the product as a brown oil (4.30 g, 98%). ¹H NMR (300 MHz, CDCl₃) δ: ppm 7.11 (d, 1H, J=7.7 Hz); 6.84-6.77 (m, 2H); 3.41 (t, 2H, J=6.9 Hz); 2.60-2.49 (m, 6H); 1.92-1.69 (m, 4H); 1.62-1.29 (m, 18H); 0.90 (m, 6H).

Nonyl 8-((2-hydroxyethyl)amino)octanoate

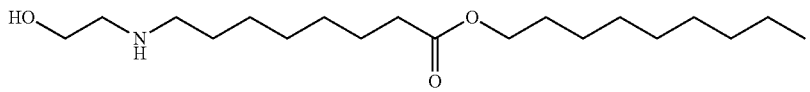

Chemical Formula: C₁₉H₃₉NO₃
Molecular Weight: 329.53

A mixture of nonyl 8-bromooctanoate (2.50 g, 7.15 mmol) and 2-aminoethanol (4.3 mL, 71.5 mmol) in 10 mL EtOH was stirred at room temperature for 60 h. The reaction mixture was partitioned with hexanes and water, and the organic layer was washed with brine. After drying over sodium sulfate, the filtrate was concentrated and purified by ISCO (SiO₂: MeOH/CH₂Cl₂/1% NH₄OH 0 to 20%) to afford the product as white solid (1.57 g, 66%). MS (APCI): m/z (MH⁺) 330.3. ¹H NMR (300 MHz, CDCl₃) δ: ppm 4.04 (t, 2H, J=6.6 Hz); 3.63 (t, 2H, J=5.2 Hz); 2.77 (t, 2H, J=5.1 Hz); 2.61 (t, 2H, J=7.1 Hz); 2.28 (t, 2H, J=7.4 Hz); 1.99 (bs, 2H); 1.67-1.20 (m, 4H); 1.62-1.29 (m, 17H); 0.87 (m, 6H).

3,4-Dipentylphenyl 8-((2-hydroxyethyl)(8-(nonyloxy)-8-oxooctyl)amino)octanoate

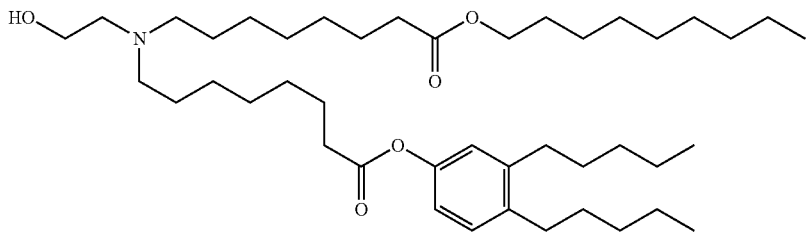

Chemical Formula: C₄₃H₇₇NO₅
Molecular Weight: 688.09

A solution of nonyl 8-((2-hydroxyethyl)amino)octanoate (500 mg, 1.52 mmol), 3,4-dipentylphenyl 8-bromooctanoate (1.00 g, 2.27 mmol) and N, N-diisopropylethylamine (0.40 mL, 2.27 mmol) in tert-butanol (3 mL) was heated to 60° C. in a sealed tube for 60 h. The reaction was cooled to room temperature and solvents were evaporated under vacuum. The residue was purified by ISCO ($SiO_2$: $MeOH/CH_2Cl_2$/ 1% $NH_4OH$ 0 to 5%) to obtain mixture (365 mg), and then the mixture was purified by ISCO (EtOAc/Hexanes/0.5% $Et_3N$ 0 to 50%) to afford product as a colorless oil (80 mg). LC/UV (214 nm): RT=10.23 min. MS (APCI): m/z ($MH^+$) 688.6. $^1H$ NMR (300 MHz, $CDCl_3$) δ: ppm 7.11 (d, 1H, J=8.0 Hz); 6.84-6.77 (m, 2H); 4.04 (t, 2H, J=6.6 Hz); 3.51 (t, 2H, J=5.5 Hz); 2.60-2.38 (m, 12H); 2.28 (t, 2H, J=7.4 Hz); 1.79-1.19 (m, 37H); 0.92-0.82 (m, 9H).

XX19. Compound 119: Nonyl 8-((2-hydroxyethyl) (8-oxo-8-(4-pentylphenoxy)octyl)amino)octanoate
4-Pentylphenyl 8-bromooctanoate

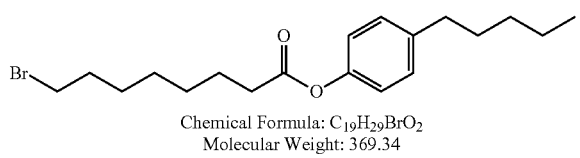 [SMILES: CCCCCc1ccc(OC(=O)CCCCCCCBr)cc1]

Chemical Formula: $C_{19}H_{29}BrO_2$
Molecular Weight: 369.34

To a solution of 8-bromooctanoic acid (2.00 g, 8.96 mmol) and 4-pentylphenol (3.07 mL g, 17.9 mmol) in dichloromethane (50 mL) were added N-(3-Dimethylaminopropyl)-N'-ethylcarbodiimide hydrochloride (1.72 g, 8.96 mmol) and DMAP (220 mg, 1.79 mmol). The reaction was allowed to stir at room temperature for 60 h. The reaction was diluted with dichloromethane and extracted with saturated sodium bicarbonate. The organic layer was separated and washed with brine, and dried over sodium sulfate. The organic layer was filtered and evaporated under vacuum. The residue was purified by ISCO ($SiO_2$: EtOAc/Hexanes 0 to 10%) to afford the product as a colorless oil (3.12 g, 94%). $^1H$ NMR (300 MHz, $CDCl_3$) δ: ppm 7.16 (d, 2H, J=8.5 Hz); 6.96 (d, 2H, J=8.5 Hz); 3.41 (t, 2H, J=6.9 Hz); 2.61-2.49 (m, 4H); 1.92-1.69 (m, 4H); 1.65-1.25 (m, 10H); 0.88 (m, 3H).

Nonyl 8-((2-hydroxyethyl)(8-oxo-8-(4-pentylphenoxy)octyl)amino)octanoate

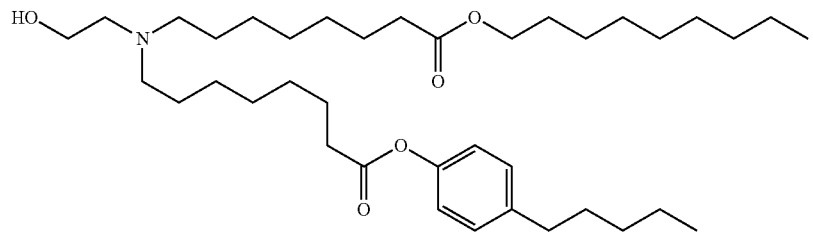

Chemical Formula: $C_{38}H_{67}NO_5$
Molecular Weight: 617.96

A solution of nonyl 8-((2-hydroxyethyl)amino)octanoate (500 mg, 1.52 mmol), 4-pentylphenyl 8-bromooctanoate (840 mg, 2.28 mmol) and N, N-diisopropylethylamine (0.40 mL, 2.28 mmol) in tert-butanol (3 mL) was heated to 60° C. in a sealed tube for 48 h. The reaction was cooled to room temperature and solvents were evaporated under vacuum. The residue was purified by ISCO ($SiO_2$: $MeOH/CH_2Cl_2$/ 1% $NH_4OH$ 0 to 5%) to obtain mixture (360 mg), and then the mixture was purified by ISCO (EtOAc/Hexanes/0.5% $Et_3N$ 0 to 50%) to afford the product as a colorless oil (95 mg). LC/UV (214 nm): RT=9.63 min. MS (APCI): m/z ($MH^+$) 618.5. $^1H$ NMR (300 MHz, $CDCl_3$) δ: ppm 7.11 (d, 1H, J=8.0 Hz); 6.84-6.77 (m, 2H); 4.04 (t, 2H, J=6.6 Hz); 3.51 (t, 2H, J=5.5 Hz); 2.60-2.38 (m, 12H); 2.28 (t, 2H, J=7.4 Hz); 1.79-1.19 (m, 37H); 0.92-0.82 (m, 9H).

XX20. Compound 120: Nonyl 8-((2-hydroxyethyl) (8-oxo-8-(3-pentylphenoxy)octyl)amino)octanoate
3-Pentylphenol (Ref: Tetrahedron Lett. 2013, 54, 52)

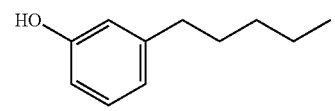

Chemical Formula: $C_{11}H_{16}O$
Molecular Weight: 164.25

At −78° C., to a suspension of potassium tert-butoxide (6.73 g, 60 mmol) in 15 mL pentane were added sequentially tetramethylethylenediamine (9.0 mL, 60 mmol) and BuLi (2.5 M in hexane, 24 mL, 60 mmol), and a solution of m-cresol (2.6 mL, 25 mmol) in 10 mL pentane was added slowly. The reaction mixture was warmed up to −20° C. for 3 h. 30 mL THF was added and the reaction was cooled to −60° C. Butyl bromide (4.8 mL, 45 mmol) was added slowly, and the mixture was allowed warm to room temperature and stir for 16 h. After cooled to 0° C., the reaction mixture was acidified with 4 M HCl to pH-3, and then extracted with ether. The combined organic layer was washed with brine and dried over sodium sulfate. After concentration, the residue was purified by ISCO (EtOAc/ Hexanes 0 to 5%) to provide a mixture of product with starting material, which was distilled under vacuum to provide the product as a colorless oil (1.23 g, 65%). $^1H$ NMR (300 MHz, $CDCl_3$) δ: ppm 7.14 (t, 1H, J=7.7 Hz); 6.75 (d, 1H, J=7.7 Hz); 6.67-6.61 (m, 2H); 4.62 (s, 1H); 2.55 (t, 2H, J=7.7 Hz); 1.67-1.52 (m, 2H); 1.38-1.24 (m, 4H); 0.88 (t, 3H, J=6.9 Hz).

3-Pentylphenyl 8-bromooctanoate

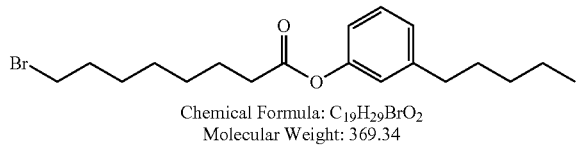 [SMILES: CCCCCc1cccc(OC(=O)CCCCCCCBr)c1]

Chemical Formula: C$_{19}$H$_{29}$BrO$_2$
Molecular Weight: 369.34

To a solution of 8-bromooctanoic acid (1.84 g, 8.20 mmol) and 3-pentylphenol (1.23 g, 7.49 mmol) in dichloromethane (40 mL) were added N-(3-Dimethylaminopropyl)-N'-ethylcarbodiimide hydrochloride (1.58 g, 8.20 mmol) and DMAP (183 mg, 1.50 mmol). The reaction was allowed to stir at room temperature for 16 h. The reaction was diluted with dichloromethane and extracted with saturated sodium bicarbonate. The organic layer was separated and washed with brine, dried over sodium sulfate. The organic layer was filtered and evaporated under vacuum. The residue was purified by ISCO (SiO$_2$: EtOAc/Hexanes 0 to 10%) to provide the product as a colorless oil (2.23 g, 80%). $^1$H NMR (300 MHz, CDCl$_3$) δ: ppm 7.26 (t, 1H, J=8.5 Hz); 7.03 (d, 1H, J=7.6 Hz); 6.91-6.84 (m, 2H); 3.41 (t, 2H, J=6.9 Hz); 2.61-2.49 (m, 4H); 1.92-1.69 (m, 4H); 1.65-1.25 (m, 12H); 0.88 (t, 3H, J=6.9 Hz).

Nonyl 8-((2-hydroxyethyl)(8-oxo-8-(3-pentylphenoxy)octyl)amino)octanoate

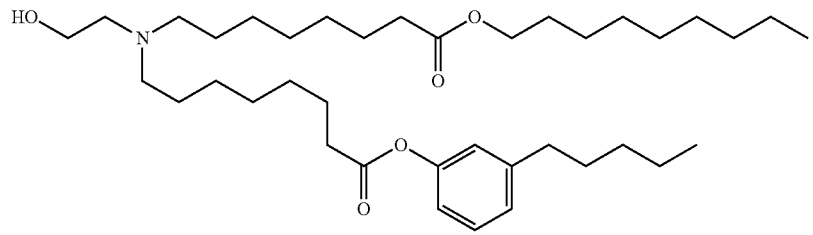

Chemical Formula: C$_{38}$H$_{67}$NO$_5$
Molecular Weight: 617.96

A solution of nonyl 8-((2-hydroxyethyl)amino)octanoate (500 mg, 1.52 mmol), 3-pentylphenyl 8-bromooctanoate (840 mg, 2.28 mmol) and N,N-diisopropylethylamine (0.40 mL, 2.28 mmol) in tert-butanol (3 mL) was stirred at 60° C. in a sealed tube for 16 h. The reaction was cooled to room temperature and solvents were evaporated under vacuum. The residue was purified by ISCO (SiO$_2$: MeOH/CH$_2$Cl$_2$/ 1% NH$_4$OH 0 to 5%) to obtain a mixture (247 mg), and then the mixture was purified by ISCO (EtOAc/Hexanes/0.5% Et$_3$N 0 to 50%) to afford the product as a colorless oil (150 mg). LC/UV (202 nm): RT=7.45 min. MS (APCI): m/z (MH$^+$) 618.5. $^1$H NMR (300 MHz, CDCl$_3$) δ: ppm 7.26 (t, 1H, J=8.5 Hz); 7.03 (d, 1H, J=7.6 Hz); 6.91-6.84 (m, 2H); 4.05 (t, 2H, J=6.6 Hz); 3.51 (t, 2H, J=5.5 Hz); 2.64-2.38 (m, 10H); 2.28 (t, 2H, J=7.8 Hz); 1.79-1.19 (m, 41H); 0.91-0.82 (m, 6H).

XX21. Compound 121: Heptadecan-9-yl 8-((3-aminopropyl)(8-(nonyloxy)-8-oxooctyl)amino)octanoateHeptadecan-9-yl 8-((3-chloropropyl)(8-(nonyloxy)-8-oxooctyl)amino)octanoate

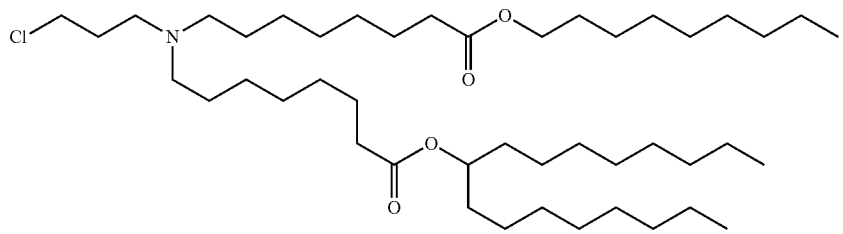

Chemical Formula: C$_{45}$H$_{88}$ClNO$_4$
Molecular Weight: 742.65

To a solution of heptadecan-9-yl 8-((3-hydroxypropyl)(8-(nonyloxy)-8-oxooctyl)amino)octanoate (8.00 g, 11.0 mmol) and triethylamine (2.0 mL, 14.4 mmol) in dichloromethane (200 mL) was added dropwise methanesulfonyl chloride (1.07 mL, 13.8 mmol) at 0° C., and the reaction mixture was allowed to room temperature for 16 h. TLC and MS showed complete reaction. The reaction mixture was diluted with dichloromethane and washed with saturated sodium bicarbonate and brine. After drying over sodium sulfate, the solvent was removed under vacuum to give the product as a brown oil (7.30 g, 89%). NMR showed the crude contained a small amount of mesylate and desired chloride. This was used for the next step without purification. MS (APCI): m/z (MH$^+$) 742.6. $^1$H NMR (300 MHz, CDCl$_3$) δ: ppm 4.86 (p, 1H, J=6.0 Hz); 4.05 (t, 2H, J=6.9 Hz); 3.58 (t, 2H, J=6.6 Hz); 2.58-2.22 (m, 9H); 1.92-1.16 (m, 65H); 0.87 (m, 9H).

Heptadecan-9-yl 8-((3-azidopropyl)(8-(nonyloxy)-8-oxooctyl)amino)octanoate

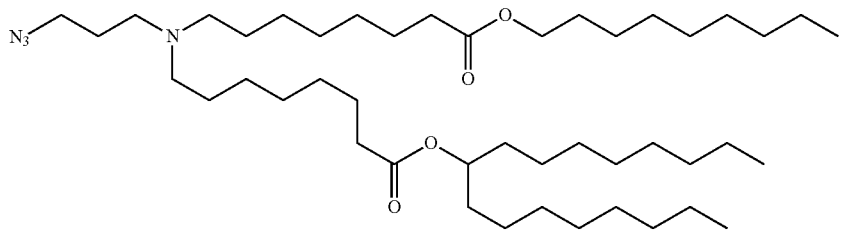

Chemical Formula: C$_{45}$H$_{88}$N$_4$O$_4$
Molecular Weight: 749.22

A mixture of heptadecan-9-yl 8-((3-chloropropyl)(8-(nonyloxy)-8-oxooctyl)amino)octanoate (4.20 g, 5.66 mmol) and sodium azide (1.75 g, 28.28 mmol) in 20 mL DMF in a sealed tube was heated to 100° C. for 16 h. After it was cooled to room temperature, the reaction mixture was diluted with water and extracted with hexanes. The combined organic layer was washed with water and brine, and then dried over sodium sulfate. After filtration and concentration, the residue was purified by ISCO (SiO$_2$: MeOH/CH$_2$Cl$_2$/1% NH$_4$OH 0 to 5%) to provide the product as a brown oil (3.66 g, 86%). MS (APCI): m/z (MH$^+$) 749.7. $^1$H NMR (300 MHz, CDCl$_3$) δ: ppm 4.85 (p, 1H, J=6.0 Hz); 4.04 (t, 2H, J=6.7 Hz); 3.32 (t, 2H, J=6.9 Hz); 2.58-2.22 (m, 10H); 1.72-1.19 (m, 64H); 0.87 (m, 9H).

Heptadecan-9-yl 8-((3-aminopropyl)(8-(nonyloxy)-8-oxooctyl)amino)octanoate

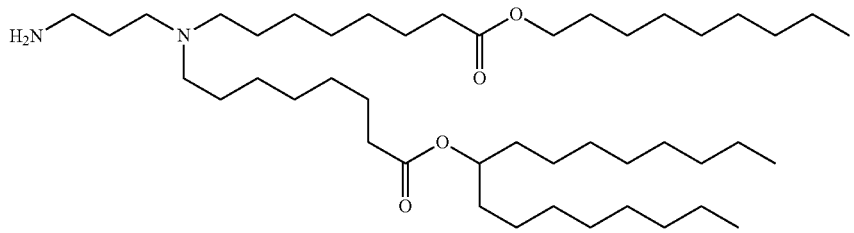

Chemical Formula: C$_{45}$H$_{90}$N$_2$O$_4$
Molecular Weight: 723.23

A mixture of heptadecan-9-yl 8-((3-azidopropyl)(8-(nonyloxy)-8-oxooctyl)amino)octanoate (3.66 g, 4.89 mmol) and Pd/C (10%, 400 mg) in 150 mL EtOH was stirred under hydrogen balloon for 16 h. MS showed complete reaction. The reaction mixture was filtered through Celite, and the filtrate was concentrated and purified by ISCO (SiO$_2$: MeOH/CH$_2$Cl$_2$/1% NH$_4$OH 0 to 20%) to afford the product as a brown oil (3.08 g, 87%). LC/UV (202 nm): RT=8.39 min. MS (APCI): m/z (MH$^+$) 723.7. $^1$H NMR (300 MHz, CDCl$_3$) δ: ppm 4.85 (p, 1H, J=6.0 Hz); 4.04 (t, 2H, J=6.6 Hz); 2.70 (t, 2H, J=6.9 Hz); 2.46-2.24 (m, 10H); 1.65-1.16 (m, 66H); 0.87 (m, 9H).

XX22. Compound 122: Heptadecan-9-yl 8-((6-(decan-2-yloxy)-6-oxohexyl)(2-hydroxyethyl)amino)octanoate

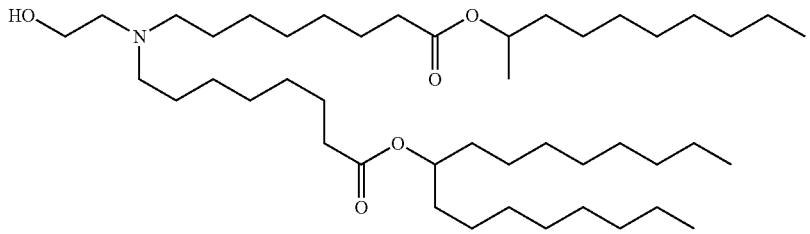

Chemical Formula: C$_{45}$H$_{85}$NO$_5$
Molecular Weight: 696.16

Compound 122 was synthesized according to the general procedure and Representative Procedure 1 described above. UPLC/ELSD: RT=3.58 min. MS (ES): m/z (MH$^+$) 697.1 for $C_{43}H_{85}NO_5$. $^1$H NMR (300 MHz, CDCl$_3$) δ: ppm 4.91 (m, 2H); 3.62 (m, 2H); 2.81-2.42 (br. m, 5H); 2.30 (m, 4H); 1.73-1.43 (m, 14H); 1.28 (m, 48H); 0.90 (m, 9H).

XX23. Compound 123: Heptadecan-9-yl) 8-(methyl (8-nonyloxy)-8-oxooctyl)amino)octanoate

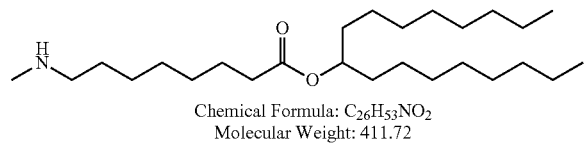 [SMILES: CCCCCCCCC(CCCCCCCC)OC(=O)CCCCCCCNC]

Chemical Formula: $C_{26}H_{53}NO_2$
Molecular Weight: 411.72

A solution of heptadecan-9-yl 8-bromooctanoate (200 mg, 0.433 mmol) in methanamine (10 mL, 19.92 mmol, 2M in THF) was allowed to stir at rt for 18 h. The reaction mixture was concentrated in vacuo. The residue was purified by silica gel chromatography (10-100% (mixture of 1% NH$_4$OH, 20% MeOH in dichloromethane) in dichloromethane) to obtain heptadecan-9-yl 8-(methylamino)octanoate (113 mg, 0.27 mmol, 63%). UPLC/ELSD: RT=2.76 min. MS (ES): m/z (MH$^+$) 412.4 for $C_{26}H_{53}NO_2$. $^1$H NMR (300 MHz, CDCl$_3$) δ: ppm 4.92 (p, 1H); 2.62 (t, 2H); 2.48 (s, 3H); 2.32-2.27 (m, 2H); 1.66-1.52 (br. m, 8H); 1.28 (m, 30H); 0.90 (m, 6H).

Heptadecan-9-yl 8-(methyl(8-(nonyloxy)-8-oxooctyl)amino)octanoate

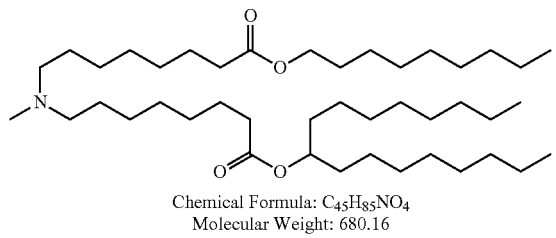 [SMILES: CCCCCCCCCOC(=O)CCCCCCCN(C)CCCCCCCC(=O)OC(CCCCCCCC)CCCCCCCC]

Chemical Formula: $C_{45}H_{85}NO_4$
Molecular Weight: 680.16

A solution of heptadecan-9-yl 8-(methylamino)octanoate (113 mg, 0.27 mmol), nonyl 8-bromooctanoate (115 mg, 0.33 mmol) and N,N-diisopropylethylamine (67 µL, 0.38 mmol) and potassium iodide (5 mg, 0.027 mmol) were dissolved in ethanol and was allowed to stir at 62° C. for 48 h. The reaction was cooled to rt and solvents were evaporated in vacuo. The residue was purified by silica gel chromatography (0-100% (mixture of 1% NH$_4$OH, 20% MeOH in dichloromethane) in dichloromethane) to obtain heptadecan-9-yl 8-(methyl(8-(nonyloxy)-8-oxooctyl) amino)octanoate (75 mg, 0.11 mmol, 41%). UPLC/ELSD: RT=3.84 min. MS (ES): m/z (MH$^+$) 681.0 for $C_{43}H_{85}NO_4$. $^1$H NMR (300 MHz, CDCl$_3$) δ: ppm 4.88 (p, 1H); 4.08 (t, 2H); 2.88-2.67 (br. m, 7H); 2.34-2.27 (m, 4H); 1.80 (m, 4H); 1.63-1.52 (br. m, 10H); 1.37-1.28 (br. m, 48H); 0.90 (m, 9H).

XX24. Compound 124: Di(heptadecan-9-yl) 8,8'-(methylazanediyl)dioctanoate

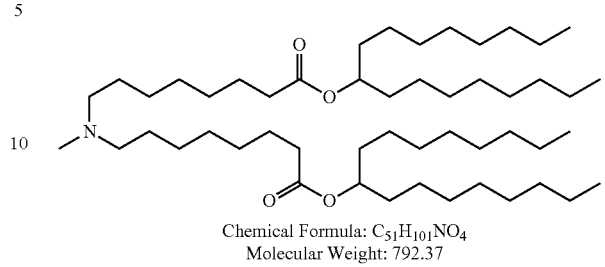

Chemical Formula: $C_{51}H_{101}NO_4$
Molecular Weight: 792.37

A solution of heptadecan-9-yl 8-bromooctanoate (500 mg, 1.08 mmol) in methanamine (11 mL, 21.67 mmol, 2M in THF) was allowed to stir at rt for 6 h. The reaction mixture was concentrated in vacuo. The residue was purified by silica gel chromatography (20-100% (mixture of 1% NH$_4$OH, 20% MeOH in dichloromethane) in dichloromethane) to obtain di(heptadecan-9-yl) 8,8'-(methylazanediyl) dioctanoate (26 mg, 0.03 mmol, 3%). UPLC/ELSD: RT=4.03 min. MS (ES): m/z (MH$^+$) 793.3 for $C_{51}H_{101}NO_4$. $^1$H NMR (300 MHz, CDCl$_3$) δ: ppm 4.89 (p, 2H); 2.32-2.24 (m, 11H); 1.66-1.28 (br. m, 76H); 0.90 (m, 12H).

XX25. Compound 125: 3-((8-(Heptadecan-9-yloxy)-8-oxooctyl)(8-(nonyloxy)-8-oxooctyl)amino) propanoic acid Heptadecan-9-yl 8-((8-(nonyloxy)-8-oxooctyl)amino)octanoate

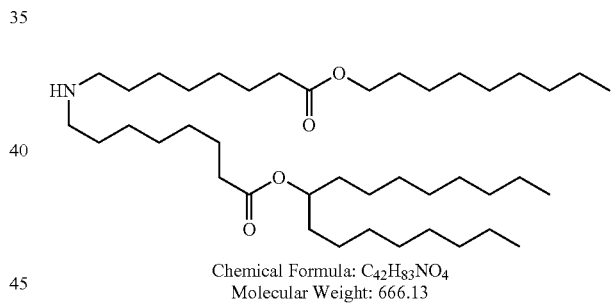

Chemical Formula: $C_{42}H_{83}NO_4$
Molecular Weight: 666.13

At −78° C., to a solution of oxalyl chloride (0.25 mL, 3.0 mmol) in 3 mL dichloromethane was added dropwise a solution of DMSO (0.43 mL, 6.0 mmol) in 2 mL dichloromethane, and then a solution of heptadecan-9-yl 8-((3-hydroxypropyl)(8-(nonyloxy)-8-oxooctyl)amino)octanoate (1.45 g, 2.0 mmol) in dichloromethane (10 mL) was added immediately. After it was stirred for 30 min at this temperature, triethylamine (1.45 mL, 10.4 mmol) was added and the reaction mixture was warmed up to room temperature. TLC and MS showed complete reaction (M+1: 722.7), and the reaction mixture was diluted with water and extracted with hexanes (2×). The combined organic layer was washed with brine. After drying over sodium sulfate, the filtrate was concentrated and the residue was purified by ISCO (SiO$_2$: EtOAc/Hexanes/0.5% Et$_3$N 0 to 50%) to afford the product as a brown oil (810 mg, 61%). MS (APCI): m/z (MH$^+$) 666.7. $^1$H NMR (300 MHz, CDCl$_3$) δ: ppm 4.85 (p, 1H, J=6.0 Hz); 4.05 (t, 2H, J=6.9 Hz); 2.56 (t, 4H, J=7.1 Hz); 2.31-2.24 (m, 4H); 1.67-1.19 (m, 63H); 0.87 (m, 9H).

Heptadecan-9-yl 8-((3-(benzyloxy)-3-oxopropyl)(8-(nonyloxy)-8-oxooctyl)amino)octanoate

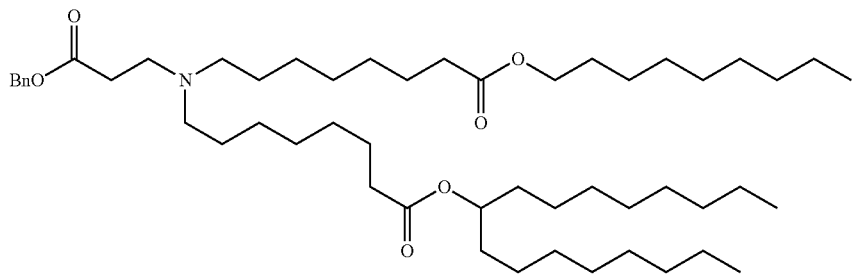

Chemical Formula: C$_{52}$H$_{93}$NO$_6$
Molecular Weight: 828.32

A solution of heptadecan-9-yl 8-((8-(nonyloxy)-8-oxooctyl)amino)octanoate (798 mg, 1.2 mmol) and benzyl acrylate (293 mg, 1.8 mmol) in dichloromethane (20 mL) was stirred at room temperature for 16 h. TLC and MS showed almost no reaction, 10 mL MeOH was added and the reaction mixture was stirred at room temperature for 16 h. MS showed the product with a small amount of methyl ester (M+1: 829.8, 752.7). The reaction mixture was concentrated to dryness and purified by ISCO (SiO$_2$: EtOAc/hexanes 0 to 35%) to afford the product as a colorless oil (280 mg, 28%). MS (APCI): m/z (MH$^+$) 829.8. $^1$H NMR (300 MHz, CDCl$_3$) δ: ppm 7.36-7.32 (m, 5H); 5.10 (s, 2H); 4.85 (p, 1H, J=6.0 Hz); 4.04 (t, 2H, J=6.9 Hz); 2.78 (t, 2H, J=6.9 Hz); 2.46 (t, 2H, J=7.0 Hz); 2.36 (t, 4H, J=6.9 Hz); 2.30-2.24 (m, 4H); 1.67-1.19 (m, 62H); 0.87 (m, 9H).

3-((8-(Heptadecan-9-yloxy)-8-oxooctyl)(8-(nonyloxy)-8-oxooctyl)amino)propanoic acid

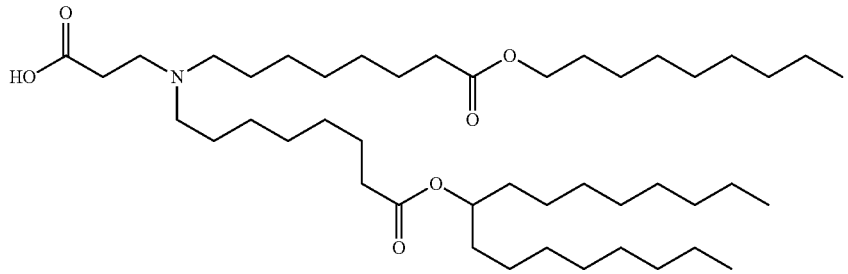

Chemical Formula: C$_{45}$H$_{87}$NO$_6$
Molecular Weight: 738.19

A mixture of heptadecan-9-yl 8-((3-(benzyloxy)-3-oxopropyl)(8-(nonyloxy)-8-oxooctyl)amino)octanoate (280 mg, 0.34 mmol) and Pd/C (10%, 28 mg) in 20 mL EtOAc was stirred under hydrogen balloon for 1 h. MS showed complete reaction. The reaction mixture was filtered and the filtrate was concentrated. The residue was purified by ISCO (SiO$_2$: MeOH/CH$_2$Cl$_2$ 0 to 10%) to afford the product as a colorless oil (230 mg, 91%). LC/UV (214 nm): RT=12.38 min. MS (APCI): m/z (MH$^+$) 838.7. $^1$H NMR (300 MHz, CDCl$_3$) δ: ppm 4.85 (p, 1H, J=6.0 Hz); 4.04 (t, 2H, J=6.6 Hz); 2.85 (t, 2H, J=6.0 Hz); 2.65 (t, 4H, J=7.7 Hz); 2.48 (t, 2H, J=6.0 Hz); 2.32-2.24 (m, 4H); 1.67-1.17 (m, 63H); 0.87 (m, 9H).

XX26. Compound 126: Heptadecan-9-yl 8-(methyl(4-(nonyloxy)-4-oxobutyl)amino)octanoate

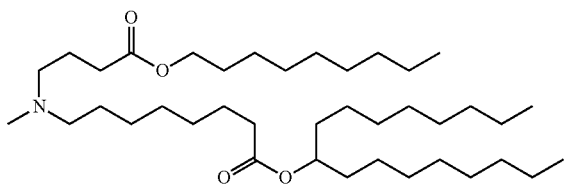

Chemical Formula: C$_{39}$H$_{77}$NO$_4$
Molecular Weight: 624.05

A solution of heptadecan-9-yl 8-(methylamino)octanoate (103 mg, 0.25 mmol), nonyl 4-bromobutanoate (88 mg, 0.30 mmol) and N,N-diisopropylethylamine (61 µL, 0.35 mmol) were dissolved in ethanol and was allowed to stir at 62° C. for 48 h. The reaction was cooled to rt and solvents were evaporated in vacuo. The residue was taken-up in ethyl acetate and washed with saturated aqueous sodium bicarbonate. The organic layer was separated and washed with brine, dried over Na$_2$SO$_4$ and evaporated in vacuo. The residue was purified by silica gel chromatography (0-100% (mixture of 1% NH$_4$OH, 20% MeOH in dichloromethane) in dichloromethane) to obtain heptadecan-9-yl 8-(methyl(4-(nonyloxy)-4-oxobutyl)amino)octanoate (90 mg, 0.14 mmol, 58%). UPLC/ELSD: RT=3.58 min. MS (ES): m/z (MH$^+$) 624.8 for C$_{39}$H$_{77}$NO$_4$. $^1$H NMR (300 MHz, CDCl$_3$) δ: ppm 4.89 (p, 1H); 4.08 (t, 2H); 2.38-2.24 (br. m, 11H); 1.82 (m, 2H); 1.64-1.28 (br. m, 52H); 0.90 (m, 9H).

XX27. Compound 127: Nonyl 8-((9-((bis(nony-loxy)phosphoryl)oxy)nonyl)(2-hydroxyethyl)amino) octanoate

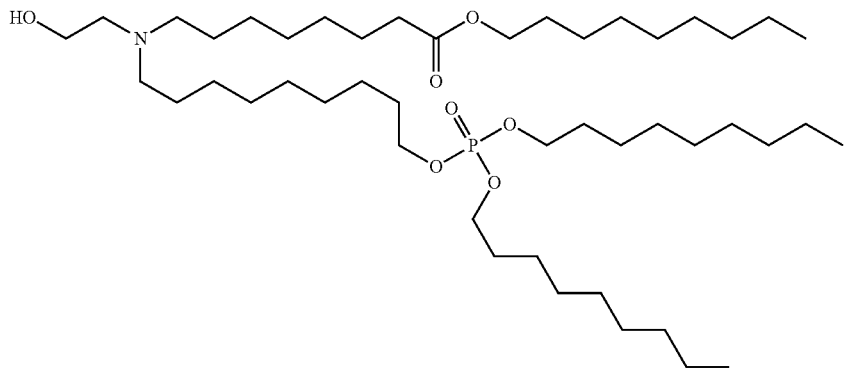

Chemical Formula: $C_{46}H_{94}NO_7P$
Molecular Weight: 804.232

Compound 127 was synthesized in the same manner as Compound 131 and according to the general procedure and Representative Procedure 1 described above. UPLC/ELSD: RT=3.58 min. MS (ES): m/z (MH$^+$) 805.1 for $C_{46}H_{94}NO_7P$. $^1$H NMR (300 MHz, CDCl$_3$) δ: ppm 4.05 (m, 8H); 3.55 (m, 2H); 2.59 (m, 2H); 2.46 (m, 4H); 2.31 (t, 2H), 1.67 (m, 11H); 1.29 (m, 55H); 0.90 (m, 9H).

XX28. Compound 128: Heptadecan-9-yl 8-((6-((1-cyclopropylnonyl)oxy)-6-oxohexyl)(2-hydroxyethyl) amino)octanoate

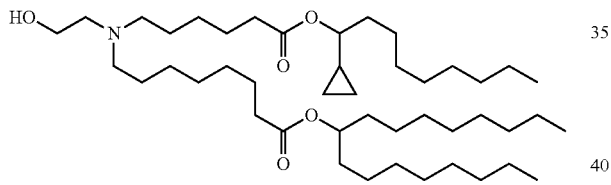

Chemical Formula: $C_{45}H_{87}NO_5$
Molecular Weight: 722.193

Compound 128 was synthesized according to the general procedure and Representative Procedure 1 described above. UPLC/ELSD: RT=3.67 min. MS (ES): m/z (MH$^{+)}$ 722.9 for $C_{45}H_{87}NO_5$. $^1$H NMR (300 MHz, CDCl$_3$) δ: ppm 4.89 (m, 1H); 4.30 (m, 1H); 3.56 (m, 2H); 2.72-2.39 (m, 6H); 2.30 (m, 4H), 1.76-1.17 (m, 58H); 0.90 (m, 10H); 0.61-0.35 (m, 3H); 0.28 (m, 1H).

XX29. Compound 129: Undecyl 6-((8-(dioctylamino)-8-oxooctyl)(2-hydroxyethyl)amino)hexanoate

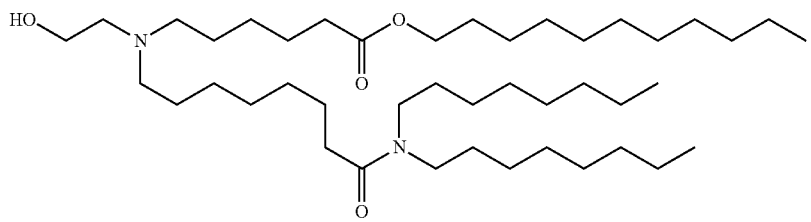

Chemical Formula: $C_{43}H_{86}N_2O_4$
Molecular Weight: 695.171

Compound 129 was synthesized according to the general procedure and Representative Procedure 1 described above. UPLC/ELSD: RT=3.45 min. MS (ES): m/z (MH$^{+}$) 695.9 for $C_{43}H_{86}N_2O_4$. $^1$H NMR (300 MHz, CDCl$_3$) δ: ppm 4.08 (t, 2H); 3.54 (m, 2H), 3.28 (m, 4H); 2.59 (m, 2H); 2.47 (m, 4H); 2.32 (q, 4H); 1.73-1.19 (m, 58H); 0.90 (m, 9H).

XX30. Compound 130: Decan-2-yl 8-((8-(dioctylamino)-8-oxooctyl)(2-hydroxyethyl)amino)octanoate

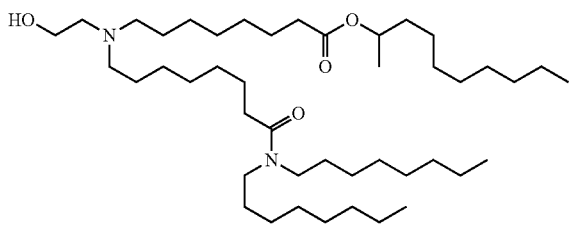

Chemical Formula: $C_{44}H_{88}N_2O_4$
Molecular Weight: 709.198

Compound 130 was synthesized according to the general procedure and Representative Procedure 1 described above. UPLC/ELSD: RT=3.46 min. MS (ES): m/z (MH$^+$) 709.9 for $C_{44}H_{88}N_2O_4$. $^1$H NMR (300 MHz, CDCl$_3$) δ: ppm 4.90 (m, 1H); 3.70 (br. m, 2H), 3.35-3.15 (m, 4H); 2.96-2.41 (br. m, 6H); 2.29 (m, 4H); 1.74-1.43 (m, 14H); 1.41-1.115 (m, 47H); 0.90 (m, 9H).

XX31. Compound 131: Nonyl 8-((7-((bis(octyloxy)phosphoryl)oxy)heptyl)(2-hydroxyethyl)amino)octanoate 7-Bromoheptyl dioctyl phosphate

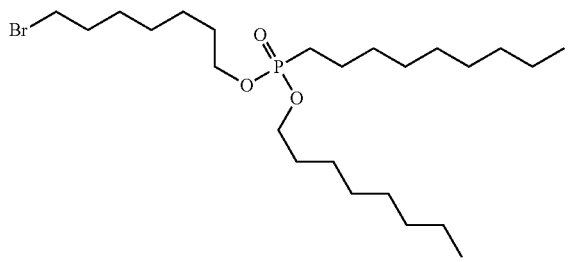

Chemical Formula: $C_{23}H_{48}BrO_4P$
Molecular Weight: 499.511

To a solution of POCl$_3$ (1.91 mL, 20.5 mmol) in DCM (20 mL) at 0° C., Et$_3$N (2.85 mL, 20.4 mmol) was slowly added followed by 7-bromoheptan-1-ol (4.0 g, 20.5 mmol). The reaction was allowed to stir for 4 h at 0° C. A solution of octan-1-ol (7.10 mL, 45.11 mmol) and Et$_3$N (8.9 mL, 63.8 mmol) in DCM were added and the reaction was allowed to stir at rt for 16 h. The reaction was diluted with DCM and washed with saturated NaHCO$_3$. The organic layer was separated, dried over Na$_2$SO$_4$, filtered, and evaporated under vacuum. The residue was purified by ISCO with (0-30%) EtOAc in hexanes to obtain 7-bromoheptyl dioctyl phosphate (0.58 g, 1.16 mmol, 6%). $^1$H NMR (300 MHz, CDCl$_3$) δ: ppm 4.03 (m, 6H); 3.43 (t, 2H); 1.88 (m, 2H); 1.70 (m, 6H); 1.54-1.23 (m, 26H); 0.90 (m, 6H).

Nonyl 8-((7-((bis(octyloxy)phosphoryl)oxy)heptyl)(2-hydroxyethyl)amino)octanoate

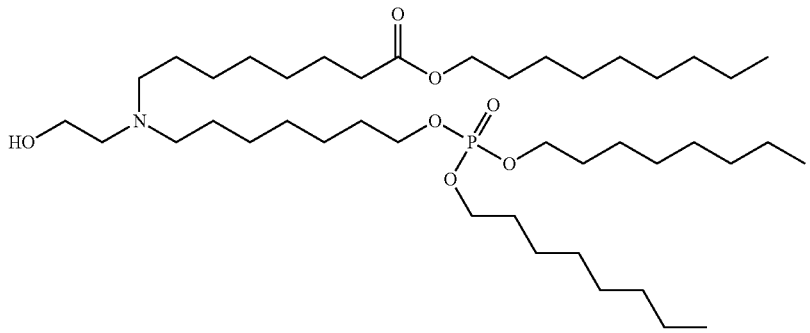

Chemical Formula: $C_{42}H_{86}NO_7P$
Molecular Weight: 748.124

Compound 131 was synthesized according to the general procedure and Representative Procedure 1 described above. UPLC/ELSD: RT=3.22 min. MS (ES): m/z (MH$^+$) 750.0 for $C_{42}H_{86}NO_7P$. $^1$H NMR (300 MHz, CDCl$_3$) δ: ppm 4.05 (m, 8H); 3.51 (m, 2H); 2.60 (br. m, 2H); 2.46 (m, 4H); 2.31 (t, 2H); 1.76-1.15 (m, 58H); 0.90 (m, 9H).

XX32. Compound 132: Decan-2-yl 8-((7-((bis(octyloxy)phosphoryl)oxy)heptyl)(2-hydroxyethyl)amino)octanoate

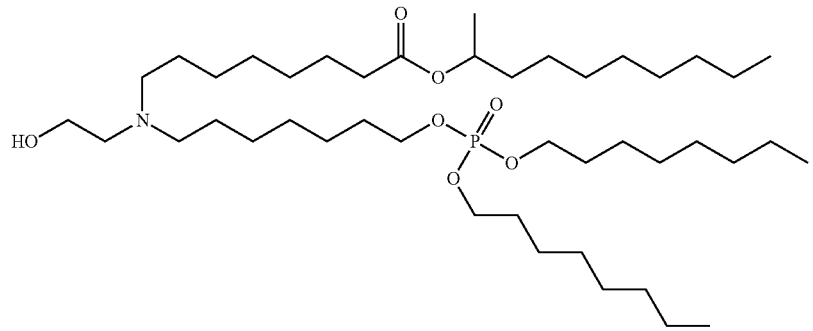

Chemical Formula: $C_{43}H_{88}NO_7P$
Molecular Weight: 762.15

Compound 132 was synthesized in the same manner as Compound 131 and according to the general procedure and Representative Procedure 1 described above. UPLC/ELSD: RT=3.27 min. MS (ES): m/z (MH$^+$) 764.00 for $C_{43}H_{88}NO_7P$. $^1$H NMR (300 MHz, CDCl$_3$) δ: ppm 4.91 (m, 1H); 4.03 (m, 6H); 3.56 (m, 2H); 2.73-2.38 (br. m, 6H); 2.29 (t, 2H); 1.79-1.16 (m, 61H); 0.90 (m, 9H).

XX33. Compound 133: ((2-Hydroxyethyl)azanediyl)bis(nonane-9,1-diyl)bis(2-hexyldecanoate)

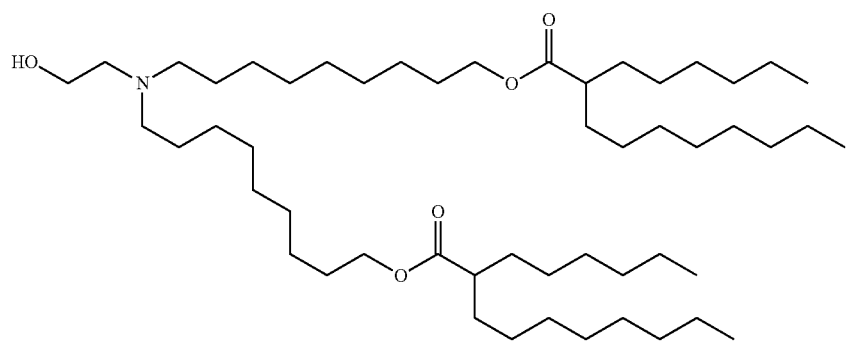

Chemical Formula: $C_{52}H_{103}NO_5$
Molecular Weight: 822.398

Compound 133 was synthesized according to the general procedure and Representative Procedure 1 described above. UPLC/ELSD: RT=3.91 min. MS (ES): m/z (MH$^+$) 824.0 for $C_{52}H_{103}NO_5$. $^1$H NMR (300 MHz, CDCl$_3$) δ: ppm 4.09 (t, 4H); 3.60 (m, 2H); 2.74-2.42 (br. m, 6H); 2.33 (m, 3H); 1.72-1.17 (m, 76H); 0.90 (m, 12H).

XX34. Compound 134: 9-((2-Hydroxyethyl)(8-(nonyloxy)-8-oxooctyl)amino)nonyl 2-hexyldecanoate

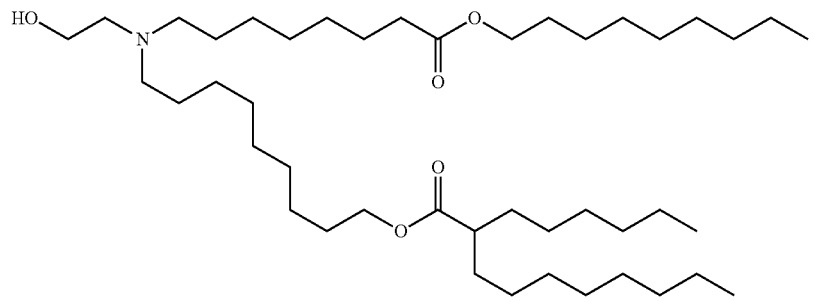

Chemical Formula: $C_{44}H_{87}NO_5$
Molecular Weight: 710.182

Compound 134 was synthesized according to the general procedure and Representative Procedure 1 described above. UPLC/ELSD: RT=3.48 min. MS (ES): m/z (MH$^+$) 712.0 for $C_{44}H_{87}NO_5$. $^1$H NMR (300 MHz, CDCl$_3$) δ: ppm 4.08 (m, 4H); 3.55 (m, 2H); 2.67-2.39 (br. m, 6H); 2.31 (m, 3H); 1.71-1.19 (m, 62H); 0.90 (m, 12H).

XX35. Compound 135: 7-((8-(Decan-2-yloxy)-8-oxooctyl)(2-hydroxyethyl)amino)heptyl 2-octyldecanoate

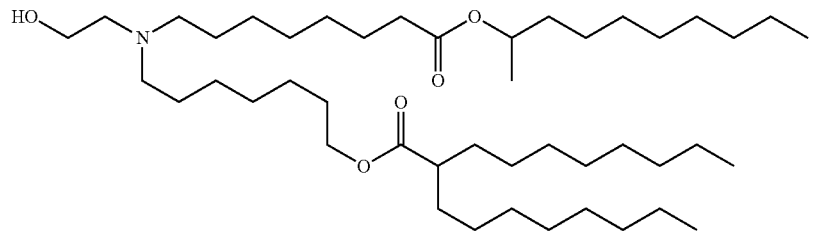

Chemical Formula: $C_{45}H_{89}NO_5$
Molecular Weight: 724.209

Compound 135 was synthesized according to the general procedure and Representative Procedure 1 described above. UPLC/ELSD: RT=3.63 min. MS (ES): m/z (MH$^+$) 726.0 for $C_{45}H_{89}NO_5$. $^1$H NMR (300 MHz, CDCl$_3$) δ: ppm 4.91 (m, 1H); 4.08 (t, 2H); 3.57 (m, 2H); 2.73-2.40 (br. m, 6H); 2.29 (m, 3H); 1.71-1.16 (m, 66H); 0.90 (m, 9H).

BA. Compound 136: Nonyl 8-((2-hydroxyethyl)((9Z,12Z)-octadeca-9,12-dien-1-yl)amino)octanoate Representative Procedure 2:

Nonyl 8-bromooctanoate (Method A)

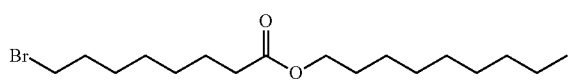 [SMILES: CCCCCCCCCOC(=O)CCCCCCCBr]

To a solution of 8-bromooctanoic acid (5 g, 22 mmol) and nonan-1-ol (6.46 g, 45 mmol) in dichloromethane (100 mL) were added N-(3-Dimethylaminopropyl)-N'-ethylcarbodiimide hydrochloride (4.3 g, 22 mmol) and DMAP (547 mg, 4.5 mmol). The reaction was allowed to stir at rt for 18 h. The reaction was diluted with dichloromethane and washed with saturated sodium bicarbonate. The organic layer was separated and washed with brine, dried over MgSO$_4$. The organic layer was filtered and evaporated under vacuum. The residue was purified by silica gel chromatography (0-10% ethyl acetate in hexanes) to obtain nonyl 8-bromooctanoate (6.1 g, 17 mmol, 77%).

$^1$H NMR (300 MHz, CDCl$_3$) δ: ppm 4.06 (t, 2H); 3.40 (t, 2H); 2.29 (t, 2H); 1.85 (m, 2H); 1.72-0.97 (m, 22H); 0.88 (m, 3H).

Nonyl 8-((2-hydroxyethyl)amino)octanoate

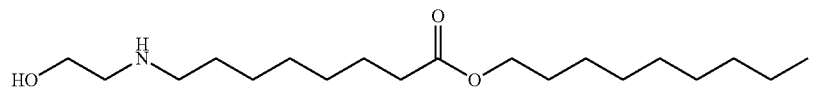 [SMILES: CCCCCCCCCOC(=O)CCCCCCCNCCO]

A solution of nonyl 8-bromooctanoate (1.2 g, 3.4 mmol) and 2-aminoethan-1-ol (5 mL, 83 mmol) in ethanol (2 mL) was allowed to stir at 62° C. for 18 h. The reaction mixture was concentrated in vacuum and the residue was extracted with ethyl acetate and water. The organic layer was separated and washed with water, brine and dried over $Na_2SO_4$. The organic layer was filtered and evaporated in vacuo. The residue was purified by silica gel chromatography (0-100% (mixture of 1% $NH_4OH$, 20% MeOH in dichloromethane) in dichloromethane) to obtain nonyl 8-((2-hydroxyethyl)amino)octanoate (295 mg, 0.9 mmol, 26%).

UPLC/ELSD: RT=1.29 min. MS (ES): m/z (MH$^+$) 330.42 for $C_{19}H_{39}NO_3$ $^1$H NMR (300 MHz, CDCl$_3$) δ: ppm 4.07 (t, 2H); 3.65 (t, 2H); 2.78 (t, 2H); 2.63 (t, 2H); 2.32-2.19 (m, 4H); 1.73-1.20 (m, 24H); 0.89 (m, 3H)

Nonyl 8-((2-hydroxyethyl)((9Z,12Z)-octadeca-9,12-dien-1-yl)amino)octanoate

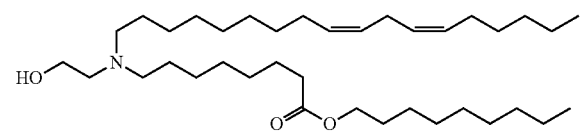

Chemical Formula: $C_{37}H_{71}NO_3$
Molecular Weight: 577.98

A solution of nonyl 8-((2-hydroxyethyl)amino)octanoate (150 mg, 0.46 mmol), (6Z,9Z)-18-bromooctadeca-6,9-diene (165 mg, 0.5 mmol) and N,N-diisopropylethylamine (65 mg, 0.5 mmol) in ethanol (2 mL) was allowed to stir at reflux for 48 h. The reaction was allowed to cool to rt and solvents were evaporated under vacuum. The residue was purified by silica gel chromatography (0-10% MeOH in dichloromethane) to obtain nonyl 8-((2-hydroxyethyl)((9Z,12Z)-octadeca-9,12-dien-1-yl)amino)octanoate (81 mg, 0.14 mmol, 30%) as a HBr salt.

UPLC/ELSD: RT=3.24 min. MS (ES): m/z (MH$^+$) 578.64 for $C_{37}H_{71}NO_3$ $^1$H NMR (300 MHz, CDCl$_3$) δ: ppm 10.71 (br., 1H); 5.36 (br. m, 4H); 4.04 (m, 4H); 3.22-2.96 (br. m, 5H); 2.77 (m, 2H); 2.29 (m, 2H); 2.04 (br. m, 4H); 1.86 (br. m, 4H); 1.66-1.17 (br. m, 40H); 0.89 (m, 6H)

BB. Compound 137: Methyl 12-(dodecyl(2-hydroxyethyl)amino)dodecanoate

Methyl 12-bromododecanoate

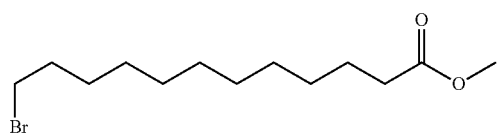

Chemical Formula: $C_{13}H_{25}BrO_2$
Molecular Weight: 293.25

To a solution of 12-bromododecanoic acid (2.5 g, 8.95 mmol) in THF (7 mL) was added methanol (7.2 mL, 179 mmol). Sulfuric acid (0.50 mL, 8.95 mmol) was added dropwise and the reaction was allowed to stir at 65° C. for two hours. The reaction mixture was washed with 5% $NaHCO_3$ and brine. The organic layer was dried over anhydrous $Na_2SO_4$, filtered, and concentrated in vacuo. Purification by silica gel chromatography (0-20% EtOAc/hexanes) provided methyl 12-bromododecanoate (2.40 g, 92%).

$^1$H NMR (300 MHz, CDCl$_3$) δ: ppm 3.69 (s, 3H); 3.44 (t, 2H); 2.33 (t, 2H); 1.88 (br. m, 2H); 1.64 (br. m, 2H); 1.45 (br. m, 2H); 1.31 (br. m, 12H).

Methyl 12-(dodecyl(2-hydroxyethyl)amino)dodecanoate

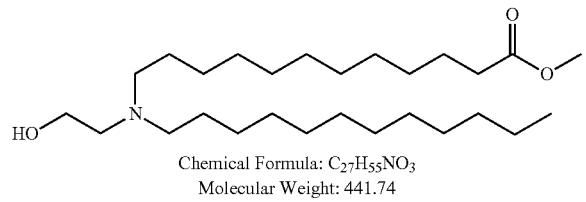 [SMILES: CCCCCCCCCCCCN(CCO)CCCCCCCCCCCC(=O)OC]

Chemical Formula: $C_{27}H_{55}NO_3$
Molecular Weight: 441.74

To a solution of methyl 12-((2-hydroxyethyl)amino)dodecanoate (413 mg, 1.51 mmol) (isolated from the synthesis of 12,12'-((2-Hydroxyethyl)azanediyl)didodecanoate) in MeCN (5 mL) was added 1-bromododecane (452 mg, 1.81 mmol), $K_2CO_3$ (418 mg, 3.02 mmol), and KI (25 mg, 0.151 mmol). The reaction was allowed to stir at 82° C. for 16 hours. The reaction mixture was cooled to room temperature, diluted with $H_2O$, and extracted with EtOAc. The combined organic layers were washed with brine, dried over anhydrous $Na_2SO_4$, filtered, and concentrated in vacuo. Purification by silica gel chromatography (0-100% [DCM, 20% MeOH, 1% $NH_4OH$]/MeOH) provided methyl 12-(dodecyl(2-hydroxyethyl)amino)dodecanoate (409 mg, 61%).

UPLC/ELSD: RT=2.39 min. MS (ES): m/z (MH⁺) 442.60 for $C_{27}H_{55}NO_3$

¹H NMR (300 MHz, CDCl₃) δ: ppm 3.69 (s, 3H); 3.61 (t, 2H); 2.68 (t, 2H); 2.54 (t, 4H); 2.32 (t, 2H); 1.64 (m, 2H); 1.50 (br. m, 4H); 1.28 (br. m, 32H); 0.90 (t, 3H).

BC. Compound 138: Dinonyl 8,8'-((2-hydroxyethyl)azanediyl)dioctanoate

Representative Procedure 3:

Dinonyl 8,8'-((2-hydroxyethyl)azanediyl)dioctanoate

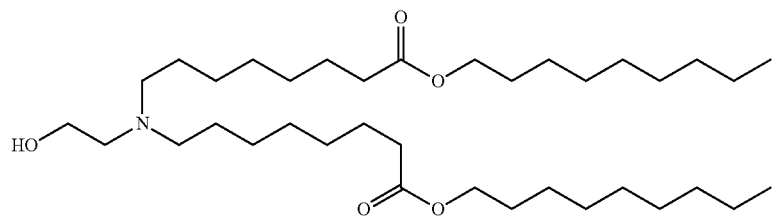

Chemical Formula: $C_{36}H_{71}NO_5$
Molecular Weight: 597.97

A solution of nonyl 8-bromooctanoate (200 mg, 0.6 mmol) and 2-aminoethan-1-ol (16 mg, 0.3 mmol) and N,N-diisopropylethylamine (74 mg, 0.6 mmol) in THF/CH₃CN (1:1) (3 mL) was allowed to stir at 63° C. for 72 h. The reaction was cooled to rt and solvents were evaporated under vacuum. The residue was extracted with ethyl acetate and saturated sodium bicarbonate. The organic layer was separated, dried over Na₂SO₄ and evaporated under vacuum. The residue was purified by silica gel chromatography (0-10% MeOH in dichloromethane) to obtain dinonyl 8,8'-((2-hydroxyethyl)azanediyl)dioctanoate (80 mg, 0.13 mmol, 43%).

UPLC/ELSD: RT=3.09 min. MS (ES): m/z (MH⁺) 598.85 for $C_{36}H_{71}NO_5$

¹H NMR (300 MHz, CDCl₃) δ: ppm 4.05 (m, 4H); 3.57 (br. m, 2H); 2.71-2.38 (br. m, 6H); 2.29 (m, 4H), 1.71-1.01 (br. m, 49H), 0.88 (m, 6H).

BD. Compound 139: Di((Z)-non-2-en-1-yl) 8,8'-((2-hydroxyethyl)azanediyl)dioctanoate Compound 139 was synthesized following the Representative Procedure 3.

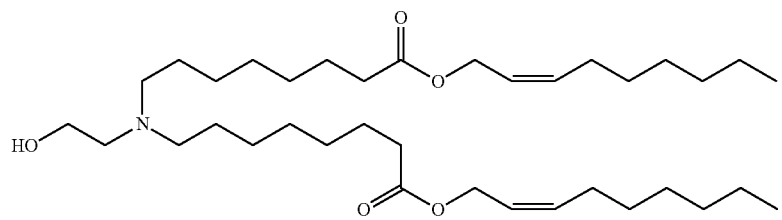

Chemical Formula: $C_{36}H_{67}NO_5$
Molecular Weight: 593.93

UPLC/ELSD: RT=2.88 min. MS (ES): m/z (MH⁺) 594.78 for $C_{36}H_{67}NO_5$

¹H NMR (300 MHz, CDCl₃) δ: ppm 5.60 (m, 2H); 5.50 (m, 2H); 4.59 (m, 4H); 3.96 (br. m, 2H); 3.20-2.94 (br. m, 5H); 2.28 (m, 4H); 2.07 (m, 4H); 1.80 (br. m 4H); 1.59 (br. m, 6H); 1.43-1.14 (br. m, 28H), 0.85 (m, 6H).

BE. Compound 140: Di((Z)-undec-2-en-1-yl) 6,6'-((2-hydroxyethyl)azanediyl)dihexanoate Compound 140 was synthesized following the Representative Procedure 3.

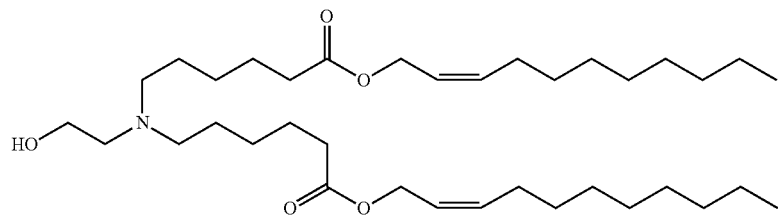

Chemical Formula: $C_{36}H_{67}NO_5$
Molecular Weight: 593.93

UPLC/ELSD: RT=2.87 min. MS (ES): m/z (MH⁺) 594.74 for $C_{36}H_{67}NO_5$

¹H NMR (300 MHz, CDCl₃) δ: ppm 5.73-5.44 (m, 4H); 4.62 (m, 4H); 3.55 (m, 2H); 2.73-2.39 (br. m, 6H); 2.39 (m, 4H); 2.09 (m, 4H); 1.64 (m, 4H); 1.55-1.14 (br. m, 33H); 0.88 (m, 6H).

BF. Compound 141: Diundecyl 6,6'-((2-hydroxyethyl)azanediyl)dihexanoate

Compound 141 was synthesized following Representative Procedure 3.

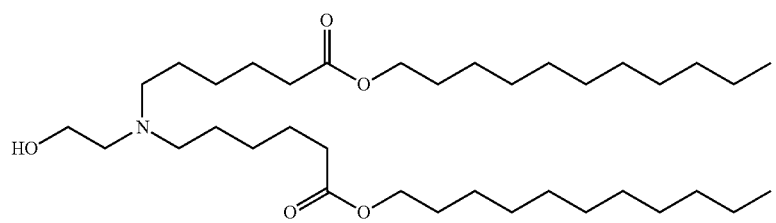

Chemical Formula: $C_{36}H_{71}NO_5$
Molecular Weight: 597.97

UPLC/ELSD: RT=3.03 min. MS (ES): m/z (MH⁺) 598.63 for $C_{36}H_{71}NO_5$

¹H NMR (300 MHz, CDCl₃) δ: ppm 4.05 (m, 4H); 3.53 (m, 2H); 2.95 (br. m, 1H); 2.65-2.35 (m, 6H); 2.30 (m, 4H); 1.73-1.54 (m, 8H); 1.54-1.15 (m, 40H); 0.88 (m, 6H).

BG. Compound 142: 12,12'-((2-Hydroxyethyl)azanediyl)didodecanoate 12,12'-((2-Hydroxyethyl)azanediyl)didodecanoate

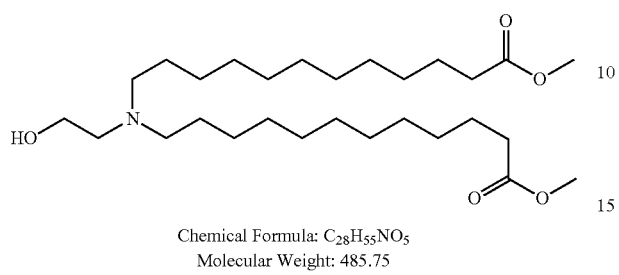

Chemical Formula: $C_{28}H_{55}NO_5$
Molecular Weight: 485.75

To a solution of methyl 12-bromododecanoate (1.5 g, 5.12 mmol) in MeCN (11 mL) was added ethanolamine (0.310 mL, 5.12 mmol), $K_2CO_3$ (1.42 g, 10.2 mmol), and KI (85 mg, 0.512 mmol). The reaction was allowed to stir at 82° C. for 16 hours. The reaction mixture was cooled to room temperature, filtered, and the solids were washed with hexanes. The filtrate was extracted with hexanes, and the combined extracts were concentrated in vacuo. Purification by silica gel chromatography (0-100% [DCM, 20% MeOH, 1% $NH_4OH$]/MeOH) provided 12,12'-((2-hydroxyethyl)azanediyl)didodecanoate (563 mg, 45%).

UPLC/ELSD: RT=1.81 min. MS (ES): m/z ($MH^+$) 486.63 for $C_{28}H_{55}NO_5$ $^1$H NMR (300 MHz, $CDCl_3$) δ: ppm 3.69 (s, 6H); 3.59 (br. m, 2H); 2.75-2.40 (br. m, 6H); 2.32 (t, 4H); 1.64 (m, 4H); 1.48 (br. m, 4H); 1.29 (br. m, 28H).

BH. Compound 143: Nonyl 8-((2-hydroxyethyl)(7-((2-octyldecyl)oxy)-7-oxoheptyl)amino)octanoate 2-Octyldecanoic acid

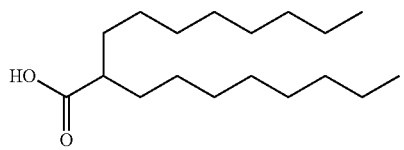

Chemical Formula: $C_{18}H_{36}O_2$
Molecular Weight: 284.48

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at rt for 30 min. After this time 1-iodooctane (5 g, 20.8 mmol) was added and the reaction mixture was heated at 45° C. for 6 h. The reaction was quenched with 1N HCl (10 mL). The organic layer was dried over $MgSO_4$, filtered and evaporated under vacuum. The residue was purified by silica gel chromatography (0-20% ethyl acetate in hexanes) to yield 2-octyldecanoic acid (1.9 g, 6.6 mmol).

$^1$H NMR (300 MHz, $CDCl_3$) δ: ppm 2.38 (br. m, 1H); 1.74-1.03 (br. m, 28H); 0.91 (m, 6H).

2-Octyldecan-1-ol

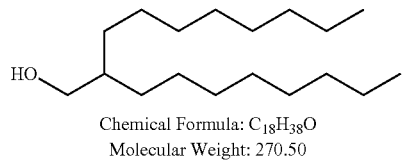 [SMILES: CCCCCCCCC(CO)CCCCCCCC]

Chemical Formula: $C_{18}H_{38}O$
Molecular Weight: 270.50

A solution of 2-octyldecanoic acid (746 mg, 2.6 mmol) in dry THF (12 mL) was added to a stirred solution of LAH (5.2 mL, 5.2 mmol, 1M solution in THF) in dry THF (6 mL) under nitrogen at 0° C. The reaction was allowed to warm to rt and stirred at rt for 12 h. A solution of saturated $Na_2SO_4*10H_2O$ solution (10 mL) was added. The solids were filtered through a plug of Celite. The filtrate was evaporated under vacuum and the residue was purified by silica gel chromatography (0-20% ethyl acetate in hexanes) to yield 2-octyldecan-1-ol (635 mg, 2.3 mmol).

$^1$H NMR (300 MHz, $CDCl_3$) δ: ppm 3.54 (d, 2H); 1.56-1.21 (br. m, 30H); 0.91 (t, 6H).

2-Octyldecyl 7-bromoheptanoate

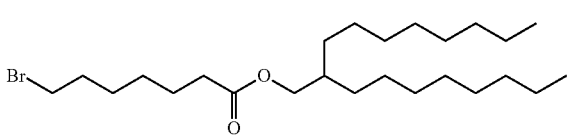 [SMILES: CCCCCCCCC(CCCCCCCC)COC(=O)CCCCCCBr]

2-Octyldecyl 7-bromoheptanoate was synthesized according to Method A.

$^1$H NMR (300 MHz, $CDCl_3$) δ: ppm 3.96 (d, 2H); 3.40 (t, 2H); 2.31 (t, 2H); 1.86 (m, 2H); 1.71-1.19 (m, 35H); 0.88 (m, 6H).

Nonyl 8-((2-hydroxyethyl)(7-((2-octyldecyl)oxy)-7-oxoheptyl)amino)octanoate was synthesized using Representative Procedure 2.

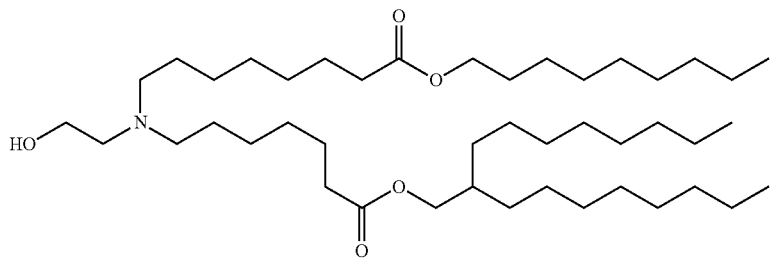

Chemical Formula: $C_{44}H_{87}NO_5$
Molecular Weight: 710.182

UPLC/ELSD: RT=5.23 min. MS (ES): m/z (MH$^+$) 711.08 for $C_{44}H_{87}NO_5$ $^1$H NMR (300 MHz, CDCl$_3$) δ: ppm 4.05 (t, 2H); 3.96 (d, 2H); 3.58 (br. m, 2H); 2.79-2.36 (br. m, 5H); 2.30 (m, 4H); 1.72-1.01 (br. m, 63H); 0.88 (m, 9H).

BI. Compound 144: Nonyl 8-((8-(dioctylamino)-8-oxooctyl)(2-hydroxyethyl)amino)octanoate
8-Bromo-N,N-dioctyloctanamide

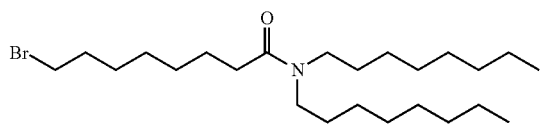

Chemical Formula: $C_{24}H_{48}BrNO$
Molecular Weight: 446.56

To a solution of 8-bromooctanoic acid (1 g, 2.2 mmol) and DMF (1 drop) in dichloromethane was added oxalyl chloride (0.416 mL, 2.5 mmol) dropwise. The reaction was allowed to stir for 1 h at room temperature. Solvents were evaporated and the residue was added to a solution of dioctylamine (1.14 g, 4.8 mmol) and DMAP (100 mg, 0.8 mmol). Triethylamine was added to the reaction dropwise and the reaction was allowed to stir for 18 h. The solvents were evaporated and the residue was taken up in ethyl acetate and saturated NaHCO$_3$. The organic layer was separated and washed with water and brine. The organic layer was dried over Na$_2$SO$_4$, filtered and evaporated in vacuo. The residue was purified by silica gel chromatography (0-100% (mixture of 1% NH$_4$OH, 20% MeOH in dichloromethane) in dichloromethane to yield a mixture of 8-bromo-N,N-dioctyloctanamide and chloro-N,N-dioctyloctanamide (736 mg, 1.6 mmol).

UPLC/ELSD: RT=4.02 min. MS (ES): m/z (MH$^+$) 446.53 for $C_{24}H_{48}BrNO$ $^1$H NMR (300 MHz, CDCl$_3$) δ: ppm 3.55 (t, 0.6H); 3.42 (t, 1.4H); 3.36-3.15 (m, 4H); 2.31 (t, 2H); 1.96-1.18 (m, 34H); 0.91 (m, 6H).

Nonyl 8-((8-(dioctylamino)-8-oxooctyl)(2-hydroxyethyl) amino)octanoate was synthesized utilizing Representative Procedure 2.

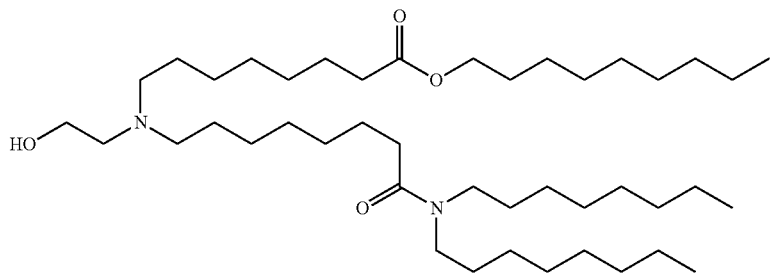

Chemical Formula: $C_{43}H_{86}N_2O_4$
Molecular Weight: 695.17

UPLC/ELSD: RT=4.24 min. MS (ES): m/z (MH$^+$) 696.16 for $C_{43}H_{86}N_2O_4$ $^1$H NMR (300 MHz, CDCl$_3$) δ: ppm 4.05 (t, 2H); 3.57 (br. m, 2H); 3.35-3.14 (m, 4H); 2.80-.2.20 (m, 10H); 1.74-1.00 (br. m, 59H); 0.88 (m, 9H).

XX45. Compound 145: Heptadecan-9-yl 8-((2-hydroxyethyl)(8-(methyl(octyl)amino)-8-oxooctyl)amino)octanoate

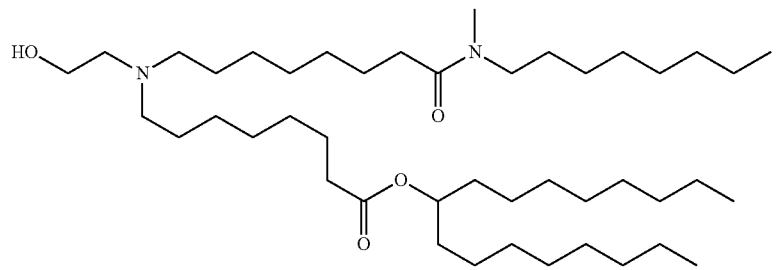

Chemical Formula: $C_{44}H_{88}N_2O_4$
Molecular Weight: 709.198

Compound 145 was synthesized according to the general procedure and Representative Procedure 1 described above. UPLC/ELSD: RT=2.17 min. MS (ES): m/z (MH$^+$) 710.0 for $C_{44}H_{88}N_2O_4$. $^1$H NMR (300 MHz, CDCl$_3$) δ: ppm 4.89 (m, 1H); 3.55 (m, 2H); 3.37 (t, 1H); 3.27 (t, 1H); 2.98 (s, 1.5H); 2.93 (s, 1.5H); 2.59 (m, 2H); 2.47 (m, 4H); 2.30 (m, 4H), 1.75-1.20 (m, 60H); 0.90 (m, 9H).

XX46. Compound 146: Heptadecan-9-yl 8-((2-hydroxyethyl)(6-(methyl(octyl)amino)-6-oxohexyl)amino)octanoate

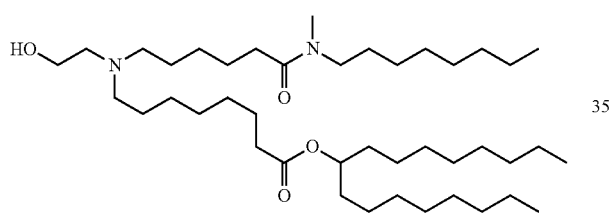

Chemical Formula: $C_{42}H_{84}N_2O_4$
Molecular Weight: 681.144

Compound 146 was synthesized according to the general procedure and Representative Procedure 1 described above. UPLC/ELSD: RT=2.01 min. MS (ES): m/z (MH$^+$) 682.0 for $C_{42}H_{84}N_2O_4$. $^1$H NMR (300 MHz, CDCl$_3$) δ: ppm 4.88 (m, 1H); 3.55 (m, 2H); 3.37 (t, 1H); 3.26 (t, 1H); 2.98 (s, 1.5H); 2.93 (s, 1.5H); 2.59 (m, 2H); 2.48 (m, 4H); 2.31 (m, 4H), 1.76-1.18 (m, 56H); 0.90 (m, 9H).

XX47. Compound 147: Tridecan-7-yl 10-((2-hydroxyethyl)(8-(nonyloxy)-8-oxooctyl)amino)decanoate

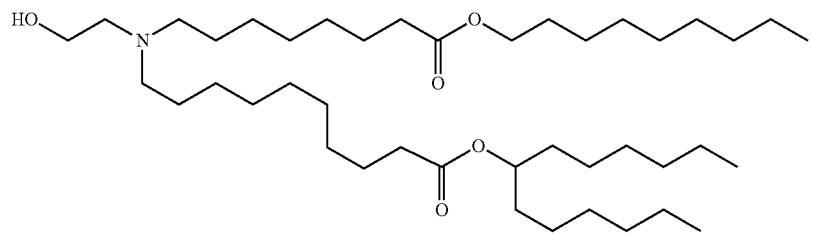

Chemical Formula: $C_{42}H_{83}NO_5$
Molecular Weight: 682.128

Compound 147 was synthesized according to the general procedure and Representative Procedure 1 described above. UPLC/ELSD: RT=2.16 min. MS (ES): m/z (MH$^+$) 683.0 for $C_{42}H_{83}NO_5$. $^1$H NMR (300 MHz, CDCl$_3$) δ: ppm 4.89 (m, 1H); 4.08 (m, 2H); 3.55 (m, 2H); 2.59 (m, 2H); 2.46 (m, 4H); 2.30 (m, 4H); 1.72-1.18 (m, 58H); 0.90 (m, 9H).

XX48. Compound 148: Heptadecan-9-yl 8-((2-hydroxyethyl)(8-((2-methoxynonyl)oxy)-8-oxooctyl)amino)octanoate 1-((tert-Butyldiphenylsilyl)oxy)nonan-2-ol

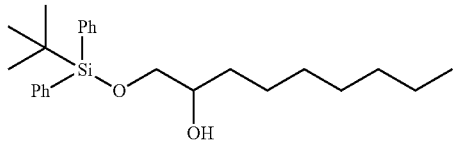

Chemical Formula: $C_{25}H_{38}O_2Si$
Molecular Weight: 398.662

TBDPSCl (8.58 g, 31.2 mmol) was added to a mixture of nonane-1,2-diol (5.0 g, 31.2 mmol) and imidazole (4.24 g, 62.4 mmol) in DMF at RT. The reaction was stirred at RT overnight. The reaction was diluted with water (150 mL) and extracted with EtOAc/hexanes (1:1) (4×). The combined organic layer was washed with brine, separated, dried with Na$_2$SO$_4$, filtered, and evaporated under vacuum. The residue was purified by ISCO with (0-10%) EtOAc in hexanes to obtain 1-((tert-butyldiphenylsilyl)oxy)nonan-2-ol (7.75 g, 19.4 mmol). $^1$H NMR (300 MHz, DMSO) δ: ppm 7.63 (m, 4H); 7.43 (m, 6H); 4.51 (d, 1H); 3.54 (m, 2H); 3.43 (m, 1H); 1.57 (m, 1H); 1.24 (m, 11H); 1.00 (s, 9H); 0.85 (m, 3H).

2-Methoxynonyl 8-bromooctanoate

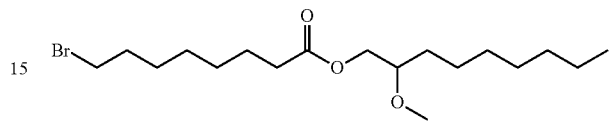

Chemical Formula: $C_{18}H_{35}BrO_3$
Molecular Weight: 379.379

2-Methoxynonyl 8-bromooctanoate was synthesized following Method A in Representative Procedure 1. $^1$H NMR (300 MHz, CDCl$_3$) δ: ppm 4.19 (m, 1H); 4.04 (m, 1H); 3.42 (m, 6H); 2.36 (t, 2H); 1.87 (m, 2H); 1.73-1.22 (m, 20H); 0.93 (m, 3H).

Heptadecan-9-yl 8-((2-hydroxyethyl)(8-((2-methoxynonyl)oxy)-8-oxooctyl)amino)octanoate

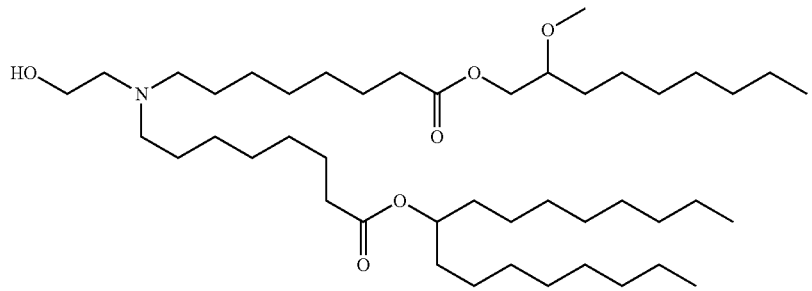

Chemical Formula: $C_{45}H_{89}NO_6$
Molecular Weight: 740.208

Compound 148 was synthesized according to the general procedure and Representative Procedure 1 described above. UPLC/ELSD: RT=2.48 min. MS (ES): m/z (MH$^+$) 741.0 for $C_{45}H_{89}NO_6$. $^1$H NMR (300 MHz, CDCl$_3$) δ: ppm 4.89 (m, 1H); 4.19 (m, 1H); 4.04 (m, 1H); 3.57 (m, 2H); 3.42 (s, 3H); 3.37 (m, 1H); 2.73-2.41 (m, 6H); 2.33 (m, 4H); 1.73-1.19 (m, 61H); 0.90 (m, 9H).

XX49. Compound 149: Heptyl 10-((8-(heptadecan-9-yloxy)-8-oxooctyl)(methyl)amino)decanoate

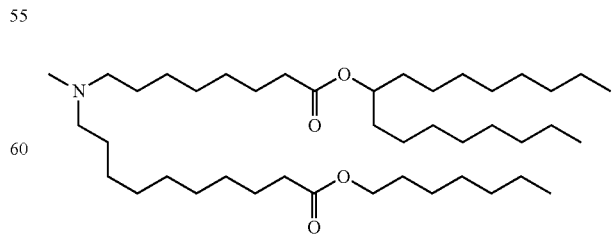

Chemical Formula: $C_{43}H_{85}NO_4$
Molecular Weight: 680.156

Compound 149 was synthesized similarly to Compound 123 and according to the general procedure and Representative Procedure 1 described above. UPLC/ELSD: RT=2.55 min. MS (ES): m/z (MH$^+$) 681.0 for $C_{43}H_{85}NO_4$. $^1$H NMR (300 MHz, CDCl$_3$) δ: ppm 4.89 (m, 1H); 4.08 (t, 2H); 2.42-2.14 (m, 11H); 1.73-1.17 (m, 62H); 0.90 (m, 9H).

XX50. Compound 150: Pentyl 12-((8-(heptadecan-9-yloxy)-8-oxooctyl)(methyl)amino)dodecanoate

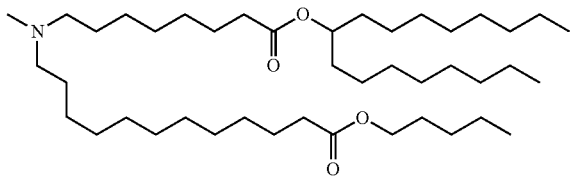

Chemical Formula: $C_{43}H_{85}NO_4$
Molecular Weight: 680.156

Compound 150 was synthesized similarly to Compound 123 and according to the general procedure and Representative Procedure 1 described above. UPLC/ELSD: RT=2.47 min. MS (ES): m/z (MH$^+$) 681.0 for $C_{43}H_{85}NO_4$. $^1$H NMR (300 MHz, CDCl$_3$) δ: ppm 4.89 (m, 1H); 4.08 (t, 2H); 2.42-2.16 (m, 10H); 1.73-1.20 (m, 63H); 0.90 (m, 9H).

XX51. Compound 151: 7-((7-(Decanoyloxy)heptyl)(2-hydroxyethyl)amino)heptyl 2-octyldecanoate

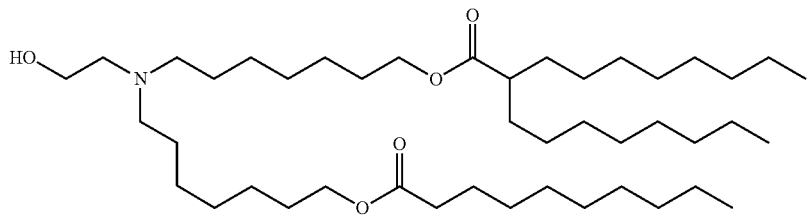

Chemical Formula: $C_{44}H_{87}NO_5$
Molecular Weight: 710.182

Compound 151 was synthesized according to the general procedure and Representative Procedure 1 described above. UPLC/ELSD: RT=2.83 min. MS (ES): m/z (MH$^+$) 711.0 for $C_{44}H_{87}NO_5$. $^1$H NMR (300 MHz, CDCl$_3$) δ: ppm 4.07 (m, 4H); 3.57 (m, 2H); 2.63 (br. m, 2H); 2.50 (m, 4H); 2.31 (m, 3H), 1.71-1.19 (m, 62H); 0.90 (m, 9H).

XX52. Compound 152: Nonyl (Z)-8-((2-hydroxyethyl)(10-octyloctadec-8-en-1-yl)amino)octanoate
N-Methoxy-N-methyl-2-octyldecanamide

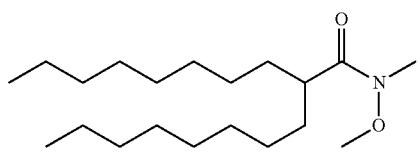

Chemical Formula: $C_{20}H_{41}NO_2$
Molecular Weight: 327.553

To a solution of 2-octyl-decanoic acid (11.1 g, 39.02 mmol) and DMF (0.05 mL, 3.9 mmol) in DCM (100 mL) oxalyl chloride (3.63 mL, 42.92 mmol) was added dropwise. The reaction was allowed to stir for 2 h at rt. Solvents and volatiles were evaporated under vacuum. The resulting residue (crude 2-octyldecanoyl chloride) (11.82 g, 39.02 mmol) was taken up in DCM (100 mL) and N,O-dimethylhydroxylamine hydrochloride (4 g, 40.97 mmol) and 4-dimethylaminopyridine (0.48 g, 3.9 mmol) were added. The mixture was allowed to cool to 0° C. and triethylamine (19.04 mL, 136.57 mmol) was slowly added. The reaction was allowed to warm to rt and stir for 1 h. Solvents were evaporated under vacuum. The residue was diluted with EtOAc and washed with sat. NaHCO$_3$, followed by brine. The organic layer was separated, dried over Na$_2$SO$_4$, filtered, and evaporated under vacuum. The residue was purified by silica gel chromatography with (0-40%) EtOAc in hexanes to obtain N-methoxy-N-methyl-2-octyldecanamide (7.10 g, 21.68 mmol, 56%). $^1$H NMR (300 MHz, CDCl$_3$) δ: ppm 3.70 (s, 3H); 3.22 (s, 3H); 2.82 (br. m, 1H); 1.62 (m, 2H); 1.51-1.19 (m, 26H); 0.90 (m, 6H).

2-Octyldecanal

Chemical Formula: $C_{18}H_{36}O$
Molecular Weight: 268.485

A solution of N-methoxy-N-methyl-2-octyldecanamide (7.1 g, 21.68 mmol) in dry THF (2 ml) was added to a suspension of LAH (27.53 mL 1 M in THF, 27.53 mmol) in dry THF (5 ml) at −45° C. The resulting suspension was stirred for 1 h at −45° C., after which time it was allowed to warm to room temperature and stir for 0.5 h. The reaction was cooled back to −45° C. and quenched with a sat. aqueous solution of sodium sulfate decahydrate (2 mL). The mixture was stirred for 20 min at room temperature and filtered through plug of Celite. The filtrate was washed with brine. The organic layer was separated, dried over sodium sulfate, filtered and evaporated under vacuum. The residue was purified by silica gel chromatography with (0-10%)

EtOAc in hexanes to obtain 2-octyldecanal (4.45 g, 16.57 mmol, 76%). $^1$H NMR (300 MHz, CDCl$_3$) δ: ppm 9.58 (d, 1H); 2.23 (m, 1H); 1.63 (m, 2H); 1.53-1.19 (m, 26H); 0.90 (m, 6H).

(Z)-10-Octyloctadec-8-en-1-ol

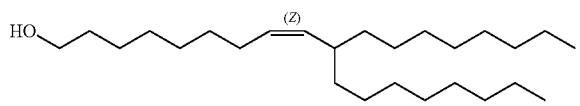

Chemical Formula: C$_{26}$H$_{52}$O
Molecular Weight: 380.701

A solution of (8-hydroxyoctyl)triphenylphosphonium bromide (3.68 g, 7.81 mmol) in THF (16 mL) and HMPA was cooled in an ice bath and NaHMDS (19.52 mL 1 M, 19.52 mmol) was added. 2-Octyldecanal (1.05 g, 3.9 mmol) in THF (5 mL) was slowly added and the reaction was warmed to 30° C. After 16 h the reaction was diluted with 20 mL of water and acidified with 2N HCl. The reaction was extracted with EtOAc (3×50 mL). The combined organic extracts were dried over sodium sulfate, filtered and concentrated under reduce pressure. The residue was purified by silica gel chromatography (0-50%) EtOAc in hexanes to obtain (Z)-10-octyloctadec-8-en-1-ol (0.5 g, 1.30 mmol, 33%). $^1$H NMR (300 MHz, CDCl$_3$)$_6$: ppm 5.24 (m, 1H); 4.90 (m, 1H); 3.53 (t, 2H); 2.14 (m, 1H); 1.89 (m, 2H); 1.45 (m, 3H); 1.33-0.95 (m, 36H); 0.77 (m, 6H).

(Z)-1-Bromo-10-octyloctadec-8-ene

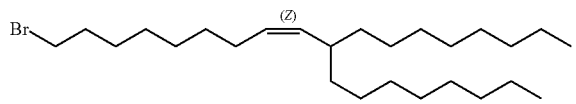

Chemical Formula: C$_{26}$H$_{51}$Br
Molecular Weight: 443.598

To a solution of PPh$_3$ (0.29 g, 1.11 mmol) and (8Z)-10-octyloctadec-8-en-1-ol (0.4 g, 1.05 mmol) in DCM (10 mL) at 0° C., NBS (0.22 g, 1.22 mmol) was added in one portion. The reaction was allowed to stir at 0° C. for 1 h and then warm to rt and stir for 1 h. 300 mL of hexanes were added and the mixture was filtered through a silica plug and evaporated under vacuum. 200 mL of hexanes were added and the mixture was filtered through a silica plug and evaporated under vacuum to obtain (Z)-1-bromo-10-octyloctadec-8-ene (0.39 g, 0.88 mmol, 83%). $^1$H NMR (300 MHz, CDCl$_3$) δ: ppm 5.24 (m, 1H); 4.90 (m, 1H); 3.53 (t, 2H); 2.14 (m, 1H); 1.89 (m, 2H); 1.45 (m, 3H); 1.33-0.95 (m, 36H); 0.77 (m, 6H).

Nonyl (Z)-8-((2-hydroxyethyl)(10-octyloctadec-8-en-1-yl)amino)octanoate

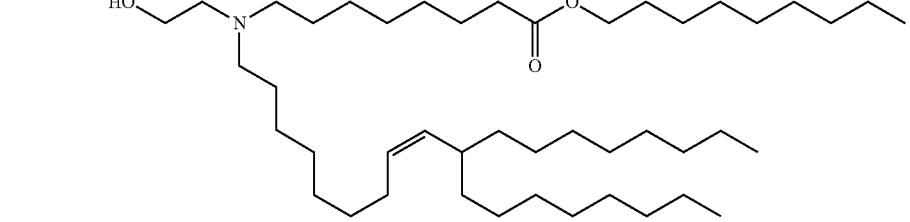

Chemical Formula: C$_{45}$H$_{89}$NO$_3$
Molecular Weight: 693.211

Compound 152 was synthesized according to the general procedure and Representative Procedure 1 described above. UPLC/ELSD: RT=3.00 min. MS (ES): m/z (MH$^+$) 694.0 for C$_{45}$H$_{89}$NO$_3$. $^1$H NMR (300 MHz, CDCl$_3$) δ: ppm 5.36 (m, 1H); 5.03 (m, 1H); 4.07 (t, 2H); 3.54 (t, 2H); 2.59 (t, 2H); 2.46 (m, 4H); 2.30 (m, 3H); 2.01 (m, 2H); 1.63 (m, 4H); 1.53-1.03 (m, 58H); 0.90 (m, 9H).

XX53. Compound 153: Nonyl 8-((2-hydroxyethyl)(10-octyloctadecyl)amino)octanoate

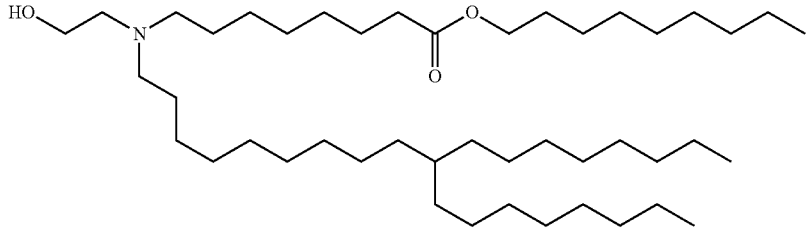

Chemical Formula: C$_{45}$H$_{91}$NO$_3$
Molecular Weight: 694.227

A flask was charged with Pd(OH)$_2$ (20 mg) and purged with N$_2$. A solution of nonyl 8-[(2-hydroxyethyl)[(8Z)-10-octyloctadec-8-en-1-yl]amino]octanoate (100 mg, 0.14 mmol) in EtOH (1 mL) was added. The reaction was purged with H$_2$ and was kept under H$_2$ (balloon) with stirring for 16 h at rt. After this time the reaction was purged with N$_2$. The reaction was filtered through a plug of Celite and washed with EtOH (50 mL). The filtrate was evaporated under vacuum. The residue was dissolved in EtOAc and washed with water. The organic layer was separated, dried over Na$_2$SO$_4$, filtered, and evaporated under vacuum. The residue was purified by silica gel chromatography with (0-50%) (1%, 20% MeOH in DCM) in DCM to obtain nonyl 8-((2-hydroxyethyl)(10-octyloctadecyl)amino)octanoate (0.069 g, 0.099 mmol, 69%). UPLC/ELSD: RT=3.21 min. MS (ES): m/z (MH$^+$) 695.08 for C$_{45}$H$_{91}$NO$_3$. $^1$H NMR (300 MHz, CDCl$_3$) δ: ppm 4.08 (t, 2H); 3.56 (t, 2H); 2.62 (m, 2H); 2.48 (m, 4H); 2.31 (m, 2H); 1.64 (m, 4H); 1.54-1.16 (m, 66H); 0.90 (m, 9H).

XX54. Compound 154: Heptadecan-9-yl 8-((2-(2-hydroxyethoxy)ethyl)(8-(nonyloxy)-8-oxooctyl)amino)octanoate

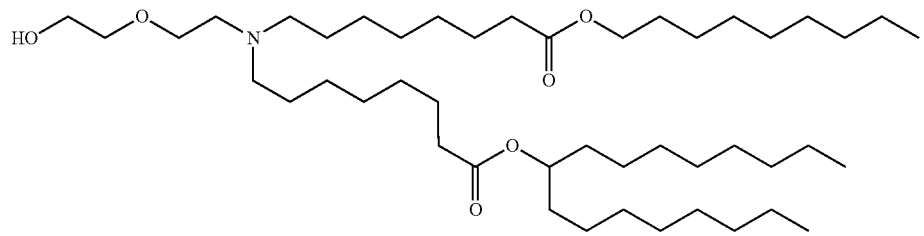

Chemical Formula: C$_{46}$H$_{91}$NO$_6$
Molecular Weight: 754.235

Compound 154 was synthesized according to the general procedure and Representative Procedure 1 described above. UPLC/ELSD: RT=3.54 min. MS (ES): m/z (MH$^+$) 755.0 for C$_{46}$H$_{91}$NO$_6$. $^1$H NMR (300 MHz, CDCl$_3$) δ: ppm 4.88 (m, 1H); 4.62 (m, 1H); 4.08 (t, 2H); 3.79-3.56 (m, 6H); 2.64 (m, 2H); 2.47 (m, 4H); 2.31 (m, 4H), 1.73-1.20 (m, 61H); 0.90 (m, 9H).

XX55. Compound 155: tert-Butyl 8-((8-(heptadecan-9-yloxy)-8-oxooctyl)(2-hydroxyethyl)amino)octanoate tert-Butyl 8-bromooctanoate

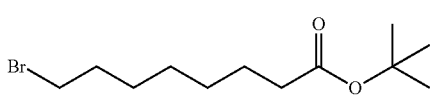

Chemical Formula: C$_{12}$H$_{23}$BrO$_2$
Molecular Weight: 279.218

To a solution of 8-bromooctanoic acid (2 g, 8.96 mmol) in DCM (20 mL) at 0° C. trifluoroacetic anhydride (2.77 mL, 19.9 mmol) was added dropwise. After 2.5 h. $^t$BuOH (3.1 mL, 32.27 mmol) was slowly added. After 1 h the reaction was warmed to rt and allowed to stir for 2.5 h. The reaction was quenched with water and extracted with diethylether. The organic layer was separated, dried over MgSO$_4$, filtered, and evaporated under vacuum. The residue was purified by silica gel chromatography with (0-10%) EtOAc in hexanes to obtain tert-butyl 8-bromooctanoate (1.5 g, 5.37 mmol, 60%). $^1$H NMR (300 MHz, CDCl$_3$) δ: ppm 3.42 (t, 2H); 2.23 (t, 2H); 1.87 (m, 2H); 1.60 (m, 2H); 1.47 (s, 11H); 1.35 (m, 4H).

tert-Butyl 8-((8-(heptadecan-9-yloxy)-8-oxooctyl)(2-hydroxyethyl)amino)octanoate

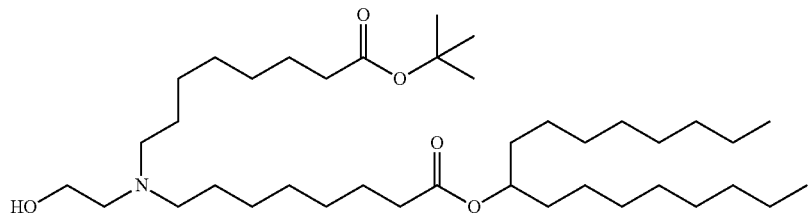

Chemical Formula: C$_{39}$H$_{77}$NO$_5$
Molecular Weight: 640.047

Compound 155 was synthesized according to the general procedure and Representative Procedure 1 described above. UPLC/ELSD: RT=3.18 min. MS (ES): m/z (MH$^+$) 641.0 for $C_{39}H_{77}NO_5$. $^1$H NMR (300 MHz, CDCl$_3$) δ: ppm 4.89 (m, 1H); 3.58 (br. m, 2H); 2.75-2.36 (br. m, 6H); 2.26 (m, 4H); 1.71-1.40 (m, 22H); 1.28 (m, 35H); 0.90 (m, 6H).

XX56. Compound 156: Heptadecan-9-yl 8-((1,3-dihydroxypropan-2-yl)(8-(nonyloxy)-8-oxooctyl)amino)octanoate

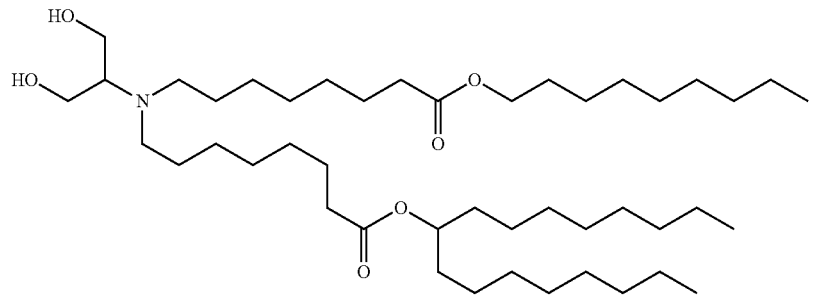

Chemical Formula: $C_{45}H_{89}NO_6$
Molecular Weight: 740.208

Compound 156 was synthesized according to the general procedure and Representative Procedure 1 described above. UPLC/ELSD: RT=3.53 min. MS (ES): m/z (MH$^+$) 741.0 for $C_{45}H_{89}NO_6$. $^1$H NMR (300 MHz, CDCl$_3$) δ: ppm 4.88 (m, 1H); 4.08 (t, 2H); 3.67 (br. m, 4H); 3.04 (m, 1H); 2.65 (m, 4H); 2.32 (m, 4H), 1.72-1.44 (m, 15H); 1.28 (m, 48H); 0.90 (m, 9H).

XX57. Compound 157: Heptadecan-9-yl 8-((1-hydroxypropan-2-yl)(8-(nonyloxy)-8-oxooctyl)amino)octanoate

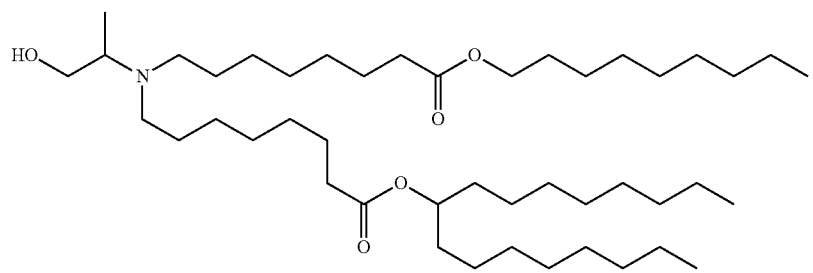

Chemical Formula: $C_{45}H_{89}NO_5$
Molecular Weight: 724.209

Compound 157 was synthesized according to the general procedure and Representative Procedure 1 described above. UPLC/ELSD: RT=3.56 min. MS (ES): m/z (MH$^+$) 725.0 for $C_{45}H_{89}NO_5$. $^1$H NMR (300 MHz, CDCl$_3$) δ: ppm 4.89 (m, 1H); 4.08 (t, 2H); 3.45-3.17 (br. m, 2H); 2.94 (br. m, 1H); 2.55-2.22 (m, 8H); 1.70-1.17 (m, 62H); 0.90 (m, 12H).

XX58. Compound 158: tert-Butyl 8-((2-hydroxy-ethyl)(8-(nonyloxy)-8-oxooctyl)amino)octanoate

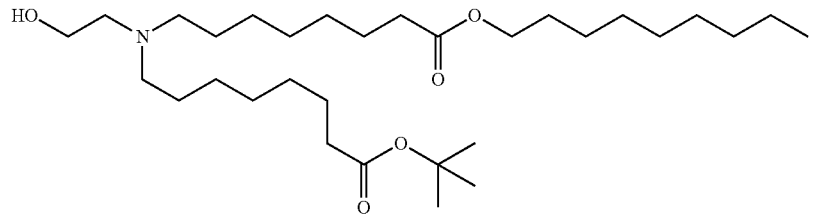

Chemical Formula: C₃₁H₆₁NO₅
Molecular Weight: 527.831

Compound 158 was synthesized according to the general procedure and Representative Procedure 1 described above. UPLC/ELSD: RT=2.23 min. MS (ES): m/z (MH⁺) 528.0 for $C_{31}H_{61}NO_5$. ¹H NMR (300 MHz, CDCl₃) δ: ppm 4.08 (t, 2H); 3.55 (br. m, 2H); 2.60 (br. m, 2H); 2.47 (m, 4H); 2.31 (t, 2H); 2.22 (t, 2H); 1.64 (br. m, 6H); 1.53-1.23 (m, 37H); 0.90 (m, 3H).

XX59. Compound 159: Heptadecan-9-yl 8-((2-hydroxyethyl)(2-((2-hydroxyethyl)(8-(nonyloxy)-8-oxooctyl)amino)ethyl)amino)octanoate

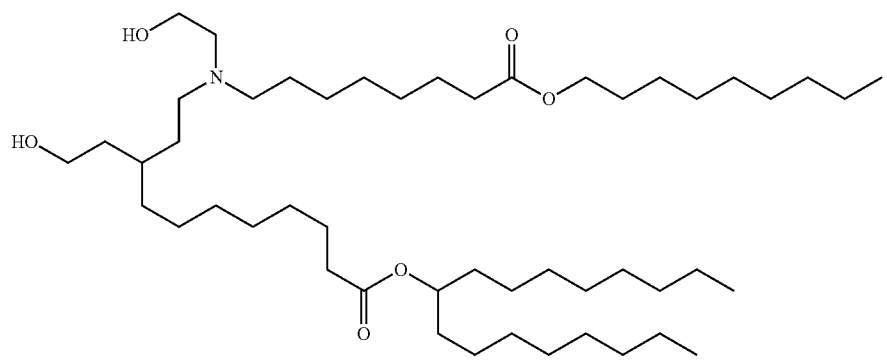

Chemical Formula: C₄₈H₉₆N₂O₆
Molecular Weight: 797.304

Compound 159 was synthesized according to the general procedure and Representative Procedure 1 described above. UPLC/ELSD: RT=3.15 min. MS (ES): m/z (MH⁺) 798.0 for $C_{48}H_{96}N_2O_6$. ¹H NMR (300 MHz, CDCl₃) δ: ppm 4.88 (m, 1H); 4.07 (t, 2H); 3.62 (br. m, 4H); 2.72-2.47 (br. m, 12H); 2.31 (m, 4H); 1.72-1.42 (m, 14H); 1.28 (m, 47H); 0.90 (m, 12H).

XX60. Compound 160: 1,5-Bis(2-butylcyclopropyl)pentan-3-yl 8-((2-hydroxyethyl)(8-(nonyloxy)-8-oxooctyl)amino)octanoate 2-(2-Butylcyclopropyl)ethan-1-ol

Chemical Formula: C₉H₁₈O
Molecular Weight: 142.242

2-(2-Butylcyclopropyl)ethan-1-ol was synthesized in the same manner as Intermediate C. ¹H NMR (300 MHz, CDCl₃) δ: ppm: 3.94 (t, 2H); 1.93 (m, 1H); 1.59 (m, 7H); 1.39 (m, 1H); 1.12 (m, 3H); 0.90 (m, 3H); 0.00 (m, 1H).

1-(2-Bromoethyl)-2-butylcyclopropane

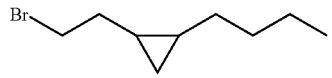

Chemical Formula: C₉H₁₇Br
Molecular Weight: 205.139

1-(2-Bromoethyl)-2-butylcyclopropane was synthesized in the same manner as (Z)-1-Bromo-10-octyloctadec-8-ene. ¹H NMR (300 MHz, CDCl₃) δ: ppm: 3.64 (t, 2H); 2.18 (m, 1H); 1.92 (m, 1H); 1.47 (m, 6H); 0.96 (m, 6H); 0.00 (m, 1H).

1,5-Bis(2-butylcyclopropyl)pentan-3-ol

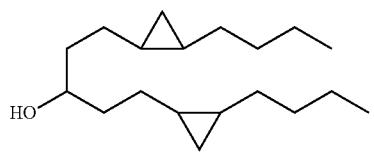

Chemical Formula: C₁₉H₃₆O
Molecular Weight: 280.496

1,5-Bis(2-butylcyclopropyl)pentan-3-ol was synthesized in the same manner as (5Z,12Z)-heptadeca-5,12-dien-9-ol. ¹H NMR (300 MHz, CDCl₃) δ: ppm: 3.96 (t, 1H); 1.64 (m, 21H); 1.16 (m, 6H); 0.91 (m, 6H); 0.03 (m, 2H).

1,5-Bis(2-butylcyclopropyl)pentan-3-yl 8-((2-hydroxyethyl)(8-(nonyloxy)-8-oxooctyl)amino)octanoate

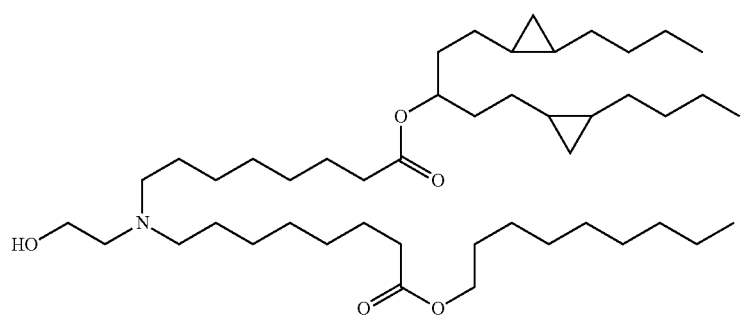

Chemical Formula: C₄₆H₈₇NO₅
Molecular Weight: 734.204

Compound 160 was synthesized according to the general procedure and Representative Procedure 1 described above. UPLC/ELSD: RT=3.51 min. MS (ES): m/z (MH⁺) 735.0 for C₄₆H₈₇NO₅. ¹H NMR (300 MHz, CDCl₃) δ: ppm 4.97 (m, 1H); 4.08 (t, 2H); 3.56 (br. m, 2H); 2.75-2.37 (br. m, 6H); 2.31 (m, 4H); 1.74-1.05 (m, 54H); 0.92 (m, 9H); 0.67 (m, 6H); 0.31 (m, 2H).

XX61. Compound 161: Heptadecan-9-yl 8-((2-hydroxyethyl)(10-(octanoyloxy)decan-2-yl)amino)octanoate 10-(Benzyloxy)decan-2-ol

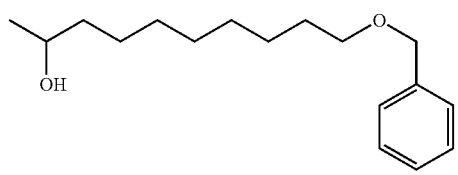

Chemical Formula: C₁₇H₂₈O₂
Molecular Weight: 264.409

A solution of 10-(benzyloxy)decan-2-one (3.5 g, 13.34 mmol) in THF (10 mL) was added to a stirred solution of LAH in THF (10 mL) under N₂ at 0° C. The mixture was allowed to warm to rt and stir for 2 h after which time 10 mL of sat. Na₂SO₄.10H₂O (aq) solution was slowly added. White solid precipitated. Additional solid Na₂SO₄.10H₂O was added and the mixture was filtered through a plug of Celite. The filtrate was diluted with EtOAc and washed with brine. The organic layer was separated, dried over Na₂SO₄, filtered, and concentrated under vacuum. The residue was purified by silica gel chromatography with (0-40%) EtOAc in hexanes to obtain 10-(benzyloxy)decan-2-ol (3.2 g, 12.1 mmol, 91%). ¹H NMR (300 MHz, CDCl₃) δ: ppm 7.32 (m, 5H); 4.53 (s, 2H); 3.80 (m, 1H); 3.49 (t, 2H); 1.64 (m, 2H); 1.55-1.25 (m, 132H); 1.21 (d, 3H).

9-Hydroxydecyl octanoate

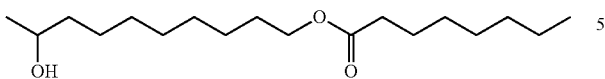

Chemical Formula C$_{18}$H$_{36}$O$_3$
Molecular Weight: 300.483

9-Hydroxydecyl octanoate was synthesized following Method A. $^1$H NMR (300 MHz, CDCl$_3$) δ: ppm 4.08 (t, 2H); 3.80 (m, 1H); 2.30 (t, 2H); 1.64 (m, 4H); 1.52-1.17 (m, 23H); 0.90 (m, 3H).

Heptadecan-9-yl 8-((2-hydroxyethyl)(10-(octanoyloxy)decan-2-yl)amino)octanoate

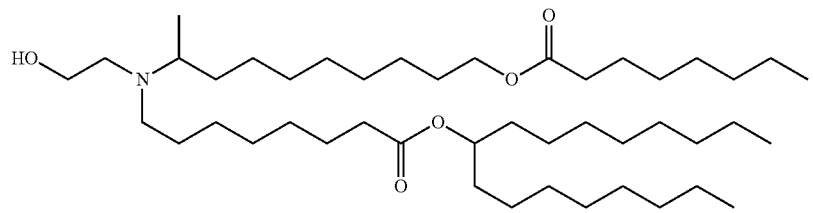

Chemical Formula: C$_{45}$H$_{89}$NO$_5$
Molecular Weight: 724.209

Compound 161 was synthesized in a manner similar to Compound 152 and according to the general procedure and Representative Procedure 1 described above. UPLC/ELSD: RT=3.46 min. MS (ES): m/z (MH$^+$) 725.0 for C$_{45}$H$_{89}$NO$_5$. $^1$H NMR (300 MHz, CDCl$_3$) δ: ppm 4.89 (m, 1H); 4.08 (t, 2H); 3.49 (br. m, 2H); 2.77-2.55 (m, 2H); 2.54-2.23 (m, 7H); 1.71-1.20 (m, 63H); 0.91 (m, 12H).

XX62. Compound 162: 7-((2-Hydroxyethyl)(10-(octanoyloxy)decan-2-yl)amino)heptyl 2-octyldecanoate

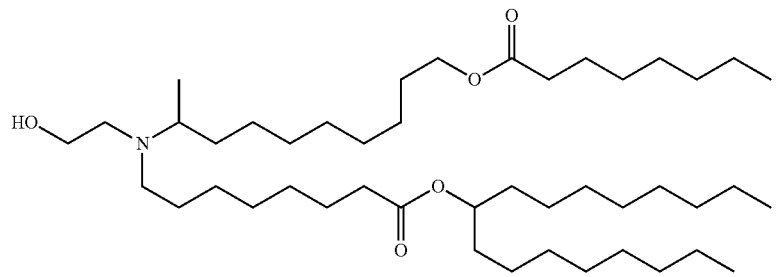

Chemical Formula: C$_{45}$H$_{89}$NO$_5$
Molecular Weight: 724.209

Compound 162 was synthesized according to the general procedure and Representative Procedure 1 described above. UPLC/ELSD: RT=3.49 min. MS (ES): m/z (MH$^+$) 725.0 for C$_{45}$H$_{89}$NO$_5$. $^1$H NMR (300 MHz, CDCl$_3$) δ: ppm 3.99 (m, 4H); 2.72-2.48 (m, 2H); 2.48-2.17 (m, 6H); 1.55 (m, 8H); 1.44-1.10 (m, 56H); 0.92-0.75 (m, 12H).

XX63. Compound 163: 7-((2-Hydroxyethyl)(7-methyl-8-(nonyloxy)-8-oxooctyl)amino)heptyl 2-octyldecanoate 8-Methoxyoctanoic acid

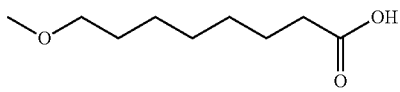

Chemical Formula: C₆H₁₈O₃
Molecular Weight: 174.240

To anhydrous MeOH (80 mL) at 0° C. KOH was added (7.54 g, 134.46 mmol) and stirred for 30 min. A solution of 8-bromooctanoic acid (10 g, 44.82 mmol) in anhydrous MeOH (70 mL) was added and the resulting solution was refluxed for 18 h. MeOH was removed under vacuum and the residue was acidified with 1N HCl and extracted with diethylether. The organic layer was washed with brine, separated, dried over Na₂SO₄, filtered, and evaporated under vacuum. The residue was purified by silica gel chromatography with (0-50%) EtOAc in hexanes to obtain 8-methoxyoctanoic acid (6.3 g, 36.16 mmol, 81%). ¹H NMR (300 MHz, CDCl₃) δ: ppm 3.35 (m, 5H); 2.37 (t, 2H); 1.61 (m, 4H); 1.36 (m, 6H).

8-Methoxy-2-methyloctanoic acid

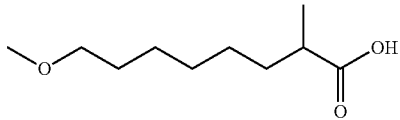

Chemical Formula: C₁₀H₂₀O₃
Molecular Weight: 188.267

To a suspension of NaH in THF (100 mL) at 0° C., 8-methoxyoctanoic acid (5.6 g, 32.14 mmol) in THF (30 mL) was added dropwise. The reaction was allowed to stir at rt for 30 min. The reaction was cooled to 0° C. and LDA (17.86 mL, 2M in THF, 35.71 mmol) was added dropwise. After complete addition, the reaction was allowed to stir at 45° C. for 2 h. The reaction was cooled to rt and methyl iodide (2.45 mL, 39.28 mmol) in THF (15 mL) was slowly added. The reaction was stirred at 45° C. for 16 h. The reaction was quenched with 1N HCl (20 mL). The quenched reaction was evaporated under vacuum to remove volatiles. The residue was dissolved in hexanes/EtOAc (1:1) and washed with 1N HCl (100 mL×2) followed by brine. The organic layer was separated, dried over sodium sulfate, filtered and evaporated under vacuum. The residue was purified by silica gel chromatography with (0-15%) EtOAc in hexanes to obtain 8-methoxy-2-methyloctanoic acid (3.25 g, 17.26 mmol, 54%). ¹H NMR (300 MHz, CDCl₃) δ: ppm 3.35 (m, 5H); 2.49 (m, 1H); 1.70 (m, 1H); 1.59 (m, 2H); 1.36 (m, 7H); 1.21 (d, 3H).

8-Hydroxy-2-methyloctanoic acid

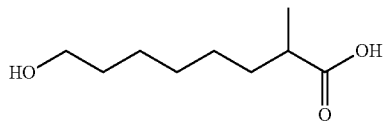

Chemical Formula: C₉H₁₈O₃
Molecular Weight: 174.240

To a solution of 8-methoxy-2-methyloctanoic acid (1 g, 5.31 mmol) in DCM (20 mL) at −78° C., boron tribromide (13.28 mL 1 M in DCM, 13.28 mmol) was added dropwise. The reaction was allowed to warm to rt and stir at rt for 2 h. The reaction was poured into ice and extracted with DCM. The organic layer was separated, dried over Na₂SO₄, filtered, and evaporated under vacuum. The residue was purified by silica gel chromatography with (0-40%) EtOAc in hexanes to obtain 8-hydroxy-2-methyloctanoic acid (0.77 g, 4.41 mmol, 83%). ¹H NMR (300 MHz, CDCl₃) δ: ppm 3.43 (t, 2H); 2.50 (m, 1H); 1.94-1.64 (m, 4H); 1.56-1.26 (m, 7H); 1.20 (d, 3H).

Nonyl 8-hydroxy-2-methyloctanoate

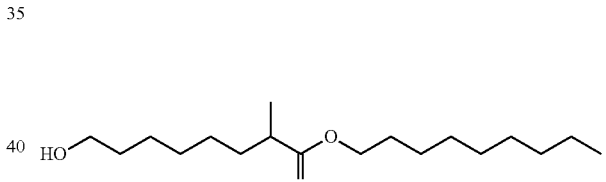

Chemical Formula: C₁₈H₃₆O₃
Molecule Weight: 300.483

A solution of 8-hydroxy-2-methyloctanoic acid (0.75 g, 4.31 mmol), nonan-1-ol (6.22 g, 43.1 mmol), 4-dimethylaminopyridine (0.11 g, 0.86 mmol) in DCM (20 mL) under N₂ was added to (3-{[(ethylimino)methylidene]amino}propyl)dimethylamine hydrochloride (0.83 g, 4.31 mmol). The reaction allowed to stir at rt for 16 h. The reaction was diluted with DCM and washed with sat. NaHCO₃, followed by brine. The organic layer was separated, dried over Na₂SO₄, filtered, and evaporated under vacuum. The residue was purified by silica gel chromatography with (0-20%) EtOAc in hexanes to obtain nonyl 8-hydroxy-2-methyloctanoate (0.68 g, 2.26 mmol, 53%). ¹H NMR (300 MHz, CDCl₃) δ: ppm 4.08 (t, 2H); 3.42 (t, 2H); 2.45 (m, 1H); 1.87 (m, 2H); 1.75-1.57 (m, 4H); 1.52-1.22 (m, 19H); 1.15 (d, 3H); 0.91 (m, 3H).

7-((2-Hydroxyethyl)(7-methyl-8-(nonyloxy)-8-oxooctyl)amino)heptyl 2-octyldecanoate

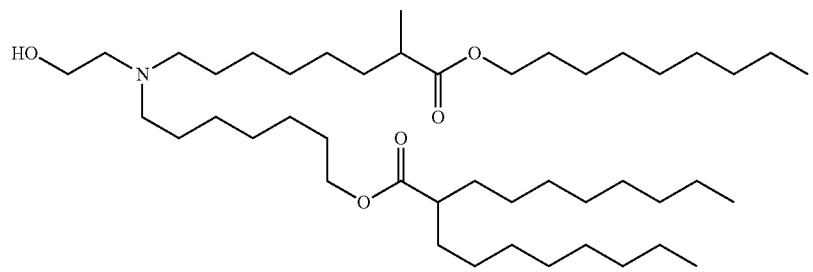

Chemical Formula: $C_{45}H_{89}NO_5$
Molecular Weight: 724.209

Compound 163 was synthesized in a manner similar to Compound 152 according to the general procedure and Representative Procedure 1 described above. UPLC/ELSD: RT=3.50 min. MS (ES): m/z (MH$^+$) 725.0 for $C_{45}H_{89}NO_5$. $^1$H NMR (300 MHz, CDCl$_3$) δ: ppm 4.08 (t, 4H); 3.55 (m, 2H); 2.67 (m, 2H); 2.53-2.24 (m, 6H); 1.72-1.10 (m, 65H); 0.90 (m, 9H).

XX64. Compound 164: Nonyl 8-((8-(heptadecan-9-yloxy)-8-oxooctyl)(2-hydroxyethyl)amino)-2-methyloctanoate

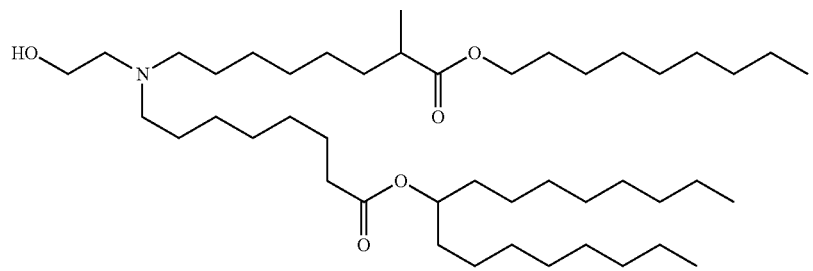

Chemical Formula: $C_{45}H_{89}NO_5$
Molecular Weight: 724.209

Compound 164 was synthesized according to the general procedure and Representative Procedure 1 described above. UPLC/ELSD: RT=3.51 min. MS (ES): m/z (MH+) 725.0 for $C_{45}H_{89}NO_5$. $^1$H NMR (300 MHz, CDCl$_3$) δ: ppm 4.89 (m, 1H); 4.08 (t, 2H); 3.55 (m, 2H); 2.69-2.38 (m, 8H); 2.30 (t, 2H); 1.74-1.09 (m, 65H); 0.90 (m, 9H).

XX65. Compound 165: 7-((7-(Decanoyloxy)octyl)(2-hydroxyethyl)amino)heptyl 2-octyldecanoate

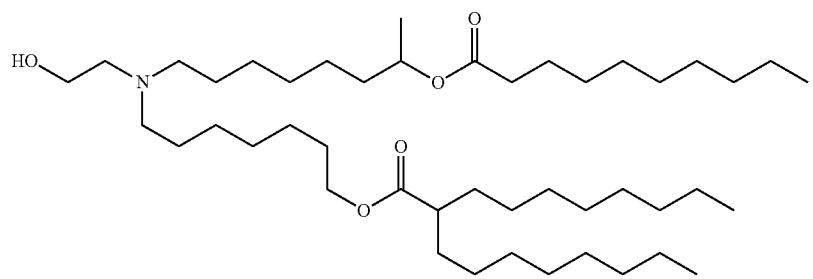

Chemical Formula: $C_{45}H_{89}NO_5$
Molecular Weight: 724.209

Compound 165 was synthesized according to the general procedure and Representative Procedure 1 described above. UPLC/ELSD: RT=3.55 min. MS (ES): m/z (MH$^+$) 725.0 for $C_{45}H_{89}NO_5$. $^1$H NMR (300 MHz, CDCl$_3$) δ: ppm 4.91 (m, 1H); 4.08 (t, 2H); 3.55 (m, 2H); 2.68-2.39 (m, 8H); 2.29 (m, 3H); 1.72-1.15 (m, 64H); 0.90 (m, 9H).

XX66. Compound 166: 8-((8-(Heptadecan-9-yloxy)-8-oxooctyl)(2-hydroxyethyl)amino)octanoic acid

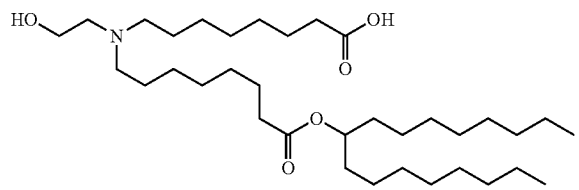

Chemical Formula: $C_{35}H_{69}NO_5$
Molecular Weight: 583.939

To a solution of heptadecan-9-yl 8-{[8-(tert-butoxy)-8-oxooctyl](2-hydroxyethyl)amino}octanoate (0.11 g, 0.17 mmol) in DCM was added trifluoroacetic acid (0.06 mL, 0.69 mmol) and the reaction was allowed to stir at rt for 40 h. Volatiles were evaporated under vacuum. The residue was dissolved in ethylacetate and water and extracted with ethylacetate. The organic layer was separated, dried with Na$_2$SO$_4$, filtered and concentrated under vacuum. The residue was purified by silica gel chromatography (0-50%) (1%, 20% MeOH in DCM) in DCM to obtain 8-{[8-(heptadecan-9-yloxy)-8-oxooctyl](2-hydroxyethyl)amino}octanoic acid (0.023 g, 0.04 mmol) as a colorless liquid. UPLC/ELSD: RT=2.72 min. MS (ES): m/z (MH+) 585.0 for $C_{35}H_{69}NO_5$. $^1$H NMR (300 MHz, CDCl$_3$) δ: ppm 4.87 (m, 1H); 3.98 (m, 2H); 3.25-3.05 (m, 6H); 2.32 (m, 4H); 1.82-1.45 (m, 12H); 1.45-1.19 (m, 37H); 0.89 (m, 6H).

XX67. Compound 167: 8-((2-Hydroxyethyl)(8-(nonyloxy)-8-oxooctyl)amino)octanoic acid

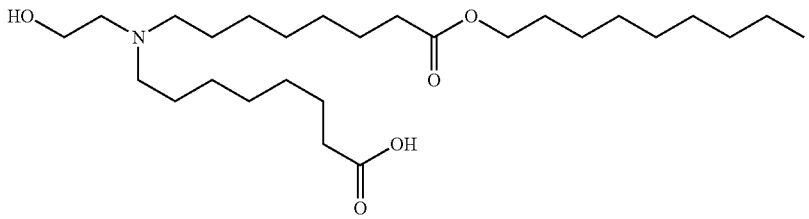

Chemical Formula: $C_{27}H_{53}NO_5$
Molecular Weight: 471.723

Compound 167 was synthesized following the same procedure as Compound 166. UPLC/ELSD: RT=1.57 min. MS (ES): m/z (MH+) 472.0 for $C_{27}H_{53}NO_5$. $^1$H NMR (300 MHz, CDCl$_3$) δ: ppm 4.08 (m, 2H); 4.00 (m, 2H); 3.44-2.98 (m, 10H); 2.35 (t, 4H); 1.85-1.55 (m, 10H); 1.33 (m, 23H); 0.90 (m, 3H).

XX68. Compound 168: Heptadecan-9-yl (Z)-8-((3-(2-cyano-3,3-dimethylguanidino)propyl)(8-(nonyloxy)-8-oxooctyl)amino)octanoate

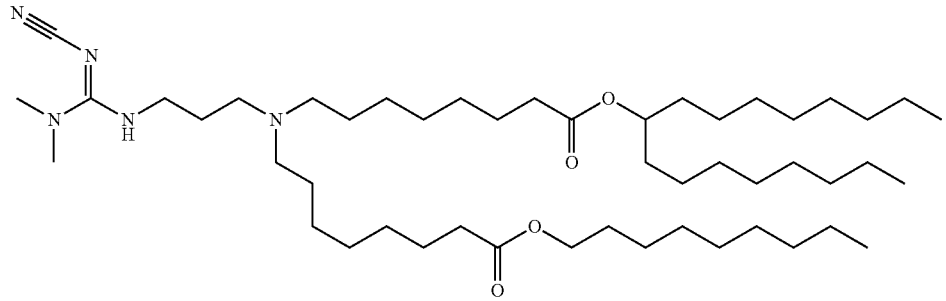

Chemical Formula: $C_{49}H_{95}N_5O_4$
Molecular Weight: 818.33

To a solution of heptadecan-9-yl 8-((3-aminopropyl)(8-(nonyloxy)-8-oxooctyl)amino)octanoate (220 mg, 0.3 mmol) in 5 mL 2-propanol was added triethylamine (0.04 mL, 0.3 mmol) followed by diphenyl cyanocarbonimidate (72 mg, 0.3 mmol) and the mixture stirred at rt for two hours. To the reaction mixture was added a 2M dimethylamine solution in THF (0.75 mL, 1.5 mmol) and the resulting solution heated to 75° C. for 18 hours. Additional 2M dimethylamine/THF solution (0.75 mL, 1.5 mmol) was added and the temperature increased to 85° C. After six hours the reaction was complete by LC/MS so the solution was reduced under vacuum, diluted with DCM and washed once with a saturated aqueous sodium bicarbonate solution. The organic phase was dried (MgSO$_4$), filtered and the filtrate evaporated in vacuo. The residue was purified by silica gel chromatography (0-50% (mixture of 1% NH$_4$OH, 20% MeOH in dichloromethane) in dichloromethane) to give heptadecan-9-yl (Z)-8-((3-(2-cyano-3,3-dimethylguanidino)propyl)(8-(nonyloxy)-8-oxooctyl)amino)octanoate (119.2 mg, 0.14 mmol, 49%) as a colorless syrup. UPLC/ELSD: RT=3.52 min. MS (ES): m/z (MH$^+$) 819.0 for C$_{49}$H$_{95}$N$_5$O$_4$. $^1$H NMR (300 MHz, CDCl$_3$) δ: ppm 7.62 (br. s., 1H); 4.86 (quint., 1H, J=6 Hz); 4.05 (t, 2H, J=7.5 Hz); 3.68 (d, 2H, J=3 Hz); 2.99 (s, 6H); 2.59 (br. s, 2H); 2.43 (br. s, 3H); 2.28 (m, 4H); 1.71 (br. s, 2H); 1.62 (m, 8H); 1.49 (m, 5H); 1.26 (br. m, 50H); 0.88 (t, 9H, J=7.5 Hz).

XX69. Compound 169: Heptadecan-9-yl 8-((3-((2-(dimethylamino)-3,4-dioxocyclobut-1-en-1-yl)amino)propyl)(8-(nonyloxy)-8-oxooctyl)amino)octanoate 3-(Dimethylamino)-4-methoxycyclobut-3-ene-1,2-dione

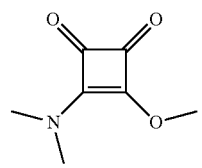

Chemical Formula: C$_7$H$_9$NO$_3$
Molecular Weight: 155.15

To a solution of 3,4-dimethoxy-3-cyclobutene-1,2-dione (1 g, 7 mmol) in 100 mL diethyl ether was added a 2M dimethylamine solution in THF (3.8 mL, 7.6 mmol) and a ppt. formed almost immediately. The mixture was stirred at rt for 24 hours and then filtered. The filter solids were washed with diethyl ether and air-dried. The filter solids were dissolved in hot MeOH, filtered, the filtrate allowed to cool to room temp., then cooled to 0° C. to give a ppt. This was isolated via filtration, washed with cold MeOH, air-dried, then dried under vacuum to give 3-(dimethylamino)-4-methoxycyclobut-3-ene-1,2-dione (0.42 g, 2.7 mmol, 39%) as a pale yellow solid. $^1$H NMR (300 MHz, DMSO-d$_6$) δ: ppm 4.28 (s, 3H); 3.21 (s, 3H); 3.05 (s, 3H).

Heptadecan-9-yl 8-((3-((2-(dimethylamino)-3,4-dioxocyclobut-1-en-1-yl)amino)propyl)(8-(nonyloxy)-8-oxooctyl)amino)octanoate

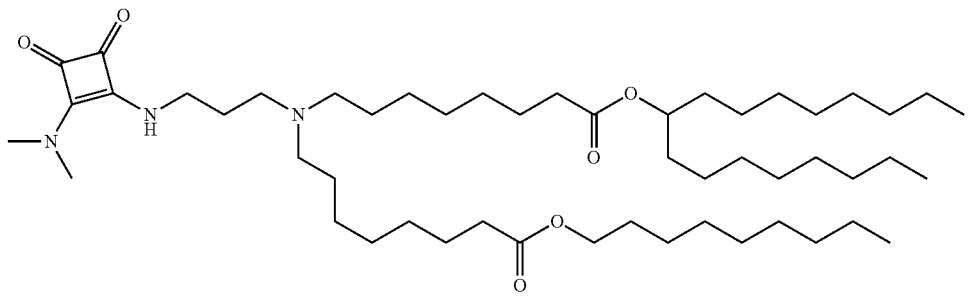

Chemical Formula: C$_{51}$H$_{95}$N$_3$O$_6$
Molecular Weight: 846.34

To a solution of heptadecan-9-yl 8-((3-aminopropyl)(8-(nonyloxy)-8-oxooctyl)amino)octanoate (220 mg, 0.3 mmol) in 10 mL ethanol was added 3-(dimethylamino)-4-methoxycyclobut-3-ene-1,2-dione (47 mg, 0.3 mmol) and the resulting colorless solution stirred at rt for 20 hours after which no starting amine remained by LC/MS. The solution was concentrated in vacuo and the residue purified by silica gel chromatography (0-50% (mixture of 1% NH$_4$OH, 20% MeOH in dichloromethane) in dichloromethane) to give heptadecan-9-yl 8-((3-((2-(dimethylamino)-3,4-dioxocyclobut-1-en-1-yl)amino)propyl)(8-(nonyloxy)-8-oxooctyl)amino)octanoate (135 mg, 0.16 mmol, 53%) as a colorless syrup. UPLC/ELSD: RT=3.51 min. MS (ES): m/z (MH$^+$) 847.3 for C$_{51}$H$_{95}$N$_3$O$_6$. $^1$H NMR (300 MHz, CDCl$_3$) δ: ppm 7.86 (br. s., 1H); 4.86 (quint., 1H, J=6 Hz); 4.05 (t, 2H, J=6 Hz); 3.92 (d, 2H, J=3 Hz); 3.20 (s, 6H); 2.63 (br. s, 2H); 2.42 (br. s, 3H); 2.28 (m, 4H); 1.74 (br. s, 2H); 1.61 (m, 8H); 1.50 (m, 5H); 1.41 (m, 3H); 1.25 (br. m, 47H); 0.88 (t, 9H, J=7.5 Hz).

XX70. Compound 170: Heptadecan-9-yl (E)-8-((3-((1-(methylamino)-2-nitrovinyl)amino)propyl)(8-(nonyloxy)-8-oxooctyl)amino)octanoate

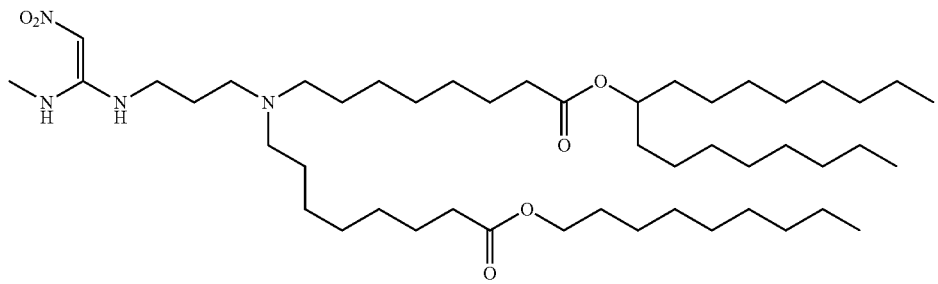

Chemical Formula: $C_{48}H_{94}N_4O_6$
Molecular Weight: 823.30

To a solution of heptadecan-9-yl 8-((3-aminopropyl)(8-(nonyloxy)-8-oxooctyl)amino)octanoate (220 mg, 0.3 mmol) in 5 mL methanol was added 1-methylthio-1-methylamino-2-nitroethene (45 mg, 0.3 mmol), the resulting solution heated to 70° C. and stirred for 24 hours after which no starting amine remained by LC/MS. The solution was diluted with DCM and washed once with a saturated aqueous sodium bicarbonate solution. The organic phase was dried ($MgSO_4$), filtered and the filtrate evaporated in vacuo. The residue was purified by silica gel chromatography (0-50% (mixture of 1% $NH_4OH$, 20% MeOH in dichloromethane) in dichloromethane) to give heptadecan-9-yl (E)-8-((3-((1-(methylamino)-2-nitrovinyl)amino)propyl)(8-(nonyloxy)-8-oxooctyl)amino)octanoate (90 mg, 0.11 mmol, 36%) as a pale yellow syrup. UPLC/ELSD: RT=3.33 min. MS (ES): m/z (MH$^+$) 824.3 for $C_{48}H_{94}N_4O_6$. $^1$H NMR (300 MHz, $CDCl_3$) δ: ppm 10.15 (d, 1H, J=9 Hz); 8.26 (d, 1H, J=27 Hz); 6.55 (d, 1H, J=9 Hz); 4.86 (quint., 1H, J=6 Hz); 4.05 (t, 2H, J=6 Hz); 3.32 (br. s, 1H); 3.24 (br. s, 1H); 2.81 (dd, 3H, J=3 Hz, 12 Hz); 2.63 (br. s, 1H); 2.47 (br. s, 4H); 2.28 (m, 4H); 1.77 (br. s, 2H); 1.62 (m, 5H); 1.59 (m, 6H); 1.49 (m, 3H); 1.43 (m, 3H); 1.26 (br. m, 46H); 0.88 (t, 9H, J=7.5 Hz).

XX71. Compound 171: Heptadecan-9-yl 8-((9-hydroxy-9-methyloctadecyl)(2-hydroxyethyl)amino) octanoate ((Dec-9-en-1-yloxy)methyl)benzene

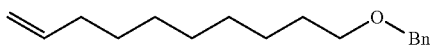

Chemical Formula: $C_{17}H_{26}O$
Molecular Weight: 246.394

To a suspension of sodium hydride (3.88 g, 96.99 mmol) in THF (100 mL) was added 9-decen-1-ol (10 g, 63.99 mmol) slowly. After 30 min. benzyl bromide (10.57 mL, 88.9 mmol) was added. The reaction was allowed to stir at rt for 18 h. The reaction was quenched with water. Solvents were evaporated under vacuum. The residue was diluted with EtOAc and washed with sat. $NaHCO_3$, followed by brine. The organic layer was separated, dried with $Na_2SO_4$, filtered, and evaporated under vacuum. The residue was purified by silica gel chromatography with (0-20%) EtOAc in hexanes to obtain ((dec-9-en-1-yloxy)methyl)benzene (8.5 g, 34.5 mmol, 54%). $^1$H NMR (300 MHz, $CDCl_3$) δ: ppm 7.32 (m, 5H); 5.83 (m, 1H); 4.98 (m, 2H); 4.53 (s, 2H); 3.49 (t, 2H); 2.06 (m, 2H); 1.64 (m, 2H); 1.46-1.26 (br. m, 10H).

10-(Benzyloxy)decan-2-one

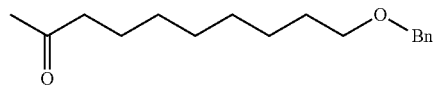

Chemical Formula: $C_{17}H_{26}O_2$
Molecular Weight: 262.393

To a solution of palladium chloride (0.09 g, 0.52 mmol) and benzoquinone (3.09 g, 28.57 mmol) in DMF/Water (7:1, 12.8 mL), [(dec-9-en-1-yloxy)methyl]benzene (6.4 g, 25.98 mmol) was slowly added and the dark brown solution was allowed to stir for 3 days at rt. The mixture was dissolved in 2N HCl (50 mL) and extracted with ether (3×50 mL). The combined organic phase was washed with 2N NaOH (3×50 mL) and dried over $MgSO_4$. Solvents were removed under vacuum and the residue was purified by silica gel chromatography (0-40%) ethyl acetate in hexanes to obtain 10-(benzyloxy)decan-2-one (3.44 g, 13.11 mmol, 50%). $^1$H NMR (300 MHz, $CDCl_3$) δ: ppm 7.36 (m, 5H); 4.52 (s, 2H); 3.48 (t, 2H); 2.43 (t, 2H); 2.15 (s, 3H); 1.61 (m, 4H); 1.45-1.24 (br. m, 8H).

1-(Benzyloxy)-9-methyloctadecan-9-ol

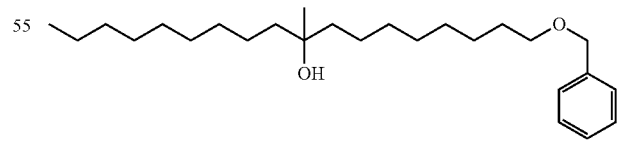

Chemical Formula: $C_{26}H_{46}O_2$
Molecular Weight: 390.652

To a solution of 10-(benzyloxy)decan-2-one (1 g, 3.81 mmol) in THF (30 mL) at 0° C., bromo(nonyl)magnesium (4.57 mL 1 M in diethylether, 4.57 mmol) was added dropwise. The reaction was allowed to warm to rt and stir for 4 h. The reaction was quenched with water (2 mL), diethylether was added (200 mL) and the resulting white solid was filtered through a silica plug. The filtrate was extracted with ether. The organic layer was washed with water, followed by brine. The organic layer was separated, dried over $Na_2SO_4$, filtered, and concentrated under vacuum. The residue was purified by silica gel chromatography with (0-40%) EtOAc in hexanes to obtain 1-(benzyloxy)-9-methyloctadecan-9-ol (0.99 g). The product was impure but taken to the next step without further purification.

9-Methyloctadecane-1,9-diol

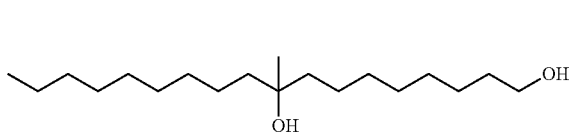

Chemical Formula: $C_{26}H_{46}O_2$
Molecular Weight: 390.652

Under $N_2$ a flask was charged with 1-(benzyloxy)-9-methyloctadecan-9-ol (1 g, 2.56 mmol), $Pd(OH)_2$ (100 mg) and EtOH. The reaction was purged with $H_2$ and was kept under $H_2$ (balloon) with stirring for 16 h at rt. The reaction was purged with $N_2$. The reaction was filtered through a plug of Celite and the Celite was washed with EtOAc (200 mL). The filtrate was evaporated under vacuum. The residue was dissolved in EtOAc and was washed with water. The organic layer was separated, dried over $Na_2SO_4$, filtered, and evaporated under vacuum. The residue was purified by silica gel chromatography with EtOAc in hexanes (0-40%) to obtain 9-methyloctadecane-1,9-diol (0.65 g, 2.16 mmol, 84%). $^1$H NMR (300 MHz, CDCl$_3$) δ: ppm 3.66 (t, 2H); 1.59 (m, 2H); 1.49-1.22 (br. m, 29H); 1.17 (s, 3H); 0.90 (m, 3H).

1-Bromo-9-methyloctadecan-9-ol

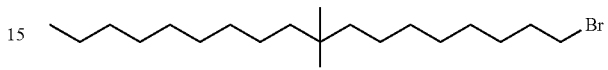

Chemical Formula: $C_{19}H_{39}BrO$
Molecular Weight: 363.42

1-Bromo-9-methyloctadecan-9-ol was synthesized in the same manner as (Z)-1-bromo-10-octyloctadec-8-ene. $^1$H NMR (300 MHz, CDCl$_3$) δ: ppm 3.43 (t, 2H); 1.88 (m, 2H); 1.53-1.23 (br. m, 28H); 1.17 (s, 3H); 0.91 (m, 3H).

Heptadecan-9-yl 8-((9-hydroxy-9-methyloctadecyl)(2-hydroxyethyl)amino)octanoate

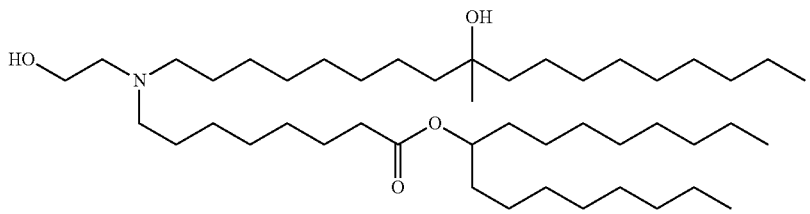

Chemical Formula: $C_{46}H_{93}NO_4$
Molecular Weight: 724.253

Compound 171 was synthesized according to the general procedure and Representative Procedure 1 described above. UPLC/ELSD: RT=3.56 min. MS (ES): m/z (MH+) 725.0 for $C_{46}H_{93}NO_4$. $^1$H NMR (300 MHz, CDCl$_3$) δ: ppm 4.89 (m, 1H); 3.55 (m, 2H); 2.60 (m, 2H); 2.47 (m, 4H); 2.30 (t, 2H); 1.74-1.21 (m, 69H); 1.17 (s, 3H); 0.90 (m, 9H).

XX72. Compound 172: (R)-Decan-2-yl 8-((8-(heptadecan-9-yloxy)-8-oxooctyl)(2-hydroxyethyl)amino)octanoate

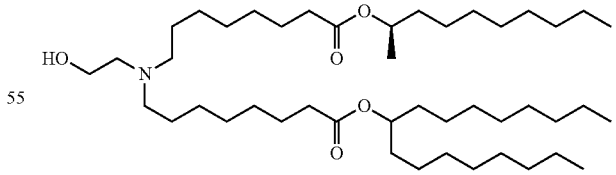

Chemical Formula: $C_{45}H_{89}NO_5$
Molecular Weight: 724.209

Compound 172 was synthesized according to the general procedure and Representative Procedure 1 described above. UPLC/ELSD: RT=3.53 min. MS (ES): m/z (MH+) 725.0 for $C_{45}H_{89}NO_5$. $^1$H NMR (300 MHz, CDCl$_3$) δ: ppm 4.91 (m, 2H); 3.54 (m, 2H); 2.59 (m, 2H); 2.46 (m, 4H); 2.30 (m, 4H); 1.70-1.19 (m, 66H); 0.90 (m, 9H).

XX73. Compound 173: Heptadecan-9-yl 8-((3-(N-methylmethylsulfonamido)propyl)(8-(nonyloxy)-8-oxooctyl)amino)octanoate

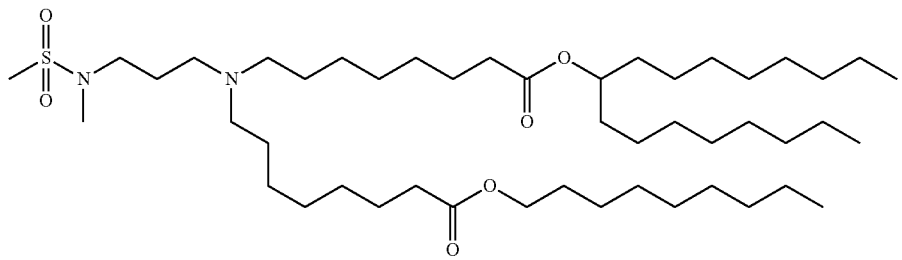

Chemical Formula: C₄₇H₉₄N₂O₆S
Molecular Weight: 815.34

To a solution of heptadecan-9-yl 8-((3-chloropropyl)(8-(nonyloxy)-8-oxooctyl)amino)octanoate (200 mg, 0.27 mmol) and N-methyl methanesulfonamide (50 uL, 0.54 mmol) in 4 mL dry DMF was added cesium carbonate (130 mg, 0.40 mmol), the resulting mixture heated to 60° C. and stirred for 24 hours, after which no starting chloride remained by LC/MS. The mixture was allowed to cool to rt, diluted with a 50% saturated aqueous sodium bicarbonate solution and extracted twice with DCM. The organics were combined, washed once with water, dried (MgSO₄), filtered and conc. to a yellow oil. The residue was purified by silica gel chromatography (0-50% (mixture of 1% NH₄OH, 20% MeOH in dichloromethane) in dichloromethane) to give heptadecan-9-yl 8-((3-(N-methylmethylsulfonamido)propyl)(8-(nonyloxy)-8-oxooctyl)amino)octanoate (85 mg, 0.11 mmol, 39%) as a pale yellow oil. UPLC/ELSD: RT=3.57 min. MS (ES): m/z (MH⁺) 816.1 for C₄₇H₉₄N₂O₆S. ¹H NMR (300 MHz, CDCl₃) δ: ppm 4.86 (quint., 1H, J=6 Hz); 4.05 (t, 2H, J=6 Hz); 3.15 (t, 2H, J=7.5 Hz); 2.85 (s, 3H); 2.79 (3, 3H); 2.40 (br. m, 5H); 2.28 (m, 4H); 1.72 (br. m, 2H); 1.64-1.49 (m, 13H); 1.26 (br. m, 50H); 0.88 (t, 9H, J=7.5 Hz).

XX74. Compound 174: Heptadecan-9-yl 8-((3-(2,5-dioxoimidazolidin-1-yl)propyl)(8-(nonyloxy)-8-oxooctyl)amino)octanoate

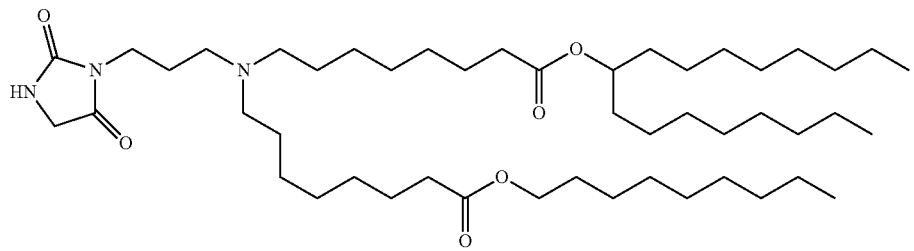

Chemical Formula: C₄₈H₉₁N₃O₆
Molecular Weight: 806.27

To a solution of heptadecan-9-yl 8-((3-chloropropyl)(8-(nonyloxy)-8-oxooctyl)amino)octanoate (200 mg, 0.27 mmol) and hydantoin (50 mg, 0.54 mmol) in 4 mL dry DMF was added cesium carbonate (130 mg, 0.40 mmol), the resulting mixture heated to 60° C. and stirred for 24 hours, after which no starting chloride remained by LC/MS. The mixture was allowed to cool to rt, diluted with a 50% saturated aqueous sodium bicarbonate solution and extracted twice with DCM. The organics were combined, washed once with water, dried (MgSO₄), filtered and conc. The residue was purified by silica gel chromatography (0-50% (mixture of 1% NH₄OH, 20% MeOH in dichloromethane) in dichloromethane) to give heptadecan-9-yl 8-((3-(2,5-dioxoimidazolidin-1-yl)propyl)(8-(nonyloxy)-8-oxooctyl)amino)octanoate (35 mg, 0.05 mmol, 18%) as a pale yellow oil. UPLC/ELSD: RT=3.52 min. MS (ES): m/z (MH⁺) 807.2 for C₄₈H₉₁N₃O₆. ¹H NMR (300 MHz, CDCl₃) δ: ppm 5.27 (br. s, 1H); 4.86 (quint., 1H, J=6 Hz); 4.05 (t, 2H, J=6 Hz); 3.95 (s, 2H); 3.55 (t, 2H, J=7.5 Hz); 2.50-2.34 (br. m, 5H); 2.26 (m, 4H); 1.77 (br. s, 2H); 1.64-1.49 (m, 15H); 1.26 (br. m, 48H); 0.88 (t, 9H, J=7.5 Hz).

XX75. Compound 175: Heptadecan-9-yl 8-((3-((methylcarbamoyl)oxy)propyl)(8-(nonyloxy)-8-oxooctyl)amino)octanoate

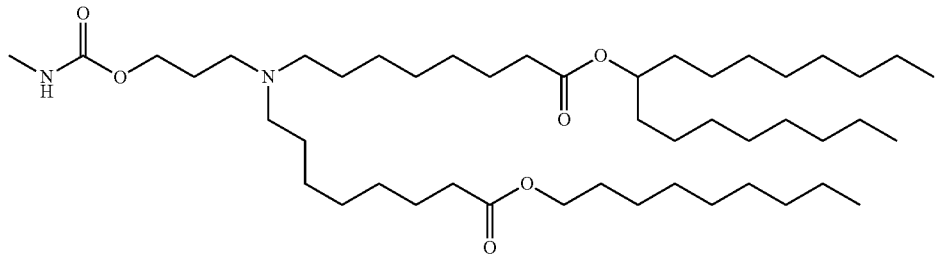

Chemical Formula: C₄₇H₉₂N₂O₆
Molecular Weight: 781.26

To a solution of heptadecan-9-yl 8-((3-hydroxypropyl)(8-(nonyloxy)-8-oxooctyl)amino)octanoate (200 mg, 0.27 mmol) and triethylamine (60 uL, 0.41 mmol) in 5 mL dry DCM at 0° C. was added methyl isocyanate (22 uL, 0.35 mmol) dropwise. The cooling bath was removed and the solution stirred at rt for 2 hours, after which no starting alcohol remained by LC/MS. The reaction was quenched with three drops of methanol, the mixture reduced in a stream of nitrogen and the residue purified by silica gel chromatography (0-50% (mixture of 1% NH₄OH, 20% MeOH in dichloromethane) in dichloromethane) to give heptadecan-9-yl 8-((3-((methylcarbamoyl)oxy)propyl)(8-(nonyloxy)-8-oxooctyl)amino)octanoate (115 mg, 0.15 mmol, 53%) as a colorless oil. UPLC/ELSD: RT=3.54 min. MS (ES): m/z (MH⁺) 782.3 for C₄₇H₉₂N₂O₆. ¹H NMR (300 MHz, CDCl₃) δ: ppm 4.86 (quint., 1H, J=6 Hz); 4.62 (br. s, 1H); 4.05 (m, 4H); 2.79 (d, 3H, J=3 Hz); 2.47 (br. s, 2H); 2.37 (br. m, 3H); 2.27 (m, 4H); 1.73 (br. s, 2H); 1.61 (m, 7H); 1.50 (br. m, 4H); 1.40 (br. m, 4H); 1.25 (br. m, 48H); 0.87 (t, 9H, J=7.5 Hz).

XX76. Compound 176: Heptadecan-9-yl 8-((3-(2,5-dioxopyrrolidin-1-yl)propyl)(8-(nonyloxy)-8-oxooctyl)amino)octanoate

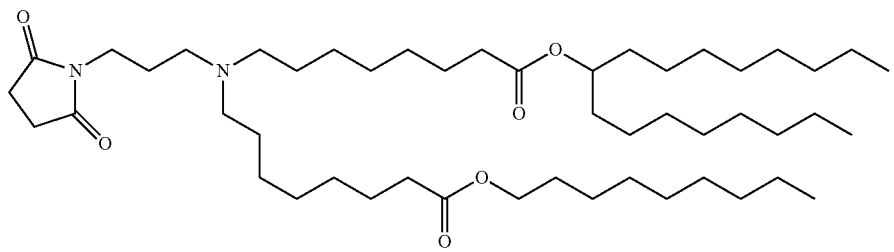

Chemical Formula: C₄₉H₉₂N₂O₆
Molecular Weight: 805.28

To a solution of heptadecan-9-yl 8-((3-chloropropyl)(8-(nonyloxy)-8-oxooctyl)amino)octanoate (200 mg, 0.27 mmol) and succinimide (50 mg, 0.54 mmol) in 4 mL dry DMSO was added cesium carbonate (130 mg, 0.40 mmol), the resulting mixture heated to 80° C. and stirred for 48 hours, after which no starting chloride remained by LC/MS. The mixture was allowed to cool to rt, diluted with a 50% saturated aqueous sodium bicarbonate solution and extracted three times with DCM. The organics were combined, washed once with water, dried (MgSO₄), filtered and conc. The residue was purified twice by silica gel chromatography (0-50% (mixture of 1% NH₄OH, 20% MeOH in dichloromethane) in dichloromethane) to give heptadecan-9-yl 8-((3-(2,5-dioxopyrrolidin-1-yl)propyl)(8-(nonyloxy)-8-oxooctyl)amino)octanoate (44 mg, 0.05 mmol, 19%) as a slightly yellow oil. UPLC/ELSD: RT=3.56 min. MS (ES): m/z (MH⁺)806.1 for C₄₉H₉₂N₂O₆. ¹H NMR (300 MHz, CDCl₃) δ: ppm 4.86 (quint., 1H, J=6 Hz); 4.05 (t, 2H, J=6 Hz); 3.52 (t, 2H, J=7.5 Hz); 2.69 (s, 4H); 2.42-2.25 (br. m, 9H); 1.71-1.58 (m, 10H); 1.50 (br. d, 4H, J=3 Hz); 1.26 (br. m, 51H); 0.88 (t, 9H, J=7.5 Hz).

XX77. Compound 177: Heptadecan-9-yl 8-((3-(4-(tert-butoxymethyl)-1H-1,2,3-triazol-1-yl)propyl)(8-(nonyloxy)-8-oxooctyl)amino)octanoate

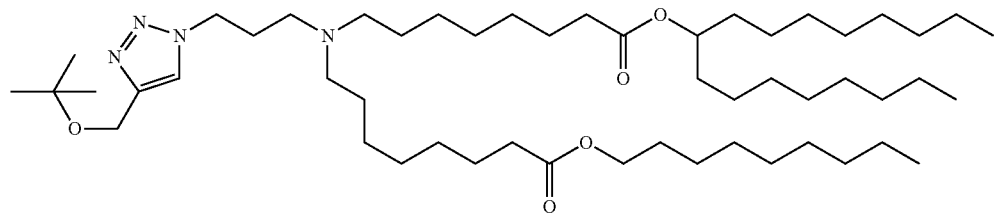

Chemical Formula: $C_{52}H_{100}N_4O_5$
Molecular Weight: 861.40

To a solution of heptadecan-9-yl 8-((3-azidopropyl)(8-(nonyloxy)-8-oxooctyl)amino)octanoate (500 mg, 0.67 mmol) and tert-butyl propargyl ether (100 uL, 0.73 mmol) in 4 mL THF was added a suspension of anhydrous copper(II) sulfate (5 mg, 0.03 mmol) and sodium ascorbate (14 mg, 0.07 mmol) in 1 mL water and the mixture stirred at rt for 24 hours, after which no starting azide remained by LC/MS. The mixture was diluted with a saturated aqueous sodium bicarbonate solution and extracted three times with DCM. The organics were combined, dried ($MgSO_4$), filtered and conc. The residue was purified by silica gel chromatography (0-50% (mixture of 1% $NH_4OH$, 20% MeOH in dichloromethane) in dichloromethane) to give heptadecan-9-yl 8-((3-(4-(tert-butoxymethyl)-1H-1,2,3-triazol-1-yl)propyl)(8-(nonyloxy)-8-oxooctyl)amino)octanoate (485 mg, 0.56 mmol, 84%) as a slightly yellow oil. UPLC/ELSD: RT=3.63 min. MS (ES): m/z (MH$^+$) 862.2 for $C_{52}H_{100}N_4O_5$. $^1$H NMR (300 MHz, $CDCl_3$) δ: ppm 7.50 (s, 1H); 4.86 (quint., 1H, J=6 Hz); 4.59 (s, 2H); 4.36 (t, 2H, J=7.5 Hz); 4.05 (t, 2H, J=6 Hz); 2.36 (br. m, 5H); 2.28 (m, 4H); 2.02 (br. m, 2H); 1.62 (br. m, 8H); 1.50 (br. d, 4H, J=3 Hz); 1.28 (br. m, 60H); 0.88 (t, 9H, J=7.5 Hz).

XX78. Compound 178: Heptadecan-9-yl 8-((3-(2-methoxyacetamido)propyl)(8-(nonyloxy)-8-oxooctyl)amino)octanoate

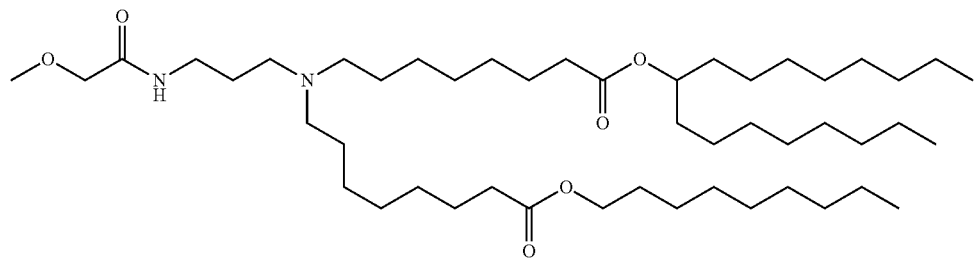

Chemical Formula: $C_{48}H_{94}N_2O_6$
Molecular Weight: 795.29

To a solution of heptadecan-9-yl 8-((3-aminopropyl)(8-(nonyloxy)-8-oxooctyl)amino)octanoate (200 mg, 0.27 mmol) and triethylamine (60 uL, 0.41 mmol) in 5 mL dry DCM at 0° C. was added methoxyacetyl chloride (30 uL, 0.33 mmol) dropwise. The cooling bath was removed and the solution stirred at rt for 24 hours, after which no starting amine remained by LC/MS. The mixture was diluted with a 50% saturated aqueous sodium bicarbonate solution and extracted twice with DCM. The organics were combined, washed once with water, dried ($MgSO_4$), filtered and conc. The residue was purified by silica gel chromatography (0-50% (mixture of 1% $NH_4OH$, 20% MeOH in dichloromethane) in dichloromethane) to give heptadecan-9-yl 8-((3-(2-methoxyacetamido)propyl)(8-(nonyloxy)-8-oxooctyl)amino)octanoate (50 mg, 0.06 mmol, 23%) as a colorless oil. UPLC/ELSD: RT=3.56 min. MS (ES): m/z (MH$^+$) 796.2 for $C_{48}H_{94}N_2O_6$. $^1$H NMR (300 MHz, $CDCl_3$) δ: ppm 7.53 (s, 1H); 4.86 (quint., 1H, J=6 Hz); 4.05 (t, 2H, J=6 Hz); 3.87 (s, 2H); 3.39 (m, 5H); 2.47 (br. s, 2H); 2.36 (br. m, 3H); 2.27 (m, 4H); 1.61 (m, 8H); 1.46 (br. m, 9H); 1.26 (br. m, 48H); 0.88 (t, 9H, J=7.5 Hz).

XX79. Compound 179: Heptadecan-9-yl 8-((3-(1H-1,2,3-triazol-1-yl)propyl)(8-(nonyloxy)-8-oxooctyl)amino)octanoate Heptadecan-9-yl 8-((8-(nonyloxy)-8-oxooctyl)(3-(4-(trimethylsilyl)-1H-1,2,3-triazol-1-yl)propyl)amino)octanoate

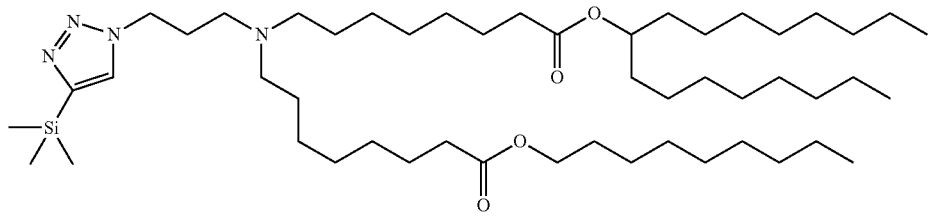

Chemical Formula: $C_{50}H_{98}N_4O_4Si$
Molecular Weight: 847.44

To a solution of heptadecan-9-yl 8-((3-azidopropyl)(8-(nonyloxy)-8-oxooctyl)amino)octanoate (200 mg, 0.27 mmol) and ethynyltrimethylsilane (41 uL, 0.29 mmol) in 2 mL THF was added a suspension of anhydrous copper(II) sulfate (2 mg, 0.01 mmol) and sodium ascorbate (5 mg, 0.02 mmol) in 0.5 mL water and the mixture stirred at rt for 20 hours, after which no starting azide remained by LC/MS. The mixture was diluted with a saturated aqueous sodium bicarbonate solution and extracted three times with DCM. The organics were combined, dried ($MgSO_4$), filtered and conc. The residue was purified by silica gel chromatography (0-50% (mixture of 1% $NH_4OH$, 20% MeOH in dichloromethane) in dichloromethane) to give heptadecan-9-yl 8-((8-(nonyloxy)-8-oxooctyl)(3-(4-(trimethyl silyl)-1H-1,2,3-triazol-1-yl)propyl)amino)octanoate (150 mg, 0.18 mmol, 66%) as a slightly yellow oil which is a 2:1 mixture of TMS/des-TMS product by $^1$H-NMR. Carried through as is. UPLC/ELSD: RT=3.63 min. MS (ES): m/z (MH$^+$) 848.3 for $C_{50}H_{98}N_4O_4Si$. $^1$H NMR (300 MHz, CDCl$_3$) δ: ppm 7.55 (s, 1H); 4.86 (quint., 1H, J=6 Hz); 4.45 (t, 2H, J=7.5 Hz); 4.05 (t, 2H, J=6 Hz); 3.42 (br. s, 1H); 2.28 (m, 5H); 1.65-1.45 (br. m, 14H); 1.25 (br. m, 48H); 0.87 (t, 9H, J=7.5 Hz); 0.33 (s, 6H).

Heptadecan-9-yl 8-((3-(1H-1,2,3-triazol-1-yl)propyl)(8-(nonyloxy)-8-oxooctyl)amino)octanoate

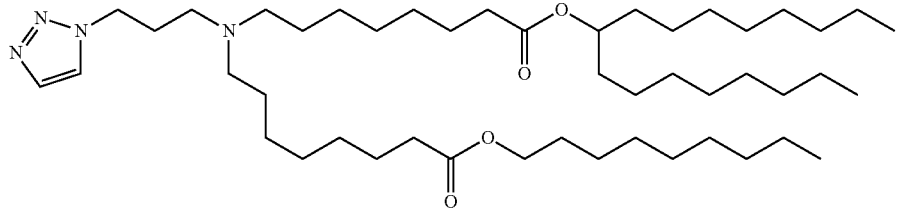

Chemical Formula: $C_{47}H_{90}N_4O_4$
Molecular Weight: 775.26

To a solution of (150 mg, 0.18 mmol) in 5 mL THF was added a 1M tetrabutylammonium fluoride solution in THF (0.21 mL, 0.21 mmol) and the solution stirred at rt for 24 hours after which the reaction had progressed ca. 25%. The solution was heated to 55° C. and stirred for 24 hours, after which the reaction was complete by LC/MS. The solution was diluted with a saturated aqueous sodium bicarbonate solution and extracted twice with DCM. The organics were combined, dried ($MgSO_4$), filtered and conc. The residue was purified by silica gel chromatography (0-50% (mixture of 1% $NH_4OH$, 20% MeOH in dichloromethane) in dichloromethane) to give heptadecan-9-yl 8-((3-(1H-1,2,3-triazol-1-yl)propyl)(8-(nonyloxy)-8-oxooctyl)amino)octanoate (53 mg, 0.07 mmol, 39%) as a colorless oil. UPLC/ELSD: RT=3.55 min. MS (ES): m/z (MH$^+$) 776.2 for $C_{47}H_{90}N_4O_4$. $^1$H NMR (300 MHz, CDCl$_3$) δ: ppm 7.69 (s, 1H); 7.55 (s, 1H); 4.86 (quint., 1H, J=6 Hz); 4.44 (t, 2H, J=7.5 Hz); 4.05 (t, 2H, J=6 Hz); 2.37 (br. m, 5H); 2.28 (m, 4H); 2.05 (br. m, 2H); 1.61 (br. m, 8H); 1.49 (br. m, 4H); 1.26 (br. m, 51H); 0.88 (t, 9H, J=7.5 Hz).

XX81. Compound 181: Heptadecan-9-yl 8-((3-((methoxycarbonyl)amino)propyl)(8-(nonyloxy)-8-oxooctyl)amino)octanoate

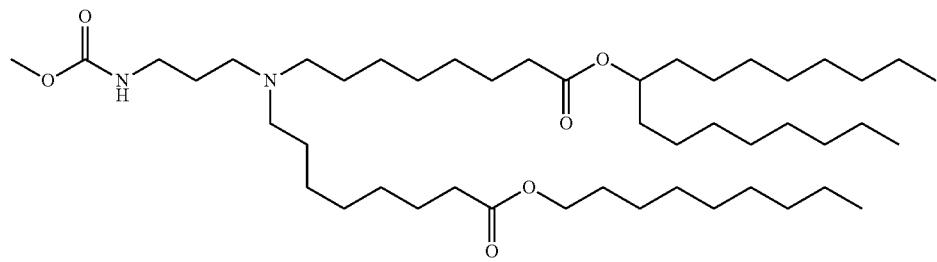

Chemical Formula: C₄₇H₉₂N₂O₆
Molecular Weight: 781.26

To a solution of heptadecan-9-yl 8-((3-aminopropyl)(8-(nonyloxy)-8-oxooctyl)amino)octanoate (200 mg, 0.27 mmol) and triethylamine (60 uL, 0.41 mmol) in 5 mL dry DCM at 0° C. was added methyl chloroformate (27 uL, 0.33 mmol) dropwise. The cooling bath was removed and the solution stirred at rt for 24 hours, after which no starting amine remained by LC/MS. The mixture was diluted with a 50% saturated aqueous sodium bicarbonate solution and extracted twice with DCM. The organics were combined, washed once with water, dried (MgSO₄), filtered and conc. The residue was purified by silica gel chromatography (0-50% (mixture of 1% NH₄OH, 20% MeOH in dichloromethane) in dichloromethane) to give heptadecan-9-yl 8-((3-((methoxycarbonyl)amino)propyl)(8-(nonyloxy)-8-oxooctyl)amino)octanoate (120 mg, 0.15 mmol, 54%) as a colorless oil. UPLC/ELSD: RT=3.55 min. MS (ES): m/z (MH⁺) 782.1 for C₄₇H₉₂N₂O₆. $^1$H NMR (300 MHz, CDCl₃) δ: ppm 6.11 (br. s, 1H); 4.86 (quint., 1H, J=6 Hz); 4.05 (t, 2H, J=6 Hz); 3.64 (s, 3H); 3.25 (br. d, 2H, J=6 Hz); 2.46 (br. s, 2H); 2.38-2.24 (m, 7H); 1.61 (br. t, 9H, J=7.5 Hz); 1.50 (m, 4H); 1.42 (br. m, 3H); 1.26 (br. m, 49H); 0.88 (t, 9H, J=7.5 Hz).

XX82. Compound 182: Heptadecan-9-yl 8-((3-((2-(methylamino)-3,4-dioxocyclobut-1-en-1-yl)amino)propyl)(8-(nonyloxy)-8-oxooctyl)amino)octanoate 3-Methoxy-4-(methylamino)cyclobut-3-ene-1,2-dione

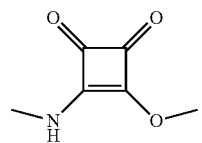

Chemical Formula: C₆H₇NO₃
Molecular Weight: 141.13

To a solution of 3,4-dimethoxy-3-cyclobutene-1,2-dione (1 g, 7 mmol) in 100 mL diethyl ether was added a 2M methylamine solution in THF (3.8 mL, 7.6 mmol) and a ppt. formed almost immediately. The mixture was stirred at rt for 24 hours, then filtered, the filter solids washed with diethyl ether and air-dried. The filter solids were dissolved in hot EtOAc, filtered, the filtrate allowed to cool to room temp., then cooled to 0° C. to give a ppt. This was isolated via filtration, washed with cold EtOAc, air-dried, then dried under vacuum to give 3-methoxy-4-(methylamino)cyclobut-3-ene-1,2-dione (0.70 g, 5 mmol, 73%) as a white solid. $^1$H NMR (300 MHz, DMSO-d₆) δ: ppm 8.50 (br. d, 1H, J=69 Hz); 4.27 (s, 3H); 3.02 (sdd, 3H, J=42 Hz, 4.5 Hz).

Heptadecan-9-yl 8-((3-((2-(methylamino)-3,4-dioxocyclobut-1-en-1-yl)amino)propyl)(8-(nonyloxy)-8-oxooctyl)amino)octanoate

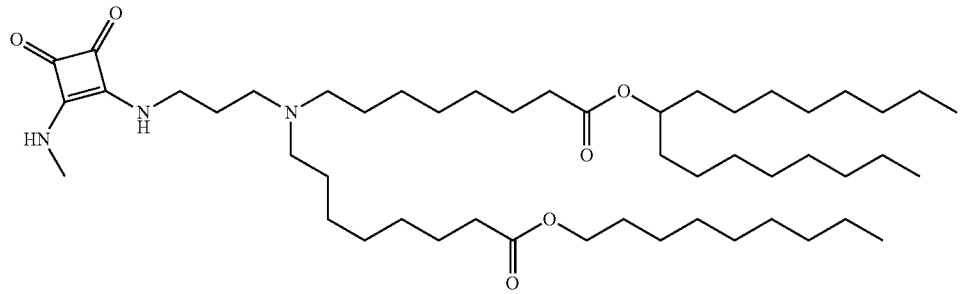

Chemical Formula: C₅₀H₉₃N₃O₆
Molecular Weight: 832.31

To a solution of heptadecan-9-yl 8-((3-aminopropyl)(8-(nonyloxy)-8-oxooctyl)amino)octanoate (200 mg, 0.28 mmol) in 10 mL ethanol was added 3-methoxy-4-(methylamino)cyclobut-3-ene-1,2-dione (39 mg, 0.28 mmol) and the resulting colorless solution stirred at rt for 20 hours after which no starting amine remained by LC/MS. The solution was concentrated in vacuo and the residue purified by silica gel chromatography (0-100% (mixture of 1% NH$_4$OH, 20% MeOH in dichloromethane) in dichloromethane) to give heptadecan-9-yl 8-((3-((2-(methylamino)-3,4-dioxocyclobut-1-en-1-yl)amino)propyl)(8-(nonyloxy)-8-oxooctyl)amino)octanoate (138 mg, 0.17 mmol, 60%) as a gummy white solid. UPLC/ELSD: RT=3. min. MS (ES): m/z (MH$^+$) 833.4 for $C_{51}H_{95}N_3O_6$. $^1$H NMR (300 MHz, CDCl$_3$) δ: ppm 7.86 (br. s., 1H); 4.86 (quint., 1H, J=6 Hz); 4.05 (t, 2H, J=6 Hz); 3.92 (d, 2H, J=3 Hz); 3.20 (s, 6H); 2.63 (br. s, 2H); 2.42 (br. s, 3H); 2.28 (m, 4H); 1.74 (br. s, 2H); 1.61 (m, 8H); 1.50 (m, 5H); 1.41 (m, 3H); 1.25 (br. m, 47H); 0.88 (t, 9H, J=7.5 Hz).

XX83. Compound 183: 1,3-Bis(hexyloxy)propan-2-yl 8-((2-hydroxyethyl)(8-(nonyloxy)-8-oxooctyl)amino)octanoate (((1,3-Bis(hexyloxy)propan-2-yl)oxy)methyl)benzene

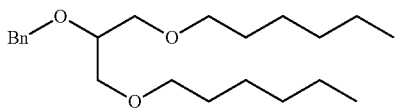

Chemical Formula: $C_{22}H_{38}O_3$
Molecular Weight: 350.543

To a slurry of NaH (1.76 g, 43.9 mmol) in THF (40 mL) under N$_2$ was added 2-(benzyloxy)propane-1,3-diol (2 g, 10.98 mmol) and the mixture was allowed to stir at 40° C. for 2 h. After this time 1-bromohexane (4.35 g, 26.34 mmol) in DMF (2 ml) and a catalytic amount of KI were added. The reaction was refluxed for 16 h. Solvents were evaporated under vacuum. The residue was diluted with EtOAc and washed with sat. NaHCO$_3$, followed by brine. The organic layer was separated, dried over Na$_2$SO$_4$, filtered, and evaporated under vacuum. The residue was purified by silica gel chromatography with (0-40%) EtOAc in hexanes to obtain (((1,3-bis(hexyloxy)propan-2-yl)oxy)methyl)benzene (1.7 g, 4.75 mmol, 43%). $^1$H NMR (300 MHz, CDCl$_3$) δ: ppm 7.34 (m, 5H); 4.73 (s, 2H); 3.75 (m, 1H); 3.61-3.40 (m, 8H); 1.59 (m, 4H); 1.32 (m, 12H); 0.91 (m, 6H).

1,3-Bis(hexyloxy)propan-2-ol

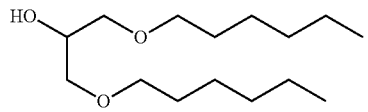

Chemical Formula: $C_{15}H_{32}O_3$
Molecular Weight: 260.418

1,3-Bis(hexyloxy)propan-2-ol was synthesized using the same manner as 9-Methyloctadecane-1,9-diol. $^1$H NMR (300 MHz, CDCl$_3$) δ: ppm 3.96 (m, 1H); 3.48 (m, 8H); 2.37 (br. S, 1H); 1.64 (m, 2H); 1.60 (m, 4H); 1.32 (m, 12H); 0.91 (m, 6H). 1,3-Bis(hexyloxy)propan-2-yl 8-((2-hydroxyethyl)(8-(nonyloxy)-8-oxooctyl)amino)octanoate

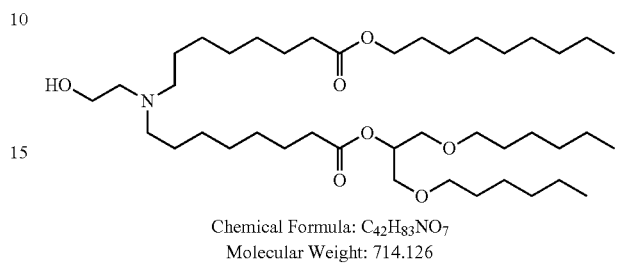

Chemical Formula: $C_{42}H_{83}NO_7$
Molecular Weight: 714.126

Compound 183 was synthesized according to the general procedure and Representative Procedure 1 described above. UPLC/ELSD: RT=3.17 min. MS (ES): m/z (MH$^+$) 715.0 for $C_{42}H_{83}NO_7$. $^1$H NMR (300 MHz, CDCl$_3$) δ: ppm 5.15 (m, 1H); 4.08 (t, 2H); 3.66-3.34 (m, 10H); 2.71-2.41 (m, 6H); 2.34 (m, 4H); 1.74-1.20 (m, 50H); 0.91 (m, 9H).

XX84. Compound 184: Heptadecan-9-yl 8-((2-hydroxyethyl)(8-((2-methylnonyl)oxy)-8-oxooctyl)amino)octanoate 2-Methylnonyl 8-bromooctanoate

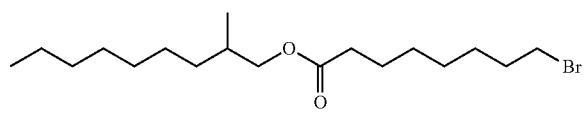

Chemical Formula: $C_{18}H_{35}BrO_2$
Molecular Weight: 363.380

To a solution of 8-bromooctanoic acid (3.83 g, 17.18 mmol), 2-methylnonan-1-ol (2.72 g, 17.18 mmol), 4-dimethylaminopyridine (0.42 g, 3.44 mmol) in DCM (25 mL) under N$_2$ was added (3-{[(ethylimino)methylidene]amino}propyl)dimethylamine hydrochloride (3.29 g, 17.18 mmol). The reaction was allowed to stir at rt for 16 h. The reaction was diluted with DCM and washed with sat. NaHCO$_3$, followed by brine. The organic layer was separated, dried over Na$_2$SO$_4$, filtered, and evaporated under vacuum. The residue was purified by silica gel chromatography with (0-20%) EtOAc in hexanes to obtain 2-methylnonyl 8-bromooctanoate (5.1 g, 14.04 mmol, 82%).

$^1$H NMR (300 MHz, CDCl$_3$) δ: ppm 3.98 (m, 2H); 3.43 (t, 2H); 2.33 (t, 2H); 1.93-1.74 (m, 3H); 1.72-1.09 (m, 20H); 0.93 (m, 6H).

287

Heptadecan-9-yl 8-((2-hydroxyethyl)(8-((2-methyl-nonyl)oxy)-8-oxooctyl)amino)octanoate

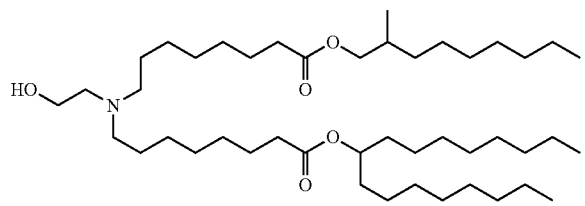

Chemical Formula: C$_{45}$H$_{89}$NO$_5$
Molecular Weight: 724.209

Compound 184 was synthesized according to the general procedure and Representative Procedure 1 described above. UPLC/ELSD: RT=3.60 min. MS (ES): m/z (MH$^+$) 725.0 for C$_{45}$H$_{89}$NO$_5$. $^1$H NMR (300 MHz, CDCl$_3$) δ: ppm 4.89 (m, 1H); 3.92 (m, 2H); 3.57 (m, 2H); 2.70-2.41 (m, 6H); 2.31 (m, 4H); 1.79 (m, 1H); 1.70-1.07 (m, 60H); 0.93 (m, 12H).

XX85. Compound 185: Henicosan-11-yl 6-((2-hydroxyethyl)(6-oxo-6-(undecyloxy)hexyl)amino)hexanoate

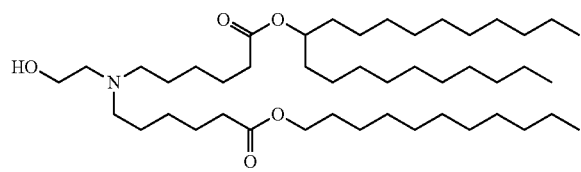

Chemical Formula: C$_{46}$H$_{91}$NO$_5$
Molecular Weight: 738.236

Compound 185 was synthesized according to the general procedure and Representative Procedure 1 described above. UPLC/ELSD: RT=3.72 min. MS (ES): m/z (MH$^+$) 739.0 for C$_{46}$H$_{91}$NO$_5$. $^1$H NMR (300 MHz, CDCl$_3$) δ: ppm 4.88 (m, 1H); 4.08 (t, 2H); 3.55 (m, 2H); 2.60 (m, 2H); 2.48 (m, 4H); 2.32 (m, 4H); 1.72-1.41 (m, 15H); 1.28 (m, 52H); 0.90 (m, 9H).

288

XX86. Compound 186: Heptyl 10-((2-hydroxyethyl)(10-oxo-10-(tridecan-7-yloxy)decyl)amino)decanoate

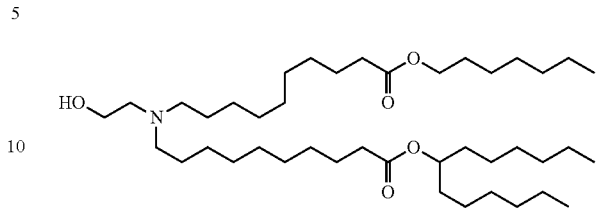

Chemical Formula: C$_{42}$H$_{83}$NO$_5$
Molecular Weight: 682.128

Compound 186 was synthesized according to the general procedure and Representative Procedure 1 described above. UPLC/ELSD: RT=3.31 min. MS (ES): m/z (MH$^+$) 739.0 for C$_{42}$H$_{83}$NO$_5$. $^1$H NMR (300 MHz, CDCl$_3$) δ: ppm 4.89 (m, 1H); 4.08 (t, 2H); 3.55 (m, 2H); 2.58 (m, 2H); 2.47 (m, 4H); 2.30 (m, 4H); 1.71-1.18 (m, 58H); 0.90 (m, 9H).

XX89. Compound 189: Heptyl 10-((8-(heptadecan-9-yloxy)-8-oxooctyl)(2-hydroxyethyl)amino)decanoate

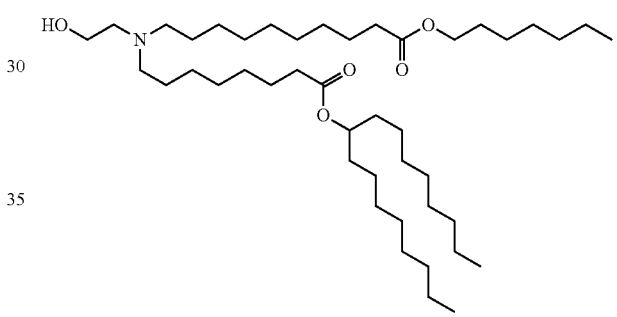

Chemical Formula: C$_{44}$H$_{87}$NO$_5$
Molecular Weight: 710.182

Compound 189 was synthesized according to the general procedure and Representative Procedure 1 described above. UPLC/ELSD: RT=3.47 min. MS (ES): m/z (MH$^+$) 710.98 for C$_{44}$H$_{87}$NO$_5$. $^1$H NMR (300 MHz, CDCl$_3$) δ: ppm 4.89 (m, 1H); 4.08 (t, 2H); 3.55 (m, 2H); 2.61 (m, 2H); 2.47 (m, 4H); 2.31 (m, 4H); 1.70-1.20 (m, 62H); 0.90 (m, 9H).

XX94. Compound 194: Heptadecan-9-yl 8-((3-isobutyramidopropyl)(8-(nonyloxy)-8-oxooctyl)amino)octanoate

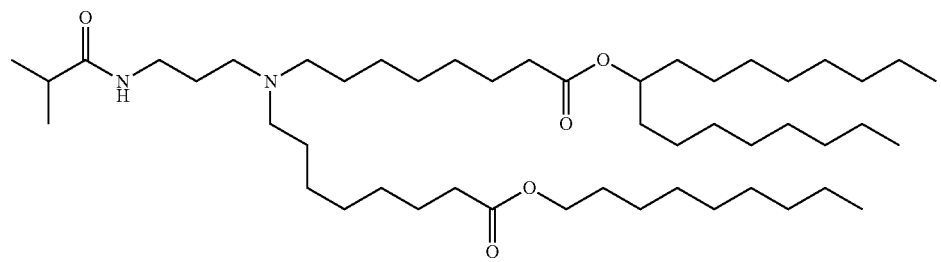

Chemical Formula: C$_{49}$H$_{96}$N$_2$O$_5$
Molecular Weight: 793.32

To a solution of heptadecan-9-yl 8-((3-aminopropyl)(8-(nonyloxy)-8-oxooctyl)amino)octanoate (150 mg, 0.21 mmol) and triethylamine (90 uL, 0.62 mmol) in 5 mL dry DCM at 0° C. was added isobutyryl chloride (35 uL, 0.31 mmol) dropwise. After 30 minutes the cooling bath was removed and the solution stirred at rt for 90 minutes, after which no starting amine remained by LC/MS. The mixture was diluted with a 50% saturated aqueous sodium bicarbonate solution and extracted twice with DCM. The organics were combined, washed once with water, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-((3-isobutyramidopropyl)(8-(nonyloxy)-8-oxooctyl)amino)octanoate (65 mg, 0.08 mmol, 39%) as a colorless oil. UPLC/ELSD: RT=3.65 min. MS (ES): m/z (MH$^+$) 794.3 for C$_{49}$H$_{96}$N$_2$O$_5$. $^1$H NMR (300 MHz, CDCl$_3$) δ: ppm 7.53 (s, 1H); 4.86 (quint., 1H, J=6 Hz); 4.05 (t, 2H, J=6 Hz); 3.87 (s, 2H); 3.39 (m, 5H); 2.47 (br. s, 2H); 2.36 (br. m, 3H); 2.27 (m, 4H); 1.61 (m, 8H); 1.46 (br. m, 9H); 1.26 (br. m, 48H); 0.88 (t, 9H, J=7.5 Hz).

XX97. Compound 197: Heptadecan-9-yl 8-((3-(2-(benzyloxy)acetamido)propyl)(8-(nonyloxy)-8-oxooctyl)amino)octanoate

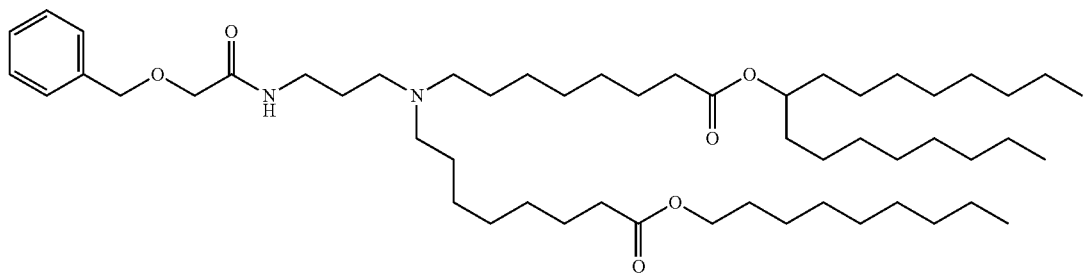

Chemical Formula: C$_{54}$H$_{98}$N$_2$O$_6$
Molecular Weight: 871.39

To a solution of heptadecan-9-yl 8-((3-aminopropyl)(8-(nonyloxy)-8-oxooctyl)amino)octanoate (300 mg, 0.41 mmol) and triethylamine (145 uL, 1 mmol) in 10 mL dry DCM at 0° C. was added benzyloxyacetyl chloride (82 uL, 0.52 mmol) dropwise. The cooling bath was removed and the solution stirred at rt for 24 hours, after which no starting amine remained by LC/MS. The mixture was diluted with a 50% saturated aqueous sodium bicarbonate solution and extracted twice with DCM. The organics were combined, washed once with water, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-((3-(2-(benzyloxy)acetamido)propyl)(8-(nonyloxy)-8-oxooctyl)amino)octanoate (179 mg, 0.21 mmol, 50%) as a colorless oil. UPLC/ELSD: RT=3.66 min. MS (ES): m/z (MH$^+$) 872.4 for C$_{54}$H$_{98}$N$_2$O$_6$. $^1$H NMR (300 MHz, CDCl$_3$) δ: ppm 7.55 (s, 1H); 7.33 (m, 5H); 4.86 (quint., 1H, J=6 Hz); 4.55 (s, 2H); 4.05 (t, 2H, J=6 Hz); 3.97 (s, 2H); 3.35 (quart., 2H, J=6 Hz); 2.46 (br. m, 2H); 2.28 (m, 7H); 1.65-1.48 (m, 15H); 1.26 (br. m, 50H); 0.88 (t, 9H, J=7.5 Hz).

XX98. Compound 198: Heptadecan-9-yl 8-((3-(2-hydroxyacetamido)propyl)(8-(nonyloxy)-8-oxooctyl)amino)octanoate

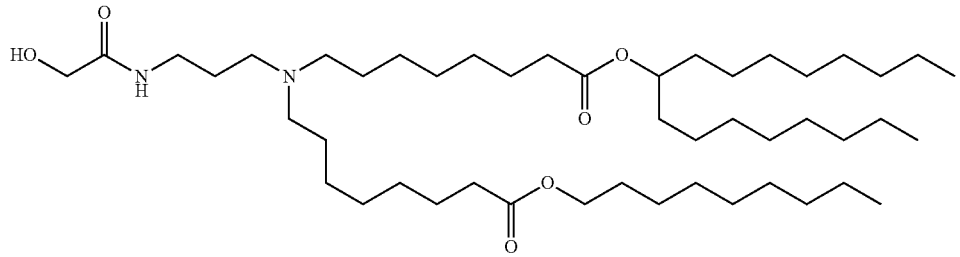

Chemical Formula: C$_{47}$H$_{92}$N$_2$O$_6$
Molecular Weight: 781.26

To a solution of heptadecan-9-yl 8-((3-(2-(benzyloxy)acetamido)propyl)(8-(nonyloxy)-8-oxooctyl)amino)octanoate (130 mg, 0.15 mmol) in 5 mL ethanol under nitrogen was added palladium 10 wt. % on carbon (approx. 20, cat.) added, the sides of the flask washed down with ethanol and the flask fitted with a hydrogen balloon. The flask was evacuated and back-filled with hydrogen three times, then stirred at rt for 24 hours after which no starting ether remained by LC/MS. The flask was flushed with nitrogen, the mixture filtered through diatomaceous earth, the filter solids washed with ethanol and the filtrate conc. The residue was purified by silica gel chromatography (0-50% (mixture of 1% $NH_4OH$, 20% MeOH in dichloromethane) in dichloromethane) to give heptadecan-9-yl 8-((3-(2-hydroxyacetamido)propyl)(8-(nonyloxy)-8-oxooctyl)amino)octanoate (55 mg, 0.07 mmol, 47%) as a colorless oil. UPLC/ELSD: RT=3.46 min. MS (ES): m/z (MH$^+$) 782.2 for $C_{47}H_{92}N_2O_6$. $^1$H NMR (300 MHz, $CDCl_3$) δ: ppm 7.73 (br. s, 1H); 4.86 (quint., 1H, J=6 Hz); 4.05 (m, 4H); 3.40 (quart., 2H, J=6 Hz); 2.50 (m, 2H); 2.37 (t, 4H, J=6 Hz); 2.28 (m, 4H); 1.63 (m, 8H); 1.46 (br. m, 8H); 1.26 (br. m, 49H); 0.88 (t, 9H, J=7.5 Hz).

XX100. Compound 200: Heptadecan-9-yl (E)-8-((3-(3-methyl-2-nitroguanidino)propyl)(8-(nonyloxy)-8-oxooctyl)amino)octanoate Methyl (E/Z)—N-methyl-N'-nitrocarbamimidothioate

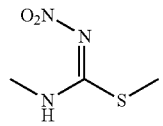

Chemical Formula: $C_3H_7N_3O_2S$
Molecular Weight: 149.17

To a suspension of 2-methyl-1-nitro-2-thiopseudourea (1.0 g, 7.4 mmol) and cesium carbonate (2.5 g, 7.8 mmol in 8 mL dry DMF was added iodomethane (0.69 mL, 11.1 mmol) and the mixture stirred at room temp for 24 hours. The yellow mixture was diluted with water and extracted twice with EtOAc. The organics were combined, washed three times with a 50% saturated aqueous sodium bicarbonate solution, once with brine, dried ($MgSO_4$), filtered and conc. to a yellow solid. This was dissolved in hot water, the solution filtered and the filtrate cooled to 4° C. for three days. The resulting solids were isolated via filtration, washed with water, air-dried, then dried under vacuum to give methyl (E/Z)—N-methyl-N-nitrocarbamimidothioate (85 mg, 0.57 mmol, 8%) as a pale yellow solid. $^1$H NMR (300 MHz, $CDCl_3$) δ: ppm 10.02 (br. s, 1H); 3.12 (d, 1H, J=6 Hz); 2.53 (s, 3H).

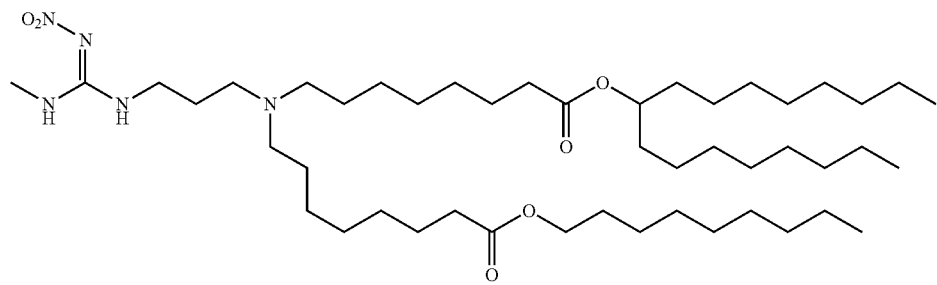

Chemical Formula: $C_{47}H_{93}N_5O_6$
Molecular Weight: 824.29

To a solution of heptadecan-9-yl 8-((3-aminopropyl)(8-(nonyloxy)-8-oxooctyl)amino)octanoate (200 mg, 0.28 mmol) in 5 mL methanol was added methyl (E/Z)—N-methyl-N-nitrocarbamimidothioate (45 mg, 0.3 mmol), the resulting solution heated to 70° C. and stirred for 24 hours after which no starting amine remained by LC/MS. The solution was diluted with DCM and washed once with a saturated aqueous sodium bicarbonate solution. The organic phase was dried (MgSO$_4$), filtered and the filtrate evaporated in vacuo. The residue was purified by silica gel chromatography (0-50% (mixture of 1% NH$_4$OH, 20% MeOH in dichloromethane) in dichloromethane) to give heptadecan-9-yl (E)-8-((3-(3-methyl-2-nitroguanidino)propyl)(8-(nonyloxy)-8-oxooctyl)amino)octanoate (75 mg, 0.09 mmol, 33%) as a pale yellow syrup. UPLC/ELSD: RT=3.55 min. MS (ES): m/z (MH$^+$) 825.3 for C$_{47}$H$_{93}$N$_5$O$_6$. $^1$H NMR (300 MHz, CDCl$_3$) δ: ppm 9.26 (br. s, 1H); 8.27 (br. s, 1H); 4.86 (quint., 1H, J=6 Hz); 4.05 (t, 2H, J=6 Hz); 3.42 (br. s, 2H); 2.86 (d, 3H, J=6 Hz); 2.60-2.40 (br. m, 5H); 2.28 (m, 4H); 1.73 (br. s, 2H); 1.65-1.40 (m, 16H); 1.26 (br. m, 47H); 0.88 (t, 9H, J=7.5 Hz).

XX107. Compound 207: Heptadecan-9-yl 8-((3-guanidinopropyl)(8-(nonyloxy)-8-oxooctyl)amino) octanoate Heptadecan-9-yl 6-((tert-butoxycarbonyl)amino)-2,2-dimethyl-11-(8-(nonyloxy)-8-oxooctyl)-4-oxo-3-oxa-5,7,11-triazanonadec-6-en-19-oate

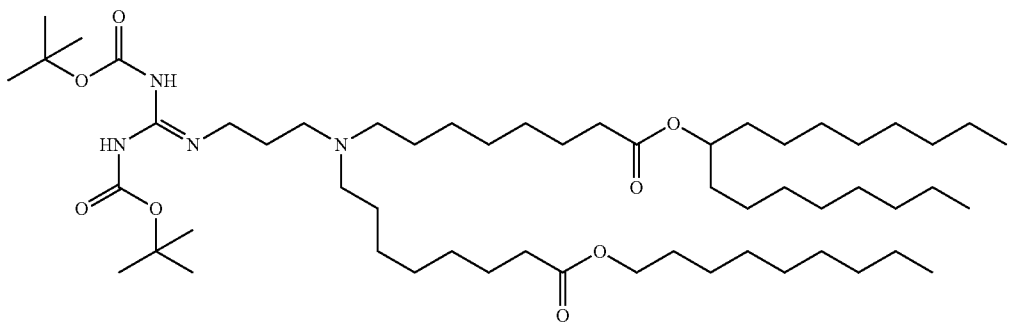

Chemical Formula: C$_{56}$H$_{108}$N$_4$O$_8$
Molecular Weight: 965.50

To a solution of heptadecan-9-yl 8-((3-aminopropyl)(8-(nonyloxy)-8-oxooctyl)amino)octanoate (300 mg, 0.41 mmol) and triethylamine (230 uL, 1.66 mmol) in 10 mL dry DCM at 0° C. was added 1,3-bis(tert-butoxycarbonyl)-2-(trifluoromethylsulfonyl)guanidine (325 mg, 0.83 mmol) in one portion and the resulting solution allowed to gradually warm to rt with stirring overnight. LC/MS showed no starting material remained so the solution was diluted with DCM, washed with a 50% saturated aqueous sodium bicarbonate solution, the organic layer dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 6-((tert-butoxycarbonyl)amino)-2,2-dimethyl-11-(8-(nonyloxy)-8-oxooctyl)-4-oxo-3-oxa-5,7,11-triazanonadec-6-en-19-oate (310 mg, 0.32 mmol, 77%) as a colorless oil in ca. 95% purity. Largest single impurity has mass corresponding to product with loss of one Boc group. Carried through as is. UPLC/ELSD: RT=3.90 min. MS (ES): m/z (MH$^+$) 966.0 for C$_{56}$H$_{108}$N$_4$O$_8$. $^1$H NMR (300 MHz, CDCl$_3$) δ: ppm 11.49 (s, 1H); 8.55 (br. s., 1H); 4.86 (quint., 1H, J=6 Hz); 4.05 (t, 2H, J=7.5 Hz); 3.45 (quart., 2H, J=6 Hz); 2.46 (m, 2H); 2.36 (m, 4H); 2.27 (m, 4H); 1.61 (m, 8H); 1.50 (m, 22H); 1.40 (m, 4H); 1.25 (br. m, 48H); 0.88 (t, 9H, J=7.5 Hz).

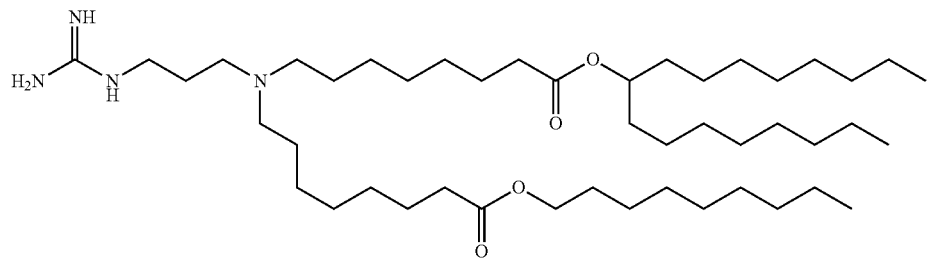

Chemical Formula: C$_{46}$H$_{92}$N$_4$O$_4$
Molecular Weight: 765.27

To a solution of heptadecan-9-yl 6-((tert-butoxycarbonyl)amino)-2,2-dimethyl-11-(8-(nonyloxy)-8-oxooctyl)-4-oxo-3-oxa-5,7,11-triazanonadec-6-en-19-oate (310 mg, 0.32 mmol) in 10 mL DCM was added trifluoroacetic acid (500 uL, excess) and the solution stirred at rt for 48 hours after which no starting material remained by LC/MS. The solution was conc., the residue codistilled with DCM twice and purified by silica gel chromatography (0-50% (mixture of 1% $NH_4OH$, 20% MeOH in dichloromethane) in dichloromethane) to give heptadecan-9-yl 8-((3-guanidinopropyl)(8-(nonyloxy)-8-oxooctyl)amino)octanoate (210 mg, 0.27 mmol, 84%) as a colorless oil. UPLC/ELSD: RT=3.16 min. MS (ES): m/z ($MH^+$) 766.3 for $C_{46}H_{92}N_4O_4$. $^1H$ NMR (300 MHz, $CDCl_3$) δ: ppm 10.92 (br. s, 1H); 8.82 (br. s, 1H); 7.25 (br. s, 2H); 4.85 (quint., 1H, J=6 Hz); 4.05 (t, 2H, J=6 Hz); 3.38 (br. s, 2H); 3.15 (br. s, 2H); 3.00 (br. s, 4H); 2.29 (m, 4H); 2.05 (br. s, 2H); 1.91 (br. s, 3H); 1.70-1.45 (br. m, 12H); 1.26 (br. m, 47H); 0.88 (t, 9H, J=7.5 Hz).

XX118. Compound 218: Heptadecan-9-yl 8-((3-(4-(hydroxymethyl)-1H-1,2,3-triazol-1-yl)propyl)(8-(nonyloxy)-8-oxooctyl)amino)octanoate

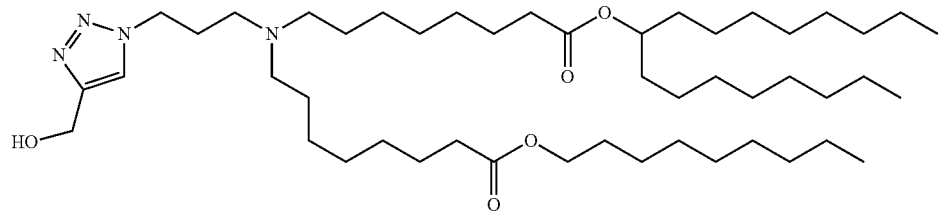

Chemical Formula: $C_{48}H_{92}N_4O_5$
Molecular Weight: 805.29

To a solution of heptadecan-9-yl 8-((3-(4-(tert-butoxymethyl)-1H-1,2,3-triazol-1-yl)propyl)(8-(nonyloxy)-8-oxooctyl)amino)octanoate (190 mg, 0.22 mmol) in 4 mL DCM was added trifluoroacetic acid (675 uL, excess) and the solution stirred at rt for 72 hours after which no starting material remained by LC/MS. The solution was conc., the residue codistilled with DCM twice and purified by silica gel chromatography (0-50% (mixture of 1% $NH_4OH$, 20% MeOH in dichloromethane) in dichloromethane) to give heptadecan-9-yl 8-((3-(4-(hydroxymethyl)-1H-1,2,3-triazol-1-yl)propyl)(8-(nonyloxy)-8-oxooctyl)amino)octanoate (113 mg, 0.14 mmol, 64%) as a colorless oil. UPLC/ELSD: RT=3.41 min. MS (ES): m/z ($MH^+$) 806.1 for $C_{48}H_{92}N_4O_5$. $^1H$ NMR (300 MHz, $CDCl_3$) δ: ppm 7.54 (s, 1H); 4.86 (quint., 1H, J=6 Hz); 4.80 (s, 2H); 4.40 (t, 2H, J=7.5 Hz); 4.05 (t, 2H, J=6 Hz); 2.38 (br. m, 5H); 2.28 (m, 5H); 2.04 (br. m, 2H); 1.61 (br. m, 7H); 1.50 (br. d, 4H, J=3 Hz); 1.26 (br. m, 51H); 0.88 (t, 9H, J=7.5 Hz) (hydroxyl proton not observed).

XX132. Compound 232: Nonyl 8-((2-hydroxyethyl)(6-oxo-6-((4-pentylcyclohexyl)oxy)hexyl)amino)octanoate

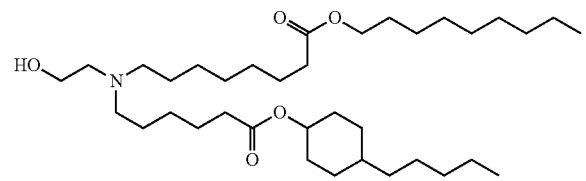

Chemical Formula: $C_{36}H_{69}NO_5$
Molecular Weight: 595.950

Compound 232 was synthesized according to the general procedure and Representative Procedure 1 described above. UPLC/ELSD: RT=2.84 min. MS (ES): m/z ($MH^+$) 596.84 for $C_{36}H_{69}NO_5$. $^1H$ NMR (300 MHz, $CDCl_3$) δ: ppm 5.01 (m, 0.5H); 4.68 (m, 0.5H); 4.08 (t, 2H); 3.56 (m, 2H), 2.67-2.55 (br. m, 2H); 2.55-2.40 (br. m, 4H); 2.31 (m, 4H); 1.97 (m, 1H); 1.82 (m, 2H); 1.73-1.15 (m, 43H); 1.02 (m, 1H); 0.90 (m, 6H).

Example 2: Production of Nanoparticle Compositions

A. Production of Nanoparticle Compositions

In order to investigate safe and efficacious nanoparticle compositions for use in the delivery of therapeutic and/or prophylactics to cells, a range of formulations are prepared and tested. Specifically, the particular elements and ratios thereof in the lipid component of nanoparticle compositions are optimized.

Nanoparticles can be made with mixing processes such as microfluidics and T-junction mixing of two fluid streams, one of which contains the therapeutic and/or prophylactic and the other has the lipid components.

Lipid compositions are prepared by combining a lipid according to Formula (I), (IA), (II), (IIa), (IIb), (IIc), (IId) or (IIe), a phospholipid (such as DOPE or DSPC, obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigeration for storage at, for example, −20° C. Lipids are combined to yield desired molar ratios (see, for example, Table 23) and diluted with water and ethanol to a final lipid concentration of between about 5.5 mM and about 25 mM.

Nanoparticle compositions including a therapeutic and/or prophylactic and a lipid component are prepared by combining the lipid solution with a solution including the therapeutic and/or prophylactic at lipid component to therapeutic and/or prophylactic wt:wt ratios between about 5:1 and about 50:1. The lipid solution is rapidly injected using a NanoAssemblr microfluidic based system at flow rates between about 10 ml/min and about 18 ml/min into the therapeutic and/or prophylactic solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kD. The first dialysis is carried out at room temperature for 3 hours. The formulations are then dialyzed overnight at 4° C. The resulting nanoparticle suspension is filtered through 0.2 m sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, may be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a therapeutic and/or prophylactic (e.g., RNA) in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of therapeutic and/or prophylactic in the nanoparticle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, Calif.) can be used to evaluate the encapsulation of an RNA by the nanoparticle composition. The samples are diluted to a concentration of approximately µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2% Triton X-100 solution is added to the wells. The plate is incubated at a temperature of 37° C. for 15 minutes. The RIBOGREEN® reagent is diluted 1:100 in TE buffer, and 100 µL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

C. In Vivo Formulation Studies

In order to monitor how effectively various nanoparticle compositions deliver therapeutic and/or prophylactics to targeted cells, different nanoparticle compositions including a particular therapeutic and/or prophylactic (for example, a modified or naturally occurring RNA such as an mRNA) are prepared and administered to rodent populations. Mice are intravenously, intramuscularly, intraarterially, or intratumorally administered a single dose including a nanoparticle composition with a formulation such as those provided in Example 3. In some instances, mice may be made to inhale doses. Dose sizes may range from 0.001 mg/kg to 10 mg/kg, where 10 mg/kg describes a dose including 10 mg of a therapeutic and/or prophylactic in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. For nanoparticle compositions including mRNA, time courses of protein expression can also be evaluated. Samples collected from the rodents for evaluation may include blood, sera, and tissue (for example, muscle tissue from the site of an intramuscular injection and internal tissue); sample collection may involve sacrifice of the animals.

Nanoparticle compositions including mRNA are useful in the evaluation of the efficacy and usefulness of various formulations for the delivery of therapeutic and/or prophylactics. Higher levels of protein expression induced by administration of a composition including an mRNA will be indicative of higher mRNA translation and/or nanoparticle composition mRNA delivery efficiencies. As the non-RNA components are not thought to affect translational machineries themselves, a higher level of protein expression is likely indicative of a higher efficiency of delivery of the therapeutic and/or prophylactic by a given nanoparticle composition relative to other nanoparticle compositions or the absence thereof.

Example 3: Sample Formulations

Nanoparticle compositions including a therapeutic and/or prophylactic can be optimized according to the selection of a compound according to Formula (I), (IA), (II), (IIa), (IIb), (IIc), (IId) or (IIe), the selection of additional lipids, the amount of each lipid in the lipid component, and the wt:wt ratio of the lipid component to the therapeutic and/or prophylactic, as described herein.

Initial studies were performed to compare the delivery efficiency of nanoparticle compositions including various compounds according to Formula (I), (IA), (II), (IIa), (IIb), (IIc), (IId) or (IIe). The cationic lipid MC3 is a current standard in the art. Accordingly, the standard MC3 formulation including about 50 mol % MC3, about 10 mol % DSPC, about 38.5 mol % cholesterol, and about 1.5 mol % PEG-DMG was used as a basis for this study. Nanoparticle compositions including DSPC as a phospholipid, cholesterol as a structural lipid, PEG-DMG as a PEG lipid, an RNA, and a compound according to Formula (I), (IA), (II), (IIa), (IIb), (IIc), (IId) or (IIe) selected from Compounds 1-159, 168-170, and 173-175 were prepared according to or via methods similar to those described in Examples 1 and 2. The ratios of the lipids were 50:10:38.5:1.5 mol % for the lipid according to Formula (I), (IA), (II), (IIa), (IIb), (IIc), (IId) or (IIe): DSPC:cholesterol:PEG-DMG. The RNA used was an mRNA encoding G5 luciferase (Luc) or G5 hEPO. Tables 1A-1B summarize the content and characteristics of the formulations.

As shown in Tables 1A-1B, the choice of compound according to Formula (I), (IA), (II), (IIa), (IIb), (IIc), (IId) or (IIe) dramatically affects the size (e.g., diameter), polydispersity index, and encapsulation efficiency (EE) of the compositions. Compositions had sizes between approximately 53 nm and 237 nm. Compositions including Compounds 5, 35, 36, 51, 59, 131, 132, 137-139, 145, 148, 155 and 158 produced the largest particles, while compositions including Compounds 9, 21, 29, 30, 65, 7175, 94, 107, 114-116, 119, 124, 133, 149, 150, 152, 174 and 175produced the smallest particles. Polydispersity indices varied between 0.04 and 0.99, while encapsulation efficiencies exceeded 75% for compositions including every tested compound except for Compounds 21, 94107, 132, 148, 155 and 158. The highest encapsulation efficiencies were observed for Compounds 1, 6, 18, 19, 24, 26, 28, 29, 49, 50, 55, 60, 61, 65-70, 72, 74, 75, 101, 109-116, 118, 119, 121, 122, 124, 126, 128, 130, 149, 152, 153, 156, 159, 169, 170 and 174.

TABLE 1A

Characteristics of nanoparticle compositions including compounds according to Formula (I), (IA), (II), (IIa), (IIb), IIc), (IId) or (IIe).

| Compound | Size (nm) | PDI | EE (%) | pKa |
|---|---|---|---|---|
| 1 | 72.7 | 0.091 | 97.04 | 6.50 |
| 2 | 83.9 | 0.14 | 93.88 | 6.73 |
| 3 | 97.5 | 0.20 | 92.25 | 6.72 |
| 4 | 120.5 | 0.21 | 95.10 | 6.33 |
| 5 | 196.4 | 0.21 | 77.07 | 6.84 |
| 6 | 73.1 | 0.066 | 97.60 | 6.32 |
| 7 | 118.9 | 0.22 | 86.10 | 6.75 |
| 8 | 121.0 | 0.15 | 95.8 | 6.64 |
| 9 | 68.5 | 0.12 | 75.7 | 4.87 |
| 10 | 102.9 | 0.18 | 89.60 | 6.09 |
| 11 | 129.6 | 0.13 | 92.47 | 5.97 |
| 12 | 116.7 | 0.17 | 92.44 | 5.99 |
| 13 | 79.4 | 0.13 | 92.28 | 5.67 |
| 14 | 130.1 | 0.15 | 95.24 | 6.58 |
| 15 | 111.1 | 0.094 | 92.47 | 5.58 |
| 16 | 119.0 | 0.16 | 91.32 | 5.52 |
| 17 | 85.2 | 0.24 | 91.84 | 7.76 |
| 18 | 86.2 | 0.042 | 97.50 | 6.56 |
| 19 | 101.1 | 0.17 | 97.21 | 6.78 |
| 20 | 111.5 | 0.13 | 96.72 | 6.87 |
| 21 | 53.5 | n.d. | −15.1 | n.d. |
| 22 | 80.2 | 0.22 | 96.00 | 6.21 |
| 23 | 104.5 | 0.09 | 92.68 | 6.84 |
| 24 | 99.5 | 0.13 | 97.16 | 6.71 |
| 25 | 85.8 | 0.10 | 95.80 | 6.68 |
| 26 | 91.9 | 0.16 | 97.43 | 6.64 |
| 27 | 82.3 | 0.18 | 94.27 | 6.78 |
| 28 | 99.4 | 0.20 | 97.03 | 6.04 |
| 29 | 66.8 | 0.11 | 96.99 | 6.00 |
| 30 | 59.4 | 0.15 | 95.69 | 6.75 |
| 31 | 73.9 | 0.15 | 95.11 | 6.64 |
| 32 | 105.6 | 0.18 | 94.87 | 6.75 |
| 33 | 107.3 | 0.13 | 95.66 | 6.80 |
| 34 | 133.8 | 0.14 | 92.52 | 6.64 |
| 35 | 151.1 | 0.18 | 90.82 | 6.85 |
| 36 | 163.5 | 0.17 | 81.45 | 7.38 |
| 47 | 80.6 | 0.10 | 96.40 | n.d. |
| 48 | 82.3 | 0.092 | 96.55 | 6.68 |
| 49 | 73.1 | 0.110 | 96.86 | 6.52 |
| 50 | 68.4 | 0.100 | 97.33 | 6.42 |
| 51 | 148.8 | 0.17 | 89.83 | n.d. |
| 52 | 130.5 | 0.19 | 93.25 | n.d. |
| 53 | 125.4 | 0.13 | 95.8 | n.d. |
| 54 | 112.9 | 0.19 | 96.71 | 6.51 |
| 55 | 91.6 | 0.16 | 97.03 | 6.44 |
| 56 | 112.1 | 0.17 | 95.18 | n.d. |
| 57 | 128.4 | 0.16 | 94.33 | n.d. |
| 58 | 130.8 | 0.14 | 92.54 | n.d. |
| 59 | 237.0 | 0.24 | 94.44 | n.d. |
| 60 | 95.1 | 0.12 | 97.6 | 6.73 |
| 61 | 89.1 | 0.11 | 97.2 | 6.70 |
| 65 | 63.9 | 0.12 | 98.2 | 6.36 |
| 66 | 76.7 | 0.120 | 96.52 | 76.7 |
| 67 | 77 | 0.13 | 98 | 6.38 |
| 68 | 76.8 | 0.14 | 97.7 | 6.69 |
| 69 | 77.2 | 0.13 | 98.4 | 6.92 |
| 70 | 73.7 | 0.15 | 97.5 | 6.51 |
| 71 | 60.1 | 0.11 | 96.1 | 5.88 |
| 72 | 65.4 | 0.11 | 97.3 | 6.29 |
| 73 | 59.2 | 0.13 | 95.7 | 5.95 |
| 74 | 65.6 | 0.15 | 97 | 6.08 |
| 75 | 64.2 | 0.10 | 98.1 | 6.67 |
| 79 | 93.7 | 0.18 | 89.1 | 7.53 |
| 80 | 118 | 0.19 | 90.7 | 7.52 |
| 81 | 99.2 | 0.14 | 95.4 | 7.14 |
| 94 | 62.4 | 0.24 | 0 | 4.43 |
| 96 | 120.5 | 0.160 | 79.04 | 6.600 |
| 101 | 91.7 | 0.230 | 98.96 | 7.27 |
| 103 | 78.8 | 0.160 | 90.77 | 6.13 |
| 107 | 55 | 0.74 | 0 | 4.802 |
| 108 | 119 | 0.14 | 96 | 7.17 |
| 109 | 81.1 | 0.13 | 98.6 | 6.78 |
| 110 | 118 | 0.13 | 97.4 | 8.03 |
| 111 | 79.3 | 0.14 | 98.2 | 7.13 |
| 112 | 85.7 | 0.12 | 99 | 7.78 |
| 113 | 69.2 | 0.15 | 99 | 6.93 |
| 114 | 65.1 | 0.11 | 98.8 | 6.42 |
| 115 | 64.5 | 0.11 | 99.7 | n.d. |
| 116 | 63.3 | 0.14 | 99.4 | 5.66 |
| 118 | 72.1 | 0.08 | 98 | 6.14 |
| 119 | 60.8 | 0.24 | 98.1 | 5.29 |
| 121 | 98.4 | 0.18 | 100 | 8.50 |
| 122 | 69.3 | 0.09 | 98.2 | 6.83 |
| 123 | 81.6 | 0.23 | 94.4 | 6.27 |
| 124 | 61.3 | 0.1 | 97.7 | 5.89 |
| 125 | 90.9 | 0.16 | 79.6 | n.d. |
| 126 | 77.4 | 0.18 | 96.8 | 6.00 |
| 127 | 110.4 | 0.19 | 89.5 | 6.98 |
| 128 | 69.4 | 0.14 | 98.2 | 6.56 |
| 129 | 86.3 | 0.19 | 77.2 | 7.3 |
| 130 | 107.1 | 0.13 | 97 | 6.83 |
| 131 | 167.9 | 0.095 | 75.44 | 7.76 |
| 132 | 298.0 | 0.180 | 30.77 | 7.34 |
| 133 | 66.0 | 0.098 | 91.48 | 6.38 |
| 134 | 85.6 | 0.110 | 94.62 | 6.66 |
| 135 | 89.5 | 0.130 | 90.20 | 6.47 |
| 136 | 140.4 | 0.5 | 90.9 | 6.95 |
| 137 | 184.4 | <1 | 85.7 | 7.06 |
| 138 | 179.4 | <0.5 | 91.8 | 7.39 |
| 139 | 174.0 | 0.54 | 78.2 | 7.04 |
| 140 | 120.3 | 0.84 | 89.2 | 7.71 |
| 141 | 91.3 | 0.99 | 94.1 | 7.47 |
| 143 | 93.3 | 0.19 | 96.4 | 6.47 |
| 144 | 135.9 | 0.22 | 90.3 | 7.09 |
| 145 | 176.5 | 0.140 | 89.15 | 7.25 |
| 146 | 97.0 | 0.210 | 91.94 | 7.78 |
| 147 | 99.5 | 0.130 | 88.31 | 6.66 |
| 148 | 192.7 | 0.200 | 25.49 | 6.646 |
| 149 | 62.1 | 0.110 | 98.00 | 6.284 |
| 150 | 63.1 | 0.082 | 96.72 | 6.101 |
| 151 | 105.7 | 0.140 | 87.86 | 6.593 |
| 152 | 62.6 | 0.072 | 99.29 | 6.465 |
| 153 | 83.7 | 0.150 | 98.39 | 6.580 |
| 154 | 92.9 | 0.110 | 94.28 | 6.827 |
| 155 | 208.3 | 0.240 | 37.36 | 6.576 |
| 156 | 74.3 | 0.072 | 98.90 | 6.572 |
| 157 | 69.6 | 0.096 | 96.43 | 6.275 |
| 158 | 251.8 | 0.080 | 35.70 | 6.953 |
| 159 | 75.9 | 0.190 | 99.29 | 7.873 |
| 168 | 80.7 | 0.1 | 94.35 | n.d. |
| 169 | 75.4 | 0.18 | 99.04 | n.d. |
| 170 | 71.7 | 0.12 | 98.24 | n.d. |
| 173 | 75.5 | 0.16 | 92.89 | n.d. |
| 174 | 61.4 | 0.12 | 98.52 | n.d. |
| 175 | 65.4 | 0.2 | 93.23 | n.d. |
| MC3 | 79.7 | 0.11 | 97.3 | n.d. | n.d. = not determined

TABLE 1B

Characteristics of nanoparticle compositions including compounds according to Formula (I), (IA), (II), (IIa), (IIb), (IIc), (IId) or (IIe).

| Compound | Size (nm) | PDI | EE (%) | Endotoxin (EU/mL) | Apparent pKa |
|---|---|---|---|---|---|
| 18[#] | 73.7 | 0.14 | 96.95 | <1 | 6.56 |
| 25[#] | 69.7 | 0.14 | 97.92 | 1.8 | 6.68 |
| 30[#] | 76.3 | 0.13 | 96.32 | <1 | 6.75 |
| 108[#] | 89.6 | 0.22 | 95.38 | <1 | 7.17 |
| 109[#] | 75 | 0.099 | 98.29 | <1 | 6.78 |
| 110[#] | 73.3 | 0.24 | 92.39 | <1 | 8.03 |
| 111[#] | 93.3 | 0.13 | 91.23 | 1.4 | 7.13 |
| 112[#] | 60.6 | 0.21 | 96.40 | 1.8 | 7.78 |
| 60[#] | 88.9 | 0.15 | 95.20 | <1 | 6.73 |
| 122[#] | 70.2 | 0.12 | 96.27 | 1.2 | 6.83 |
| MC3[#] | 57.7 | 0.12 | 99.01 | <1 | 6.35 |

[#] = Formulated with hEPO mRNA

Example 4: Expression of Luc Induced by Sample Formulations

The efficacy of the nanoparticle compositions presented in Table 1A was evaluated with a bioluminescence study. Formulations were administered intravenously to mice (n=6) at a dosage of 0.5 mg/kg (mpk) and bioluminescence measured at 3, 6, and 24 hour time points. The standard MC3 formulation and, in some instances, a control (e.g., a PBS control) were evaluated for comparison. As is evident in Table 2, at 3 hours, the total flux was highest for compositions including Compounds 4, 28, 32, 48, 66, 128 and 135 and the total flux at 3 h was higher than or comparable to that of MC3 formulations for Compounds 2, 3, 18, 19, 20, 24, 26, 25, 27, 31, 33, 47, 49, 50, 53-55, 60, 61, 65-68, 70, 72, 74, 75, 96, 111, 122, 130, 133, 134, 143, 147, 148, 150, 151 and 153. These compositions also demonstrated higher total flux at 6 and 24 hour time points. Compositions including Compounds 9, 17, 57, 58, 59, 121, 125, 137, 140, 141 and 158 had significantly lower flux at all time points measured. In general, flux decreased as time progressed to less than 10% of the initial flux. These results suggest that the compounds described herein may be useful in transfection applications.

TABLE 2

Expression of luciferase induced by administration of nanoparticle compositions including compounds according to Formula (I), (IA), (II), (IIa), (IIb), (IIc), (IId) or (IIe).

| | Total Flux | | |
|---|---|---|---|
| Compound | 3 hours | 6 hours | 24 hours |
| 1 | 3.48E+09 | 3.40E+09 | 4.10E+08 |
| 2 | 1.93E+10 | 4.31E+10 | 2.43E+09 |
| 3 | 6.55E+10 | 7.37E+10 | 4.96E+09 |
| 4 | 1.37E+11 | 6.01E+10 | 1.13E+09 |
| 5 | 2.77E+08 | 1.76E+08 | 2.40E+07 |
| 6 | 5.38E+09 | 7.60E+09 | 7.69E+08 |
| 7 | 4.13E+10 | 4.03E+10 | 1.68E+09 |
| 8 | 7.43E+10 | 6.71E+10 | 7.84E+09 |
| 9 | 1.43E+08 | 3.46E+06 | 1.01E+06 |
| 10 | 6.03E+08 | 2.37E+09 | 4.04E+07 |
| 11 | 3.38E+09 | 7.11E+09 | 1.15E+08 |
| 12 | 5.14E+09 | 1.27E+10 | 2.45E+08 |
| 13 | 1.02E+08 | 1.56E+08 | 1.47E+06 |
| 14 | 4.43E+08 | 2.29E+09 | 1.39E+08 |
| 15 | 4.31E+08 | 4.41E+07 | 2.05E+06 |
| 16 | 2.58E+08 | 5.45E+08 | 2.37E+07 |
| 17 | 7.72E+06 | 3.58E+06 | 6.79E+05 |

TABLE 2-continued

Expression of luciferase induced by administration of nanoparticle compositions including compounds according to Formula (I), (IA), (II), (IIa), (IIb), (IIc), (IId) or (IIe).

| | Total Flux | | |
|---|---|---|---|
| Compound | 3 hours | 6 hours | 24 hours |
| 18 | 1.71E+10 | 2.13E+10 | 2.51E+09 |
| 19 | 3.38E+10 | 3.56E+09 | 4.68E+08 |
| 20 | 1.71E+10 | 2.48E+10 | 5.40E+08 |
| 22 | 6.57E+08 | 3.89E+08 | 2.73E+07 |
| 23 | 1.83E+10 | 1.15E+09 | 3.71E+08 |
| 24 | 1.72E+10 | 2.25E+10 | 1.83E+09 |
| 25 | 2.27E+10 | 1.59E+10 | 9.77E+08 |
| 26 | 6.75E+10 | 1.57E+10 | 1.54E+09 |
| 27 | 1.64E+10 | 1.03E+10 | 1.94E+09 |
| 28 | 8.98E+10 | 1.13E+11 | 1.20E+09 |
| 29 | 4.61E+09 | 2.89E+09 | 3.55E+08 |
| 30 | 1.19E+10 | 2.09E+10 | 1.21E+09 |
| 31 | 4.19E+10 | 5.31E+10 | 1.68E+09 |
| 32 | 8.65E+10 | 6.08E+10 | 1.92E+09 |
| 33 | 6.53E+10 | 1.20E+11 | 3.71E+09 |
| 34 | 1.06E+10 | 1.48E+10 | 6.69E+08 |
| 35 | 9.82E+08 | 1.24E+09 | 5.09E+07 |
| 36 | 6.97E+07 | 1.72E+08 | 4.44E+05 |
| 47 | 6.55E+10 | 5.38E+10 | 2.09E+09 |
| 48 | 8.73E+10 | 1.10E+11 | 2.92E+09 |
| 49 | 4.48E+10 | 1.08E+11 | 1.24E+09 |
| 50 | 3.81E+10 | 7.49E+10 | 5.02E+08 |
| 51 | 1.34E+08 | 2.80E+08 | 6.20E+06 |
| 52 | 2.91E+09 | 4.63E+09 | 2.55E+07 |
| 53 | 1.91E+10 | 2.32E+10 | 1.01E+09 |
| 54 | 5.36E+10 | 4.18E+10 | 9.07E+08 |
| 55 | 5.07E+10 | 1.68E+10 | 4.06E+08 |
| 56 | 1.27E+10 | 8.06E+09 | 2.53E+08 |
| 57 | 6.69E+06 | 6.21E+06 | 4.16E+05 |
| 58 | 5.69E+05 | 7.60E+05 | 3.64E+05 |
| 59 | 2.75E+05 | 2.79E+05 | 1.45E+05 |
| 60 | 7.91E+10 | 9.04E+10 | 2.90E+09 |
| 61 | 6.54E+10 | 6.20E+10 | 1.78E+09 |
| 65 | 6.56E+10 | 7.01E+10 | 7.50E+08 |
| 66 | 9.66E+10 | 4.577E+10 | 5.56E+09 |
| 67 | 4.24E+10 | 4.62E+10 | 4.51E+08 |
| 68 | 5.22E+10 | 8.16E+10 | 2.15E+09 |
| 69 | 3.38E+09 | 7.95E+09 | 1.15E+08 |
| 70 | 4.70E+10 | 2.49E+10 | 9.27E+08 |
| 71 | 4.09E+09 | 9.28E+09 | 6.51E+07 |
| 72 | 1.73E+10 | 4.07E+10 | 7.12E+08 |
| 73 | 8.10E+09 | 1.07E+10 | 1.27E+08 |
| 74 | 3.27E+10 | 2.23E+10 | 2.75E+08 |
| 75 | 3.51E+10 | 8.80E+10 | 2.13E+09 |
| 79 | 3.23E+08 | 5.27E+08 | 3.08E+07 |
| 80 | 2.76E+08 | 3.26E+08 | 1.54E+07 |
| 81 | 7.87E+09 | 9.96E+09 | 5.13E+08 |
| 96 | 4.54E+10 | 1.05E+11 | 3.86E+09 |
| 101 | 1.89E+08 | 1.41E+08 | 3.64E+06 |
| 103 | 2.68E+09 | 1.82E+09 | 9.45E+07 |
| 108 | 5.04E+09 | 5.53E+09 | 1.50E+08 |
| 109 | 3.82E+09 | 4.88E+09 | 8.06E+07 |
| 110 | 1.89E+09 | 2.57E+09 | 1.11E+08 |
| 111 | 1.89E+10 | 3.57E+10 | 8.86E+08 |
| 112 | 9.69E+08 | 1.04E+09 | 2.75E+07 |
| 113 | 5.16E+09 | 8.09E+09 | 1.30E+08 |
| 114 | 8.41E+07 | 5.98E+07 | n.d. |
| 115 | 2.13E+07 | 2.91E+07 | n.d. |
| 116 | 3.13E+07 | 3.86E+07 | n.d. |
| 118 | 1.46E+09 | 1.16E+09 | 4.37E+07 |
| 119 | 1.02E+07 | 3.74E+07 | n.d. |
| 121 | 1.29E+06 | 1.36E+06 | n.d. |
| 122 | 3.64E+10 | 8.64E+10 | 1.95E+09 |
| 123 | 4.06E+09 | 1.81E+10 | 5.18E+08 |
| 124 | 6.62E+07 | 3.91E+09 | 5.13E+06 |
| 125 | 2.44E+05 | 3.16E+05 | n.d. |
| 126 | 7.59E+09 | 1.09E+10 | 1.40E+08 |
| 127 | 3.81E+09 | 2.09E+09 | 4.56E+08 |
| 128 | 1.04E+11 | 8.99E+10 | 1.00E+09 |
| 129 | 5.97E+09 | 4.51E+09 | 2.22E+08 |
| 130 | 6.26E+10 | 8.92E+10 | 1.08E+09 |
| 131 | 6.97E+09 | 7.64E+09 | 2.47E+08 |

TABLE 2-continued

Expression of luciferase induced by administration of nanoparticle compositions including compounds according to Formula (I), (IA), (II), (IIa), (IIb), (IIc), (IId) or (IIe).

| Compound | Total Flux | | |
|---|---|---|---|
| | 3 hours | 6 hours | 24 hours |
| 132 | 1.77E+09 | 1.36E+09 | 5.31E+07 |
| 133 | 3.32E+10 | 2.93E+10 | 4.74E+08 |
| 134 | 2.01E+10 | 2.91E+10 | 8.00E+08 |
| 135 | 1.24E+11 | 9.90E+10 | 2.51E+09 |
| 136 | 7.21E+08 | 7.33E+08 | 3.39E+07 |
| 137 | 3.77E+05 | 5.02E+05 | 4.49E+05 |
| 138 | 2.97E+07 | 2.30E+07 | 1.63E+06 |
| 139 | 3.50E+07 | 1.17E+07 | 5.89E+05 |
| 140 | 3.74E+06 | 1.70E+06 | 5.67E+05 |
| 141 | 2.16E+.06 | 1.21E+06 | 3.49E+05 |
| 143 | 1.76E+10 | 2.03E+10 | 2.47E+08 |
| 144 | 9.50E+09 | 1.82E+09 | 3.36E+08 |
| 145 | 7.11E+09 | 6.50E+09 | 2.38E+08 |
| 146 | 9.48E+07 | 8.39E+07 | 2.30E+06 |
| 147 | 3.24E+10 | 4.87E+10 | 3.32E+08 |
| 148 | 6.28E+10 | 3.71E+10 | 1.43E+09 |
| 149 | 1.01E+10 | 8.33E+09 | 3.45E+08 |
| 150 | 1.66E+10 | 2.31E+10 | 3.86E+08 |
| 151 | 5.63E+10 | 5.68E+10 | 2.23E+09 |
| 152 | 1.56E+09 | 2.45E+09 | 4.95E+07 |
| 153 | 1.69E+10 | 2.28E+10 | 5.10E+08 |
| 154 | 2.49E+09 | 4.89E+09 | 6.26E+07 |
| 155 | 2.49E+09 | 1.15E+10 | 1.99E+08 |
| 156 | 5.68E+09 | 1.03E+10 | 6.53E+07 |
| 157 | 8.54E+09 | 2.22E+10 | 1.90E+08 |
| 158 | 2.69E+05 | 9.82E+05 | 1.55E+05 |
| 159 | 3.32E+06 | 1.20E+07 | 4.98E+05 |
| MC3 | 1.58E+10 | 2.12E+10 | 7.19E+08 | n.d. = not determined

Figure 8:
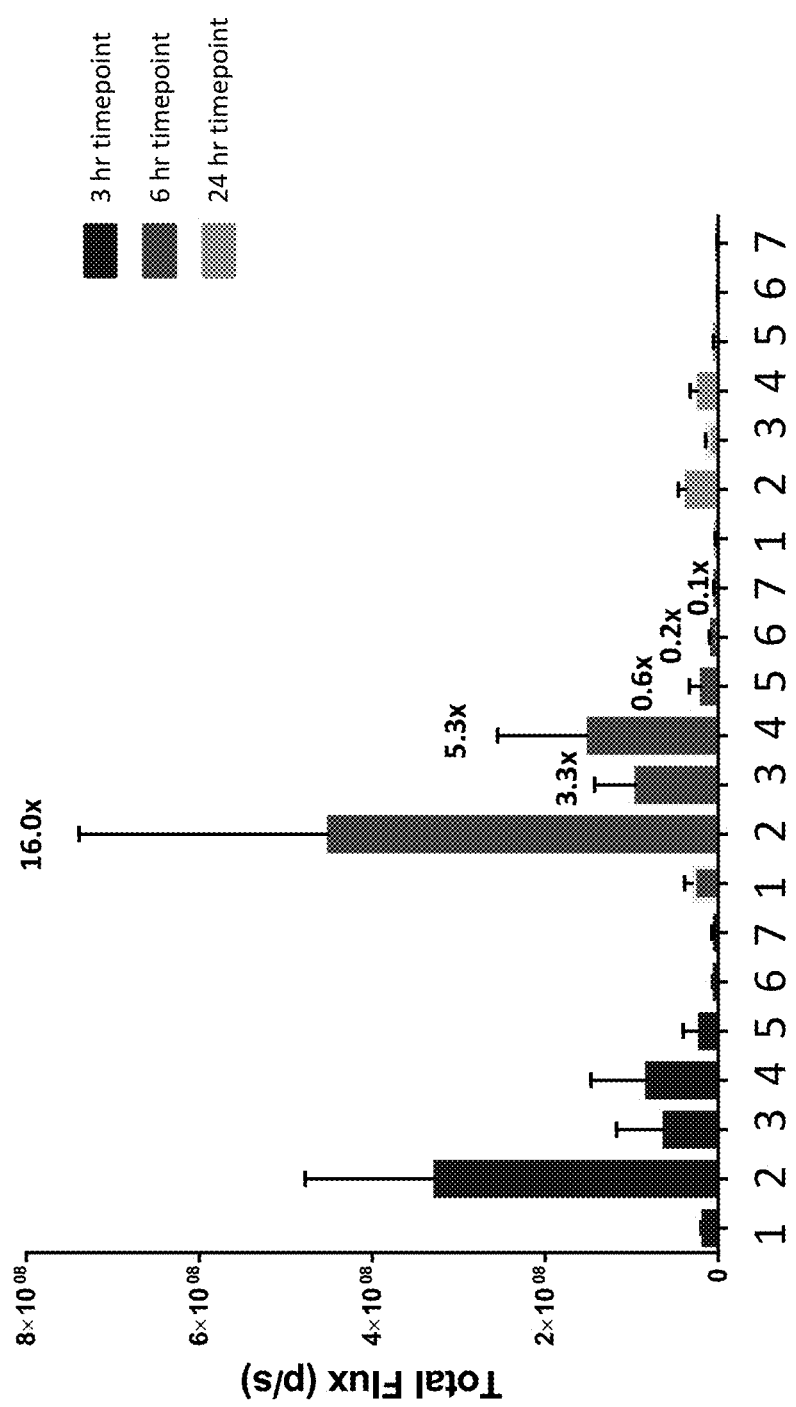
FIG. 8 shows the results of luciferase expression measured upon intramuscular administration of various nanoparticle compositions including MC3, Compounds 168-170, and 173-175 to mice at 0.01 mpk at various time points: 3 hr (left block), 6 hr (middle block) and 24 hr (right block). The numbers 1-7 in this figure correspond to MC3, Compounds 168-170, and 173-175 respectively.

The total flux (measured by area under the curve, AUC) induced by administration of a formulation including a given lipid relative to that induced by administration of a formulation including MC3 was also measured for several lipids. As shown in Table 3A (i.v. administration), the flux induced by formulations including Compounds 48 and 49 measured at 6 h was ten times higher than that induced by the MC3 formulation. Formulations including Compounds 50, 54, and 55 also demonstrated higher flux than MC3 formulations. As shown in Table 3B, the flux induced by formulations including Compounds 108 and 168 measured at 6 h was fourteen and sixteen times higher than that induced by the MC3 formulation via intramuscular administration (i.m.). Results are also shown in FIG. 8. As shown in Table 3C (i.v. administration), the flux induced by formulations including Compounds 66, 133-135, and 147 measured at 6 h and the total flux were noticeably higher than those induced by the MC3 formulation. As shown in Table 3D, the total flux induced by formulations including Compounds 96, 148, and 151 measured at 6 h was noticeably higher than that induced by the MC3 formulation.

TABLE 3A

Expression of luciferase upon administration of formulations including compounds according to Formula (I), (IA), (II), (IIa), (IIb), (IIc), (IId) or (IIe) relative to administration of formulations including MC3.

| Compound | Fold increase in total body Luc Flux relative to MC3 at 6 h |
|---|---|
| 1 | 0.40 |
| 2 | 1.31 |
| 3 | 2.24 |
| 4 | 1.31 |
| 5 | 0.005 |
| 6 | 1.15 |
| 16 | 0.02 |
| 18 | 3.22 |
| 19 | 0.96 |
| 20 | 0.80 |
| 24 | 2.67 |
| 25 | 1.89 |
| 26 | 4.24 |
| 27 | 0.31 |
| 28 | 2.46 |
| 29 | 0.78 |
| 30 | 2.49 |
| 31 | 1.21 |
| 32 | 1.39 |
| 33 | 2.74 |
| 34 | 0.34 |
| 35 | 0.028 |
| 36 | 0.004 |
| 48 | 10.0 |
| 49 | 9.81 |
| 50 | 6.81 |
| 51 | 0.025 |
| 53 | 2.11 |
| 54 | 3.80 |
| 55 | 1.52 |
| 56 | 0.733 |
| 57 | 0.00056 |
| 58 | 0.00007 |
| 59 | 0.00003 |
| 65 | 3.16 |
| 66 | 0.103 |
| 67 | 2.08 |
| 68 | 3.68 |
| 71 | 0.418 |
| 73 | 0.48 |
| 74 | 1.005 |
| 127 | 0.094 |
| 128 | 4.05 |
| 129 | 0.203 |
| 130 | 4.02 |
| MC3 | 1.00 |

TABLE 3B

Expression of luciferase upon administration of formulations including compounds according to Formula (I), (IA), (II), (IIa), (IIb), (IIc), (IId) or (IIe) relative to administration of formulations including MC3.

| Compound | i.v. Lipid/MC3 0.5 mpk, Luc, 6 h | i.m. Lipid/MC3 0.01 mpk, Luc, 6h |
|---|---|---|
| 108 | 0.4 | 14.2 |
| 109 | 0.3 | 3.6 |
| 111 | 2.6 | 4.9 |
| 168 | ND | 16.0 |
| 169 | ND | 3.3 |
| 170 | ND | 5.3 |
| 173 | ND | 0.6 |
| 174 | ND | 0.2 |
| 175 | ND | 0.1 |

ND = not determined

TABLE 3C

Expression of luciferase upon administration of formulations including compounds according to Formula (I), (IA), (II), (IIa), (IIb), (IIc), (IId) or (IIe) relative to administration of formulations including MC3.

| Compound | 6 h Lipid/MC3 Avg. Luc Expression | 6 h Lipid/MC3 G.M. Luc Expression | AUC (h * p/s) | Fold increase AUC Lipid/lVIC3 |
|---|---|---|---|---|
| 66 | 6.28 | 5.23 | 6.76E+11 | 8.20 |
| 101 | 0.019 | 0.011 | 1.8E+09 | 0.022 |
| 103 | 0.250 | 0.171 | 2.4E+10 | 0.291 |
| 131 | 1.05 | 1.27 | 9.29E+10 | 1.13 |
| 132 | 0.187 | 0.112 | 1.75E+10 | 0.212 |
| 133 | 4.02 | 4.18 | 3.62E+11 | 4.39 |
| 134 | 3.99 | 3.27 | 3.43E+11 | 4.16 |
| 135 | 13.6 | 10.5 | 1.25E+12 | 15.2 |
| 145 | 0.89 | 0.979 | 8.1E+10 | 0.983 |
| 146 | 0.011 | 0.012 | 1.04E+09 | 0.013 |
| 147 | 6.68 | 8.13 | 5.63E+11 | 6.83 |
| MC3 | 1 | 1 | 8.24E+10 | 1 |

Avg. = average;
G.M. = geometric mean

TABLE 3D

Expression of luciferase and lipid clearance upon administration of formulations including compounds according to Formula (I), (IA), (II), (IIa), (IIb), (IIc), (IId) or (IIe) relative to administration of formulations including MC3.

| Lipid | AUC (p/s * h) | Lipid/MC3 AUC | % Dose Remaining in Liver 6 h | % Dose Remaining in Liver 6 h |
|---|---|---|---|---|
| 148 | 4.965E+011 | 2.6 | <1 | <1 |
| 149 | 1.057E+011 | 0.55 | | |
| 150 | 2.704E+011 | 1.4 | <1 | <1 |
| 96 | 1.209E+012 | 6.3 | <1 | <1 |
| 151 | 7.010E+011 | 3.7 | <1 | <1 |
| 152 | 2.855E+010 | 0.15 | | |
| 153 | 2.697E+011 | 1.4 | <1 | <1 |
| 154 | 5.560E+010 | 0.29 | | |
| 155 | 1.266E+011 | 0.66 | | |
| 156 | 1.170E+011 | 0.61 | | |
| 157 | 2.481E+011 | 1.3 | <1 | <1 |
| 158 | 1.211E+007 | <0.01 | | |
| 159 | 1.355E+008 | <0.01 | | |
| MC3 | 1.909E+011 | 1 | 80 | 54 |

Example 5: Expression of Luc Induced by Sample Formulations in Different Organs The efficacy of the nanoparticle compositions presented in Table 1A was further evaluated by measuring the expression of modified luciferase in the liver, lung, spleen, and femur upon administration of a given composition. Formulations were administered intravenously to mice (n=3) at a dosage of 0.5 mpk and bioluminescence measured after 6 hours. The standard MC3 formulation and a PBS control were also tested. As is evident in Table 4, flux for nearly all species was higher in the liver compared to other tissues. Flux in the liver was highest for compositions including 3, 28, 33, 48, 96 and 135 and comparable to that of MC3 formulations for compositions including Compounds 2, 4, 6, 7, 18, 20, 24-27, 30-32, 34, 47, 49, 50, 53-56, 60, 65, 67, 68, 74, 75, 111, 113, 122, 128, 130, 133, 134, 143, 147-151, 153 and 157. Flux in the liver was lowest for compositions including Compounds 58, 59, 137, and 141. Flux in the spleen was highest for compositions including Compounds 4, 7, 33, 34, 48, 53, 108, 129, 130, and 148, and lowest for compositions including Compounds 9, 59, 124, and 141. Similar results were observed in the lung and femur.

TABLE 4

Expression of luciferase in various organs 6 hours after administration of nanoparticle compositions including compounds according to Formula (I), (IA), (II), (IIa), (IIb), (IIc), (IId) or (IIe).

| | Total Flux | | | |
|---|---|---|---|---|
| Compound | Liver | Lung | Spleen | Femur |
| 1 | 4.02E+08 | 1.72E+06 | 4.27E+06 | 7.52E+05 |
| 2 | 4.87E+09 | 2.52E+07 | 5.77E+07 | 3.86E+06 |
| 3 | 1.39E+10 | 4.76E+07 | 1.47E+08 | 7.36E+06 |
| 4 | 5.26E+09 | 6.22E+07 | 4.09E+08 | n.d. |
| 5 | 5.84E+07 | 1.89E+06 | 1.55E+08 | 1.22E+06 |
| 6 | 1.09E+09 | 4.30E+06 | 3.03E+07 | 2.15E+06 |
| 7 | 2.49E+09 | 3.95E+07 | 4.83E+08 | n.d. |
| 8 | 7.87E+08 | 4.06E+06 | 1.51E+08 | n.d. |
| 9 | 4.30E+05 | 2.56E+04 | 5.51E+04 | 2.57E+04 |
| 10 | 3.22E+08 | 8.85E+05 | 8.17E+06 | 5.09E+05 |
| 11 | 8.03E+08 | 1.35E+07 | 1.04E+08 | n.d. |
| 12 | 6.84E+08 | 7.45E+06 | 6.82E+07 | |
| 13 | 2.25E+07 | 2.21E+05 | 7.09E+05 | 1.35E+05 |
| 14 | 1.91E+08 | 4.74E+06 | 1.92E+08 | 4.91E+06 |
| 15 | 6.23E+06 | 6.41E+04 | 9.01E+05 | 5.93E+04 |
| 16 | 3.17E+07 | 4.18E+05 | 5.43E+06 | 2.55E+05 |
| 17 | 5.52E+05 | 9.95E+04 | 5.58E+06 | 9.55E+04 |
| 18 | 2.76E+09 | 1.25E+07 | 5.15E+07 | 4.68E+06 |
| 19 | 6.33E+08 | 5.99E+06 | 1.77E+07 | 1.68E+06 |
| 20 | 1.84E+09 | 2.66E+07 | 1.43E+08 | 1.31E+07 |
| 22 | 4.00E+07 | 4.73E+05 | 1.57E+06 | 1.16E+05 |
| 23 | 2.92E+08 | 1.82E+06 | 3.08E+07 | 1.19E+06 |
| 24 | 4.19E+09 | 1.71E+07 | 8.78E+07 | 4.54E+06 |
| 25 | 2.41E+09 | 1.51E+07 | 3.11E+07 | 4.40E+06 |
| 26 | 2.90E+09 | 1.18E+07 | 1.56E+07 | 4.67E+06 |
| 27 | 2.16E+09 | 6.35E+06 | 3.78E+06 | 2.00E+06 |
| 28 | 1.22E+10 | 2.17E+08 | 1.80E+08 | n.d. |
| 29 | 5.20E+08 | 9.83E+05 | 5.99E+06 | 9.56E+05 |
| 30 | 2.68E+09 | 1.02E+07 | 3.55E+07 | 6.38E+06 |
| 31 | 5.17E+09 | 7.55E+06 | 9.42E+07 | n.d. |
| 32 | 8.52E+09 | 1.16E+07 | 1.70E+08 | n.d. |
| 33 | 1.78E+10 | 2.92E+07 | 3.77E+08 | n.d. |
| 34 | 2.08E+09 | 9.49E+06 | 2.40E+08 | n.d. |
| 35 | 1.63E+08 | 2.06E+06 | 1.23E+08 | n.d. |
| 36 | 2.65E+07 | 5.82E+05 | 6.14E+07 | n.d. |
| 47 | 4.86E+09 | 8.71E+06 | 8.33E+07 | n.d. |
| 48 | 1.08E+10 | 3.31E+07 | 3.49E+08 | n.d. |
| 49 | 5.68E+09 | 2.52E+07 | 1.87E+08 | n.d. |
| 50 | 6.30E+09 | 2.81E+07 | 1.14E+08 | n.d. |
| 51 | 2.49E+07 | 3.67E+05 | 2.80E+07 | n.d. |
| 52 | 5.86E+08 | 2.80E+06 | 8.30E+07 | n.d. |
| 53 | 2.02E+09 | 2.47E+07 | 8.54E+08 | n.d. |
| 54 | 5.57E+09 | 1.12E+07 | 1.64E+08 | n.d. |
| 55 | 1.92E+09 | 7.02E+06 | 2.63E+07 | n.d. |
| 56 | 1.04E+09 | 4.62E+06 | 1.98E+08 | n.d. |
| 57 | 9.36E+05 | 3.18E+04 | 2.47E+06 | n.d. |
| 58 | 8.71E+04 | 1.21E+04 | 2.38E+05 | n.d. |
| 59 | 2.87E+05 | 4.41E+04 | 9.68E+04 | n.d. |
| 60 | 1.54E+09 | 6.25E+06 | 7.12E+06 | n.d. |
| 61 | 6.37E+08 | 3.56E+06 | 1.61E+07 | n.d. |
| 65 | 9.56E+09 | 3.79E+07 | 6.57E+07 | n.d. |
| 66 | 5.01E+09 | 4.20E+06 | 2.00E+07 | n.d. |
| 67 | 3.60E+09 | 1.68E+07 | 2.55E+07 | n.d. |
| 68 | 8.42E+09 | 3.98E+07 | 6.69E+07 | n.d. |
| 69 | 2.24E+08 | 7.34E+05 | 2.54E+06 | n.d. |
| 70 | 8.55E+08 | 6.32E+06 | 2.06E+06 | n.d. |
| 71 | 7.93E+08 | 4.86E+06 | 8.04E+06 | n.d. |
| 72 | 7.97E+08 | 1.05E+07 | 6.40E+06 | n.d. |
| 73 | 7.93E+08 | 6.17E+06 | 9.45E+06 | n.d. |
| 74 | 1.99E+09 | 6.93E+06 | 2.26E+07 | n.d. |
| 75 | 1.45E+09 | 3.92E+06 | 5.66E+06 | n.d. |
| 79 | 3.15E+06 | 6.13E+04 | 6.45E+05 | n.d. |
| 80 | 1.09E+07 | 8.97E+04 | 4.71E+06 | n.d. |
| 81 | 2.74E+08 | 6.23E+06 | 4.49E+07 | n.d. |
| 96 | 1.56E+10 | 3.43E+07 | 3.39E+08 | n.d. |
| 101 | 1.27E+07 | 1.77E+05 | 5.60E+06 | n.d. |
| 103 | 8.48E+07 | 2.06E+05 | 2.65E+06 | n.d. |
| 108 | 4.63E+08 | 9.81E+06 | 7.82E+08 | n.d. |

TABLE 4-continued

Expression of luciferase in various organs 6 hours after administration of nanoparticle compositions including compounds according to Formula (I), (IA), (II), (IIa), (IIb), (IIc), (IId) or (IIe).

| Compound | Total Flux | | | |
|---|---|---|---|---|
| | Liver | Lung | Spleen | Femur |
| 109 | 8.17E+08 | 6.03E+06 | 4.81E+07 | n.d. |
| 110 | 2.30E+08 | 5.76E+06 | 1.41E+08 | n.d. |
| 111 | 4.83E+09 | 2.57E+07 | 2.44E+08 | n.d. |
| 112 | 1.48E+08 | 1.83E+06 | 2.75E+07 | n.d. |
| 113 | 1.11E+09 | 5.55E+06 | 5.22E+07 | n.d. |
| 118 | 1.72E+08 | 1.98E+06 | 2.49E+07 | n.d. |
| 122 | 2.63E+09 | 2.77E+07 | 1.56E+07 | n.d. |
| 123 | 2.50E+08 | 1.78E+06 | 4.04E+06 | n.d. |
| 124 | 8.46E+06 | 5.67E+04 | 8.06E+04 | n.d. |
| 126 | 7.41E+08 | 2.68E+06 | 1.87E+07 | n.d. |
| 127 | 1.94E+08 | 5.26E+06 | 3.21E+08 | n.d. |
| 128 | 5.98E+09 | 2.16E+07 | 7.09E+07 | n.d. |
| 129 | 6.65E+08 | 9.89E+06 | 5.09E+08 | n.d. |
| 130 | 8.17E+09 | 5.88E+07 | 1.35E+09 | n.d. |
| 131 | 3.52E+08 | 1.45E+07 | 8.32E+08 | n.d. |
| 132 | 1.49E+08 | 1.39E+07 | 3.37E+08 | n.d. |
| 133 | 2.94E+09 | 3.18E+06 | 1.77E+07 | n.d. |
| 134 | 1.73E+09 | 2.82E+06 | 1.85E+07 | n.d. |
| 135 | 1.65E+10 | 2.71E+07 | 1.39E+08 | n.d. |
| 136 | 1.34E+08 | 8.91E+05 | 2.77E+07 | 6.60E+05 |
| 137 | 6.48E+04 | 1.66E+04 | 1.32E+05 | 2.02E+04 |
| 138 | 3.66E+06 | 9.47E+04 | 4.04E+06 | 1.58E+05 |
| 139 | 8.27E+05 | 5.26E+04 | 2.10E+06 | 5.12E+04 |
| 140 | 4.21E+05 | 2.14E+04 | 2.22E+05 | 3.26E+04 |
| 141 | 1.59E+05 | 3.85E+04 | 6.29E+04 | 2.86E+04 |
| 143 | 1.76E+09 | 3.60E+07 | 1.42E+08 | n.d. |
| 144 | 3.75E+08 | 4.81E+06 | 5.11E+07 | 2.44E+06 |
| 145 | 5.01E+08 | 1.36E+07 | 4.25E+08 | n.d. |
| 146 | 7.24E+06 | 3.88E+06 | 5.11E+07 | n.d. |
| 147 | 5.24E+08 | 6.73E+06 | 8.57E+07 | n.d. |
| 148 | 4.39E+09 | 3.27E+07 | 2.71E+09 | n.d. |
| 149 | 1.11E+09 | 2.69E+06 | 2.71E+07 | n.d. |
| 150 | 1.54E+09 | 2.20E+06 | 3.43E+07 | n.d. |
| 151 | 4.72E+09 | 9.20E+06 | 9.27E+07 | n.d. |
| 152 | 1.43E+08 | 3.16E+05 | 6.63E+06 | n.d. |
| 153 | 1.18E+09 | 6.42E+06 | 1.42E+08 | n.d. |
| 154 | 3.62E+08 | 2.89E+06 | 1.30E+07 | n.d. |
| 155 | 8.58E+08 | 1.00E+07 | 2.77E+08 | n.d. |
| 156 | 6.51E+08 | 1.92E+06 | 1.82E+07 | n.d. |
| 157 | 2.27E+09 | 6.70E+06 | 5.15E+07 | n.d. |
| 158 | 1.99E+05 | 1.71E+04 | 1.17E+05 | n.d. |
| 159 | 1.13E+06 | 2.17E+05 | 7.24E+05 | n.d. |
| MC3 | 2.57E+09 | 1.27E+07 | 2.85E+07 | 2.56E+06 | n.d.=not determined

Example 6A: Expression Induced by Sample Formulations Upon Intramuscular Administration Sample formulations including both modified luciferase (Luc) mRNA and H10 mRNA were prepared and administered intramuscularly and the resulting expression and immunogenicity were evaluated simultaneously. Formulations including compounds according to Formula (I), (IA), (II), (IIa), (IIb), (IIc), (IId) or (IIe) were prepared and administered at doses of 0.001 and 0.01 mpk (e.g., doses of 0.0005 mpk of a formulation including Luc mRNA and a formulation including H10 mRNA or doses of 0.005 mpk of a formulation including Luc mRNA and a formulation including H10 mRNA). As shown in Table 5A, Compound 20 exhibited the highest expression at both dose levels. The low dose of Compound 20 showed equivalent expression to the high dose of MC3. Formulations including other compounds also showed multi-fold enhancement in expression relative to MC3.

TABLE 5A

Total flux (p/s) measured 6 hours after intramuscular administration of nanoparticle compositions including compounds according to Formula (I), (IA), (II), (IIa), (IIb), (IIc), (IId) or (IIe).

| Compound | 0.001 mpk Dose | 0.01 mpk Dose |
|---|---|---|
| 2 | 3.55E+06 | 6.16E+07 |
| 3 | 3.58E+06 | 4.95E+07 |
| 5 | 9.84E+05 | 3.55E+06 |
| 7 | 3.65E+06 | 7.48E+07 |
| 8 | 7.81E+05 | 3.32E+06 |
| 12 | 8.02E+04 | 8.90E+05 |
| 18 | n.d. | 8.84E+05 |
| 19 | 3.28E+06 | 2.96E+07 |
| 20 | 2.59E+07 | 9.72E+07 |
| 23 | 8.27E+06 | 2.20E+06 |
| 24 | 3.78E+06 | 3.97E+07 |
| 25 | 3.53E+06 | 9.96E+07 |
| 26 | 3.90E+06 | 6.13E+07 |
| 27 | 2.55E+06 | 3.17E+07 |
| 28 | 6.73E+05 | 5.56E+06 |
| 29 | 7.64E+05 | 1.12E+07 |
| 30 | 2.47E+06 | 3.77E+07 |
| 32 | 7.37E+05 | 1.03E+07 |
| 35 | 2.45E+06 | 8.12E+06 |
| 48 | 4.69E+05 | 8.78E+06 |
| 50 | 6.56E+05 | 1.13E+07 |
| 57 | 1.16E+05 | 2.23E+05 |
| 137 | 7.57E+04 | 8.09E+04 |
| 138 | 2.72E+05 | 1.19E+06 |
| 140 | 2.03E+05 | 6.09E+05 |
| 144 | 2.72E+06 | 2.18E+07 |
| MC3 | 2.76E+06 | 3.68E+07 | n.d.=not determined

Example 6B: Expression Induced by Sample Formulations Upon Intramuscular Administration Sample formulations including modified luciferase (Luc) mRNA prepared and administered intramuscularly and the resulting expression and immunogenicity were evaluated simultaneously. Formulations including compounds according to Formula (I), (IA), (II), (IIa), (IIb), (IIc), (IId) or (IIe) were prepared and administered at dose of and 0.01 mpk. As shown in Table 5B, Compound 108 exhibited the highest expression. Formulations including other compounds also showed multi-fold enhancement in expression relative to MC3.

TABLE 5B

Total flux (p/s) measured 6 hours after intramuscular administration of nanoparticle compositions including compounds according to Formula (I), (IA), (II), (IIa), (IIb), (IIc), (IId) or (IIe).

| Compound | 0.01 mpk Dose |
|---|---|
| 60 | 9.48E+07 |
| 69 | 8.83E+06 |
| 108 | 4.60E+08 |
| 109 | 1.18E+08 |
| 110 | 1.21E+08 |
| 111 | 1.58E+08 |
| 112 | 9.47E+07 |
| 114 | 3.31E+06 |
| 121 | 1.06E+06 |
| 122 | 9.19E+07 |
| 123 | 1.08E+07 |
| MC3 | 3.23E+07 |

The fluxes measured upon intravenous and intramuscular administration are compared in Table 6. Fluxes are presented as fold increase over that measured for MC3 formulations. Formulations including Compound 20 displayed the highest fold increase in Luc expression upon intramuscular administration, while those including Compounds 18 and 26 displayed the highest fold increase upon intravenous administration. Notably, the intravenous data included in Table 6 was measured at higher doses than the intramuscular data.

TABLE 6

Relative flux measured after intravenous or intramuscular administration of nanoparticle compositions including compounds according to Formula (I), (IA), (II), (IIa), (IIb), (IIc), (IId) or (IIe).

| | | Fold increase in Luc expression relative to MC3 | | |
|---|---|---|---|---|
| Compound | pKa | Intravenous (0.5 mpk dose) | Intramuscular (0.01 mpk dose) | Intramuscular (0.001 mpk dose) |
| 3 | 6.72 | 2.24 | 1.13 | 0.51 |
| 18 | 6.56 | 3.23 | 2.01 | n.d. |
| 20 | 6.87 | 0.80 | 2.21 | 3.70 |
| 26 | 6.64 | 4.24 | 1.39 | 0.56 |
| 29 | 6.00 | 1.03 | 0.25 | 0.11 | n.d.=not determined

Example 7: Cytokine Production Induced by Sample Formulations

The introduction of foreign material into a mammalian body induces an innate immune response that promotes cytokine production. Such immune responses to, for example, nanoparticle compositions including therapeutic and/or prophylactics, are undesirable. The induction of certain cytokines is thus measured to evaluate the efficacy of nanoparticle compositions. The concentrations of various cytokines in mice upon intravenous administration of nanoparticle compositions presented in Table 1A at a dosage of 0.5 mpk was measured at 6 hours. The standard MC3 formulation and a PBS control were also tested. As is evident in Table 7, IL-6 induction was highest for compositions including Compounds 1, 3, 9, 19, and 26, while IP-10 induction was highest for compositions including Compounds 3, 4, 7, 20, and 26. IL-6 induction was lowest for compositions including Compounds 4, 11, 12, and 28. IP-10 induction was lowest for compositions including Compounds 10, 11, 12, 13, 15, 17, and 18.

TABLE 7

Cytokine induction 6 hours after administration of nanoparticle compositions including compounds according to Formula (I), (IA), (II), (IIa), (IIb), (IIc), (IId) or (IIe).

| Compound | IL-6 | IP-10 |
|---|---|---|
| 1 | 267.24 | 687.14 |
| 2 | 70.95 | 468.86 |
| 3 | 282.88 | 2052.87 |
| 4 | 13.1375 | 2253.09 |
| 5 | 94.07 | 487.16 |
| 6 | 136.18 | 316.01 |
| 7 | 116.35 | 4959.16 |
| 9 | 317.45 | 366.53 |
| 10 | 88.81 | 138.16 |
| 11 | 0.14 | 44.84 |
| 12 | 3.88 | 32.03 |
| 13 | 29.07 | 126.29 |
| 14 | 75.29 | 621.49 |
| 15 | 64.65 | 184.30 |
| 16 | 32.01 | 206.75 |
| 17 | 138.43 | 156.41 |
| 18 | 78.76 | 139.92 |
| 19 | 285.56 | 1468.94 |
| 20 | 126.83 | 2468.24 |
| 22 | 90.54 | 976.50 |
| 23 | 94.00 | 1015.95 |
| 24 | 163.53 | 1172.93 |
| 25 | 233.45 | 1194.13 |
| 26 | 273.56 | 2330.01 |
| 27 | 161.07 | 345.56 |
| 28 | 17.47 | 283.13 |
| 29 | 69.54 | 1362.81 |
| 30 | 152.51 | 1638.77 |
| 136 | 28.69 | 887.91 |
| 137 | 130.82 | 234.35 |
| 138 | 23.38 | 172.56 |
| 139 | 23.57 | 153.36 |
| 140 | 282.82 | 187.83 |
| 141 | 327.15 | 1072.04 |
| 143 | 6.245 | 209.63 |
| 144 | 319.46 | 4220.55 |
| MC3 | 124.42 | 504.90 |

Example 8: Complement Activation Induced by Sample Formulations

Complement activation assists in the clearance of pathogens from an organism. As it is undesirable that a subject's body recognize a nanoparticle composition as a foreign invader, low complement system activation upon administration of such a composition is preferred. The complex sC5b-9 is a marker for the activation of the complement system. Thus, human cells were contacted in vitro with nanoparticle compositions according to Table 1A and were evaluated for sC5b-9 levels. Table 8 shows the fold increase in sC5b-9 levels relative to saline for nanoparticle compositions including Compounds 1, 6, 9, 18, 24, 25, 29, and 30. Compositions including Compounds 6 and 18 somewhat increase sC5b-9 levels relative to saline, while compositions including Compounds 1, 9, 24, 29, and 30 slightly decrease sC5b-9 levels relative to saline.

TABLE 8

Fold increases in sC5b-9 levels upon administration of nanoparticle compositions including compounds according to Formula (I), (IA), (II), (IIa), (IIb), (IIc), (IId) or (IIe).

| Compound | Fold increase versus saline |
|---|---|
| 1 | 0.82 |
| 6 | 1.39 |
| 9 | 0.92 |
| 18 | 1.28 |
| 24 | 0.81 |
| 25 | 1.02 |
| 29 | 0.93 |
| 30 | 0.94 |
| 136 | 0.69 |
| 139 | 0.73 |
| 140 | 0.75 |
| 141 | 1.81 |
| MC3 | 0.73 |

Example 9: Clinical Chemistry and Hematology

Sample formulations of nanoparticle compositions including different lipids were administered intravenously to rat at a dose of 2 mpk. The expression of various clinical markers was evaluated at 48 h post dose and compared to that induced by administration of MC3 formulations or phosphate buffered saline (PBS).

TABLE 9

Levels of clinical markers induced by administration of nanoparticle compositions including a compound of Formula (I), (IA), (II), (IIa), (IIb), (IIc), (IId) or (IIe).

| | Concentration | | | | |
|---|---|---|---|---|---|
| Compound | Alanine aminotransferase | Aspartate aminotransferase | Neutrophils | Lymphocytes | Monocytes |
| 3 | 53.5 | 87.5 | 3388.5 | 12051 | 2103 |
| 24 | 51.5 | 90 | 1790.5 | 14100 | 1834 |
| 25 | 52 | 124.5 | 1998 | 15924 | 2122 |
| 30 | 56 | 95 | 3195 | 10408.5 | 877 |
| MC3 | 339 | 325 | 4962.5 | 19976 | 1429 |
| PBS | 55.5 | 108 | 920 | 8004 | 276 |

Example 10: Expression of hEPO Induced by Sample Formulations

Sample formulations of nanoparticle compositions including different lipids are generally first evaluated according to Luc expression in vivo. The activity of several such compositions was further evaluated using an mRNA encoding hEPO. Nanoparticle compositions including Compounds 6, 18, 25, 30, 108-112, 60, and 122, or MC3 were prepared according to Example 2. As shown in Tables 10 and 1B supra, each composition had a similar particle size and encapsulation efficiency.

TABLE 10

Characteristics of nanoparticle compositions including compounds according to Formula (I), (IA), (II), (IIa), (IIb), (IIc), (IId) or (IIe).

| Compound | Formulation | Size (nm) | PDI | EE (%) |
|---|---|---|---|---|
| 6 | Compound 6:DSPC:Chol:PEG-DMG (50:10:38.5:1.5) | 70.5 | 0.082 | 97.84 |
| 18 | Compound 18:DSPC:Chol:PEG-DMG (50:10:38.5:1.5) | 78.6 | 0.095 | 97.34 |
| MC3 | MC3:DSPC:Chol:PEG-DMG (50:10:38.5:1.5) | 73.7 | 0.114 | 97.22 |

Figure 9:
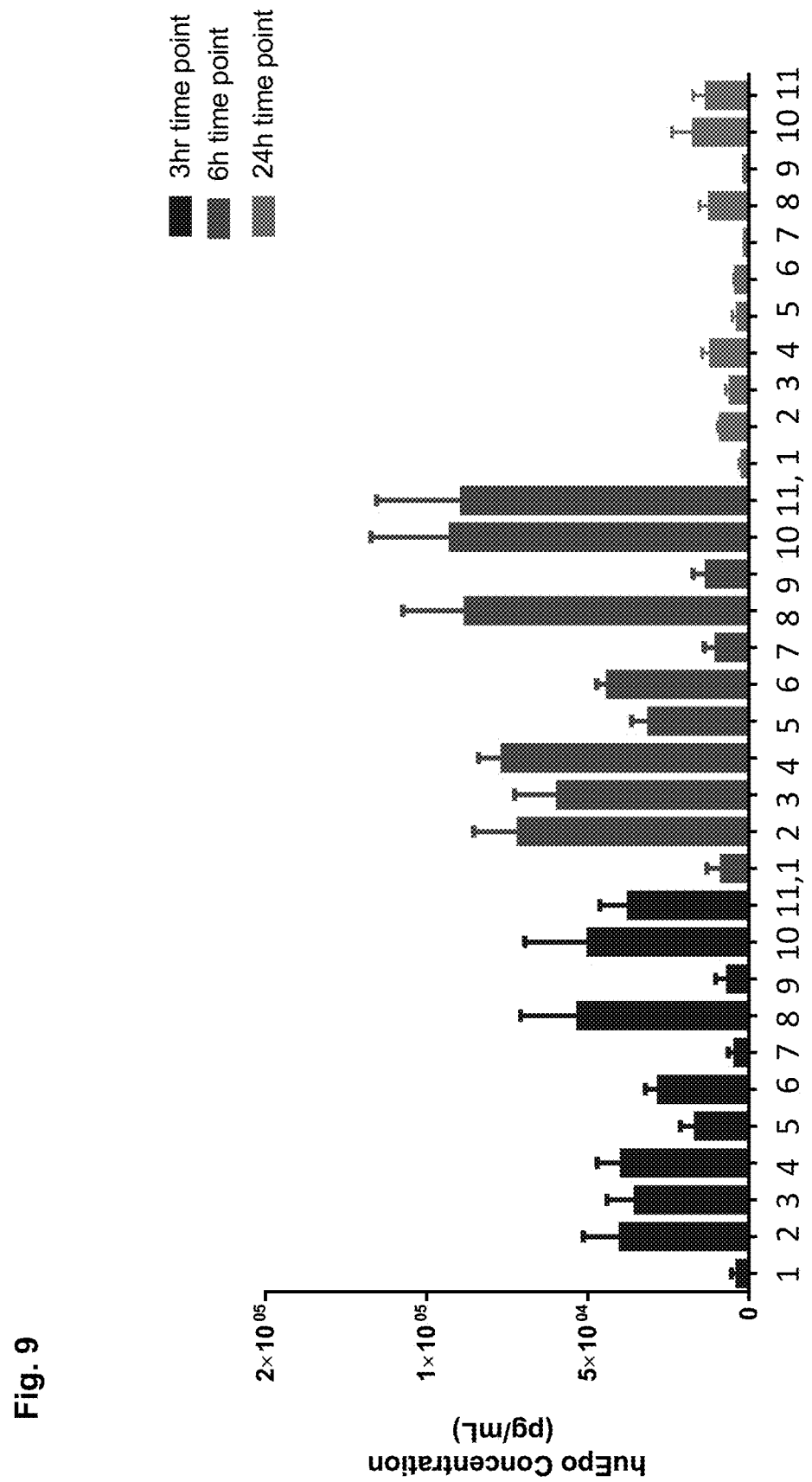
FIG. 9 shows the results of hEPO expression measured upon intramuscular administration of various nanoparticle compositions including MC3, Compounds 18, 25, 30, 108-112, 60, and 122 to mice at 0.01 mpk at various time points: 3 hr (left block), 6 hr (middle block) and 24 hr (right block). The numbers 1-11 in this figure correspond to MC3, Compounds 18, 25, 30, 108-112, 60, and 122 respectively.
Figure 10:
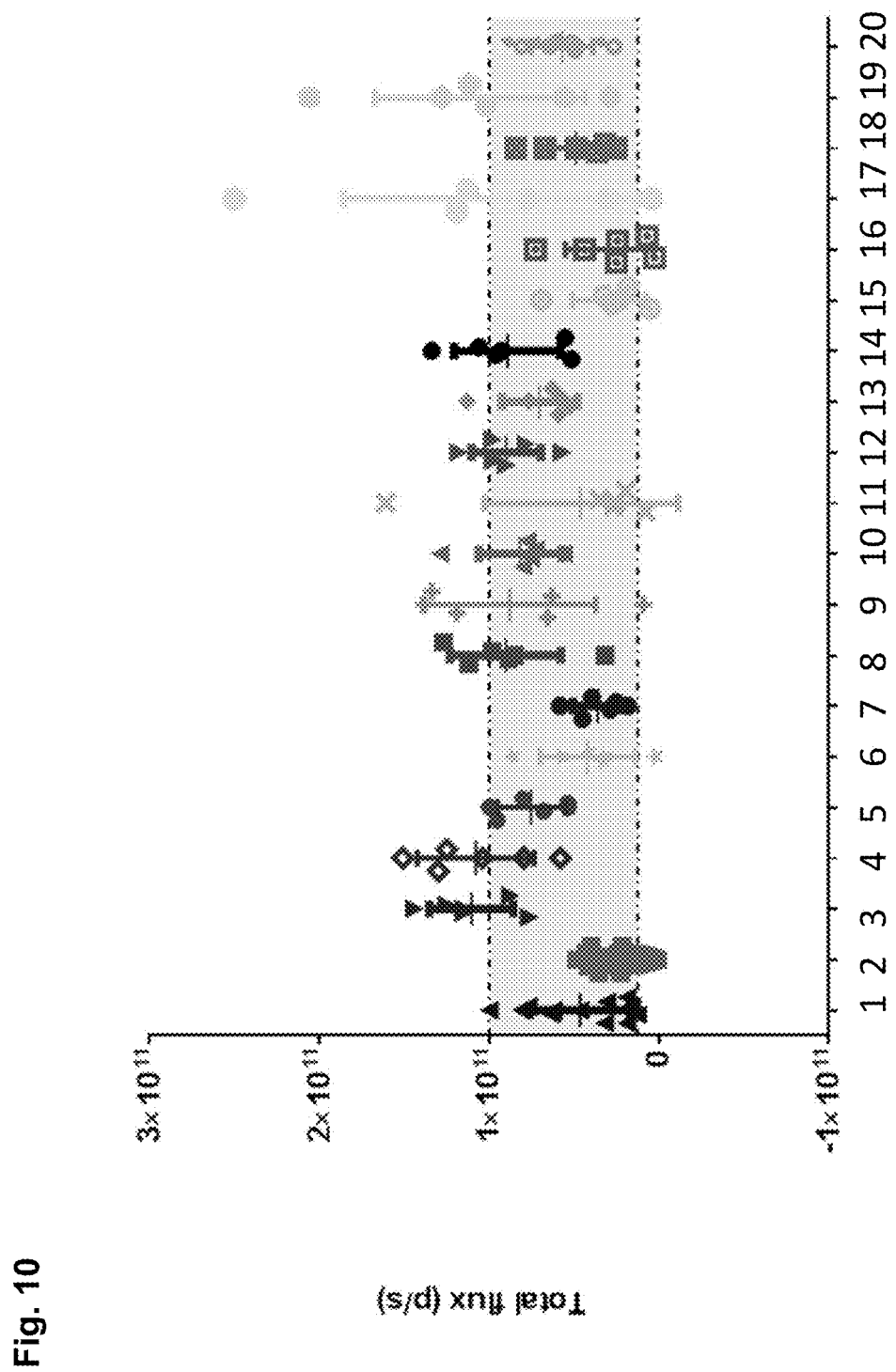
FIG. 10 shows the results of luciferase expression (total flux) measured upon intravenous administration of various nanoparticle compositions including MC3 or various compounds disclosed herein. The numbers 1-12 in this figure correspond to Compound 18, MC3, Compounds 48-50, 54, 111, 60, 75, 68, 66, 128, 65, 130, 133-135, 147, 96, and 151 respectively.

The expression of hEPO and cytokine induction in mice intravenously administered a nanoparticle composition at a dose of 0.5 mpk were measured at 3, 6, and 24 hours. The resultant hEPO and cytokine levels are summarized in Table 11A. Compositions including Compounds 6 and 18 yielded higher hEPO concentrations than MC3 formulations at each time point. The expression of hEPO in mice intramuscularly administered a nanoparticle composition from Table 1B at a dose of 0.01 mpk were measured at 3, 6, and 24 hours. The resultant hEPO levels are summarized in Table 11B. Compositions including Compounds 18, 25, 30, 108-112, 60, and 122 yielded higher hEPO concentrations than MC3 formulations at 6 hr time point. (see also FIG. 9)

TABLE 11A

Evaluation of nanoparticle compositions including compounds according to Formula (I), (IA), (II), (IIa), (IIb), (IIc), (IId) or (IIe).

| | hEPO expression (pg/ml) | | | Cytokine expression (pg/ml) | |
|---|---|---|---|---|---|
| Compound | 3 h | 6 h | 24 h | IP-10 (6 h) | IL-6 (6 h) |
| 6 | 2.31E+06 | 3.17E+06 | 1.11E+06 | 116.66 | 10.15 |
| 18 | 3.00E+06 | 3.38E+06 | 1.80E+06 | 299.93 | 10.16 |
| MC3 | 1.57E+06 | 1.83E+06 | 0.81E+06 | 117.94 | 19.85 |

TABLE 11B

Evaluation of nanoparticle compositions including compounds according to Formula (I), (IA), (II), (IIa), (IIb), (IIc), (IId) or (IIe).

| Compound | Fold increase in hEPO concentration relative to MC3 |
|---|---|
| 18 | 8.6 |
| 25 | 7.1 |
| 30 | 9.2 |
| 108 | 3.7 |
| 109 | 5.3 |
| 110 | 1.2 |
| 111 | 10.6 |
| 112 | 1.6 |
| 60 | 11.2 |
| 122 | 10.7 |
| MC3 | 1 |

Table 12 compares the nanoparticle compositions including compounds according to Formula (I), (IA), (II), (IIa), (IIb), (IIc), (IId) or (IIe) to the compositions including MC3 on the basis of expression and flux levels. As is evident in Table 12, both Compounds 6 and 18 outperform MC3 in both hEPO expression and average total flux. Thus, these lipids may be useful in nanoparticle composition therapeutics.

TABLE 12

Comparison of nanoparticle compositions including compounds according to Formula (I), (IA), (II), (IIa), (IIb), (IIc), (IId) or (IIe).

| | Compound 6 | Compound 18 | MC3 |
|---|---|---|---|
| Average hEPO concentration (pg/ml, 6 h) | $3.17 \times 10^6$ | $3.38 \times 10^6$ | $1.83 \times 10^6$ |
| Fold increase in hEPO concentration relative to MC3 | 1.73 | 1.85 | 1 |
| Average total flux (6 h, ffluc) | $7.60 \times 10^9$ | $2.13 \times 10^{10}$ | $6.59 \times 10^9$ |
| Fold increase in average total flux relative to MC3 | 1.15 | 3.23 | 1 |

Example 11: Expression of hEPO Induced by Sample Formulations in Rat and Residual Lipid Levels in the Liver The expression of hEPO and cytokine induction in rats intravenously administered a nanoparticle composition at a dose of 2.0 mpk was measured at 6 h.

At 48 h liver tissue was harvested for lipid quantification. To pre-weighed tissues, Milli-Q water was added (900 μL water per 100 mg tissue). Tissues were homogenized using an Omni probe homogenizer until uniform. 50 μL of samples and matrix calibration standards were aliquoted into a 96-well plate. 50 μL of blank matrix for matrix blanks and control blanks were aliquoted. 400 μL IS spiking solution were manually added to all samples except matrix blanks. 400 μL of 50:50 ACN:IPA were manually added to matrix blanks. The plate was covered and the samples vortexed and centrifuged for 5 minutes at >3000 rpm. 200 μL of the samples were transferred into a clean 96-well plate for analysis. Samples were analyzed on a Waters Acquity UPLC using a Higgins Analytical Clipeus C8 column (5 μM, 30×2.1 mm) and a gradient of either 70-95% or 60-95% (Mobile Phase A: 5 mM ammonium formate in 50:50:1 $H_2O$:MeOH:formic acid; Mobile Phase B: 5 mM ammonium formate in 100:1 MeOH:formic acid) over 1.3 min at 1.2 mL/min (column temperature 55° C.). Detection was based on electrospray ionization (ESI) in positive mode using a Sciex API5500 Mass Spectrometer.

TABLE 13

Expression of hEPO induced by administration of nanoparticle compositions including compounds according to Formula (I), (IA), (II), (IIa), (IIb), (IIc), (IId) or (IIe) in rat, 6 h, 2 mpk.

| Compound | hEPO expression (pg/mL) |
| --- | --- |
| 3 | 1.74E+07 |
| 18 | 9.96E+06 |
| 24 | 1.44E+07 |
| 25 | 3.05E+07 |
| 30 | 1.63E+07 |
| MC3 | 1.33E+07 |

TABLE 14

Cytokine induction 6 hours after administration of hEPO nanoparticle compositions including compounds according to Formula (I), (IA), (II), (IIa), (IIb), (IIc), (IId) or (IIe).

| Compound | IP-10 (pg/mL) |
| --- | --- |
| 3 | 542 |
| 18 | 517.3 |
| 24 | 323.5 |
| 25 | 533.5 |
| 30 | 214.5 |
| MC3 | 688.3 |

TABLE 15

Liver levels in rats administered compositions including compounds according to Formula (I), (IA), (II), (IIa), (IIb), (IIc), (IId) or (IIe) after 48 h.

| Compound | % remaining dose in liver, 48 h |
| --- | --- |
| 3 | 14.2 |
| 18 | <1 |
| 24 | <1 |
| 25 | 1.3 |
| 30 | <1 |
| MC3 | 74 |

The expression of hEPO in rats intravenously administered a nanoparticle composition at a dose of 0.2 mpk or 2.0 mpk was measured at 6 hours. Table 16 summarize the ratio of hEPO expression levels using various nanoparticle compositions as compared to the hEPO expression level using MC3 formulation and the lipid levels in the liver measured 48 hours after administration, as described above. Tables 17 and 18 summarize the lipid levels in the liver and spleen measured 48 hours after administration of Compounds 28, 33, 53, and 54. Liver and spleen levels represent the average values calculated for 3 rats in each group. As is shown in Tables 17 and 18, less than 10% of Compounds 28, 33, 53, and 54 remained in the liver after 48 hours, while greater than 60% of MC3 remained.

TABLE 16

Ratio of expression of hEPO and lipid levels remaining in liver after 48 h.

| Compound | Lipid/MC3 hEPO conc. ratio | | % Lipid Remaining in liver, 48 h* |
| --- | --- | --- | --- |
| | 0.2 mpk | 2 mpk | 2 mpk |
| MC3 | 1 | 1 | 87 |
| 18 | n.d. | 0.81 | 0.018 |
| 25 | 2.41 | 2.13 | 1.32 |
| 24 | 1.75 | 1.01 | 0.016 |
| 30 | 1.87 | 1.14 | <0.01 |
| 3 | 2.41 | 1.21 | 14 |
| 26 | n.d. | 4.95 | 20 |
| 48 | 5.39 | 3.84 | 7.22 |
| 49 | 4.13 | 3.28 | 12.6 |
| 50 | 3.41 | 3.03 | 15.9 |

*Assuming 300 g rat and 15 g liver

TABLE 17

Liver levels in rats administered 0.2 mpk doses of compositions including compounds according to Formula (I) (IA), (II), (IIa), (IIb), (IIc), (IId) or (IIe) after 48 h.

| Compound | Liver level (ng/g) | Spleen level (ng/g) |
| --- | --- | --- |
| 28 | 49.6 | 268 |
| 33 | n.d. | 115 |
| 53 | 4810 | 1181 |
| 54 | 6067 | 6357 |
| MC3 | 25033 | 9440 |

TABLE 18

Liver levels in rats administered 2 mpk doses of compositions including compounds according to Formula (I) (IA), (II), (IIa), (IIb), (IIc), (IId) or (IIe) after 48 h.

| Compound | Liver level (ng/g) | Spleen level (ng/g) |
|---|---|---|
| 28 | 665 | 551 |
| 33 | 103 | 287 |
| 53 | 47033 | 201333 |
| 54 | 56100 | 49367 |
| MC3 | 285333 | 129000 |

Table 19 summarizes the hEPO expression, IP-10 induction, liver and spleen levels, and alanine aminotransferase (ALT) and aspartate aminotransferase (AST) measured upon intravenous administration of formulations including Compounds 48, 49, and 50 to rat at 0.2 and 2 mpk and hEPO mRNA. hEPO concentrations were measured 6 hours after administration, while cytokine induction and liver and spleen levels were measured 48 hours after administration. hEPO and IP-10 concentrations are presented in pg/ml, while liver levels are provided in ng/g. ALT and AST levels are presented in international units.

TABLE 19 hEPO expression, IP-10 induction, and liver levels measured after administration of compositions including compounds according to one of formulas (I), (IA), (II), (IIa), (IIb), (IIc), (IId) or (IIe).

| | Compound 48 | | Compound 49 | | Compound 50 | | MC3 | |
|---|---|---|---|---|---|---|---|---|
| | 0.2 mpk | 2 mpk | 0.2 mpk | 2 mpk | 0.2 mpk | 2 mpk | 0.2 mpk | 2 mpk |
| hEPO expression (pg/ml) | 4.06E+06 | 3.57E+07 | 3.17E+06 | 3.04E+07 | 2.62E+06 | 2.81E+07 | 7.68E+06 | 9.29E+06 |
| IP-10 induction (pg/ml) | 134 | 970 | 66 | 932 | 20 | 1065 | 2 | 596 |
| Liver level (ng/g) | 5448 | 34520 | 6490 | 61400 | 5822 | 79200 | 11300 | 140520 |
| Spleen level (ng/g) | 0.31 | 0.21 | 0.36 | 0.37 | 0.22 | 0.17 | 0.74 | 0.65 |
| ALT | 59.6 | 66.0 | 54.0 | 77.8 | 59.2 | 78.8 | 63.6 | 79.6 |
| AST | 140.8 | 131.2 | 99.4 | 132.4 | 143.2 | 158.4 | 134.8 | 139.0 |

Example 12: Dose Response of Sample Formulations in Rats

The expression of hEPO induced by intravenous administration to rats of nanoparticle compositions at various doses was measured at 2, 4, 6, 8, 24, and 48 hour time points. FIGS. 3-6 respectively summarize the hEPO expression measured upon intravenous administration of formulations including Compounds 26, 18, 25, and MC3 to rat at various doses. The lipid levels of Compound 26 in the liver after 48 hours were about 19%.

Figure 7:
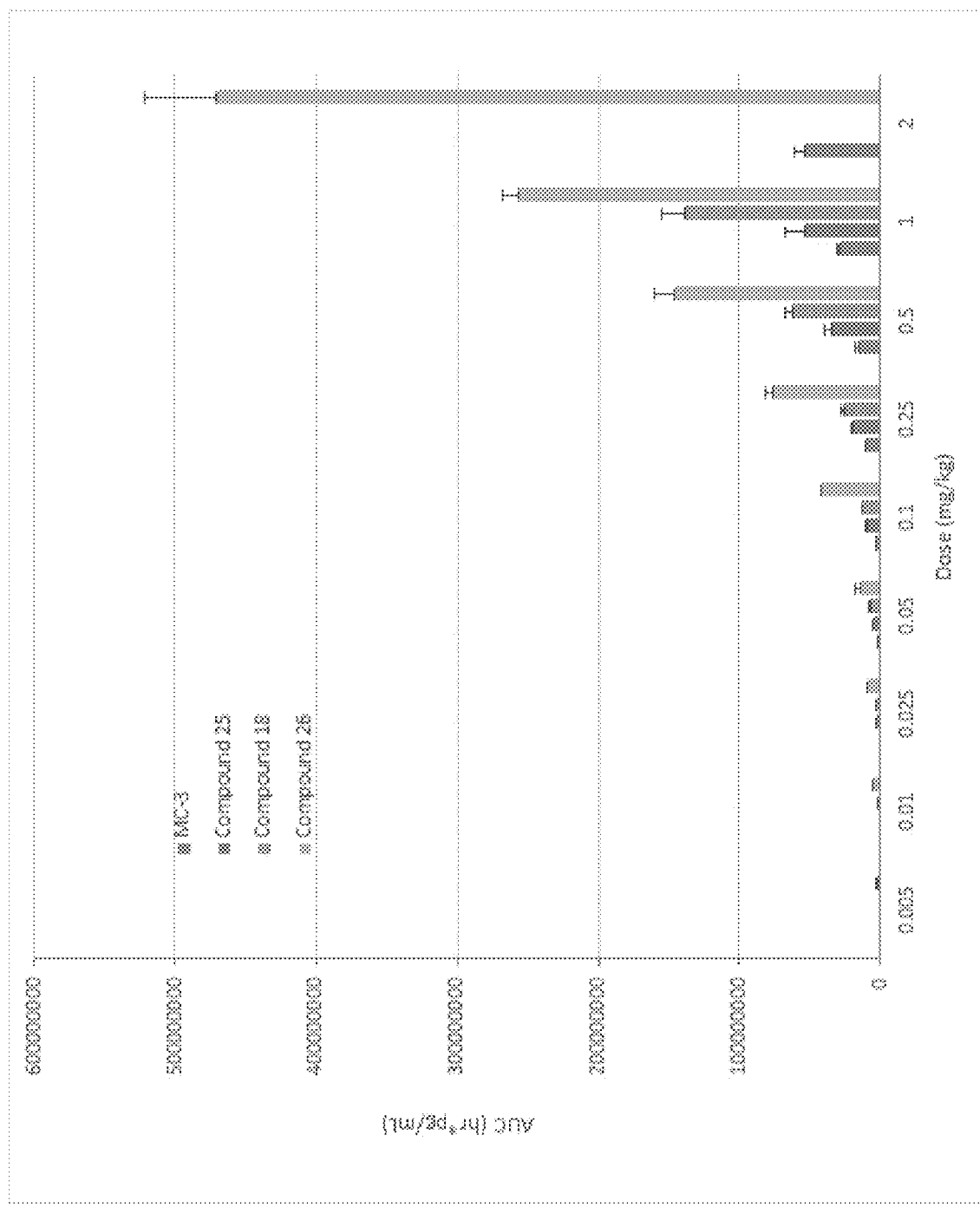
FIG. 7 shows the area under the curve (AUC) for nanoparticle compositions including Compounds 18, 25, and 26 and MC3 at various doses between 0.005 mpk and 2 mpk.

FIG. 7 shows the area under the curve for compositions including Compounds 18, 25, and 26 and MC3 at different dosages: 0.005 mpk, 0.01 mpk, 0.025 mpk, 0.05 mpk, 0.1 mpk, 0.25 mpk, 0.5 mpk, 1 mpk or 2 mpk.

Example 13: Pharmacokinetics of Sample Formulations in Rats

The expression of hEPO and lipid levels in the liver and spleen in rats intravenously administered a nanoparticle composition at a dose of 0.2 mpk was measured at various timepoints. Compounds 18 and 25 were selected for comparison with MC3. Lipids were formulated according to the standard MC3 formulation described above. Rats were administered intravenously a single 0.2 mpk dose and expression monitored at 0.25, 0.5, 1, 2, 4, 8, 24, and 48 hours after administration.

TABLE 20

Expression of hEPO induced by administration of nanoparticle compositions in rat, 6 h, 0.2 mpk.

| hEPO expression (pg/mL) | Compound 18 | Compound 25 | MC3 |
|---|---|---|---|
| 0.25 h | 20227 | 0 | 0 |
| 0.5 h | 20743 | 19553 | 42457 |
| 1 h | 194353 | 434299 | 93720 |
| 2 h | 238107 | 2042807 | 524093 |
| 4 h | 514807 | 3176560 | 601307 |
| 8 h | 915320 | 2631633 | 1536833 |
| 24 h | 412051 | 869374 | 703619 |
| 48 h | 52361 | 103089 | 64687 |

TABLE 21

Lipid level in liver induced by administration of nanoparticle compositions in rat, 6 h, 0.2 mpk.

| Lipid level (ng/g) | Compound 18 | Compound 25 | MC3 |
|---|---|---|---|
| 0.25 h | 5374 | 12037 | 13180 |
| 0.5 h | 6023 | 16447 | 20500 |
| 1 h | 6053 | 17900 | 16777 |
| 2 h | 2037 | 11733 | 25967 |
| 4 h | 839 | 6687 | 24730 |
| 8 h | 296 | 2357 | 32633 |
| 24 h | 5 | 199 | 33000 |
| 48 h | 5374 | 12037 | 13180 |

TABLE 22

Lipid level in spleen induced by administration of nanoparticle compositions in rat, 6 h, 0.2 mpk.

| Lipid level (ng/g) | Compound 18 | Compound 25 | MC3 |
|---|---|---|---|
| 0.25 h | 1230 | 4037 | 4100 |
| 0.5 h | 2017 | 6880 | 6237 |
| 1 h | 3213 | 8590 | 4197 |
| 2 h | 3070 | 13733 | 8613 |
| 4 h | 3770 | 20400 | 11920 |
| 8 h | 1345 | 10787 | 21200 |
| 24 h | 271 | 2023 | 19067 |
| 48 h | 92 | 1547 | 11563 |

Example 14: Optimization of Lipid:Therapeutic Agent Ratios

The relative amounts of lipid component and therapeutic and/or prophylactic in a nanoparticle composition can be optimized according to considerations of efficacy and tolerability. For compositions including an RNA as a therapeutic and/or prophylactic, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition. Thus, the wt/wt ratio of total lipid to RNA is varied between 10:1, 15:1, 20:1, 32:1, 40:1, 50:1, and 60:1 for a lipid formulation including about 50 mol % of a compound according to Formula (I), (IA), (II), (IIa), (IIb), (IIc), (IId) or (IIe), about 10 mol % phospholipid (e.g., DOPE or DSPC), about 38.5 mol % structural lipid (e.g., cholesterol), and about 1.5 mol % PEG lipid (e.g., PEG-DMG). N:P ratios are calculated for each nanoparticle composition assuming a single protonated nitrogen atom. The encapsulation efficiency (EE), size, and polydispersity index of each composition are also measured.

Generally, compositions with higher total lipid:RNA ratios yield smaller particles with higher encapsulation efficiencies, both of which are desirable. However, the N:P ratio for such formulations generally exceeds 4. Current standards in the art such as the MC3 formulation described above have N:P ratios of 5.67. Thus, a balance between the N:P ratio, size, and encapsulation efficiency should be struck.

In order to explore the efficacy of nanoparticle compositions with different N:P ratios, the expression of luciferase (Luc) or human erythropoietin (hEPO) in mice after low (0.05 mg/kg) or high (0.5 mg/kg) doses of intravenously administered nanoparticle compositions is examined. The concentration of Luc or hEPO expressed is measured 3, 6, and/or 24 hours after administration.

Example 15: Optimization of Content of a Compound According to Formula (I), (IA), (II), (IIa), (IIb), (IIc), (IId) or (IIe)

As smaller particles with higher encapsulation efficiencies are generally desirable, the relative amounts of various elements in lipid components of nanoparticle compositions are optimized according to these parameters.

A compound according to Formula (I), (IA), (II), (IIa), (IIb), (IIc), (IId) or (IIe) is selected for optimization. The relative amount of the compound according to Formula (I), (IA), (II), (IIa), (IIb), (IIc), (IId) or (IIe) is varied between 30 mol % and 60 mol % in compositions including DOPE or DSPC as phospholipids to determine the optimal amount of the compound according to Formula (I), (IA), (II), (IIa), (IIb), (IIc), (IId) or (IIe) in the formulations. Formulations are prepared using a standardized process with a water to ethanol ratio in the lipid-mRNA solution of 3:1 and a rate of injection of the lipid solution into the mRNA solution of 12 mL/min on a NanoAssemblr microfluidic based system. This method induces nano-precipitation and particle formation. Alternative processes including, but not limited to, T-junction or direct injection, may also be used to achieve the same nano-precipitation.

Formulations producing the smallest particles with the highest encapsulation efficiencies are generally preferred, however larger or smaller particle sizes may be desirable based on a given application (e.g., based on the fenestration size of a target organ). Compositions are also evaluated for their Luc or hEPO expression levels and cytokine profiles.

Example 16: Optimization of Phospholipid

The relative amount of phospholipid in a lipid component of a nanoparticle composition is varied to further optimize the formulation. A compound according to Formula (I), (IA), (II), (IIa), (IIb), (IIc), (IId) or (IIe) is selected for use in the nanoparticle composition and DOPE and DSPC are selected as phospholipids. Additional phospholipids can also be evaluated. Nanoparticle compositions are prepared with the relative phospholipid content varying between 0 mol % and 30 mol %. Compositions are evaluated for their size, encapsulation efficiency, Luc or hEPO expression levels, and cytokine profiles.

Example 17: Optimization of Structural Lipid

The relative amount of structural lipid in a lipid component of a nanoparticle composition is varied to further optimize the formulation. A compound according to Formula (I), (IA), (II), (IIa), (IIb), (IIc), (IId) or (IIe) is selected for use in the nanoparticle composition and cholesterol is selected as a structural lipid. Additional structural lipids can also be evaluated. Nanoparticle compositions are prepared with the relative structural lipid content varying between 18.5 mol % and 48.5 mol %. Compositions are evaluated for their size, encapsulation efficiency, Luc or hEPO expression levels, and cytokine profiles.

Example 18: Optimization of PEG Lipid

The relative amount of PEG lipid in a lipid component of a nanoparticle composition is varied to further optimize the formulation. A compound according to Formula (I), (IA), (II), (IIa), (IIb), (IIc), (IId) or (IIe) is selected for use in the nanoparticle composition and PEG-DMG is selected as a PEG lipid. Additional PEG lipids can also be evaluated. Nanoparticle compositions are prepared with the relative PEG lipid content varying between 0 mol % and 10 mol %. Compositions are evaluated for their size, encapsulation efficiency, Luc or hEPO expression levels, and cytokine profiles.

Exemplary formulations useful in the optimization of nanoparticle composition formulations are presented in Table 23.

TABLE 23

Exemplary formulations including compounds according to Formula (I), (IA), (II), (IIa), (IIb), (IIc), (IId) or (IIe).

| Composition (mol %) | Components |
| --- | --- |
| 40:20:38.5:1.5 | Compound:Phospholipid:Chol:PEG-DMG |
| 45:15:38.5:1.5 | Compound:Phospholipid:Chol:PEG-DMG |
| 50:10:38.5:1.5 | Compound:Phospholipid:Chol:PEG-DMG |
| 55:5:38.5:1.5 | Compound:Phospholipid:Chol:PEG-DMG |
| 60:5:33.5:1.5 | Compound:Phospholipid:Chol:PEG-DMG |
| 45:20:33.5:1.5 | Compound:Phospholipid:Chol:PEG-DMG |
| 50:20:28.5:1.5 | Compound:Phospholipid:Chol:PEG-DMG |
| 55:20:23.5:1.5 | Compound:Phospholipid:Chol:PEG-DMG |
| 60:20:18.5:1.5 | Compound:Phospholipid:Chol:PEG-DMG |
| 40:15:43.5:1.5 | Compound:Phospholipid:Chol:PEG-DMG |
| 50:15:33.5:1.5 | Compound:Phospholipid:Chol:PEG-DMG |
| 55:15:28.5:1.5 | Compound:Phospholipid:Chol:PEG-DMG |
| 60:15:23.5:1.5 | Compound:Phospholipid:Chol:PEG-DMG |
| 40:10:48.5:1.5 | Compound:Phospholipid:Chol:PEG-DMG |
| 45:10:43.5:1.5 | Compound:Phospholipid:Chol:PEG-DMG |
| 55:10:33.5:1.5 | Compound:Phospholipid:Chol:PEG-DMG |
| 60:10:28.5:1.5 | Compound:Phospholipid:Chol:PEG-DMG |
| 40:5:53.5:1.5 | Compound:Phospholipid:Chol:PEG-DMG |
| 45:5:48.5:1.5 | Compound:Phospholipid:Chol:PEG-DMG |
| 50:5:43.5:1.5 | Compound:Phospholipid:Chol:PEG-DMG |
| 40:20:40:0 | Compound:Phospholipid:Chol:PEG-DMG |
| 45:20:35:0 | Compound:Phospholipid:Chol:PEG-DMG |
| 50:20:30:0 | Compound:Phospholipid:Chol:PEG-DMG |
| 55:20:25:0 | Compound:Phospholipid:Chol:PEG-DMG |
| 60:20:20:0 | Compound:Phospholipid:Chol:PEG-DMG |
| 40:15:45:0 | Compound:Phospholipid:Chol:PEG-DMG |
| 45:15:40:0 | Compound:Phospholipid:Chol:PEG-DMG |
| 50:15:35:0 | Compound:Phospholipid:Chol:PEG-DMG |
| 55:15:30:0 | Compound:Phospholipid:Chol:PEG-DMG |
| 60:15:25:0 | Compound:Phospholipid:Chol:PEG-DMG |
| 40:10:50:0 | Compound:Phospholipid:Chol:PEG-DMG |
| 45:10:45:0 | Compound:Phospholipid:Chol:PEG-DMG |
| 50:0:48.5:1.5 | Compound:Phospholipid:Chol:PEG-DMG |
| 50:10:40:0 | Compound:Phospholipid:Chol:PEG-DMG |
| 55:10:35:0 | Compound:Phospholipid:Chol:PEG-DMG |
| 60:10:30:0 | Compound:Phospholipid:Chol:PEG-DMG |

Example 19: Optimization of Particle Sizes

The fenestration sizes for different bodily organs often vary; for example, the kidney is known to have a smaller fenestration size than the liver. Thus, targeting delivery of a therapeutic and/or prophylactic (e.g., specifically delivering) to a particular organ or group of organs may require the administration of nanoparticle compositions with different particle sizes. In order to investigate this effect, nanoparticle compositions with formulations such as those included in Table 23 are prepared with a variety of particle sizes using a Nanoassemblr instrument. Nanoparticle compositions include an RNA encoding Luc. Each differently sized nanoparticle composition is subsequently administered to mice to evaluate the effect of particle size on delivery selectivity. Luc expression in two or more organs or groups of organs can be measured using bioluminescence to evaluate the relative expression in each organ.

Example 20: Administration Following Pretreatment

Administration of nanoparticle compositions to subjects can result in inflammation, infusion related reactions, and other undesirable effects indicative of low tolerability. These effects can be attributed to undesirable immunoactivity.

In order to combat negative effects, nanoparticle compositions are co-administered with one or more substances (e.g., co-medications or additional therapeutic and/or prophylactics) to subjects. Potentially useful additional therapeutic and/or prophylactics include steroids (e.g., corticosteroids), anti-histamines, $H_1$ receptor blockers, $H_2$ receptor blockers, anti-inflammatory compounds, statins, BTK inhibitors, S1P1 agonists, glucocorticoid receptor modulators (GRMs), and estradiols. Non-human primates are pretreated with one or more additional therapeutic agents selected from dexamethasone and acetaminophen. The additional therapeutic agent is administered either 24 hours, 1 hour, or both 24 hours and 1 hour before administration of a nanoparticle composition. Sample protocol are summarized in Table 24. Cytokine profiles, inflammation, and other parameters are measured and compared to evaluate the effectiveness of pretreatment.

TABLE 24

Sample protocol for pretreatment study.

| Group | Pretreatment Time | Additional Therapeutic Agent(s) Administered |
| --- | --- | --- |
| 1 | None | None |
| 2 | 24 hours | Dexamethasone |
| 3 | 24 hours | Acetaminophen |
| 4 | 24 hours | Dexamethasone and Acetaminophen |
| 5 | 1 hour | Dexamethasone |
| 6 | 1 hour | Acetaminophen |
| 7 | 1 hour | Dexamethasone and Acetaminophen |
| 8 | 24 hours and 1 hour | Dexamethasone |
| 9 | 24 hours and 1 hour | Acetaminophen |
| 10 | 24 hours and 1 hour | Dexamethasone and Acetaminophen |

For example, a useful therapeutic treatment course may involve administering an additional therapeutic and/or prophylactic both the day before and the day of (one hour prior) to administration of a nanoparticle composition at a dose level of 1.3 mpk. Additional therapeutic and/or prophylactics can be formulated for delivery by a variety of different routes. For example, dexamethasone may be delivered orally. In general, additional therapeutic and/or prophylactics are administered at clinically approved or typical dosage levels.

Example 21: Administration to Non-Human Primates

The tolerability and efficacy of nanoparticle compositions to non-human primates was evaluated in Cynomolgus monkeys. Monkeys were administered an optimized nanoparticle composition including an mRNA encoding hEPO once weekly for four weeks. The levels of hEPO protein, mRNA, and cytokine profiles were measured using ELISA-based techniques before and 2, 6, 12, 24, 48, 72, and 120 hours after each administration.

The effects of pretreatment to non-human primates were evaluated using a standard MC3 formulation including an mRNA encoding hEPO. The study design is summarized in Table 25. Male monkeys were administered the nanoparticle composition once weekly for four weeks at a dose rate of 5 ml/kg/h and were pretreated with either methotrexate or dexamethasone.

TABLE 25

Protocol for pretreatment study in Cynomolgus monkeys.

| Group | Test Material | Dose level (mg/kg) | Additional Therapeutic Agent Administered | Dose concentration (mg/ml) | Number of monkeys |
|---|---|---|---|---|---|
| 1 | MC3 | 0 | None | 0 | 3 |
| 2 | hEPO mRNA in MC3 | 0.3 | None | 0.06 | 3 |
| 3 | hEPO mRNA in MC3 | 0.3 | Methotrexate | 0.06 | 3 |
| 4 | hEPO mRNA in MC3 | 0.3 | Dexamethasone | 0.06 | 3 |

Results of the pretreatment study are shown in FIG. 1. As shown, in the absence of any pretreatment, maximal expression levels decreased nearly 70% over the course of the study. Methotrexate did not confer any particular beneficial effect. However, pre-administration of dexamethasone resulted in increased protein expression compared to treatment courses not involving pretreatment. Notably, minimal decrease in plasma/serum protein expression was observed over time for animals pretreated with dexamethasone. These results suggest that pretreatment of corticosteroids such as dexamethasone improves the tolerability and efficacy of nanoparticle compositions containing, for example, a compound according to Formula (I), (IA), (II), (IIa), (IIb), (IIc), (IId) or (IIe).

The tolerability and efficacy of nanoparticle compositions to non-human primates was also investigated using a sample formulation including Compound 18. The formulation was prepared according to the standard MC3 formulation described above and included an hEPO mRNA. Primates were administered a single dose of 0.05 (Group 1), 0.3 (Group 2), or 1.0 (Group 3) mpk via intravenous infusion for 60 minutes. Three primates were administered each dose. Expression of hEPO was measured prior to dosing and at 2, 6, 24, 48, and 96 hours post-treatment (Table 26). Pharmacokinetic parameters including Tmax, Cmax, and the AUC were also determined and are presented in Table 27. Table 28 includes levels of indicators of complement activation, while Table 29 includes cytokine induction data.

TABLE 26 hEPO expression measured at various time points upon administration of nanoparticle compositions to non-human primates.

| hEPO concentration (pg/ml) | Group 1 (0.05 mpk) | Group 2 (0.3 mpk) | Group 3 (1.0 mpk) |
|---|---|---|---|
| Predose | 1000 | 1000 | 1000 |
| 2 h | 142588 | 363272 | 312006 |
| 6 h | 379362 | 341285 | 502663 |
| 24 h | 103055 | 148789 | 467598 |
| 48 h | 25382 | 57095 | 175953 |
| 96 h | 2084 | 6095 | 24795 |

TABLE 27

Pharmacokinetic parameters measured upon administration of nanoparticle compositions to non-human primates.

| | | Group 1 (0.05 mpk) | Group 2 (0.3 mpk) | Group 3 (1.0 mpk) |
|---|---|---|---|---|
| Tmax (hours) | Mean | 6.00 | 3.33 | 12.0 |
| | SD | 0.00 | 2.31 | 10.4 |
| | CV % | 0.00 | 69.3 | 86.6 |
| Cmax (pg/ml) | Mean | 3.79E+05 | 3.84E+05 | 5.51E+05 |
| | SD | 2.64E+05 | 2.45E+05 | 6.24E+04 |
| | CV % | 69.7 | 63.8 | 11.3 |
| AUCall (hr · pg/ml) | Mean | 7.72E+06 | 1.02E+07 | 2.32E+07 |
| | SD | 6.26E+06 | 7.34E+06 | 4.20E+06 |
| | CV % | 81.1 | 72.3 | 18.1 |

TABLE 28

Complement activation indicators measured at various time points upon administration of nanoparticle compositions to non-human primates.

| | Time point | Group 1 (0.05 mpk) | Group 2 (0.3 mpk) | Group 3 (1.0 mpk) |
|---|---|---|---|---|
| C3a (ng/ml) | Predose | 10600 | 9827 | 12792 |
| | 2 h | 19236 | 42897 | 75936 |
| | 6 h | 12385 | 32436 | 51996 |
| | 24 h | 11596 | 19721 | 35843 |
| | Day 5 | 11945 | 16207 | 19101 |
| Bb fragment (ng/ml) | Predose | 1375 | 1461 | 1529 |
| | 2 h | 5341 | 5356 | 8849 |
| | 6 h | 3037 | 7157 | 12820 |
| | 24 h | 1496 | 3680 | 8601 |
| | Day 5 | 1273 | 2400 | 2834 |
| C5b9 (ng/ml) | Predose | 169 | 157 | 238 |
| | 2 h | 1959 | 393 | 801 |
| | 6 h | 786 | 1333 | 2928 |
| | 24 h | 265 | 614 | 4798 |
| | Day 5 | 163 | 405 | 534 |

TABLE 29

Cytokine induction measured at various time points upon administration of nanoparticle compositions to non-human primates.

| | Time point | Group 1 (0.05 mpk) | Group 2 (0.3 mpk) | Group 3 (1.0 mpk) |
|---|---|---|---|---|
| IFNg (pg/ml) | Predose | 18.8 | 18.8 | 18.8 |
| | 2 h | 18.8 | 18.8 | 35.8 |
| | 6 h | 18.8 | 18.8 | 38.9 |
| | 24 h | 18.8 | 18.8 | 18.8 |
| | Day 5 | 39.3 | 18.8 | 18.8 |
| IFNα (pg/ml) | Predose | 18.8 | 18.8 | 18.8 |
| | 2 h | 18.8 | 18.8 | 18.8 |
| | 6 h | 18.8 | 18.8 | 18.8 |
| | 24 h | 18.8 | 18.8 | 18.8 |
| | Day 5 | 18.8 | 18.8 | 18.8 |

TABLE 29-continued

Cytokine induction measured at various time points upon administration of nanoparticle compositions to non-human primates.

| | Time point | Group 1 (0.05 mpk) | Group 2 (0.3 mpk) | Group 3 (1.0 mpk) |
|---|---|---|---|---|
| IL-1b (pg/ml) | Predose | 18.8 | 18.8 | 18.8 |
| | 2 h | 18.8 | 18.8 | 33.4 |
| | 6 h | 18.8 | 18.8 | 18.8 |
| | 24 h | 18.8 | 18.8 | 18.8 |
| | Day 5 | 18.8 | 18.8 | 18.8 |
| IL-6 (pg/ml) | Predose | 18.8 | 18.8 | 18.8 |
| | 2 h | 18.8 | 191 | 834 |
| | 6 h | 18.8 | 33.0 | 398 |
| | 24 h | 18.8 | 18.8 | 31.4 |
| | Day 5 | 18.8 | 18.8 | 18.8 |
| MCP-1 (pg/ml) | Predose | 192 | 168 | 235 |
| | 2 h | 342 | 3018 | 4221 |
| | 6 h | 543 | 2011 | 3945 |
| | 24 h | 236 | 404 | 1444 |
| | Day 5 | 232 | 211 | 225 |
| TNF-α (pg/ml) | Predose | 18.8 | 18.8 | 18.8 |
| | 2 h | 18.8 | 38.2 | 18.8 |
| | 6 h | 41.5 | 32.5 | 18.8 |
| | 24 h | 17.6 | 59.6 | 46.2 |
| | Day 5 | 63.5 | 18.8 | 41.9 |

In general, the formulation was tolerated similarly to the MC3 formulation with dose-response effects. Aspartate aminotransferase (AST) increased in the high dose group on Day 2 and returned to baseline by Day 5. Alanine aminotransferase (ALT) levels did not increase, however. In general, lower doses were better tolerated. High doses induced body temperature elevation and hunched posture, which is similar to the behavior observed for primates administered higher doses of MC3 formulations. White blood cell counts were slightly elevated in animals in the high dose group, however all groups showed a marked increase in reticulocyte counts on Day 5, indicating a strong pharmacological response. Complement activation and cytokine release (IL-6 and MCP-1) were dose-related and reversible within 24 hours for the low and mid-dose groups and by Day 5 in the high dose group. hEPO levels were higher than those measured upon administration of comparable doses of MC3 formulations to non-human primates.

Example 22: Administration to Non-Human Primates

The tolerability and efficacy of nanoparticle compositions to non-human primates was also investigated using sample formulations including Compounds 18, 25, 26, and 48 and MC3 to determine if these compounds are differentiated in terms of protein expression. The formulations were prepared according to the standard MC3 formulation described above and included an hEPO mRNA. Table 30 includes details of the compositions tested, while Table 31 summarizes the relative expression of Luc and hEPO mRNA in mice and rats. Expression was measured 6 hours after administration.

TABLE 30

Characteristics of nanoparticle compositions including compounds according to Formula (I), (IA), (II), (IIa), (IIb), (IIc), (IId) or (IIe).

| Compound | Size (nm) | PDI | EE (%) | pH | Osmolality (mOsm/kg) | Zeta potential (mV) |
|---|---|---|---|---|---|---|
| 18 | 102.6 | 0.230 | 85.56 | 7.64 | 312 | −3.53 |
| 25 | 98.8 | 0.230 | 87.01 | 7.60 | 304 | −3.88 |
| 26 | 79.2 | 0.120 | 95.60 | 7.54 | 305 | −3.73 |
| 48 | 70.6 | 0.176 | 91.92 | 7.58 | 311 | −3.61 |
| MC3 | 106.0 | 0.220 | 91.66 | 7.52 | 318 | −3.64 | n.d. = not determined

TABLE 31

Comparison of nanoparticle compositions including compounds according to Formula (I), (IA), (II), (IIa), (IIb), (IIc), (IId) or (IIe).

| | Compound 18 | Compound 25 | Compound 26 | Compound 48 | MC3 |
|---|---|---|---|---|---|
| Lipid/MC3 Luc expression (0.5 mpk dose to mouse) | 3.23 | 1.89 | 4.24 | 10.0 | 1 |
| Lipid/MC3 hEPO expression (0.2 mpk dose to rat) | n.d. | 2.41 | n.d. | 5.39 | 1 |
| Lipid/MC3 hEPO expression (2 mpk dose to rat) | 0.81 | 2.13 | 4.95 | 3.84 | 1 |
| % lipid remaining in liver after 48 hours | 0.018 | 1.32 | 20 | 11.4 | 87 | n.d. = not determined

Figure 2:
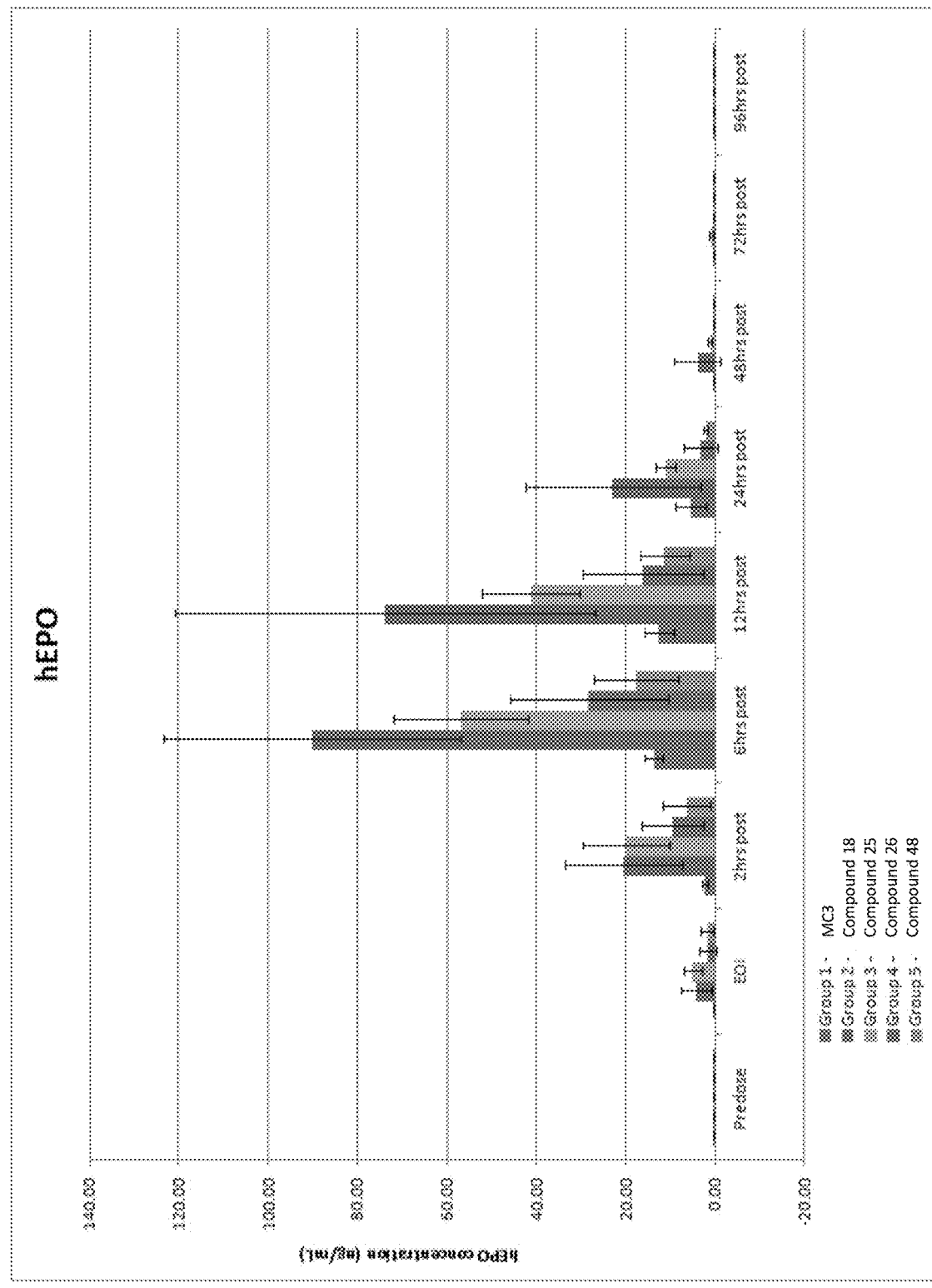
FIG. 2 shows the hEPO mRNA expression measured after intravenous administration of various nanoparticle compositions at a 0.01 mpk dose with 60 minutes infusion to naive cynomolgus monkeys.
Figure 3:
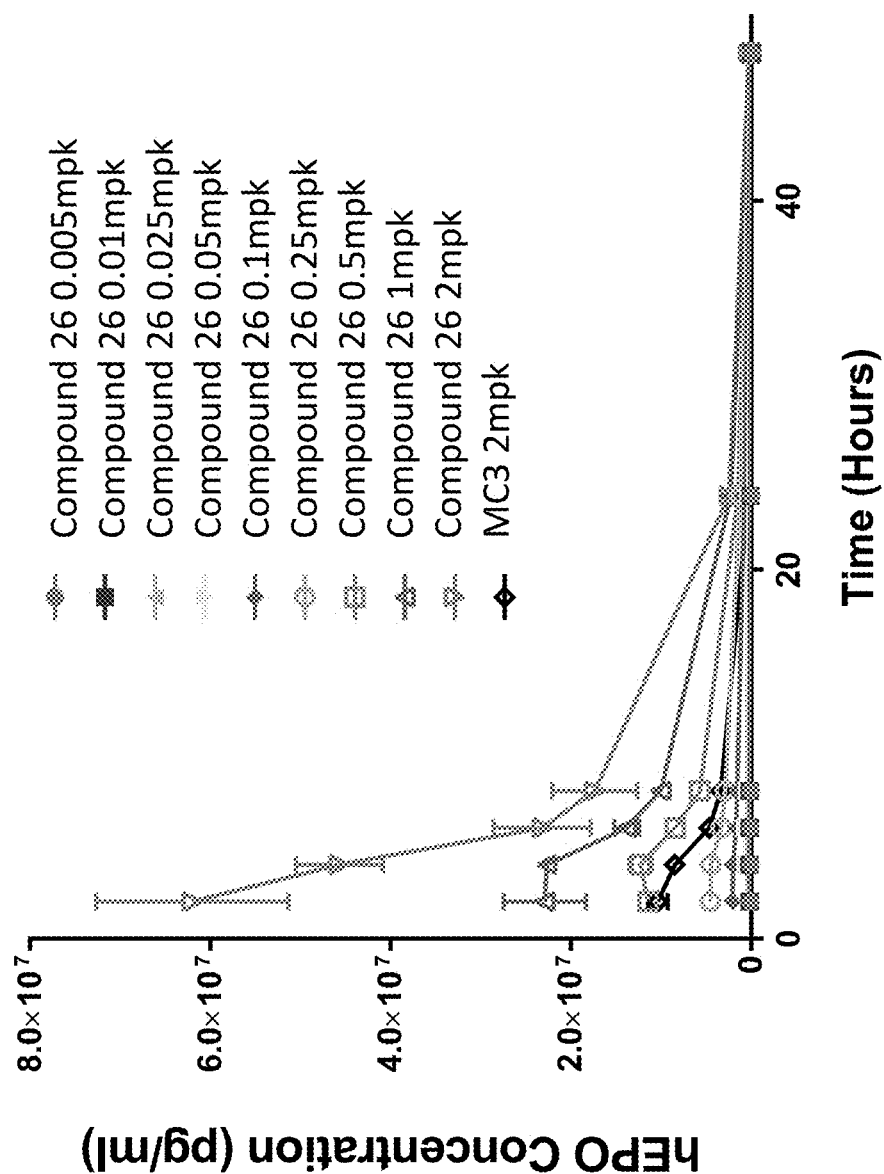
FIGS. 3-6 respectively shows the results of hEPO expression measured upon intravenous administration of various nanoparticle compositions including Compounds 26, 18, 25, and MC3 to rat at various doses.
Figure 4:
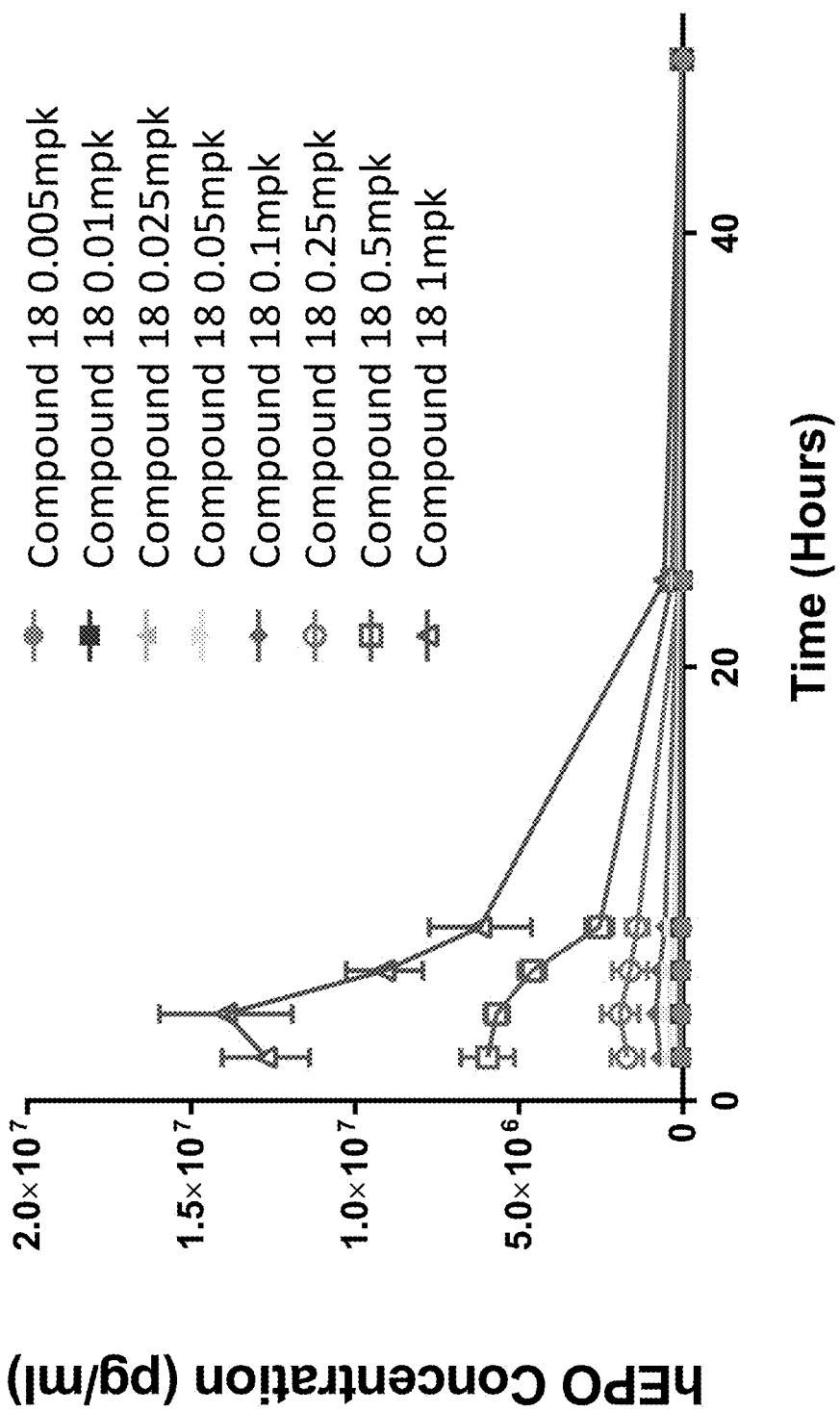
Figure 5:
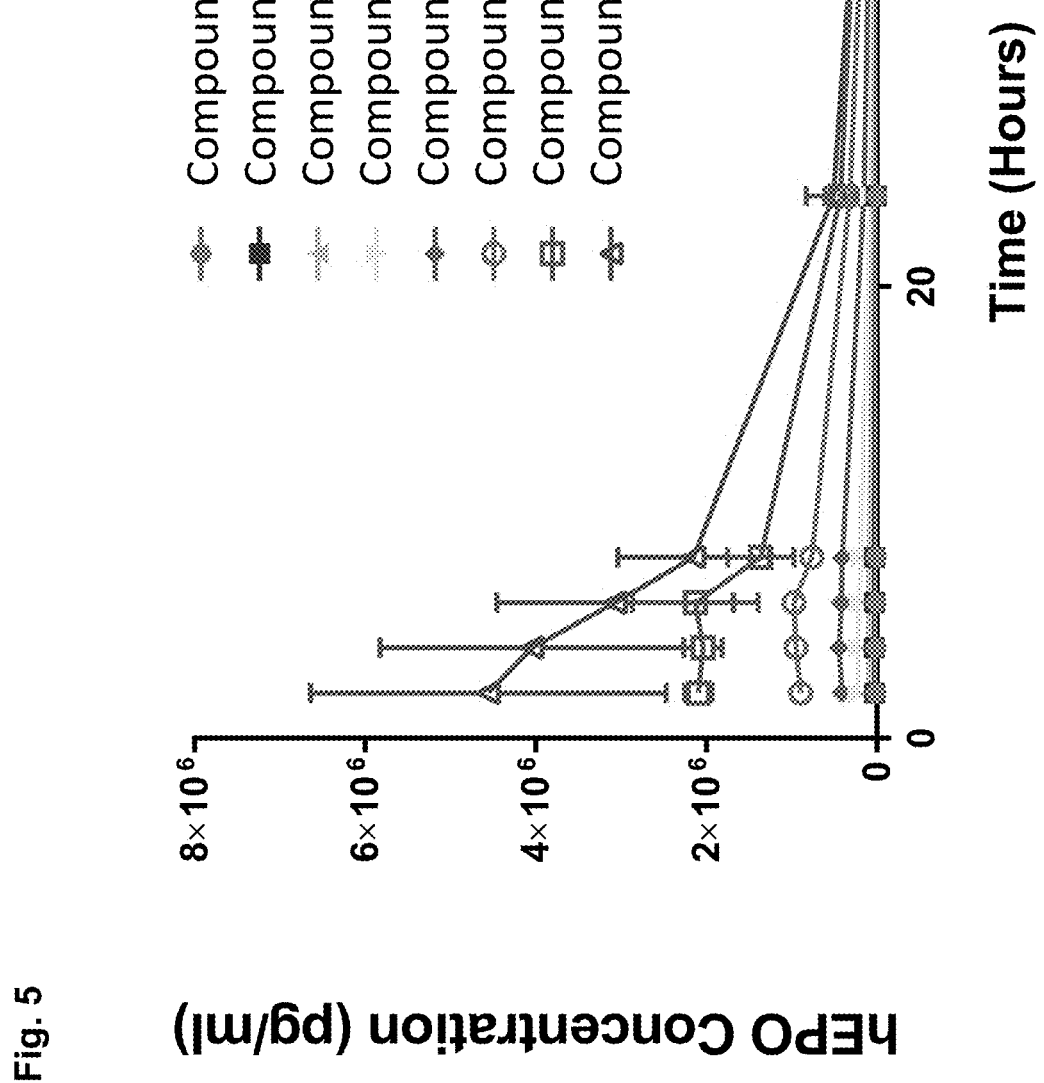
Figure 6:
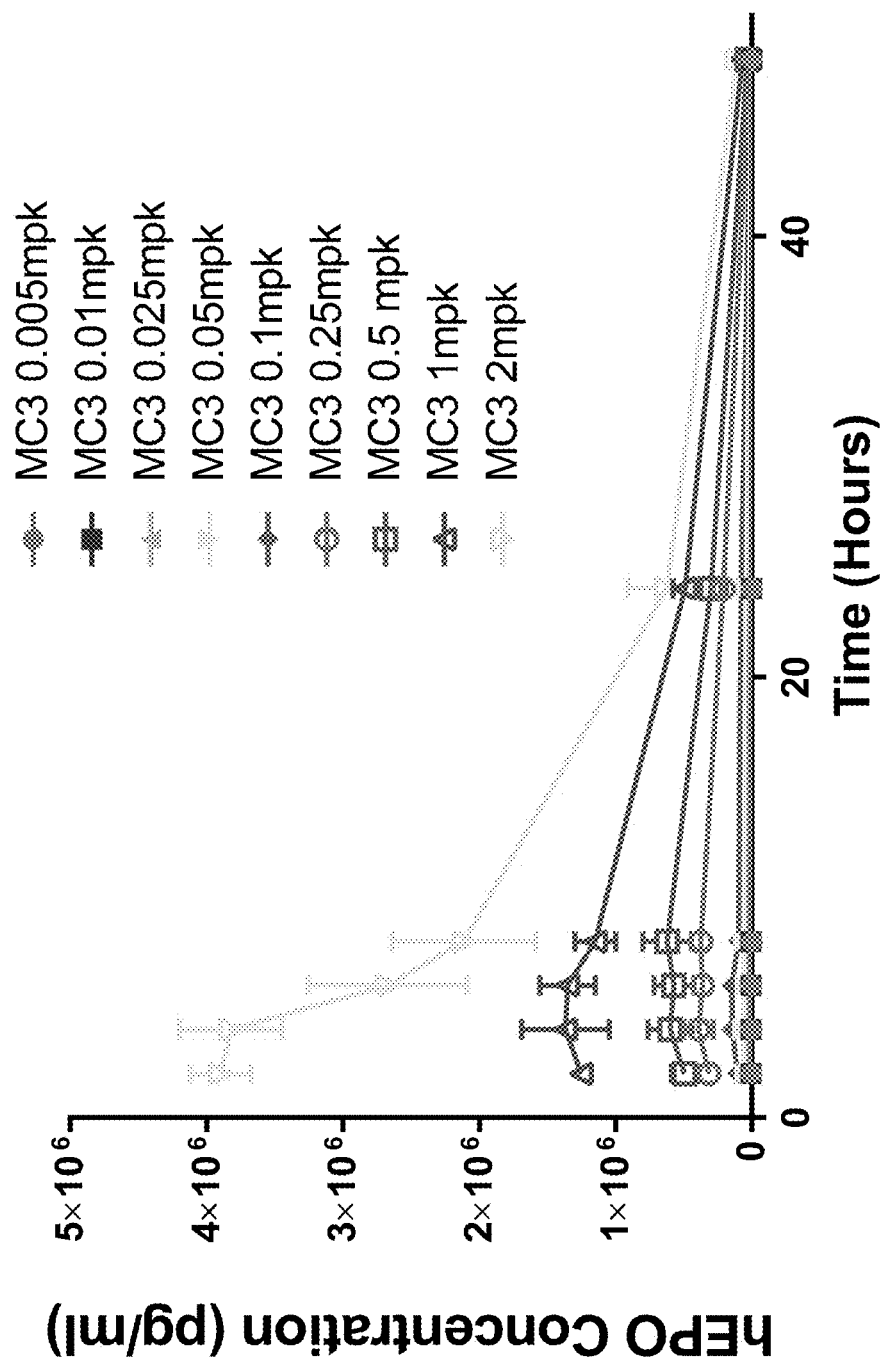

FIG. 2 shows the hEPO mRNA expression measured after intravenous administration of a 0.01 mpk dose with 60 minutes infusion to naive cynomolgus monkeys. As is evident in the figure, expression was highest 6 hours post administration for all formulations tested, and was highest for those formulations including Compound 18.

Table 32 summarizes pharmacokinetic parameters measured upon administration of 0.01 mpk doses of formulations to non-human primates.

TABLE 32

Pharmacokinetic parameters measured upon administration of formulations including compounds according to Formula (I), (IA), (II), (IIa), (IIb), (IIc), (IId) or (IIe) to non-human primates.

| Lipid | $T_{max}$ (hr) Mean | $C_{max}$ (ng/mL) Mean | SD | CV % | $AUC_{0-t}$ (hr*ng/mL) Mean | SD | CV % | AUC Lipid/MC3 Ratio |
|---|---|---|---|---|---|---|---|---|
| MC3 | 8 | 14.1 | 2.36 | 16.8 | 284 | 97.4 | 34.2 | 1.0 |
| Compound 18 | 8 | 91 | 34.7 | 38.1 | 1690 | 1060 | 63.1 | 6.0 |
| Compound 25 | 6 | 56.9 | 15.1 | 26.5 | 930 | 249 | 26.8 | 3.3 |
| Compound 26 | 6 | 28.2 | 17.7 | 62.7 | 365 | 302 | 82.7 | 1.3 |
| Compound 48 | 6 | 17.7 | 9.49 | 53.6 | 245 | 117 | 47.9 | 0.9 |

Example 23: Administration to Non-Human Primates

Results of hEPO expression studies were validated using a standard MC3 formulation and a nanoparticle composition containing Compound 18 including an mRNA encoding an anti-hemagglutinin (anti-HA) antibody. Cynomolgus monkeys were administered a single dose of 0.1 mpk or 0.3 mpk of a nanoparticle composition containing Compound 18 (see Table 33; prepared according to Example 2) including an mRNA encoding anti-HA antibody via intravenous infusion for 60 minutes.

TABLE 33

| Lipid | EE (%) | Diameter (nm) | PDI |
|---|---|---|---|
| Compound 18 | 79.3 | 76.8 | 0.16 |

The results of anti-HA (anti-hemagglutinin) antibody expression are shown in Table 34 and in FIG. 11.

TABLE 34

| Lipid | Dose (mpk) | AUC (µg/mL * h) | AUC Compound 18/MC3 Ratio |
|---|---|---|---|
| MC3 | 0.1 | 77.05 | — |
| Compound 18 | 0.1 | 354.3 | 4.6 |
| MC3 | 0.3 | 235.7 | — |
| Compound 18 | 0.3 | 1055 | 4.5 |

A five times higher protein expression was observed with the nanoparticle composition containing Compound 18 versus the MC3 counterpart, and a clear dose response between 0.1 and 0.3 mpk with Compound 18 was found (e.g., 0.3 mpk AUC is about three times of that from 0.1 mpk dose).

Example 24: Methods of Treating Diseases and Disorders

A nanoparticle composition formulation having high tolerability (e.g., provoking a low immune response) and efficacy (e.g., facilitating efficient and effective encapsulation of a therapeutic and/or prophylactic and delivery of the agent to a desired target) is selected for use. A therapeutic and/or prophylactic for formulation with the nanoparticle composition is selected for use based on the condition of a subject. For example, an mRNA encoding a vascular endothelial growth factor A (VEGF-A) may be selected to promote angiogenesis to treat atherosclerotic renovascular disease, while an siRNA capable of knocking down apolipoprotein B (apoB) may be selected to treat a metabolic disease or disorder such as dyslipidemia.

A subject in need of treatment is pretreated with a small dose of dexamethasone one or more hours prior to treatment with the nanoparticle composition. The nanoparticle composition is preferably administered to the subject intravenously, however intramuscular, intradermal, subcutaneous, intranasal, or inhalation administration routes are also acceptable. Treatment is provided in a dose of about 0.001 mg/kg to about 10 mg/kg of therapeutic and/or prophylactic and is repeated daily, weekly, biweekly, or monthly according to needs of the subject.

EQUIVALENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A compound of Formula (I):

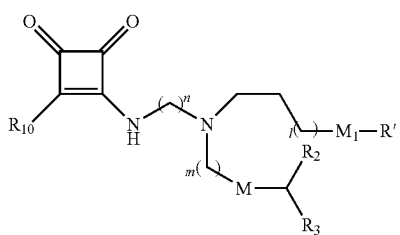

(I)

or its N-oxide,
or a salt thereof, wherein
l is selected from 1, 2, 3, 4, and 5;
m is selected from 5, 6, 7, 8, and 9;
n is selected from 1, 2, 3, 4, and 5;
$M_1$ is a bond or M';
$R_2$ and $R_3$ are both $C_{1-14}$ alkyl or $C_{2-14}$ alkenyl;
M and M' are independently selected from —C(O)O—, —OC(O)—, —OC(O)-M"-C(O)O—, —C(O)N(R')—, —C(O)N(H)—, —N(R')C(O)—, —N(H)C(O)—, —C(O)—, —C(S)—, —C(S)S—, —SC(S)—, —CH(OH)—, —P(O)(OR')O—, —P(O)(OH)O—, —S(O)$_2$—, —S—S—, an aryl group, and a heteroaryl group, in which M" is a bond, $C_{1-13}$ alkyl or $C_{2-13}$ alkenyl;
$R_{10}$ is selected from the group consisting of alkylamino and dialkylamino; and
R' is a linear alkyl.

2. The compound of claim 1, wherein $R_2$ and $R_3$ are the same.
3. The compound of claim 1, wherein R' is $C_9$ alkyl.
4. The compound of claim 1, wherein n is 3.
5. The compound of claim 1, wherein l is 5 and m is 7.
6. A nanoparticle composition comprising a lipid component comprising a compound of claim 1.

7. The nanoparticle composition of claim 6, wherein the lipid component further comprises a phospholipid selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine,1,2-dioleoyl-sn-glycero-3-phosphoethanola mine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

8. The nanoparticle composition of claim 6, wherein the lipid component further comprises a structural lipid selected from the group consisting of cholesterol, fecosterol, sitosterol, ergosterol, campesterol, stigmasterol, brassicasterol, tomatidine, ursolic acid, alpha-tocopherol, and mixtures thereof.

9. The nanoparticle composition of claim 6, wherein the lipid component further comprises a PEG lipid selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

10. The nanoparticle composition of claim 6, wherein the lipid component further comprises a cationic and/or ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), 2-({8-[(3β)-cholest-5-en-3-yloxy] octyl} oxy)-N,N-dimethyl-3-[(9Z,12Z)-octadeca-9,12-dien-1-yl oxy] propan-1-amine (Octyl-CLinDMA), (2R)-2-({8-[(3β)-cholest-5-en-3-yloxy]octyl}oxy)-N,N-dimethyl-3-[(9Z, 12Z)-octadeca-9,12-dien-1-yloxy]propan-1-amine (Octyl-CLinDMA (2R)), and (2 S)-2-({8-[(3β)-cholest-5-en-3-yloxy] octyl} oxy)-N,N-dimethyl-3-[(9Z,12Z)-octadeca-9, 12-dien-1-yloxy]propan-1-amine (Octyl-CLinDMA (2S)).

11. The nanoparticle composition of claim 6, wherein the lipid component comprises about 30 mol % to about 60 mol % said compound, about 0 mol % to about 30 mol % phospholipid, about 18.5 mol % to about 48.5 mol % structural lipid, and about 0 mol % to about 10 mol % PEG lipid.

12. The nanoparticle composition of claim 6, further comprising a therapeutic and/or prophylactic agent.

13. The nanoparticle composition of claim 12, wherein the therapeutic and/or prophylactic agent is a ribonucleic acid (RNA), wherein the RNA is selected from the group consisting of a small interfering RNA (siRNA), an asymmetrical interfering RNA (aiRNA), a microRNA (miRNA), a Dicer-substrate RNA (dsRNA), a small hairpin RNA (shRNA), a messenger RNA (mRNA), and mixtures thereof.

14. The nanoparticle composition of claim 13, wherein the RNA is an mRNA.

15. The nanoparticle composition of claim 14, wherein the mRNA includes one or more of a stem loop, a chain terminating nucleoside, a polyA sequence, a polyadenylation signal, and/or a 5' cap structure.

16. The nanoparticle composition of claim 12, wherein the encapsulation efficiency of the therapeutic and/or prophylactic agent is at least 80% or at least 90%.

17. The nanoparticle composition of claim 12, wherein the wt/wt ratio of the lipid component to the therapeutic and/or prophylactic agent is from about 10:1 to about 60:1.

18. The nanoparticle composition of claim 6, wherein the N:P ratio is from about 2:1 to about 30:1.

19. A pharmaceutical composition comprising the nanoparticle composition of claim 6 and a pharmaceutically acceptable carrier.

20. A method of delivering a therapeutic and/or prophylactic agent to a mammalian cell, the method comprising administering to a subject the nanoparticle composition of claim 12, said administering comprising contacting the cell with the nanoparticle composition, whereby the therapeutic and/or prophylactic agent is delivered to the cell.

21. The compound of claim 1, wherein M and M' are each independently —C(O)O— or —OC(O)—.

22. A compound selected from:

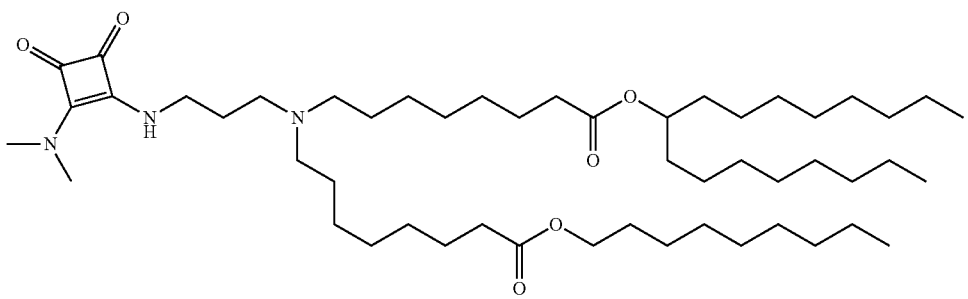

(Compound 169)

, and

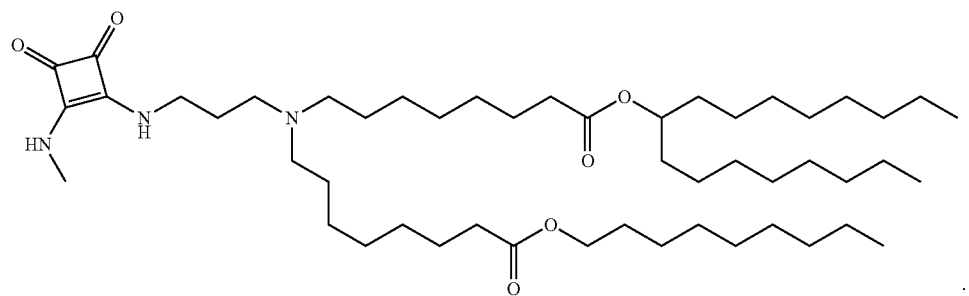
(Compound 182)
* * * * *